(12) United States Patent
Staudt et al.

(10) Patent No.: US 11,574,704 B2
(45) Date of Patent: Feb. 7, 2023

(54) METHOD FOR SUBTYPING LYMPHOMA TYPES BY MEANS OF EXPRESSION PROFILING

(71) Applicants: The United States of America, as represented by the Secretary, Department of Health and Human Services, Bethesda, MD (US); British Columbia Cancer Agency Branch, Vancouver (CA); Arizona Board of Regents on Behalf of the University of Arizona, Tucson, AZ (US); Universitat de Barcelona, Barcelona (ES); Hospital Clinic de Barcelona, Barcelona (ES); The Cleveland Clinic Foundation, Cleveland, OH (US); Board of Regents of the University of Nebraska, Lincoln, NE (US); Oregon Health & Science University, Portland, OR (US); Julius-Maximilians—University of Würzburg, Würzburg (DE); Oslo University Hospital HF, Oslo (NO)

(72) Inventors: Louis M. Staudt, Bethesda, MD (US); George W. Wright, Rockville, MD (US); David William Scott, Vancouver (CA); Joseph M. Connors, Vancouver (CA); Randy D. Gascoyne, North Vancouver (CA); Lisa Rimsza, Scottsdale, AZ (US); Elias Campo Guerri, Barcelona (ES); Raymond Tubbs, Cleveland, OH (US); Timothy C. Greiner, Council Bluffs, IA (US); James Robert Cook, Shaker Heights, OH (US); Kai Fu, Omaha, NE (US); Paul Michael Williams, Great Falls, VA (US); Chih-Jian Lih, Gaithersburg, MD (US); Elaine S. Jaffe, Great Falls, VA (US); Rita M. Braziel, West Linn, OR (US); Andreas Rosenwald, Würzburg (DE); Erlend B. Smeland, Oslo (NO); Wing C. Chan, Pasadena, CA (US); German Ott, Bietigheim-Bissingen (DE); Jan Delabie, Toronto (CA); Dennis Weisenburger, Glendora, CA (US)

(73) Assignees: The United States of America, as represented by the Secretary, Department of Health and Human Services, Bethesda, MD (US); British Columbia Cancer Agency Branch, Vancouver (CA); Arizona Board of Regents on Behalf of the University of Arizona, Tucson, AZ (US); Universitat de Barcelona, Barcelona (ES); Hospital Clinic de Barcelona, Barcelona (ES)

( * ) Notice: Subject to any disclaimer, the term of this patent is extended or adjusted under 35 U.S.C. 154(b) by 470 days.

(21) Appl. No.: 16/746,347

(22) Filed: Jan. 17, 2020

(65) Prior Publication Data
US 2020/0143906 A1 May 7, 2020

Related U.S. Application Data

(63) Continuation of application No. 15/035,101, filed as application No. PCT/US2014/064161 on Nov. 5, 2014, now Pat. No. 10,607,717.

(60) Provisional application No. 61/900,553, filed on Nov. 6, 2013.

(51) Int. Cl.
*G01N 33/48* (2006.01)
*G16B 25/10* (2019.01)
(Continued)

(52) U.S. Cl.
CPC .......... *G16B 25/10* (2019.02); *C12Q 1/6886* (2013.01); *G16B 5/00* (2019.02); *G16B 25/00* (2019.02);
(Continued)

(58) Field of Classification Search
None
See application file for complete search history.

(56) References Cited

U.S. PATENT DOCUMENTS

| | | | |
|---|---|---|---|
| 5,143,854 | A | 9/1992 | Pirrung et al. |
| 5,242,974 | A | 9/1993 | Holmes |

(Continued)

FOREIGN PATENT DOCUMENTS

| | | | |
|---|---|---|---|
| JP | 2012-533308 A | 1/2011 | |
| JP | 2011-510663 A | 4/2011 | |

(Continued)

OTHER PUBLICATIONS

U.S. Appl. No. 10/934,930, filed Sep. 3, 2004.
(Continued)

*Primary Examiner* — Anna Skibinsky
(74) *Attorney, Agent, or Firm* — Leydig, Voit & Mayer, Ltd.

(57) ABSTRACT

The invention is directed to methods for selecting a treatment option for an activated B cell-like diffuse large B cell lymphoma (ABC DLBCL) subject, a germinal center B cell-like diffuse large B cell lymphoma (GCB DLBCL) subject, a primary mediastinal B cell lymphoma (PMBL) subject, a Burkitt lymphoma (BL) subject, or a mantle cell lymphoma (MCL) subject by analyzing digital gene expression data obtained from the subject, e.g., from a biopsy sample.

12 Claims, 1 Drawing Sheet
Specification includes a Sequence Listing.

(51) Int. Cl.
*G16B 25/00* (2019.01)
*G16B 5/00* (2019.01)
*C12Q 1/6886* (2018.01)

(52) U.S. Cl.
CPC .. *C12Q 2600/106* (2013.01); *C12Q 2600/112* (2013.01); *C12Q 2600/158* (2013.01); *C12Q 2600/166* (2013.01)

(56) References Cited

U.S. PATENT DOCUMENTS

| | | | |
|---|---|---|---|
| 5,252,743 | A | 10/1993 | Barrett et al. |
| 5,324,633 | A | 6/1994 | Fodor et al. |
| 5,384,261 | A | 1/1995 | Winkler et al. |
| 5,424,186 | A | 6/1995 | Fodor et al. |
| 5,445,934 | A | 8/1995 | Fodor et al. |
| 5,451,683 | A | 9/1995 | Barrett et al. |
| 5,482,867 | A | 1/1996 | Barrett et al. |
| 5,491,074 | A | 2/1996 | Aldwin et al. |
| 5,527,681 | A | 6/1996 | Holmes |
| 5,550,215 | A | 8/1996 | Holmes |
| 5,571,639 | A | 11/1996 | Hubbell et al. |
| 5,578,832 | A | 11/1996 | Trulson et al. |
| 5,593,839 | A | 1/1997 | Hubbell et al. |
| 5,599,695 | A | 2/1997 | Pease et al. |
| 5,624,711 | A | 4/1997 | Sundberg et al. |
| 5,631,734 | A | 5/1997 | Stern et al. |
| 5,708,153 | A | 1/1998 | Dower et al. |
| 5,744,305 | A | 4/1998 | Fodor et al. |
| 5,770,358 | A | 6/1998 | Dower et al. |
| 5,789,162 | A | 8/1998 | Dower et al. |
| 5,795,716 | A | 8/1998 | Chee et al. |
| 5,800,992 | A | 9/1998 | Fodor et al. |
| 5,831,070 | A | 11/1998 | Pease et al. |
| 5,837,832 | A | 11/1998 | Chee et al. |
| 5,856,101 | A | 1/1999 | Hubbell et al. |
| 5,856,174 | A | 1/1999 | Lipshutz et al. |
| 5,858,659 | A | 1/1999 | Sapolsky et al. |
| 5,922,591 | A | 7/1999 | Anderson et al. |
| 5,936,324 | A | 8/1999 | Montagu |
| 5,968,740 | A | 10/1999 | Fodor et al. |
| 5,974,164 | A | 10/1999 | Chee |
| 5,981,185 | A | 11/1999 | Matson et al. |
| 5,981,956 | A | 11/1999 | Stern |
| 6,020,198 | A | 2/2000 | Bennett et al. |
| 6,025,601 | A | 2/2000 | Trulson et al. |
| 6,033,860 | A | 3/2000 | Lockhart et al. |
| 6,040,193 | A | 3/2000 | Winkler et al. |
| 6,090,555 | A | 7/2000 | Fiekowsky et al. |
| 6,410,229 | B1 | 6/2002 | Lockhart et al. |
| 7,711,492 | B2 | 5/2010 | Staudt et al. |
| 7,919,237 | B2 | 4/2011 | Dimitrov et al. |
| 2002/0110820 | A1 | 8/2002 | Ramaswamy et al. |
| 2003/0104411 | A1 | 6/2003 | Fodor et al. |
| 2003/0194701 | A1 | 10/2003 | Golub et al. |
| 2003/0219760 | A1 | 11/2003 | Gordon et al. |
| 2005/0112630 | A1 | 5/2005 | Shaughnessy et al. |
| 2005/0164231 | A1 | 7/2005 | Staudt et al. |
| 2007/0105136 | A1 | 5/2007 | Staudt et al. |
| 2008/0132504 | A1 | 6/2008 | Garcia-Echeverria et al. |
| 2008/0193462 | A1 | 8/2008 | Kung et al. |
| 2009/0181393 | A1 | 7/2009 | Mulligan et al. |
| 2009/0233279 | A1 | 9/2009 | Glinskii |
| 2009/0253583 | A1 | 10/2009 | Yoganathan |
| 2011/0104671 | A1 | 5/2011 | Dornan et al. |
| 2011/0152115 | A1 | 6/2011 | Staudt et al. |
| 2011/0195064 | A1 | 8/2011 | Rimsza et al. |
| 2011/0293629 | A1* | 12/2011 | Bastid ............... A61P 35/00 435/7.1 |
| 2012/0087915 | A1 | 4/2012 | Buggy et al. |
| 2012/0225432 | A1 | 9/2012 | Campo Guerri et al. |
| 2012/0258878 | A1 | 10/2012 | Saad |
| 2013/0011409 | A1 | 1/2013 | Shipp et al. |
| 2013/0259858 | A1 | 10/2013 | Zacksenhaus et al. |

FOREIGN PATENT DOCUMENTS

| | | |
|---|---|---|
| WO | WO 02/024956 A2 | 3/2002 |
| WO | WO 03/024956 A1 | 3/2003 |
| WO | WO 2005/024043 A2 | 3/2005 |
| WO | WO 2008/013910 A2 | 1/2008 |
| WO | WO 2009/100029 A1 | 8/2009 |
| WO | WO 2009/149359 A2 | 12/2009 |
| WO | WO 2011/009104 A1 | 1/2011 |
| WO | WO 2011/097476 A1 | 8/2011 |
| WO | WO 2012/149299 A2 | 11/2012 |
| WO | WO 2013/082722 A1 | 6/2013 |
| WO | WO 2013/120086 A1 | 8/2013 |
| WO | WO 2013/188600 A1 | 12/2013 |
| WO | WO 2014/197936 A1 | 12/2014 |
| WO | WO 2015/085172 A2 | 6/2015 |
| WO | WO 2016/057705 A1 | 4/2016 |

OTHER PUBLICATIONS

U.S. Appl. No. 11/493,387, filed Jul. 25, 2006.
U.S. Appl. No. 12/592,778, filed Dec. 2, 2009.
U.S. Appl. No. 12/996,489, filed Feb. 24, 2011.
U.S. Appl. No. 13/008,403, filed Jan. 18, 2011.
U.S. Appl. No. 13/409,416, filed Mar. 1, 2012.
U.S. Appl. No. 14/540,302, filed Nov. 13, 2014.
U.S. Appl. No. 14/570,316, filed Dec. 15, 2014.
U.S. Appl. No. 15/035,101, filed May 6, 2016.
Alizadeh et al., "The lymphochip: a specialized cDNA microarray for the genomic-scale analysis of gene expression in normal and malignant lymphocytes," *Cold Spring Harbor Symp. Quant. Biol.*, 64, 71-78 (1999).
Alizadeh et al., "Distinct types of diffuse large B-cell lymphoma identified by gene expression profiling," *Nature*, 403 (6769), 503-511 (2000).
Alon et al., "Broad patterns of gene expression revealed by clustering analysis of tumor and normal colon tissues probed by oligonucleotide arrays," *Proc. Natl. Acad. Sci. USA*, 96 (12), 6745-6750 (1999).
Ando et al., "Fuzzy neural network applied to gene expression profiling for predicting the prognosis of diffuse large B-cell lymphoma," *Jpn. J. Cancer Res.*, 93, 1207-1212 (2002).
Andreasson et al., "Genomic amplification of CCND2 is rare in non-Hodgkin lymphomas," *Cancer Genet. Cytogenet.*, 102 (1), 81-82 (1998).
Basso et al., "Tracking CD40 signaling during germinal center development," *Blood*, 104 (13), 4088-4096 (2004).
Bea et al., "Clinicopathologic significance and prognostic value of chromosomal imbalances in diffuse large B-cell lymphomas," *J. Clin. Oncol.*, 22 (17), 3498-3506 (2004).
Berglund et al., "Chromosomal imbalances in diffuse large B-cell lymphoma detected by comparative genomic hybridization," *Mod. Pathol.*, 15 (8), 807-816 (2002).
Bergsagel et al., "Critical roles for immunoglobulin translocations and cyclin D dysregulation in multiple myeloma," *Immunol. Rev.*, 194, 96-104 (2003).
Bishop et al., "Burkitt's lymphoma: molecular pathogenesis and treatment," *Cancer Invest.*, 18 (6), 574-583 (2000).
Blenk et al., "Germinal center B cell-like (GCB) and activated B cell-like (ABC) type of diffuse large B cell lymphoma (DLBCL): analysis of molecular predictors, signatures, cell cycle state and patient survival," *Cancer Inform.*, 3, 399-420 (2007).
Boxer et al., "Translocations involving c-myc and c-myc function," *Oncogene*, 20 (40), 5595-5610 (2001).
Brault et al., "PIM kinases are progression markers and emerging therapeutic targets in diffuse large B-cell lymphoma," *Br. J. Canc.*, 107 (3), 491-500 (2012).
Cao et al., "Serial analysis of gene expression of lobular carcinoma in situ identifies down regulation of claudin 4 and overexpression of matrix metalloproteinase 9," *Breast Cancer Res.*, 10 (5), 10 pp. (2008).

(56) References Cited

OTHER PUBLICATIONS

Castillo et al., "Prognostic factors in chemotherapy-treated patients with HIV-associated plasmablastic lymphoma," *The oncologist*, 15:293-299 (2010).
Chee et al., "Accessing genetic information with high-density DNA arrays," *Science*, 274 (5287), 610-614 (1996).
Chiarle et al., "Increased proteasome degradation of cyclin-dependent kinase inhibitor p27 is associated with a decreased overall survival in mantle cell lymphoma," Blood, 95 (2), 619-626 (2000).
Cho et al., "A genome-wide transcriptional analysis of the mitotic cell cycle," Mol. Cell., 2 (1), 65-73 (1998).
Choi et al., "A new immunostain algorithm classifies diffuse large B-cell lymphoma into molecular subtypes with high accuracy," Clin. Cancer Res., 15 (17), 5494-5502 (2009).
Chu et al., "The transcriptional program of sporulation in budding yeast," Science, 282 (5389), 699-705 (1998).
Cigudosa et al., "Cytogenetic analysis of 363 consecutively ascertained diffuse large B-cell lymphomas," Genes Chromosomes Cancer, 25 (2), 123-133 (1999).
Coiffier et al., "CHOP chemotherapy plus rituximab compared with CHOP alone in elderly patients with diffuse large-B-cell lymphoma," N. Engl. J. Med., 346 (4), 235-242 (2002).
Collins et al., "A differential microRNA profile distinguishes cholangiocarcinoma from pancreatic adenocarcinoma," Ann. Surg. Oncol., 21 (1), 133-138 (2014) Author Manuscript.
Copie-Bergman et al., "MAL expression in lymphoid cells: further evidence for MAL as a distinct molecular marker of primary mediastinal large B-cell lymphomas," Mod Pathol., 15 (11), 1172-1180 (2002).
Dave et al., "Cytogenetic characterization of diffuse large cell lymphoma using multi-color fluorescence in situ hybridization," Cancer Genet. Cytogenet., 132 (2), 125-132 (2002).
Dave et al., "Molecular diagnosis of Burkitt's lymphoma," N. Engl. J. Med., 354 (23), 2431-2442 (2006).
Davis et al., "Constitutive nuclear factor kappaB activity is required for survival of activated B cell-like diffuse large B cell lymphoma cells," J. Exp. Med., 194 (12), 1861-1874 (2001).
Davis et al., "Molecular diagnosis of lymphoid malignancies by gene expression profiling," Curr. Opin. Hematol., 9 (4), 333-338 (2002).
Deeb et al., "Super-SILAC Allows Classification of Diffuse Large B-cell Lymphoma Subtypes by Their Protein Expression Profiles," *Mol. Cell. Proteomics*, 11(5), 77-89 (2012).
De Leeuw et al., "Comprehensive whole genome array CGH profiling of mantle cell lymphoma model genomes," *Hum. Mol. Genet.*, 13 (17), 1827-1837 (2004).
Delmer et al., "Overexpression of cyclin D2 in chronic B-cell malignancies," *Blood*, 85 (10), 2870-2876 (1995).
Derisi et al., "Exploring the metabolic and genetic control of gene expression on a genomic scale," *Science*, 278 (5338), 680-686 (1997).
Derisi et al., "Use of a cDNA microarray to analyse gene expression patterns in human cancer," *Nat. Genet.*, 14 (4), 457-460 (1996).
Doglioni et al., "Cyclin D3 expression in normal, reactive and neoplastic tissues," *J. Pathol.*, 185 (2), 159-166 (1998).
Dreyling et al., "How to manage mantle cell lymphoma," *Leukemia*, 28 (11), 2117-2130 (2014).
Dudoit et al., "Comparison of Discrimination Methods for the Classification of Tumors Using Gene Expression Data," *J. Am. Stat. Assoc.*, 97 (457), 77-87 (2002).
Dybkaer et al., "Molecular diagnosis and outcome prediction in diffuse large B-cell lymphoma and other subtypes of lymphoma," *Clinical Lymphoma*, 5 (1), 19-28 (2004).
Eisen et al., "Cluster analysis and display of genome-wide expression patterns," *Proc. Natl. Acad. Sci. USA*, 95 (25), 14863-14868 (1998).
Ek et al., "Parallel gene expression profiling of mantle cell lymphoma—how do we transform 'omics data into clinical practice," *Curr. Genomics*, 8 (3), 171-179 (2007).

Fernandez et al., "Genomic and gene expression profiling defines indolent forms of mantle cell lymphoma," *Cancer Res.*, 70 (4), 1408-1418 (2010).
Fernandez et al., "Using digital RNA counting and flow cytometry to compare mRNA with protein expression in acute leukemias," *PLoS One*, 7(11), e49010 (2012), 10 pp.
Feuerhake et al., "NFkappaB activity, function, and target-gene signatures in primary mediastinal large B-cell lymphoma and diffuse large B-cell lymphoma subtypes," *Blood*, 106 (4), 1392-1399 (2005).
Fisher et al., "Comparison of a standard regimen (CHOP) with three intensive chemotherapy regimens for advanced non-Hodgkin's lymphoma," *N. Engl. J. Med.*, 328 (14), 1002-1006 (1993).
Fortina et al., "Digital mRNA profiling," *Nat. Biotechnol.*, 26 (3), 293-294 (2008).
Fu et al., "Cyclin D1-negative mantle cell lymphoma: a clinicopathologic study based on gene expression profiling," *Blood*, 106 (13), 4315-4321 (2005).
Geiss et al., "Direct multiplexed measurement of gene expression with color-coded probe pairs," Nat. Biotechnol., 26 (3), 317-325 (2008).
Goff et al., "The use of real-time quantitative polymerase chain reaction and comparative genomic hybridization to identify amplification of the REL gene in follicular lymphoma," Br. J. Haematol., 111 (2), 618-625 (2000).
Golub et al., "Molecular classification of cancer: class discovery and class prediction by gene expression monitoring," Science, 286 (5439), 531-537 (1999).
Gress et al., "A pancreatic cancer-specific expression profile," Oncogene, 13 (8), 1819-1830 (1996).
Hans et al., "Confirmation of the molecular classification of diffuse large B-cell lymphoma by immunohistochemistry using a tissue microarray," Blood, 103 (1), 275-82 (2004).
Hans et al., "Expression of PKC-beta or cyclin D2 predicts for inferior survival in diffuse large B-cell lymphoma," Mod. Pathol., 18 (10), 1377-1384 (2005).
Haralambieva et al., "Clinical, immunophenotypic, and genetic analysis of adult lymphomas with morphologic features of Burkitt lymphoma," Am. J. Surg. Pathol., 29 (8), 1086-1094 (2005).
Harpole et al., "A prognostic model of recurrence and death in stage I non-small cell lung cancer utilizing presentation, histopathology, and oncoprotein expression," Cancer Res., 55 (1), 51-56 (1995).
Hartmann et al., "Pathway discovery in mantle cell lymphoma by integrated analysis of high-resolution gene expression and copy number profiling," Blood, 116 (6), 953-961 (2010).
Heller et al., "Discovery and analysis of inflammatory disease-related genes using cDNA microarrays," Proc. Natl. Acad. Sci. USA, 94 (6), 2150-2155 (1997).
Henrickson et al., "Gene expression profiling in malignant lymphomas," Adv. Exp. Med. Biol., 593, 134-146 (2007).
Henson et al., "Candidate genes contributing to the aggressive phenotype of mantle cell lymphoma," Acta Histochem, 113 (7), 729-742 (2011), Author Manuscript.
Hofmann et al., "Altered apoptosis pathways in mantle cell lymphoma detected by oligonucleotide microarray," Blood, 98 (3), 787-794 (2001).
Holstege et al., "Dissecting the regulatory circuitry of a eukaryotic genome," Cell, 95 (5), 717-728 (1998).
Huang et al., "The t(14;18) defines a unique subset of diffuse large B-cell lymphoma with a germinal center B-cell gene expression profile," Blood, 99 (7), 2285-2290 (2002).
Huang et al., "Retraction: Simultaneous recovery of DNA and RNA from formalin-fixed paraffin-embedded tissue and application in epidemiologic studies," Cancer Epidemiol Biomarkers Prev, 23 (6), 1132 (2014).
Huang et al., "Simultaneous recovery of DNA and RNA from formalin-fixed paraffin-embedded tissue and application in epidemiologic studies," Cancer Epidemiol Biomarkers Prev., 19 (4), 973-977 (2010), retracted May 1, 2014.
Hudson et al., "Transcription signatures encoded by ultraconserved genomic regions in human prostate cancer," Mol. Cancer, 12, 13 pp. (2013).

(56) References Cited

OTHER PUBLICATIONS

Hummel et al., "A biologic definition of Burkitt's lymphoma from transcriptional and genomic profiling," N. Engl. J. Med., 354 (23), 2419-2430 (2006).
Hyman et al., "Impact of DNA amplification on gene expression patterns in breast cancer," Cancer Res., 62 (21), 6240-6245 (2002).
Hymowitz et al., "A20: from ubiquitin editing to tumour suppression," Nat. Rev. Cancer, 10 (5), 332-340 (2010).
Igarashi et al., "Factors affecting toxicity, response and progression-free survival in relapsed patients with indolent B-cell lymphoma and mantle cell lymphoma treated with rituximab: a Japanese phase II study," Ann. Oncol., 13 (6), 928-943 (2002).
International Preliminary Report on Patentability, Application No. PCT/US2014/064161, dated May 10, 2016, 11 pp.
International Search Report, Application No. PCT/US2014/064161, dated Mar. 5, 2015, 7 pp.
Iqbal et al., "BCL2 translocation defines a unique tumor subset within the germinal center B-cell-like diffuse large B-cell lymphoma," Am. J. Pathol., 165 (1), 159-166 (2004).
Iqbal et al., "Gene expression profiling in lymphoma diagnosis and management," Best Pract. Res. Clin. Haematol., 22 (2), 191-210 (2009).
Japanese Patent Office, Office Action dated Oct. 16, 2018 in Application No. 2016-553231, with English translation, 15 pages.
Jares et al., "Expression of retinoblastoma gene product (pRb) in mantle cell lymphomas. Correlation with cyclin D1 (PRAD1/CCND1) mRNA levels and proliferative activity," Am. J. Pathol., 148 (5), 1591-1600 (1996).
Jares et al., "Genetic and molecular pathogenesis of mantle cell lymphoma: perspectives for new targeted therapeutics," Nat. Rev. Cancer, 7 (10), 750-762 (2007).
Khan et al., "Classification and diagnostic prediction of cancers using gene expression profiling and artificial neural networks," Nat. Med., 7 (6), 673-679 (2001).
Khouri et al., "Hyper-CVAD and high-dose methotrexate/cytarbine followed by stem cell transplantation: an active regimen for aggressive mantle cell lymphoma," J. Clin. Oncol 16 (12), 3803-3809 (1998).
Kovacs, "Consistent chromosome 3p deletion and loss of heterozygosity in renal cell carcinoma," Proc. Natl. Acad. Sci. USA, 85 (5), 1571-1573 (1988).
Kramer et al., "Clinical relevance of BCL2, BCL6, and MYC rearrangements in diffuse large B-cell lymphoma," Blood, 92 (9), 3152-3162 (1998).
Kusumoto et al., "Diffuse large B-cell lymphoma with extra Bcl-2 gene signals detected by FISH analysis is associated with a 'non-germinal center phenotype',"Am. J. Surg. Pathol., 29 (8), 1063-1073 (2005).
Lafage-Pochitaloff-Huvale et al., "The gene for human thioredoxin maps on the short arm of chromosome 3 at bands 3p11-p12," FEBS Lett., 255 (1), 89-91 (1989).
Lashkari et al., "Yeast microarrays for genome wide parallel genetic and gene expression analysis," Proc. Natl. Acad. Sci. USA, 94 (24), 13057-13062 (1997).
Lenz et al., "Oncogenic CARD11 mutations in human diffuse large B cell lymphoma," Science, 319 (5870), 1676-1679 (2008).
Lenz et al., "Stromal gene signatures in large-B-cell lymphomas," N. Engl. J. Med., 359 (22), 2313-2323 (2008).
Li, "Survival prediction of diffuse large-B-cell lymphoma based on both clinical and gene expression information," Bioinformatics, 22 (4), 466-471 (2006).
Lipshutz et al., "Using oligonucleotide probe arrays to access genetic diversity," Biotechniques, 19 (3), 442-447 (1995).
Lockhart et al., "Expression monitoring by hybridization to high-density oligonucleotide arrays," Nat. Biotechnol., 14 (13), 1675-1680 (1996).
Mahadevan et al., "Transcript profiling in peripheral T-cell lymphoma, not otherwise specified, and diffuse large B-cell lymphoma identifies distinct tumor profile signatures," Mol. Cancer. Ther., 4 (12), 1867-1879 (2005).
Martinez et al., "The molecular signature of mantle cell lymphoma reveals multiple signals favoring cell survival," Cancer Res., 63 (23), 8226-8232 (2003).
Matsumura et al., "Gene expression analysis of plant host-pathogen interactions by SuperSAGE," Proc. Natl. Acad. Sci. USA, 100 (26), 15718-15723 (2003).
Meyer et al., "Immunohistochemical methods for predicting cell of origin and survival in patients with diffuse large B-cell lymphoma treated with rituximab," J. Clin. Oncol., 29 (2), 200-207 (2011).
Mircean et al., "Pathway analysis of informative genes from microarray data reveals that metabolism and signal transduction genes distinguish different subtypes of lymphomas," Int. J. Oncol., 24 (3), 497-504 (2004).
Monni et al., "DNA copy number changes in diffuse large B-cell lymphoma—comparative genomic hybridization study," Blood, 87 (12), 5269-5278 (1996).
Montgomery et al., "Pathology consultation on intermediate-to-large B-cell lymphomas," Am. J. Clin. Pathol., 141 (3), 305-317 (2014).
Monti et al., "Molecular profiling of diffuse large B-cell lymphoma identifies robust subtypes including one characterized by host inflammatory response," Blood, 105 (5), 1851-1861 (2005).
Mortazavi et al., "Mapping and quantifying mammalian transcriptomes by RNA-Seq," Nat Methods, 5 (7), 621-628 (2008).
Mounier et al., "Rituximab plus CHOP (R-CHOP) overcomes bcl-2-associated resistance to chemotherapy in elderly patients with diffuse large B-cell lymphoma (DLBCL)," Blood, 101 (11), 4279-4284 (2003).
Neri et al., "Different regions of the immunoglobulin heavy-chain locus are involved in chromosomal translocations in distinct pathogenetic forms of Burkitt lymphoma," Proc. Natl. Acad. Sci. USA, 85 (8), 2748-2752 (1988).
Ngo et al., "A loss-of-function RNA interference screen for molecular targets in cancer," Nature, 441 (7089), 106-110 (2006).
Northcott et al., "Rapid, reliable, and reproducible molecular subgrouping of clinical medulloblastoma samples," Acta Neruopathol., 123 (4), 615-626 (2012).
Nyman et al., "Prognostic impact of immunohistochemically defined germinal center phenotype in diffuse large B-cell lymphoma patients treated with immunochemotherapy," Blood, 109 (11), 4930-4935 (2007).
Orsetti et al., "Genomic and expression profiling of chromosome 17 in breast cancer reveals complex patterns of alterations and novel candidate genes," Cancer Res., 64 (18), 6453-6460 (2004).
Ortega-Paino et al., "Functionally associated targets in mantle cell lymphoma as defined by DNA microarrays and RNA interference," Blood, 111 (3), 1617-1624 (2008).
Ott et al., "Cyclin D1 expression in mantle cell lymphoma is accompanied by downregulation of cyclin D3 and is not related to the proliferative activity," Blood, 90 (8), 3154-3159 (1997).
Payton et al., "High throughput digital quantification of mRNA abundance in primary human acute myeloid leukemia samples," J. Clin. Invest., 119 (6), 1714-1726 (2009).
Pease et al., "Light-generated oligonucleotide arrays for rapid DNA sequence analysis," Proc. Natl. Acad. Sci. USA, 91 (11), 5022-5026 (1994).
Pietu et al., "Novel gene transcripts preferentially expressed in human muscles revealed by quantitative hybridization of a high density cDNA array," Genome Res., 6 (6), 492-503 (1996).
Pruneri et al., "Immunoreactivity for cyclin D3 is frequently detectable in high-grade primary gastric lymphomas in the absence of the t(6;14)(p21.1;q32.3) chromosomal translocation," J. Pathol., 200 (5), 596-601 (2003).
Puvvada et al., "Molecular classification, pathway addiction, and therapeutic targeting in diffuse large B-cell lymphoma," Cancer Genet., 206, 257-265 (2013), Author Manuscript.
Quek et al., "A multiplex assay to measure RNA transcripts of prostate cancer in urine," PLoS One, 7 (9), e45656 (2012), 9 pp.
Quintanilla-Martinez et al., "Mantle cell lymphomas lack expression of p27Kip1, a cyclin-dependent kinase inhibitor," Am. J. Pathol., 153 (1), 175-182 (1998).
Radmacher et al., "A paradigm for class prediction using gene expression profiles," J. Comput. Biol., 9 (3), 505-511 (2002).

(56) References Cited

OTHER PUBLICATIONS

Ramaswamy et al., "Recurrence patterns across medulloblastoma subgroups: an integrated clinical and molecular analysis," *Lancet Oncol.*, 14 (12), 1200-1207 (2013), Author Manuscript.
Ramaswamy et al., "Multiclass cancer diagnosis using tumor gene expression signatures," *Proc. Natl. Acad. Sci. USA*, 98 (26), 15149-15154 (2001).
Ransohoff, "Rules of evidence for cancer molecular-marker discovery and validation," *Nat. Rev. Cancer*, 4 (4), 309-314 (2004).
Rao et al., "Chromosomal and gene amplification in diffuse large B-cell lymphoma," *Blood*, 92 (1), 234-240 (1998).
Rimsza et al., "Loss of MHC class II gene and protein expression in diffuse large B-cell lymphoma is related to decreased tumor immunosurveillance and poor patient survival regardless of other prognostic factors: a follow-up study from the Leukemia and Lymphoma Molecular Profiling Project," *Blood*, 103 (11), 4251-4258 (2004).
Rizzatti et al., "Gene expression profiling of mantle cell lymphoma cells reveals aberrant expression of genes from the PI3K-AKT, WNT and TGFbeta signalling pathways," *Br. J. Haematol.*, 130 (4), 516-526 (2005).
Robetorye et al., "Microarray analysis of b-cell lymphoma cell lines with the t(14;18)," *J. Mol. Diag.*, 4 (3), 123-136 (2002).
Rogge et al., "Gene Profiling of Lymphoma, myeloma, and AML," *Medscape from WebMed*, 5 (3), 1-8 (2003).
Rosenwald, "DNA microarrays in lymphoid malignancies," *Oncology*, 8 pp. (2003), Web.
Rosenwald et al., "Gene expression profiling of diffuse large B-cell lymphoma," *Leukemia & Lymphoma*, 44 (Supp. 3), S41-S47 (2003).
Rosenwald et al., "Molecular diagnosis of primary mediastinal B cell lymphoma identifies a clinically favorable subgroup of diffuse large B cell lymphoma related to Hodgkin lymphoma," *J. Exp. Med.*, 198 (6), 851-862 (2003).
Rosenwald et al., "The proliferation gene expression signature is a quantitative integrator of oncogenic events that predicts survival in mantle cell lymphoma," *Cancer Cell*, 3 (2), 185-197 (2003).
Rosenwald et al., "The use of molecular profiling to predict survival after chemotherapy for diffuse large-B-cell lymphoma," *N. Engl. J. Med.*, 346 (25), 1937-1947 (2002).
Rubio-Moscardo et al., "Mantle-cell lymphoma genotypes identified with CGH to BAC microarrays define a leukemic subgroup of disease and predict patient outcome," *Blood*, 105 (11), 4445-4454 (2005).
Rummel et al., "Bendamustine plus rituximab versus CHOP plus rituximab as first-line treatment for patients with indolent and mantle-cell lymphomas: an open-label, multicentre, randomised, phase 3 non-inferiority trial," *Lancet*, 381 (9873), 1203-1210 (2013).
Salaverria et al., "Specific secondary genetic alterations in mantle cell lymphoma provide prognostic information independent of the gene expression-based proliferation signature," *J. Clin. Oncol.*, 25 (10), 1216-1222 (2007).
Savage et al., "The molecular signature of mediastinal large B-cell lymphoma differs from that of other diffuse large B-cell lymphomas and shares features with classical Hodgkin lymphoma," *Blood*, 102 (12), 3871-3879 (2003).
Schena et al., "Parallel human genome analysis: Microarray-based expression monitoring of 1000 genes," *Proc. Natl. Acad. Sci. USA*, 93, 10614-10619 (1996).
Schena et al., "Quantitative monitoring of gene expression patterns with a complementary DNA microarray," *Science*, 270 (5235), 467-470 (1995).
Schmechel et al., "Identification of genes whose expression patterns differ in benign lymphoid tissue and follicular, mantle cell, and small lymphocytic lymphoma," *Leukemia*, 18, 841-855 (2004).
Schwaenen et al., "DNA microarray analysis in malignant lymphomas," *Ann Hematol.*, 82 (6), 323-332 (2003).
Scott et al., "Determining cell-of-origin subtypes of diffuse large B-cell lymphoma using gene expression in formalin-fixed paraffin-embedded tissue," *Blood*, 123 (8), 1214-1217 (2014).

Sehn et al., "The revised International Prognostic Index (R-IPI) is a better predictor of outcome than the standard IPI for patients with diffuse large B-cell lymphoma treated with R-CHOP," *Blood*, 109 (5), 1857-1861 (2007).
Shaffer et al., "A library of gene expression signatures to illuminate normal and pathological lymphoid biology," *Immunol. Rev.*, 210, 67-85 (2006).
Shaffer et al., "Lymphoid malignancies: the dark side of B-cell differentiation," *Nat. Rev. Immunol.*, 2 (12), 920-932 (2002).
Shaffer et al., "Signatures of the immune response," *Immunity*, 15 (3), 375-385 (2001).
Shalon et al., "A DNA microarray system for analyzing complex DNA samples using two-color fluorescent probe hybridization," *Genome Res.*, 6 (7), 639-645 (1996).
Shipp et al., "A predictive model for aggressive non-Hodgkin's lymphoma. The International Non-Hodgkin's Lymphoma Prognostic Factors Project," *N. Engl. J. Med.*, 329 (14), 987-994 (1993).
Shipp et al., "Diffuse large B-cell lymphoma outcome prediction by gene-expression profiling and supervised machine learning," *Nat. Med.*, 8 (1), 68-74 (2002).
Sonoki et al., "Cyclin D3 is a target gene of t(6;14)(p21.1;q32.3) of mature B-cell malignancies," *Blood*, 98 (9), 2837-2844 (2001).
Southern et al., "Arrays of complementary oligonucleotides for analysing the hybridisation behaviour of nucleic acids," *Nucleic Acids. Res.*, 22 (8), 1368-1373 (1994).
Spellman et al., "Comprehensive identification of cell cycle-regulated genes of the yeast Saccharomyces cerevisiae by microarray hybridization," *Mol. Biol. Cell*, 9 (12), 3273-3297 (1998).
Staudt et al., "The biology of human lymphoid malignancies revealed by gene expression profiling," *Adv. Immunol.*, 87, 163-208 (2005), Author Manuscript.
Staudt et al., "Focus on lymphomas," *Cancer Cell*, 2 (5), 363-366 (2002).
Staudt, "Gene expression profiling of lymphoid malignancies," *Annu. Rev. Med.*, 53, 303-318 (2002).
Staudt et al., "Genomic views of the immune system*," *Annu. Rev. Immunol.*, 18, 829-859 (2000).
Staudt et al., "Molecular diagnosis of the hematologic cancers," *N. Engl. J. Med.*, 348 (18), 1777-1785 (2003).
Staudt, "It's All in the diagnosis," *Cancer Cell*, 1 (2), 109-110 (2002).
Subramanian et al., "Gene set enrichment analysis: a knowledge-based approach for interpreting genome-wide expression profiles," *Proc. Natl. Acad. Sci. USA*, 102 (43), 15545-15550 (2005).
Tagawa et al., "Comparison of genome profiles for identification of distinct subgroups of diffuse large B-cell lymphoma," *Blood*, 106 (5), 1770-1777 (2005).
Tamayo et al., "Interpreting patterns of gene expression with self-organizing maps: methods and application to hematopoietic differentiation," *Proc. Natl. Acad. Sci. USA*, 96 (6), 2907-2912 (1999).
Tavazoie et al., "Systematic determination of genetic network architecture," *Nature Genet.*, 22 (3), 281-285 (1999).
Thieblemont et al., "Small lymphocytic lymphoma, marginal zone B-cell lymphoma, and mantle cell lymphoma exhibit distinct gene-expression profiles allowing molecular diagnosis," *Blood*, 103 (7), 2727-2737 (2004).
Tibshirani et al., "Diagnosis of multiple cancer types by shrunken centroids of gene expression," *Proc. Natl. Acad. Sci. USA*, 99 (10), 6567-6572 (2002).
Triscott et al., "Personalizing the treatment of pediatric medulloblastoma: Polo-like kinase 1 as a molecular target in high-risk children," *Cancer Res.*, 73 (22), 6734-6744 (2013).
Van Der Velden et al., "B-cell prolymphocytic leukemia: a specific subgroup of mantle cell lymphoma," *Blood*, 124 (3), 412-419 (2014).
Velculescu et al., "Serial analysis of gene expression," *Science*, 270 (5235), 484-487 (1995).
Wells, "Lymphoma microenvironment impacts therapy and prognosis," *Hematology Times*, 3 pp. (2008), http://www.hematologytimes.com/ht/p_article_print.do?id=437§ion.

(56) References Cited

OTHER PUBLICATIONS

Wiestner et al., "Towards molecular diagnosis and targeted therapy of lymphoid malignancies," *Semin. Hematol.*, 40 (4), 296-307 (2003).
Wilson et al., "A cancer and leukemia Group B multi-center study of DA-EPOCH-rituximab in untreated diffuse large B-cell lymphoma with analysis of outcome by molecular subtype," *Haeatologica*, 97:758-765 (2012).
Winter et al., "Prognostic significance of Bcl-6 protein expression in DLBCL treated with CHOP or R-CHOP: a prospective correlative study," *Blood*, 107 (11), 4207-4213(2006).
Wodicka et al., "Genome-wide expression monitoring in *Saccharomyces cerevisiae*," *Nat. Biotechnol.*, 15 (13), 1359-1367 (1997).
Wright et al., "A gene expression-based method to diagnose clinically distinct subgroups of diffuse large B cell lymphoma," *Proc. Natl. Acad. Sci. USA*, 100 (17), 9991-9996 (2003).
Written Opinion of the International Searching Authority, Application No. PCT/US2014/064161, dated Jul. 2009, 10 pp.
Wuthrich et al., "MHC class II, antigen presentation and tumor necrosis factor in renal tubular epithelial cells," *Kidney Int.*, 37 (2), 783-792 (1990).
Xiu et al., "Analysis of survivin expression in subtypes of lymphoma," *Chinese J. Can.*, 23 (6), 655-661 (2004).
Yatabe et al., "Significance of cyclin D1 overexpression for the diagnosis of mantle cell lymphoma: a clinicopathologic comparison of cyclin D1-positive MCL and cyclin D1-negative MCL-like B-cell lymphoma," *Blood*, 95 (7), 2253-2261 (2000).
Ye et al., "Variable frequencies of t(11;18)(q21;q21) in MALT lymphomas of different sites: significant association with CagA strains of H pylori in gastric MALT lymphoma," *Blood*, 102 (3), 1012-1018 (2003).
Zeller et al., "An integrated database of genes responsive to the Myc oncogenic transcription factor: identification of direct genomic targets," *Genome Biol.*, 4 (10), 10 pp. (2003).
Zhang et al., "Lenalidomide efficacy in activated B-cell-like subtype diffuse large B-cell lymphoma is dependent upon IRF4 and cereblon expression," *Br. J. Haemotology*, 160 (4), 487-502 (2012).
Al-Humood et al., "Genotypic and Phenotypic Differences between Nodal and Extranodal Diffuse Large B-Cell Lymphomas," *J Histochem Cytochem.*, 59 (10), 918-31 (Oct. 2011).
Culpin et al., "Prognostic significance of immunohistochemistry-based markers and algorithms in immunochemotherapy-treated diffuse large B cell lymphoma patients," *Histopathology*, 63 (6), 788-801 (Dec. 2013).
Nyman et al., "Prognostic impact of activated B-cell focused classification in diffuse large B-cell lymphoma patients treated in R-CHOP," *Modern Pathology*, 22 (8), 1094-1101 (Aug. 2009).
Takeuchi et al., "The potential of copy number gains and losses, detected by array-based comparative genomic hybridization, for computational differential diagnosis of B-cell lymphomas and genetic regions involved in lymphomagenesis," *Haematologica*, 94 (1), 61-69 (Jan. 2009).
Zheng, "Analysis of survivin expression in subtypes of lymphoma," *Chinese Journal of Cancer*, 23 (6), 655-661 (Jun. 2004).

\* cited by examiner

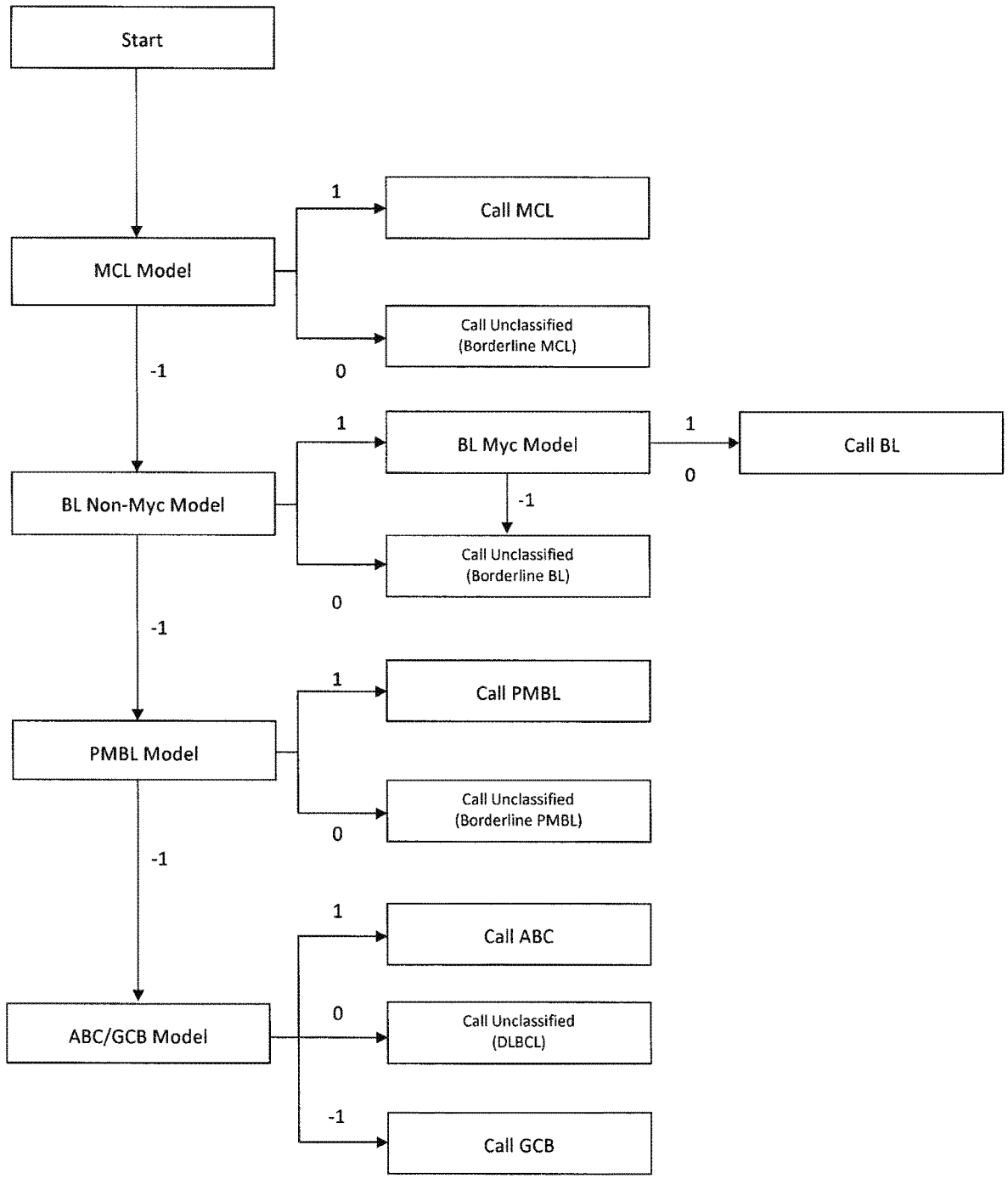

US 11,574,704 B2

METHOD FOR SUBTYPING LYMPHOMA TYPES BY MEANS OF EXPRESSION PROFILING

CROSS-REFERENCE TO RELATED APPLICATIONS

This patent application is a continuation application of U.S. patent application Ser. No. 15/035,101, filed May 6, 2016, which is a U.S. National Phase of International Patent Application No. PCT/US2014/064161, filed Nov. 5, 2014, which claims the benefit of U.S. Provisional Patent Application No. 61/900,553, filed Nov. 6, 2013, each of which is incorporated herein by reference in its entirety.

STATEMENT REGARDING FEDERALLY SPONSORED RESEARCH AND DEVELOPMENT

This invention was made with Government support under grant no. U01 CA084967, awarded by National Institutes of Health. This invention was made with Government support under project number ZIA BC011006-05 by the National Institutes of Health, National Cancer Institute. The Government has certain rights in the invention.

INCORPORATED-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 520,999 Byte ASCII (Text) file named "747265 ST25.TXT," created Jan. 17, 2020.

BACKGROUND OF THE INVENTION

A variety of systems for identifying and classifying lymphomas have been proposed over the last 25 years. In the 1980's, the Working Formulation was introduced as a method of classifying lymphomas based on morphological and clinical characteristics. In the 1990's, the Revised European-American Lymphoma (REAL) system was introduced in an attempt to take into account immunophenotypic and genetic characteristics in classifying lymphomas (Harris 1994). The most recent standard, set forth by the World Health Organization (WHO), attempts to build on these previous systems (see, Swerdlow et al., eds., *WHO Classification of Tumours of Haematopoietic and Lymphoid Tissues*, 4th ed., International Agency for Research on Cancer; World Health Organization (2008); and Jaffe, E. S., *Pathology & Genetics: Tumours of Haematopoietic and Lymphoid Tissues*, WHO Classification of Tumours, Pathology and Genetics series (2001)). The WHO classification of lymphomas is based on several factors, including tumor morphology, immunophenotype, recurrent genetic abnormalities, and clinical features.

Other diagnoses that have not been given WHO diagnostic numbers include HIV-associated lymphoma, germinal center B cell-like subtype of diffuse large B cell lymphoma, activated B cell-like subtype of diffuse large B-cell lymphoma, follicular hyperplasia (non-malignant), and infectious mononucleosis (non-malignant).

Although the WHO classification has proven useful in patient management and treatment, patients assigned to the same WHO diagnostic category often have noticeably different clinical outcomes. In many cases, these different outcomes appear to be due to molecular differences between tumors that cannot be readily observed by analyzing tumor morphology.

Diffuse large B cell lymphoma (DLBCL) can be classified as the germinal center B cell (GCB) subtype or the activated B cell (ABC) subtype based on the cell-of-origin (COO) distinction as molecularly described previously by the Lymphoma/Leukemia Molecular Profiling Project (LLMPP) (see Alizadeh et al., *Nature*, 403: 503-511 (2000)). However, more accurate diagnostic assays are needed to qualify patients for clinical trials using targeted agents and to use as a predictive biomarker.

Therefore, more precise methods are needed for identifying and classifying lymphomas based on their molecular characteristics. The invention provides such methods.

BRIEF SUMMARY OF THE INVENTION

The invention provides a method for selecting a treatment option for an activated B cell-like diffuse large B cell lymphoma (ABC DLBCL) subject, a germinal center B cell-like diffuse large B cell lymphoma (GCB DLBCL) subject, a primary mediastinal B cell lymphoma (PMBL) subject, a Burkitt lymphoma (BL) subject, or a mantle cell lymphoma (MCL) subject. The method comprises: (a) isolating a gene expression product from a biopsy sample from a lymphoma subject; (b) obtaining digital gene expression data from the isolated gene expression product, wherein the digital gene expression data comprises data for genes in a gene expression signature, and wherein the gene expression signature comprises at least one of the genes listed in Table 2; (c) generating a weighted average of the expression levels of genes from the gene expression signature to thereby obtain a gene expression signature value; (d) calculating a predictor score based on the gene expression signature value; (e) classifying the subject as belonging to one of the following groups based on the predictor score of (d): (i) ABC DLBCL, (ii) GCB DLBCL, (iii) PMBL, (iv) BL, or (v) MCL; (f) selecting a treatment option for the subject based on the subject's classification in (e); and (g) providing the treatment option to the subject.

The invention also provides a method for selecting a treatment option for a diffuse large B cell lymphoma (DLBCL) subject. The method comprises: (a) isolating a gene expression product from a biopsy sample from a DLBCL subject; (b) obtaining digital gene expression data from the isolated gene expression product, wherein the digital gene expression data comprises data for genes in a gene expression signature, and wherein the gene expression signature comprises at least one of the following genes: ASB13 (GenBank Accession No. NM 024701.3), CCDC50 (GenBank Accession No. NM 174908.3), CREB3L2 (GenBank Accession No. NM_194071.2), CYB5R2 (GenBank Accession No. NM_016229.3), IRF4 (GenBank Accession No. NM_002460.1), ISY1 (GenBank Accession No. NM_020701.2), ITPKB (GenBank Accession No. NM_002221.3), LIMD1 (GenBank Accession No. NM_014240.2), MAML3 (GenBank Accession No. NM_018717.4), MME (GenBank Accession No. NM_000902.2), MYBL1 (GenBank Accession No. XM_034274.14), PIM2 (GenBank Accession No. NM_006875.2), R3HDM1 (GenBank Accession No. NM_015361.2), RAB7L1 (GenBank Accession No. NM_001135664.1), S1PR2 (GenBank Accession No. NM_004230.2), SERPINA9 (GenBank Accession No. NM_001042518.1), TNFRSF13 B (GenBank Accession No. NM_012452.2), TRIM56 (GenBank Accession No.

NM_030961.1), UBXN4 (GenBank Accession No. NM_014607.3), and WDR55 (GenBank Accession No. NM_017706.4); (c) generating a weighted average of the expression levels of genes from the gene expression signature to thereby obtain a gene expression signature value; (d) calculating a predictor score based on the gene expression signature value; (e) classifying the subject as belonging to one of the following groups based on the predictor score of (d): (i) activated B cell-like diffuse large B cell lymphoma (ABC DLBCL) or (ii) germinal center B cell-like diffuse large B cell lymphoma (GCB DLBCL); (f) selecting a treatment option for the subject based on the subject's classification in (e); and (g) providing the treatment option to the subject.

The invention provides a method for selecting a germinal center B cell-like diffuse large B cell lymphoma (GCB DLBCL) subject for treatment with R-CHOP (rituxan, cyclophosphamide, hydroxydaunorubicin, oncovin (vincristine), and prednisone) therapy. The method comprises the steps of: (a) isolating a gene expression product from a biopsy sample from a DLBCL subject; (b) obtaining digital gene expression data from the isolated gene expression product, wherein the digital gene expression data comprises data for genes in a gene expression signature, and wherein the gene expression signature comprises at least one of the following genes: ASB13 (GenBank Accession No. NM_024701.3), CCDC50 (GenBank Accession No. NM_174908.3), CREB3L2 (GenBank Accession No. NM_194071.2), CYB5R2 (GenBank Accession No. NM_016229.3), IRF4 (GenBank Accession No. NM_002460.1), ISY1 (GenBank Accession No. NM_020701.2), ITPKB (GenBank Accession No. NM_002221.3), LIMD1 (GenBank Accession No. NM_014240.2), MAML3 (GenBank Accession No. NM_018717.4), MME (GenBank Accession No. NM_000902.2), MYBL1 (GenBank Accession No. XM_034274.14), PIM2 (GenBank Accession No. NM_006875.2), R3HDM1 (GenBank Accession No. NM_015361.2), RAB7L1 (GenBank Accession No. NM_001135664.1), S1PR2 (GenBank Accession No. NM_004230.2), SERPINA9 (GenBank Accession No. NM_001042518.1), TNFRSF13B (GenBank Accession No. NM_012452.2), TRIM56 (GenBank Accession No. NM_030961.1), UBXN4 (GenBank Accession No. NM_014607.3), and WDR55 (GenBank Accession No. NM_017706.4); (c) generating a weighted average of the expression levels of genes from the gene expression signature to thereby obtain a gene expression signature value; (d) calculating a predictor score based on the gene expression signature value; (e) classifying the subject as belonging to one of the following groups based on the predictor score of (d): (i) activated B cell-like diffuse large B cell lymphoma (ABC DLBCL) or (ii) germinal center B cell-like diffuse large B cell lymphoma (GCB DLBCL); (f) selecting a GCB DLBCL subject for R-CHOP therapy; and (g) providing R-CHOP therapy to the GCB DLBCL subject and providing a different therapy to an ABC DLBCL subject.

BRIEF DESCRIPTION OF THE SEVERAL VIEWS OF THE DRAWING(S)

The FIGURE is a diagram which illustrates the logic employed in classifying a subject having (i) ABC DLBCL, (ii) GCB DLBCL, (iii) PMBL, (iv) BL, or (v) MCL based on the predictor models disclosed herein.

DETAILED DESCRIPTION OF THE INVENTION

Gene expression profiling of a cancer cell or biopsy reflects the molecular phenotype of a cancer at the time of diagnosis. As a consequence, the detailed picture provided by the genomic expression pattern provides a basis for a new systematic classification of cancers and more accurate predictors of survival and response to treatment. The invention discloses methods for identifying, diagnosing, and/or classifying a lymphoma, lymphoid malignancy, or lymphoproliferative disorder based on its gene expression patterns. The information obtained using these methods will be useful in evaluating the optimal therapeutic approach to be employed with regards to a particular subject.

The term "lymphoproliferative disorder" as used herein refers to any tumor of lymphocytes, and may refer to both malignant and benign tumors. The terms "lymphoma" and "lymphoid malignancy" as used herein refer specifically to malignant tumors derived from lymphocytes and lymphoblasts. Examples of lymphomas include, but are not limited to, follicular lymphoma (FL), Burkitt lymphoma (BL), mantle cell lymphoma (MCL), follicular hyperplasia (FH), small cell lymphocytic lymphoma (SLL), mucosa-associated lymphoid tissue lymphoma (MALT), splenic lymphoma, multiple myeloma, lymphoplasmacytic lymphoma, post-transplant lymphoproliferative disorder (PTLD), lymphoblastic lymphoma, nodal marginal zone lymphoma (NMZ), germinal center B cell-like diffuse large B cell lymphoma (GCB), activated B cell-like diffuse large B cell lymphoma (ABC), and primary mediastinal B cell lymphoma (PMBL).

The phrase "lymphoma type" (or simply "type") as used herein refers to a diagnostic classification of a lymphoma. The phrase may refer to a broad lymphoma class (e.g., DLBCL, FL, MCL, etc.) or to a subtype or subgroup falling within a broad lymphoma class (e.g., GCB DLBCL and ABC DLBCL). In one embodiment, the invention comprises selecting a treatment option for a subject having activated B cell-like diffuse large B cell lymphoma (ABC DLBCL), a germinal center B cell-like diffuse large B cell lymphoma (GCB DLBCL), primary mediastinal B cell lymphoma (PMBL), Burkitt lymphoma (BL), or mantle cell lymphoma (MCL).

The inventive method comprises isolating a gene expression product from a subject, e.g., from a biopsy sample from a subject, such as from a snap-frozen biopsy sample from a subject or a formalin-fixed and paraffin-embedded (FFPE) biopsy sample from a subject. The term "gene expression product," as used herein, refers to any molecule that is produced as a result of gene transcription. The gene expression product can be, for example, total cellular mRNA, rRNA, cDNA obtained by reverse transcription of total cellular mRNA, or a protein. The gene expression product can be obtained from the subject in any suitable manner. For example, one or more biopsy samples can be obtained from a patient that has been diagnosed as having a particular lymphoma type, and the biopsy samples can be formalin-fixed and paraffin-embedded using protocols that are known in the art or are commercially available (see, e.g., Keirnan, J. (ed.), *Histological and Histochemical Methods: Theory and Practice*, 4th edition, Cold Spring Harbor Laboratory Press (2008)). The gene expression product can be extracted from an FFPE biopsy sample using methods that are known in the art or are commercially available (see, e.g., Huang et al., *Cancer Epidemiol Biomarkers Prev.*, 19: 973-977 (2010); QIAamp DNA FFPE Tissue Kit, RNAEASY™

FFPE Kit (Qiagen, Venlo, Netherlands); and MAGMAX™ FFPE DNA Isolation Kit (Life Technologies, Carlsbad, Calif.)).

The inventive method further comprises obtaining digital gene expression data from the isolated gene expression product, wherein the digital gene expression data comprises data for genes in a gene expression signature. The phrase "gene expression data" as used herein refers to information regarding the relative or absolute level of expression of a gene or set of genes in a cell or group of cells. The level of expression of a gene may be determined based on the level of RNA, such as mRNA, encoded by the gene. Alternatively, the level of expression may be determined based on the level of a polypeptide or fragment thereof encoded by the gene. "Gene expression data" may be acquired for an individual cell, or for a group of cells such as a tumor or biopsy sample. Any effective method of quantifying the expression of at least one gene, gene set, or group of gene sets may be used to acquire gene expression data for use in the invention. For example, gene expression data may be measured or estimated using one or more microarrays. The microarrays may be of any effective type, including but not limited to nucleic acid based or antibody based. Gene expression may also be measured by a variety of other techniques, including but not limited to PCR, quantitative RT-PCR, real-time PCR, RNA amplification, in situ hybridization, immunohistochemistry, immunocytochemistry, FACS, serial analysis of gene expression (SAGE) (Velculescu et al., *Science*, 270: 484-487 (1995)), Northern blot hybridization, or western blot hybridization.

Nucleic acid microarrays generally comprise nucleic acid probes derived from individual genes and placed in an ordered array on a support. This support may be, for example, a glass slide, a nylon membrane, or a silicon wafer. Gene expression patterns in a sample are obtained by hybridizing the microarray with the gene expression product from the sample. This gene expression product may be, for example, total cellular mRNA, rRNA, or cDNA obtained by reverse transcription of total cellular mRNA. The gene expression product from a sample is labeled with a radioactive, fluorescent, or other label to allow for detection. Following hybridization, the microarray is washed, and hybridization of gene expression product to each nucleic acid probe on the microarray is detected and quantified using a detection device such as a phosphorimager or scanning confocal microscope.

The microarray can be a cDNA microarray or an oligonucleotide microarray. cDNA arrays consist of hundreds or thousands of cDNA probes immobilized on a solid support, and are described in detail in, e.g., Southern et al., *Genomics*, 13: 1008-1017 (1992); Southern et al., *Nucl. Acids. Res.*, 22: 1368-1373 (1994); Gress et al., *Oncogene*, 13: 1819-1830 (1996); Pietu et al., *Genome Res.*, 6: 492-503 (1996); Schena et al., *Science*, 270: 467-470 (1995); DeRisi et al., *Nat. Genet.*, 14: 457-460 (1996); Schena et al., *Proc. Natl. Acad. Sci. USA*, 93: 10614-10619 (1996); Shalon et al., *Genome Res.*, 6: 639-645 (1996); DeRisi et al., *Science*, 278: 680-686 (1997); Heller et al., *Proc. Natl. Acad. Sci. USA*, 94: 2150-2155 (1997); and Lashkari et al., *Proc. Natl. Acad. Sci. USA*, 94: 13057-13062 (1997). Oligonucleotide arrays differ from cDNA arrays in that the probes are 20- to 25-mer oligonucleotides. Oligonucleotide arrays are generally produced by in situ oligonucleotide synthesis in conjunction with photolithographic masking techniques (see, e.g., Pease et al., *Proc. Natl. Acad. Sci. USA*, 91: 5022-5026 (1994); Lipshutz et al., *Biotechniques*, 19: 442-447 (1995); Chee et al., *Science*, 274: 610-14 (1996); Lockhart et al., *Nat. Biotechnol.*, 14: 1675-1680 (1996); and Wodicka et al., *Nat. Biotechnol.*, 15: 1359-1367 (1997)). The solid support for oligonucleotide arrays is typically a glass or silicon surface.

Methods and techniques applicable to array synthesis and use have been described in, for example, U.S. Pat. Nos. 5,143,854, 5,242,974, 5,252,743, 5,324,633, 5,384,261, 5,424,186, 5,445,934, 5,451,683, 5,482,867, 5,491,074, 5,527,681, 5,550,215, 5,571,639, 5,578,832, 5,593,839, 5,599,695, 5,624,711, 5,631,734, 5,795,716, 5,831,070, 5,837,832, 5,856,101, 5,858,659, 5,936,324, 5,968,740, 5,974,164, 5,981,185, 5,981,956, 6,025,601, 6,033,860, 6,040,193, 6,090,555, and 6,410,229, and U.S. Patent Application Publication 2003/0104411. Techniques for the synthesis of microarrays using mechanical synthesis methods are described in, for example, U.S. Pat. Nos. 5,384,261 and 6,040,193. Microarrays may be nucleic acids on beads, gels, polymeric surfaces, fibers such as fiber optics, glass or any other appropriate substrate (see, e.g., U.S. Pat. Nos. 5,708,153, 5,770,358, 5,789,162, 5,800,992, and 6,040,193).

Microarrays may be packaged in such a manner as to allow for diagnostic use, or they can be an all-inclusive device (see, e.g., U.S. Pat. Nos. 5,856,174 and 5,922,591). Microarrays directed to a variety of purposes are commercially available from Affymetrix (Affymetrix, Santa Clara, Calif.).

"Digital gene expression data," as used herein, refers to gene expression information that is based on the generation of sequence tags, as opposed to "analog gene expression data" which is based on hybridization to arrayed cDNA or oligonucleotide libraries as described above.

Digital gene expression data can be obtained and analyzed using a variety of methods known in the art, such as, for example, serial analysis of gene expression (SAGE) (see, e.g., Velculescu et al., *Science*, 270(5235): 484-487 (1995)), SuperSAGE (see e.g., Matsumura et al., *Proc. Natl. Acad. Sci. USA*, 100 (26): 15718-15723 (2003)), digital northern analysis (see, e.g., Cao et al., *Breast Cancer Research*, 10: R91 (2008)), and RNA-seq (see, e.g., Mortazavi et al. *Nat Methods*, 5(7):621-628 (2008)). In one embodiment, the digital gene expression data is obtained using the NCOUNTER™ gene expression assay available from NanoString Technologies, Inc. The NCOUNTER™ assay can detect the expression of up to 800 genes in a single reaction with high sensitivity and linearity across a broad range of expression levels. The NCOUNTER™ assay is based on direct digital detection of mRNA molecules of interest using target-specific, color-coded probe pairs, and does not require the conversion of mRNA to cDNA by reverse transcription or the amplification of the resulting cDNA by PCR. Each target gene of interest is detected using a pair of reporter and capture probes carrying 35- to 50-nucleotide target-specific sequences. In addition, each reporter probe carries a unique color code at the 5' end that enables the molecular barcoding of the genes of interest, while the capture probes all carry a biotin label at the 3' end that provides a molecular handle for attachment of target genes to facilitate downstream digital detection. After solution-phase hybridization between target mRNA and reporter-capture probe pairs, excess probes are removed and the probe/target complexes are aligned and immobilized in an NCOUNTER™ cartridge, which is then placed in a digital analyzer for image acquisition and data processing. Hundreds of thousands of color codes designating mRNA targets of interest are directly imaged on the surface of the cartridge. The expression level of a gene is measured by counting the number of times the color-coded barcode for that gene is detected, and the barcode counts are then tabulated. NANOSTRING™ technology and analysis of digital gene expression data is described in detail in, e.g., Kulkarni, M. M., "Digital Multiplexed Gene Expression Analysis Using the NANOSTRING™ NCOUNTER™ System," *Current Protocols in Molecular Biology.* 94: 25B.10.1-25B.10.17 (2011); Geiss et al., *Nature Biotechnology*, 26: 317-325 (2008); and U.S. Pat. No. 7,919,237.

The term "gene expression signature" or "signature" as used herein refers to a group of coordinately expressed genes. The genes making up a particular signature may be expressed in a specific cell lineage, stage of differentiation, or during a particular biological response. The genes can reflect biological aspects of the tumors in which they are expressed, such as the cell of origin of the cancer, the nature of the non-malignant cells in the biopsy, and the oncogenic mechanisms responsible for the cancer (see, e.g., Shaffer et al., *Immunity*, 15: 375-385 (2001)). Examples of gene expression signatures include lymph node (see Shaffer et al., supra), proliferation (see, e.g., Rosenwald et al., *New Engl. J. Med.*, 346: 1937-1947 (2002)), MHC class ii, ABC DLBCL high, B-cell differentiation, T-cell, macrophage, immune response-1, immune response-2, and germinal center B cell.

The invention provides gene expression signatures that can be used to classify particular types of lymphoma and then select an appropriate treatment option based on that classification. In this respect, the invention provides a novel 800 gene array for the identification and diagnosis various lymphoma types. The 800 gene array contains genes previously identified as being differentially expressed between ABC DLBCL, GCB DLBCL, PMBL, BL, and MCL, shown to be associated with survival in DLBCL or MCL, or were known in the art to be of particular importance in lymphoid biology. The genes and probe sequences that comprise the 800 gene array are set forth in Table 1.

TABLE 1

| Gene | GenBank Accession No. | Target Sequence | Capture Probe Sequence | Reporter Probe Sequence |
|---|---|---|---|---|
| DDX58 | NM_014314.3 | CTGGCATATTGACTGGACGTGGCAAAACAAATCAGAACACAGGAATGACCCTCCCGGCACAGAAGTGTATATTGGATGCATTCAAAGCCAGTGGAGATCA (SEQ ID NO: 1) | GGTCATTCCTGTGTTCTGATTTGTTTTGCCACGTCCAGTCAATATGCCAG (SEQ ID NO: 2) | TGATCTCCACTGGCTTTGAATGCATCCAATATACACTTCTGTGCCGGGAG (SEQ ID NO: 3) |
| HLA-DQA1 | NM_002122.3 | GGTGGCCTGAGTTCAGCAAATTTGGAGGTTTTGACCCGCAGGGTGCACTGAGAAACATGGCTGTGGCAAAACACAACTTGAACATCATGATTAAACGCTA (SEQ ID NO: 4) | CAGTGCACCCTGCGGGTCAAAACCTCCAAATTTGCTGAACTCAGGCCACC (SEQ ID NO: 5) | TAGCGTTTAATCATGATGTTCAAGTTGTGTTTTGCCACAGCCATGTTTCT (SEQ ID NO: 6) |
| IFI16 | NM_005531.1 | ACGACTGAACACAATCAACTGTGAGGAAGGAGATAAACTGAAACTCACCAGCTTTGAATTGGCACCGAAAAGTGGGAATACCGGGGAGTTGAGATCTGTA (SEQ ID NO: 7) | TGGTGAGTTTCAGTTTATCTCCTTCCTCACAGTTGATTGTGTTCAGTCGT (SEQ ID NO: 8) | TACAGATCTCAACTCCCCGGTATTCCCACTTTTCGGTGCCAATTCAAAGC (SEQ ID NO: 9) |
| IFNAR1 | NM_000629.2 | CTAATCAGCTCTCAGTGATCAACCCACTCTTGTTATGGGTGGTCTCTGTCACTTTGAATGCCAGGCTGGCTTCTCGTCTAGCAGTATTCAGATACCCCTT (SEQ ID NO: 10) | GACAGAGACCACCCATAACAAGAGTGGGTTGATCACTGAGAGCTGATTAG (SEQ ID NO: 11) | AAGGGGTATCTGAATACTGCTAGACGAGAAGCCAGCCTGGCATTCAAAGT (SEQ ID NO: 12) |
| IFNAR2 | NM_000874.3 | AAATACCACAAGATCATTTTGTGACCTCACAGATGAGTGGAGAAGCACACACGAGGCCTATGTCACCGTCCTAGAAGGATTCAGCGGGAACACAACGTTG (SEQ ID NO: 13) | GTGTGCTTCTCCACTCATCTGTGAGGTCACAAAATGATCTTGTGGTATTT (SEQ ID NO: 14) | TTCCCGCTGAATCCTTCTAGGACGGTGACATAGGCCTCGT (SEQ ID NO: 15) |

TABLE 1-continued

| Gene | GenBank Accession No. | Target Sequence | Capture Probe Sequence | Reporter Probe Sequence |
|---|---|---|---|---|
| IFNB1 | NM_002176.2 | ACAGACTTACAGGTTACCTCCGAAACTGAAGATCTCCTAGCCTGTGCCTCTGGGACTGGACAATTGCTTCAAGCATTCTTCAACCAGCAGATGCTGTTTA (SEQ ID NO: 16) | GAGGCACAGGCTAGGAGATCTTCAGTTTCGGAGGTAACCTGTAAGTCTGT (SEQ ID NO: 17) | TAAACAGCATCTGCTGGTTGAAGAATGCTTGAAGCAATTGTCCAGTCCCA (SEQ ID NO: 18) |
| IL13 | NM_002188.2 | TTTCTTTCTGATGTCAAAAATGTCTTGGGTAGGCGGGAAGGAGGGTTAGGGAGGGGTAAAATTCCTTAGCTTAGACCTCAGCCTGTGCTGCCCGTCTTCA (SEQ ID NO: 19) | CCTAACCCTCCTTCCCGCCTACCCAAGACATTTTTGACATCAGAAAGAAA (SEQ ID NO: 20) | TGAAGACGGGCAGCACAGGCTGAGGTCTAAGCTAAGGAATTTTACCCCTC (SEQ ID NO: 21) |
| IRF3 | NM_001571.4 | CTGCCCTCAACCGCAAAGAAGGGTTGCGTTTAGCAGAGGACCGGAGCAAGGACCCTCACGACCCACATAAAATCTACGAGTTTGTGAACTCAGGAGTTGG (SEQ ID NO: 22) | CTTGCTCCGGTCCTCTGCTAAACGCAACCCTTCTTTGCGGTTGAG (SEQ ID NO: 23) | CCAACTCCTGAGTTCACAAACTCGTAGATTTTATGTGGGTCGTGAGGGTC (SEQ ID NO: 24) |
| IRF5 | NM_002200.3 | GCCTGGCTCTCGGGAAATTCAGCCATGAGCAGGGAAAGAACTCTCCCAACCCTGGGGCCTAGCTGTATAGGAGGAATTGCCTAAGGGTGGCCCACTCTTG (SEQ ID NO: 25) | GTTGGGAGAGTTCTTTCCCTGCTCATGGCTGAATTTCCGAGAGCCAG (SEQ ID NO: 26) | CTTAGGCAATTCCTCCTATACAGCTAGGCCCCAGG (SEQ ID NO: 27) |
| IRF7 | NM_001572.3 | CGCAGCGTGAGGGTGTGTCTTCCCTGGATAGCAGCAGCCTCAGCCTCTGCCTGTCTTGGCGCTGGACCAGCGCCAACAGCCTCTATGACGACATCGAGTGCTTCCTTATGGA (SEQ ID NO: 28) | GCAGAGGCTGAGGCTGCTGCTATCCAGGGAAGACACAC (SEQ ID NO: 29) | TCCATAAGGAAGCACTCGATGTCGTCATAGAGGCTGAG (SEQ ID NO: 30) |
| RBCK1 | NM_031229.2 | TACCAGCGATTTCTAGACCTGGGCATCTCCATTGCTGAAAACCGCAGTGCCTTCAGCTACCATTGCAAGACCCCAGATTGCAAGGGATGGTGCTTCTTTG (SEQ ID NO: 31) | GCACTGCGGTTTTCAGCAATGGAGATGCCCAGGTCTAGAAATCGC (SEQ ID NO: 32) | CAAAGAAGCACCATCCCTTGCAATCTGGGGTCTTGCAATGGTAGCTGAAG (SEQ ID NO: 33) |
| RNF31 | NM_017999.4 | ACCTCACCGATGACACACAGTTGCTCAGCTACTTCTCTACCCTTGACATCCAGCTTCGCGAGAGCCTAGAGCCAGATGCCTATGCGTTGTTCCATAAGAA (SEQ ID NO: 34) | GATGTCAAGGGTAGAGAAGTAGCTGAGCAACTGTGTGTCATCGGTGAG (SEQ ID NO: 35) | TTCTTATGGAACAACGCATAGGCATCTGGCTCTAGGCTCTCGCGAAGCTG (SEQ ID NO: 36) |
| SHARPIN | NM_030974.3 | TCTCAGAGCTCGGTTTCCCGCCAGCCGTGCAACGCTGGGTCATCGGACGGTGCCTGTGTGCCTGAGCGCAGCCTTGCCTCTTACGGGGTTCGGCAGGA (SEQ ID NO: 37) | CCGTCCGATGACCCAGCCGTTGCACGGCTGGCGGGAAACCG (SEQ ID NO: 38) | CCGTAAGAGGCAAGGCTGCGCTCAGGCACACACAGGCA (SEQ ID NO: 39) |

TABLE 1-continued

| Gene | GenBank Accession No. | Target Sequence | Capture Probe Sequence | Reporter Probe Sequence |
|---|---|---|---|---|
| TNIP2 | NM_024309.3 | GTCACTTGTATGGTCCCCAGGGTGGGAGCCCCATCCTGTTCTATGGAATAAAGCGTCGCCTCTCTGCCTCGAACCAGTCAAATGGAGTATTGCGGCTGCA (SEQ ID NO: 40) | TATTCCATAGAACAGGATGGGCTCCCACCCTGGGGACCATACAAGTGAC (SEQ ID NO: 41) | AGCCGCAATACTCCATTTGACTGGTTCGAGGCAGAGAGGCGACGCTT (SEQ ID NO: 42) |
| TRIM25 | NM_005082.4 | GTGAGTATGAGGAATTTAGCCTCTTATAGTGAAATGAGTCCAACTCTGGGCTTTGCTTAGAGGAGAGCTCCTGTCAGGCTTCCTATAATATGAAAAGAAG (SEQ ID NO: 43) | CCCAGAGTTGGACTCATTTCACTATAAGAGGCTAAATTCCTCATACTCAC (SEQ ID NO: 44) | CTTCTTTTCATATTATAGGAAGCCTGACAGGAGCTCTCCTCTAAGCAAAG (SEQ ID NO: 45) |
| A2LD1 | NM_033110.2 | AGCAAGGCACGAAGTACCAATTACTACCCACCTCCATCTGATAATTGTCAGCATCGATTCAACTCGGTGCACGGCTCTTGCTTCTGCTTCCCAGCAAAGT (SEQ ID NO: 46) | TGACAATTATCAGATGGAGGTGGGTAGTAATTGGTACTTCGTGCCTTGCT (SEQ ID NO: 47) | ACTTTGCTGGGAAGCAGAAGCAAGAGCCGTGCACCGAGTTGAATCGATGC (SEQ ID NO: 48) |
| ABCA12 | NM_015657.3 | TTTTCCTCTAACATCGAGCCTGAACCTAAAGATCTCACAGTCGGGGTTGCCCTGCATGGGGTCACAAAGATCTATGGCTCAAAAGTTGCTGTTGATAACC (SEQ ID NO: 49) | GCAACCCCGACTGTGAGATCTTTAGGTTCAGGCTCGATGTTAGAGGAAAA (SEQ ID NO: 50) | GGTTATCAACAGCAACTTTTGAGCCATAGATCTTTGTGACCCCATGCAGG (SEQ ID NO: 51) |
| ACPP | NM_001099.2 | CAGATGGCGCTAGATGTTTACAACGGACTCCTTCCTCCCTATGCTTCTTGCCACTTGACGGAATTGTACTTTGAGAAGGGGGAGTACTTTGTGGAGATGT (SEQ ID NO: 52) | CAAGAAGCATAGGGAGGAAGGAGTCCGTTGTAAACATCTAGCGCCATCTG (SEQ ID NO: 53) | ACATCTCCACAAAGTACTCCCCCTTCTCAAAGTACAATTCCGTCAAGTGG (SEQ ID NO: 54) |
| ACSL5 | NM_016234.3 | TCTGTGACACACCCCAAAAGGCATTGGTGCTGATAGGGAATGTAGAGAAAGGCTTCACCCCGAGCCTGAAGGTGATCATCTTATGGACCCCTTTGATGA (SEQ ID NO: 55) | TTTCTCTACATTCCCTATCAGCACCAATGCCTTTTGGGGTGTGTCACAGA (SEQ ID NO: 56) | TCCATAAGGATGATCACCTTCAGGCTCGGGGTGAAGCC (SEQ ID NO: 57) |
| ACTG2 | NM_001615.3 | GGGCCCTCCATTGTCCACAGGAAGTGCTTCTAAAGTCAGAACAGGTTCTCCAAGGATCCCCTCGAGACTACTCTGTTACCAGTCATGAAACATTAAACC (SEQ ID NO: 58) | GAGAACCTGTTCTGACTTTAGAAGCACTTCCTGTGGACAATGGAGGGC (SEQ ID NO: 59) | GGTTTTAATGTTTCATGACTGGTAACAGAGTAGTCTCGAGGGGATCCTTG (SEQ ID NO: 60) |
| ADAM12 | NM_003474.4 | GTACTGATGTCTCCCTCGCTCGAAATTACACGGTAATTCTGGGTCACTGTTACTACCATGGACATGTACGGGGATATTCTGATTCAGCAGTCAGTCTCAG (SEQ ID NO: 61) | ACAGTGACCCAGAATTACCGTGTAATTTCGAGCGAGGGAGACATCAGTAC (SEQ ID NO: 62) | CTGAGACTGACTGCTGAATCAGAATATCCCCGTACATGTCCATGGTAGTA (SEQ ID NO: 63) |

TABLE 1-continued

| Gene | GenBank Accession No. | Target Sequence | Capture Probe Sequence | Reporter Probe Sequence |
|---|---|---|---|---|
| ADAM28 | NM_014265.4 | GCAGAGTGGATGACACACTCATTCCCTGCAAAGCAAATGATACCATGTGTGGGAAGTTGTTCTGTCAAGGTGGGTCGGATAATTTGCCCTGGAAAGGACG (SEQ ID NO: 64) | ACACATGGTATCATTTGCTTTGCAGGGAATGAGTGTGTCATCCACTCTGC (SEQ ID NO: 65) | CGTCCTTTCCAGGGCAAATTATCCGACCCACCTTGACAGAACAACTTCCC (SEQ ID NO: 66) |
| ADH1B | NM_000668.4 | ATAATCTTTAGTCATCGAATCCCAGTGGAGGGGACCCTTTTACTTGCCCTGAACATACACATGCTGGGCCATTGTGATTGAAGTCTTCTAACTCTGTCTC (SEQ ID NO: 67) | AGGGCAAGTAAAAGGGTCCCCTCCACTGGGATTCGATGACTAAAGATTAT (SEQ ID NO: 68) | GAGACAGAGTTAGAAGACTTCAATCACAATGGCCCAGCATGTGTATGTTC (SEQ ID NO: 69) |
| ADIPOQ | NM_004797.2 | GCTTTCTTCTCTACCATGACACCAACTGATCACCACTAACTCAGAGCCTCCTCCAGGCCAAACAGCCCCAAAGTCAATTAAAGGCTTTCAGTACGGTTAG (SEQ ID NO: 70) | GAGGCTCTGAGTTAGTGGTGATCAGTTGGTGTCATGGTAGAGAAGAAAG (SEQ ID NO: 71) | CTAACCGTACTGAAAGCCTTTAATTGACTTTGGGGCTGTTTGGCCTGGAG (SEQ ID NO: 72) |
| ADO | NM_032804.5 | AGGAACTTTAATGTTCCCGACTCGGGTGATTCCAGCTGTGTTGCTGGCAGTGTTGTCTCAACCCTCTCCCTAAAATGACTGAGCCCTGGGTTCATCTAAT (SEQ ID NO: 73) | CTGCCAGCAACACAGCTGGAATCACCCGAGTCGGGAACATTAAAGTTCCT (SEQ ID NO: 74) | ATTAGATGAACCCAGGGCTCAGTCATTTTAGGGAGAGGGTTGAGACAACA (SEQ ID NO: 75) |
| AHCYL2 | NM_001130723.2 | CACGCATGATCACCAAAACCTTCCCATCCTGATTCTCTTCTTCTACCTCTACCCTCTCCAACTTCTCCTGGTCTTCACATATACTCTCAAAGCTAGTCTG (SEQ ID NO: 76) | AGAGGTAGAAGAAGAGAATCAGGATGGGAAGGTTTTGGTGATCATGCGTG (SEQ ID NO: 77) | CAGACTAGCTTTGAGAGTATATGTGAAGACCAGGAGAAGTTGGAGAGGGT (SEQ ID NO: 78) |
| AHR | NM_001621.3 | CTGCTACCACATCCACTCTAAGCAAGGACTCTCTCAATCCTAGTTCCCTCCTGGCTGCCATGATGCAACAAGATGAGTCTATTTATCTCTATCCTGCTTC (SEQ ID NO: 79) | GAGGGAACTAGGATTGAGAGAGTCCTTGCTTAGAGTGGATGTGGTAGCAG (SEQ ID NO: 80) | GAAGCAGGATAGAGATAAATAGACTCATCTTGTTGCATCATGGCAGCCAG (SEQ ID NO: 81) |
| AICDA | NM_020661.1 | GCTGCATGAAAATTCAGTTCGTCTCTCCAGACAGCTTCGGCGCATCCTTTTGCCCCTGTATGAGGTTGATGACTTACGAGACGCATTTCGTACTTTGGGA (SEQ ID NO: 82) | AAAGGATGCGCCGAAGCTGTCTGGAGAGACGAACTGAATTTTCATGCAGC (SEQ ID NO: 83) | TCCCAAAGTACGAAATGCGTCTCGTAAGTCATCAACCTCATACAGGGGCA (SEQ ID NO: 84) |
| AKAP2 | NM_001136562.2 | GCTTGAGCCAGGGTGCACGCAGGAATCGTCTGGAAAAAGGCAGTTCTCACTGAGGAGGGTTTGAGGCGCGCGCTCTGGGCAGGAAGCCTCCCCAGCTTTC (SEQ ID NO: 85) | TGAGAACTGCCTTTTTCCAGACAGATTCCTGCGTGCACCCTGGCTCAAG (SEQ ID NO: 86) | TTCCTGCCCAGAGCGCGCGCCTCAAACCTCCTCAG (SEQ ID NO: 87) |

TABLE 1-continued

| Gene | GenBank Accession No. | Target Sequence | Capture Probe Sequence | Reporter Probe Sequence |
|---|---|---|---|---|
| AKAP9 | NMJ05751.3 | CTGGGAAGCAGCA TGAGATTGAAGAG CTAAACAGAGAGC TGGAAGAAATGAG GGTTACCTATGGGA CTGAAGGACTGCA GCAGTTACAAGAAT TTGAAGC (SEQ ID NO: 88) | CATTTCTTCCAGC TCTCTGTTTAGCT CTTCAATCTCATG CTGCTTCCCAG (SEQ ID NO: 89) | GCTTCAAATTCT TGTAACTGCTGC AGTCCTTCAGTC CCATAGGTAACC CT (SEQ ID NO: 90) |
| AKR1C2 | NM_001354.4 | ACATACTGCATCCT ATAGTTATACCATC CACTCTGAAATCAA TGTGAATTTAACTT CAGTTCCATACAGA AACTTCTTTTCCAC AGGTAAGAAACGG TTG (SEQ ID NO: 91) | AATTCACATTGAT TTCAGAGTGGAT GGTATAACTATA GGATGCAGTATG T (SEQ ID NO: 92) | CAACCGTTTCTT ACCTGTGGAAAA GAAGTTTCTGTA TGGAACTGAAGT TA (SEQ ID NO: 93) |
| ALOX5 | NM_000698.2 | GTCAAGATCAGCA ACACTATTTCTGAG CGGGTCATGAATCA CTGGCAGGAAGAC CTGATGTTTGGCTA CCAGTTCCTGAATG GCTGCAACCCTGTG TTGA (SEQ ID NO: 94) | TCCTGCCAGTGAT TCATGACCCGCTC AGAAATAGTGTT GCTGATCTTGAC (SEQ ID NO: 95) | TCAACACAGGGT TGCAGCCATTCA GGAACTGGTAGC CAAACATCAGGT CT (SEQ ID NO: 96) |
| AMIGO2 | NM_001143668.1 | TTTCGTGCGCTTGG CTTTATTCATGAGG CTCAGGTCGGGGA AAGACTGATGGTCC ACTGTGACAGCAA GACAGGTAATGCA AATACGGATTTCAT CTGGG (SEQ ID NO: 97) | ATCAGTCTTTCCC CGACCTGAGCCT CATGAATAAAGC CAAGCGCACGAA A (SEQ ID NO: 98) | CCAGATGAAATC CGTATTTGCATT ACCTGTCTTGCT GTCACAGTGGAC C (SEQ ID NO: 99) |
| ANKRD13A | NM_033121.1 | GCCAAACTGCGCGT CGATATCACATTGC TGGGATTTGAAAAC ATGAGCTGGATAA GAGGGAGGCGTAG TTTTATATTTAAGG GAGAAGACAACTG GGCGG (SEQ ID NO: 100) | CAGCTCATGTTTT CAAATCCCAGCA ATGTGATATCGA CGCGCAGTTTGG C (SEQ ID NO: 101) | CCGCCCAGTTGT CTTCTCCCTTAA ATATAAAACTAC GCCTCCCTCTTA TC (SEQ ID NO: 102) |
| ANLN | NM_018685.2 | ATGACCTCTTCAGT GATGTCCTAGAGGA AGGTGAACTAGAT ATGGAGAAGAGCC AAGAGGAGATGGA TCAAGCATTAGCAG AAAGCAGCGAAGA ACAGGA (SEQ ID NO: 103) | CTTCTCCATATCT AGTTCACCTTCCT CTAGGACATCAC TGAAGAGGTCAT (SEQ ID NO: 104) | CTGTTCTTCGCT GCTTTCTGCTAA TGCTTGATCCAT CTCCTCTTGGCT (SEQ ID NO: 105) |
| ANO3 | NM_031418.2 | ACGCTTACTCAAAG AGCTTGAGCCAGTC TACTTCCCTCTTCC AGTCAACCGAGAG TGAATCTCAGGCTC CCACATCTATAACC TTAATCTCCACTGA CAA (SEQ ID NO: 106) | GGTTGACTGGAA GAGGGAAGTAGA CTGGCTCAAGCTC TTTGAGTAAGCGT (SEQ ID NO: 107) | TTGTCAGTGGAG ATTAAGGTTATA GATGTGGGAGCC TGAGATTCACTC TC (SEQ ID NO: 108) |

TABLE 1-continued

| Gene | GenBank Accession No. | Target Sequence | Capture Probe Sequence | Reporter Probe Sequence |
|---|---|---|---|---|
| ANTXR1 | NM_018153.3 | GATGGGGGTCCAGCCTGCTACGGCGGATTTGACCTGTACTTCATTTTGGACAAATCAGGAAGTGTGCTGCACCACTGGAATGAAATCTATTACTTTGTGG (SEQ ID NO: 109) | TCCAAAATGAAGTACAGGTCAAATCCGCCGTAGCAGGCTGGACCCCCATC (SEQ ID NO: 110) | CCACAAAGTAATAGATTTCATTCCAGTGGTGCAGCACACTTCCTGATTTG (SEQ ID NO: 111) |
| ANUBL1 | NM_001128324.1 | TGTACCTTGAAGCTAGTTTTGGCTATGCGTGGCGGACCTATAAATACTAGAAGAGTTCCTACAGACGATCCACTTAGGAAGATGGCAGAGTACTTGGATT (SEQ ID NO: 112) | CTAGTATTTATAGGTCCGCCACGCATAGCCAAAACTAGCTTCAAGGTACA (SEQ ID NO: 113) | AATCCAAGTACTCTGCCATCTTCCTAAGTGGATCGTCTGTAGGAACTCTT (SEQ ID NO: 114) |
| APOL1 | NM_003661.3 | CCGCTTTGACCGGGATTACCAGCAGTACCATGGACTACGGAAAGAAGTGGTGGACACAAGCCCAAGCCCACGACCTGGTCATCAAAAGCCTTGACAAATT (SEQ ID NO: 115) | CCACTTCTTTCCGTAGTCCATGGTACTGCTGGTAATCCCGGTCAAAG (SEQ ID NO: 116) | AATTTGTCAAGGCTTTTGATGACCAGGTCGTGGGCTTGGGCTTGTGTCCA (SEQ ID NO: 117) |
| ARID3A | NM_005224.2 | AGAATTTAATAAAACAGGGGAAAACCAAGGAACACTTGAATTTCTCAGGTTTTGGACATTCAGAGAGATGAATTGTGAGAACAGCAAAGAAATCCATCAG (SEQ ID NO: 118) | ACCTGAGAAATTCAAGTGTTCCTTGGTTTTCCCCTGTTTTATTAAATTCT (SEQ ID NO: 119) | CTGATGGATTTCTTTGCTGTTCTCACAATTCATCTCTCTGAATGTCCAAA (SEQ ID NO: 120) |
| ARID3B | NM_006465.2 | GGGCCCATTTGAAGGTGTCTCAGACATTTGGCCAGTATGTCTTTCTCAGGGGTTTGGTCACAAAGGATGGACTCTTCCCACCCAGAGGATGCAGGGAAAG (SEQ ID NO: 121) | CCTGAGAAAGACATACTGGCCAAATGTCTGAGACACCTTCAAATGGGCCC (SEQ ID NO: 122) | ATCCTCTGGGTGGGAAGAGTCCATCCTTTGTGACCAAACC (SEQ ID NO: 123) |
| ARID5A | NM_212481.1 | CAGCAGGGCCTGGCCTCTGGGTCTTCTGTGTCCTTTGTGGGTGCCAGCGGCTGTCCTGAGGCCTACAAGCGGCTCCTATCCAGCTTCTACTGCAAGGGGA (SEQ ID NO: 124) | CCGCTGGCACCCACAAAGGACACAGAAGACCCAGAGGCCAGG (SEQ ID NO: 125) | TAGAAGCTGGATAGGAGCCGCTTGTAGGCCTCAGGACAG (SEQ ID NO: 126) |
| ARL6IP1 | NM_015161.1 | GACCATGATCGTTTCCCTTGCTGCGGTTGCTTGGGTGGGACAACAAGTCCACAACCTGCTTCTCACCTACCTGATAGTGACTTCCTTACTATTGCTTCCT (SEQ ID NO: 127) | GGACTTGTTGTCCCACCCAAGCAACCGCAGCAAGGGAAACGATCATGG (SEQ ID NO: 128) | AGGAAGCAATAGTAAGGAAGTCACTATCAGGTAGGTGAGAAGCAGGTTGT (SEQ ID NO: 129) |

TABLE 1-continued

| Gene | GenBank Accession No. | Target Sequence | Capture Probe Sequence | Reporter Probe Sequence |
|---|---|---|---|---|
| ARNT2 | NM_014862.3 | CGGGCTCAAAGCTGGATTAGAAAGGGGAGAGGCACTTGTGACTTTGTTTGACTCTGTGACTCACTTCCTCGCTCACACCTTGTTTGAACTACTGGACTTT (SEQ ID NO: 130) | CAAACAAAGTCACAAGTGCCTCTCCCCTTTCTAATCCAGCTTTGAGCCCG (SEQ ID NO: 131) | AAAGTCCAGTAGTTCAAACAAGGTGTGAGCGAGGAAGTGAGTCACAGAGT (SEQ ID NO: 132) |
| ARNTL | NM_001178.4 | GCCACGGTGGTGCTGGCTAGAGTGTATACGTTTGGACCCAAGCTTAACTTTTCCAATGTGGAATCCTGGGCCTTCATTGGTTCCGATGTCATAGGAATCT (SEQ ID NO: 133) | AAGTTAAGCTTGGGTCCAAACGTATACACTCTAGCCAGCACCACCGTGG (SEQ ID NO: 134) | AGATTCCTATGACATCGGAACCAATGAAGGCCCAGGATTCCACATTGGAA (SEQ ID NO: 135) |
| ASB13 | NM_024701.3 | GGACACGTAGGCGGTACCACTAAGGTTTTGGTAATGAGCCATTCAAACCGACAGCAGTGTGAAGGTGTGTCAAGGTGTATATTCTCGTGGCTCGGCATTC (SEQ ID NO: 136) | CGGTTTGAATGGCTCATTACCAAAACCTTAGTGGTACCGCCTACGTGTCC (SEQ ID NO: 137) | GAATGCCGAGCCACGAGAATATACACCTTGACACACCTTCACACTGCTGT (SEQ ID NO: 138) |
| ASCL2 | NM_005170.2 | CGGGGGGCACCAACACTTGGAGATTTTTCCGGAGGGGAGAGGATTTTCTAAGGGCACAGAGAATCCATTTTCTACACATTAACTTGAGCTGCTGGAGGGA (SEQ ID NO: 139) | TAGAAAATCCTCTCCCCTCCGGAAAAATCTCCAAGTGTTGGTGCCCC (SEQ ID NO: 140) | CCTCCAGCAGCTCAAGTTAATGTGTAGAAAATGGATTCTCTGTGCCCT (SEQ ID NO: 141) |
| ASMTL-AS1 | NR_026711.1 | GGAAGTTCTCCTTCAAGTCTAACCTAAGGCCACACTGTGACGGCTCTCGGGTCAGTTCCTTCCGTGACCTCGGCACCGTGGATGCCCATGAATGCTGATC (SEQ ID NO: 142) | CCGAGAGCCGTCACAGTGTGGCCTTAGGTTAGACTTGAAG (SEQ ID NO: 143) | CATTCATGGGCATCCACGGTGCCGAGGTCACGGAAGGAACTGAC (SEQ ID NO: 144) |
| ASPM | NM_018136.4 | CAGAGATGGTACAGGGCGTACAAGACTCTTCATGATACAAGAACACATTTTTTGAAGACAAAGGCAGCTGTGATTTCCCTCCAGTCTGCTTATCGTGGCT (SEQ ID NO: 145) | AAATGTGTTCTTGTATCATGAAGAGTCTTGTACGCCCTGTACCATCTCTG (SEQ ID NO: 146) | AGCCACGATAAGCAGACTGGAGGGAAATCACAGCTGCCTTTGTCTTCAAA (SEQ ID NO: 147) |
| ATF3 | NM_001674.2 | TTTGATATACATGCTCAACCTTCATCGGCCCACGTGTATTGTCCGGGCTCAGAATGGGAGGACTCCAGAAGATGAGAGAAACCTCTTTATCCAACAGATA (SEQ ID NO: 148) | GAGCCCGGACAATACACGTGGGCCGATGAAGGTTGAGCATGTATATCAA (SEQ ID NO: 149) | TATCTGTTGGATAAAGAGGTTTCTCTCATCTTCTGGAGTCCTCCCATTCT (SEQ ID NO: 150) |
| ATM | NM_000051.3 | ACGCTAAGTCGCTGGCCATTGGTGGACATGGCGCAGGCGCGTTTGCTCCGACGGGCCGAATGTTTTGGGGCAGTGTTTTGAGCGCGGAGACCGCGTGATA (SEQ ID NO: 151) | CGGAGCAAACGCGCCTGCGCCATGTCCACCAATGG (SEQ ID NO: 152) | CGGTCTCCGCGCTCAAAACACTGCCCCAAAACATTCGGCCCGT (SEQ ID NO: 153) |

TABLE 1-continued

| Gene | GenBank Accession No. | Target Sequence | Capture Probe Sequence | Reporter Probe Sequence |
|---|---|---|---|---|
| ATOH8 | NM_032827.6 | GGCATCCTGAGGAACTTGATAGACAAACAATGACAGTGTTTTCCAGAACTGTGGGTACGTGTCTAATCTCAGATGGTACTATGAATTCCTGGAGATCAAA (SEQ ID NO: 154) | AGTTCTGGAAAACACTGTCATTGTTTGTCTATCAAGTTCCTCAGGATGCC (SEQ ID NO: 155) | TTTGATCTCCAGGAATTCATAGTACCATCTGAGATTAGACACGTACCCAC (SEQ ID NO: 156) |
| ATP6V0E1 | NM_003945.3 | GACATGCTCTACAGTGCTCAGTCTTTGAGGTCACGAGAAGAGAATGCCTTCTAGATGCAAAATCACCTCCAAACCAGACCACTTTTCTTGACTTGCCTGT (SEQ ID NO: 157) | AAGGCATTCTCTTCTCGTGACCTCAAAGACTGAGCACTGTAGAGCATGTC (SEQ ID NO: 158) | ACAGGCAAGTCAAGAAAAGTGGTCTGGTTTGGAGGTGATTTTGCATCTAG (SEQ ID NO: 159) |
| ATXN7L2 | NM_153340.4 | ATGTCCATCTTCGGGCACTGCCCTGCCCATGATGACTTCTACTTGGTTGTGTGTAACCCACTGCAGCCAAGTGGTGAAGCCTCAAGCTTTCAGAAGCACT (SEQ ID NO: 160) | ACAACCAAGTAGAAGTCATCATGGGCAGGGCAGTGCCCGAAGATGGACAT (SEQ ID NO: 161) | GAAAGCTTGAGGCTTCACCACTTGGCTGCAGTGGTTACAC (SEQ ID NO: 162) |
| AUH | NM_001698.2 | GGTGGTCTTGAACTGGCTTTAGCCTGTGATATACGAGTAGCAGCTTCCTCTGCAAAAATGGGCCTGGTTGAAACAAAATTGGCGATTATTCCTGGTGGAG (SEQ ID NO: 163) | GAGGAAGCTGCTACTCGTATATCACAGGCTAAAGCCAGTTCAAGACCAC (SEQ ID NO: 164) | CTCCACCAGGAATAATCGCCAATTTTGTTTCAACCAGGCCCATTTTTGCA (SEQ ID NO: 165) |
| AURKA | NM_198433.1 | AGGCGCCCTGTAGGATACTGCTTGTTACTTATTACAGCTAGAGGGTCTCACTCCATTGCCCAGGCCAGAGTGCGGGGATATTTGATAAGAAACTTCAGTG (SEQ ID NO: 166) | TGAGACCCTCTAGCTGTAATAAGTAACAAGCAGTATCCTACAGGGCGC (SEQ ID NO: 167) | CACTGAAGTTTCTTATCAAATATCCCCGCACTCTGGCCTGGGCAATGAG (SEQ ID NO: 168) |
| AUTS2 | NM_001127231.1 | CTTGTCCTTTCATTCAAAGAAGAGCAGACTCAGCCACCCACACCACTACAGCTCAGATCGAGAAAATGACCGCAATCTCTGCCAGCACCTTGGGAAGAGA (SEQ ID NO: 169) | TGTAGTGGTGTGGGTGGCTGAGTCTGCTCTTCTTTGAATGAAAGGACAAG (SEQ ID NO: 170) | TCTCTTCCCAAGGTGCTGGCAGAGATTGCGGTCATTTTCTCGATCTGAGC (SEQ ID NO: 171) |
| BANK1 | NM_001083907.1 | GGCAAATGAAATGGAAGGGGAAGGAAACAGAATGGATCAGGCATGGAGACCAAACACAGCCCACTAGAGGTTGGCAGTGAGAGTTCTGAAGACCAGTAT (SEQ ID NO: 172) | TCTCCATGCCTGATCCATTCTGTTTTCCTTCCCCTTCCATTTCATTTGCC (SEQ ID NO: 173) | TCTTCAGAACTCTCACTGCCAACCTCTAGTGGGCTGTGTTTGG (SEQ ID NO: 174) |
| BASP1 | NM_006317.3 | GATCCGCGTCTGAAAGTGCAGTACATCGTTTGTACCTGAAACTGCCGCCACACATGCACTCCTCCACCGCTGAGAGTTGAATAGCTTTTCTTCTGCAATGGG (SEQ ID NO: 175) | TGGCGGCAGTTTCAGGTACAAACGATGTACTGCACTTTCAGACGCGGATC (SEQ ID NO: 176) | CCCATTGCAGAAGAAAAGCTATTCAACTCTCAGCGGTGGAGGAGTGCATG (SEQ ID NO: 177) |

TABLE 1-continued

| Gene | GenBank Accession No. | Target Sequence | Capture Probe Sequence | Reporter Probe Sequence |
|---|---|---|---|---|
| BATF | NM_006399.3 | CACTGTGGGTTGCAGGCCCAATGCAGAAGAGTATTAAGAAAGATGCTCAAGTCCCATGGCACAGAGCAAGGCGGGCAGGGAACGGTTATTTTCTAAATA (SEQ ID NO: 178) | TTGAGCATCTTTCTTAATACTCTTCTGCATTGGGCCTGCAACCCA (SEQ ID NO: 179) | TATTTAGAAAAATAACCGTTCCCTGCCCGCCTTGCTCTGTGCCATGGGAC (SEQ ID NO: 180) |
| BATF3 | NM_018664.2 | CTGCTGTTATGCAGAGCCATTTCCTCTAGAATTTGGATAATAAAGATGCTTATTGTCTCTCCCTTCTCCAGTTCTGGGAATTTACAGGCACAATACACTT (SEQ ID NO: 181) | AGCATCTTTATTATCCAAATTCTAGAGGAAATGGCTCTGCATAACAGCAG (SEQ ID NO: 182) | AAGTGTATTGTGCCTGTAAATTCCCAGAACTGGAGAAGGGAGAGACAATA (SEQ ID NO: 183) |
| BCAT1 | NM_005504.4 | CCGACGGAACAATGAAGGATTGCAGTAACGGATGCTCCGCAGAGTGTACCGGAGAAGGAGGATCAAAAGAGGTGGTGGGGACTTTTAAGGCTAAAGACCT (SEQ ID NO: 184) | GGTACACTCTGCGGAGCATCCGTTACTGCAATCCTTCATTGTTCCGTCG (SEQ ID NO: 185) | AGGTCTTTAGCCTTAAAAGTCCCCACCACCTCTTTTGATCCTCCTTCTCC (SEQ ID NO: 186) |
| BCL10 | NM_003921.2 | TGAAAATACCATCTTCTCTTCAACTACACTTCCCAGACCTGGGGACCCAGGGGCTCCTCCTTTGCCACCAGATCTACAGTTAGAAGAAGAAGGAACTTGT (SEQ ID NO: 187) | CTGGGTCCCCAGGTCTGGGAAGTGTAGTTGAAGAGAAGATGGTATTTTCA (SEQ ID NO: 188) | ACAAGTTCCTTCTTCTTCTAACTGTAGATCTGGTGGCAAAGGAGGAGCCC (SEQ ID NO: 189) |
| BCL2A1 | NM_004049.2 | TCATGTGTCATAACTCAGTCAAGCTCAGTGAGCATTCTCAGCACATTGCCTCAACAGCTTCAAGGTGAGCCAGCTCAAGACTTTTGCTCTCCACCAGGCAG (SEQ ID NO: 190) | GGCAATGTGCTGAGAATGCTCACTGAGCTTGACTGAGTTATGACACATGA (SEQ ID NO: 191) | CTGGTGGAGAGCAAAGTCTTGAGCTGGCTCACCTTGAAGCTGTTGA (SEQ ID NO: 192) |
| BCL2L10 | NM_020396.2 | TTTTATCTGAATGCATACAAGGAGTCCTGAGGTGGTGATTTGGCCAGTGTTTTAACTTGTGACAAGTACTCAGGTGTGAGGACAAGAATGCAAATGGCTC (SEQ ID NO: 193) | ACACTGGCCAAATCACCACCTCAGGACTCCTTGTATGCATTCAGATAAA (SEQ ID NO: 194) | GAGCCATTTGCATTCTTGTCCTCACACCTGAGTACTTGTCACAAGTTAAA (SEQ ID NO: 195) |
| BCL6 | NM_001706.2 | GTTGTGGACACTTGCCGGAAGTTTATTAGGCCAGTGAAGCAGAGATGGTTTCTGCCATCAAGCCTCCTCGTGAAGAGTTCCTCAACAGCCGGATGCTGA (SEQ ID NO: 196) | ACCATCTCTGCTTCACTGGCCTTAATAAACTTCCGGCAAGTGTCCACAAC (SEQ ID NO: 197) | TCAGCATCCGGCTGTTGAGGAACTCTTCACGAGGAGCTTGATGGCAGAA (SEQ ID NO: 198) |

TABLE 1-continued

| Gene | GenBank Accession No. | Target Sequence | Capture Probe Sequence | Reporter Probe Sequence |
|---|---|---|---|---|
| BEST3 | NM_152439.2 | TCTTGCAACTAAAG CCCGGAATGAAGG TAGAATCAGAGAC AGTGTTGATCTGCA ATCATTGATGACTG AAATGAATCGATAC CGCTCTTGGTGCAG CCTC (SEQ ID NO: 199) | GATCAACACTGT CTCTGATTCTACC TTCATTCCGGGCT TTAGTTGCAAGA (SEQ ID NO: 200) | GAGGCTGCACCA AGAGCGGTATCG ATTCATTTCAGT CATCAATGATTG CA (SEQ ID NO: 201) |
| BIRC2 | NM_001166.3 | TGGGATCCACCTCT AAGAATACGTCTCC AATGAGAAACAGT TTTGCACATTCATT ATCTCCCACCTTGG AACATAGTAGCTTG TTCAGTGGTTCTTA CTC (SEQ ID NO: 202) | ATGTGCAAAACT GTTTCTCATTGGA GACGTATTCTTAG AGGTGGATCCCA (SEQ ID NO: 203) | GAGTAAGAACC ACTGAACAAGCT ACTATGTTCCAA GGTGGGAGATA ATGA (SEQ ID NO: 204) |
| BIRC3 | NM_001165.3 | GTGATGTTTCTCCT GCCACCTGGAAAC AAAGCATTGAAGTC TGCAGTTGAAAAGC CCAACGTCTGTGAG ATCCAGGAAACCAT GCTTGCAAACCACT GGT (SEQ ID NO: 205) | TCAACTGCAGAC TTCAATGCTTTGT TTCCAGGTGGCA GGAGAAACATCA C (SEQ ID NO: 206) | ACCAGTGGTTTG CAAGCATGGTTT CCTGGATCTCAC AGACGTTGGGCT TT (SEQ ID NO: 207) |
| BIRC5 | NM_001168.2 | CCATTCTAAGTCAT TGGGGAAACGGGG TGAACTTCAGGTGG ATGAGGAGACAGA ATAGAGTGATAGG AAGCGTCTGGCAG ATACTCCTTTTGCC ACTGCT (SEQ ID NO: 208) | TCTCCTCATCCAC CTGAAGTTCACCC CGTTTCCCCAATG ACTTAGAATGG (SEQ ID NO: 209) | AGCAGTGGCAA AAGGAGTATCTG CCAGACGCTTCC TATCACTCTATT CTG (SEQ ID NO: 210) |
| BMP7 | NM_001719.1 | GCTTCGTCAACCTC GTGGAACATGACA AGGAATTCTTCCAC CCACGCTACCACCA TCGAGAGTTCCGGT TTGATCTTTCCAAG ATCCCAGAAGGGG AAGC (SEQ ID NO: 211) | GTAGCGTGGGTG GAAGAATTCCTT GTCATGTTCCACG AGGTTGACGAAG C (SEQ ID NO: 212) | GCTTCCCCTTCT GGGATCTTGGAA AGATCAAACCGG AACTCTCGATGG TG (SEQ ID NO: 213) |
| BPGM | NM_199186.1 | TTTCCAGAGCTAGG CTGTGGAGTAGAGT TTGTATAGGTAACT AGGTAACTTATTGT GGCCCAGATAAGG CTTTAGGATGCCTC AGTGCTATGTCAT AGC (SEQ ID NO: 214) | AGTTACCTAGTTA CCTATACAAACTC TACTCCACAGCCT AGCTCTGGAAA (SEQ ID NO: 215) | GCTATGACATAA GCACTGAGGCAT CCTAAAGCCTTA TCTGGGCCACAA TA (SEQ ID NO: 216) |
| BPNT1 | NM_006085.4 | ACACTGTGTTGATG CGGTTGGTAGCCTC CGCATATTCTATTG CTCAAAAGGCAGG AATGATAGTCAGAC GTGTTATTGCTGAA GGAGACCTGGGTAT TGT (SEQ ID NO: 217) | CTTTTGAGCAATA GAATATGCGGAG GCTACCAACCGC ATCAACACAGTG T (SEQ ID NO: 218) | ACAATACCCAGG TCTCCTTCAGCA ATAACACGTCTG ACTATCATTCCT GC (SEQ ID NO: 219) |

TABLE 1-continued

| Gene | GenBank Accession No. | Target Sequence | Capture Probe Sequence | Reporter Probe Sequence |
|---|---|---|---|---|
| BSPRY | NM_017688.2 | CACTGGCCTGGTGGGCATGCTTACTCACCTGGATGACCTCCAGCTGATTCAGAAGGAGCAAGAGATTTTCGAGAGGACCGAAGAAGCAGAGGGCATTTTG (SEQ ID NO: 220) | GAATCAGCTGGAGGTCATCCAGGTGAGTAAGCATGCCCAC (SEQ ID NO: 221) | CAAAATGCCCTCTGCTTCTTCGGTCCTCTCGAAAATCTCTTGCTCCTTCT (SEQ ID NO: 222) |
| BST2 | NM_004335.2 | TTCGTATGACTATTGCAGAGTGCCCATGGAAGACGGGGATAAGCGCTGTAAGCTTCTGCTGGGGATAGGAATTCTGGTGCTCCTGATCATCGTGATTCTG (SEQ ID NO: 223) | TACAGCGCTTATCCCGTCTTCCATGGGCACTCTG (SEQ ID NO: 224) | CAGAATCACGATGATCAGGAGCACCAGAATTCCTATCCCCAGCAGAAGCT (SEQ ID NO: 225) |
| BTBD19 | NM_001136537.1 | TTTTTCCGCAGCACTCCGAAGCCTTGTCAACAACCCGCGATACAGTGATGTTTGCTTCGTGGTTGGTCAAGAACGGCAGGAGGTATTTGCCCATCGGTGC (SEQ ID NO: 226) | CATCACTGTATCGCGGGTTGTTGACAAGGCTTCGGAGTGCTGCGGAAAAA (SEQ ID NO: 227) | GCACCGATGGGCAAATACCTCCTGCCGTTCTTGACCAACCACGAAGCAAA (SEQ ID NO: 228) |
| BTG1 | NM_001731.2 | CAACGTGCAAATGGTAGACAGCCGAATCAGCTGTAAGGAGGAACTTCTCTTGGGCAGAACGAGCCCTTCCAAAAACTACAATATGATGACTGTATCAGGT (SEQ ID NO: 229) | AGAGAAGTTCCTCCTTACAGCTGATTCGGCTGTCTACCATTTGCACGTTG (SEQ ID NO: 230) | ACCTGATACAGTCATCATATTGTAGTTTTGGAAGGGCTCGTTCTGCCCA (SEQ ID NO: 231) |
| BTG2 | NM_006763.2 | TGCTCTCCTTGGGATGATGGCTGGCTAGTCAGCCTTGCATGTATTCCTTGGCTGAATGGGAGAGTGCCCCATGTTCTGCAAGACTACTTGGTATTCTTGT (SEQ ID NO: 232) | CAAGGAATACATGCAAGGCTGACTAGCCAGCCATCATCCCAAGGAGAG (SEQ ID NO: 233) | ACAAGAATACCAAGTAGTCTTGCAGAACATGGGGCACTCTCCCATTCAGC (SEQ ID NO: 234) |
| BTK | NM_000061.1 | TGATCTGGTTCAGAAATATCACCCTTGCTTCTGGATCGATGGGCAGTATCTCTGCTGCTCTCAGACAGCCAAAAATGCTATGGGCTGCCAAATTTTGGAG (SEQ ID NO: 235) | GATACTGCCCATCGATCCAGAAGCAAGGGTGATATTTCTGAACCAGATCA (SEQ ID NO: 236) | CTCCAAAATTTGGCAGCCCATAGCATTTTTGGCTGTCTGAGAGCAGCAGA (SEQ ID NO: 237) |
| BUB1 | NM_004336.2 | CCCGGAAAATGTCCTTCAGATGCTTGAAGCCCACATGCAGAGCTACAAGGGCAATGACCCTCTTGGTGAATGGGAAAGATACATACAGTGGGTAGAAGAG (SEQ ID NO: 238) | CCTTGTAGCTCTGCATGTGGGCTTCAAGCATCTGAAGGACATTTTCCGGG (SEQ ID NO: 239) | CTCTTCTACCCACTGTATGTATCTTTCCCATTCACCAAGAGGGTCATTGC (SEQ ID NO: 240) |

TABLE 1-continued

| Gene | GenBank Accession No. | Target Sequence | Capture Probe Sequence | Reporter Probe Sequence |
|---|---|---|---|---|
| BUB1B | NM_001211.4 | GAGTCTTCTGTACCACAACGAAGCACACTAGCTGAACTAAAGAGCAAAGGGAAAAAGACAGCAAGAGCTCCAATCATCCGTGTAGGAGGTGCTCTCAAGG (SEQ ID NO: 241) | CCTTTGCTCTTTAGTTCAGCTAGTGTGCTTCGTTGTGGTACAGAAGACTC (SEQ ID NO: 242) | CCTTGAGAGCACCTCCTACACGGATGATTGGAGCTCTTGCTGTCTTTTTC (SEQ ID NO: 243) |
| C10orf18 | NM_017782.3 | CCAGAAAATACCACAGCGGCTCACAATGATCTTCCTGAAAACTCCATCGTCAACTATGACTCCCAGGCCCTAAATATGTTAGCCGATCTAGCATTAAGCT (SEQ ID NO: 244) | ACGATGGAGTTTTCAGGAAGATCATTGTGAGCCGCTGTGGTATTTTCTGG (SEQ ID NO: 245) | AGCTTAATGCTAGATCGGCTAACATATTTAGGGCCTGGGAGTCATAGTTG (SEQ ID NO: 246) |
| C13orf18 | NM_025113.2 | CCTCCCCATATCCTGAGACTGACAGTGCTTTTTTTGAGCCTTCCCATCTGACATCTGCTGCTGATGAAGGTGCTGTTCAAGTCAGTAGAAGAACCATTTC (SEQ ID NO: 247) | CAGATGGGAAGGCTCAAAAAAGCACTGTCAGTCTCAGGATATGGGGAG (SEQ ID NO: 248) | GAAATGGTTCTTCTACTGACTTGAACAGCACCTTCATCAGCAGCAGATGT (SEQ ID NO: 249) |
| C15orf41 | NM_001130010.1 | ATTAATGGCTCGGCTTATACTGGAGAGGTTTCTACAGGAACACGAGGAAACTCCACCCTCCAAGTCTATTATAAATAGTATGCTACGGGACCCTTCTCAG (SEQ ID NO: 250) | TTTCCTCGTGTTCCTGTAGAAACCTCTCCAGTATAAGCCGAGCCATTAAT (SEQ ID NO: 251) | CTGAGAAGGGTCCCGTAGCATACTATTTATAATAGACTTGGAGGGTGGAG (SEQ ID NO: 252) |
| C19orf26 | NM_152769.2 | CGGGGCAGGTACCGTTCTGCAGTTCCTCACCCGCCTGCGCCGCCATGCCAGCCTGGATGGGGCCAGCCCCTATTTCAAGGTCAAGAAGTGGAAGCTGGAG (SEQ ID NO: 253) | TGGCATGGCGGCGCAGGCGGGTGAGGAACTGCAGAACGG (SEQ ID NO: 254) | CTTCTTGACCTTGAAATAGGGGCTGGCCCCATCCAGGC (SEQ ID NO: 255) |
| C3orf37 | NM_020187.2 | CCAAGCTGCAGTTCAATACTACCAACTGTCGTAGTGATACCGTAATGGAGAAACGGTCATTTAAGGTGCCTCTGGGAAAGGGAAGACGCTGTGTCGTTTT (SEQ ID NO: 256) | CTCCATTACGGTATCACTACGACAGTTGGTAGTATTGAACTGCAGCTTGG (SEQ ID NO: 257) | AAAACGACACAGCGTCTTCCCTTTCCCAGAGGCACCTTAAATGACCGTTT (SEQ ID NO: 258) |
| C4orf31 | NM_024574.3 | TCCAGGCTTCTCGTTCCTGGATATTGTGCTTAGCATCTTGGCAGGGTCCGGGACGTGGACTATTTCGCACACCACACCACGGGGAGGGATTTTTTCT (SEQ ID NO: 259) | GGACCCTGCCAAGATGCTAAGCACCAATATCCAGGAACGAGAAGCCTGGA (SEQ ID NO: 260) | AGAAAAAAATCCCTCCCCGTGGTGTGGTGTGCGAAATAGTCCACGTCCCC (SEQ ID NO: 261) |
| C5AR1 | NM_001736.2 | TTGCCTGTCTTTCCCAGACTTGTCCCTCCTTTTCCAGCGGGACTCTTCTCATCCTTCCTCATTTGCAAGGTGAACACTTCCTTCTAGGGAGCACCCTCCC (SEQ ID NO: 262) | GAGAAGAGTCCCGCTGGAAAAGGAGGGCAAGTCTGGGAAAGACAGGCAA (SEQ ID NO: 263) | GGGAGGGTGCTCCCTAGAAGGAAGTGTTCACCTTGCAAATGAGGAAGGAT (SEQ ID NO: 264) |

TABLE 1-continued

| Gene | GenBank Accession No. | Target Sequence | Capture Probe Sequence | Reporter Probe Sequence |
|---|---|---|---|---|
| C5orf41 | NM_153607.2 | GCTCCTGTGTGTTC TTCTAAGACTCTGC AGGCTGAGGTCCCT TTGTCAGACTGTGT CCAAAAAGCAAGT AAACCCACTTCAAG CACACAAATCATGG TGA (SEQ ID NO: 265) | TCTGACAAAGGG ACCTCAGCCTGC AGAGTCTTAGAA GAACACACAGGA GC (SEQ ID NO: 266) | TCACCATGATTT GTGTGCTTGAAG TGGGTTTACTTG CTTTTTGGACAC AG (SEQ ID NO: 267) |
| C7orf68 | NM_013332.1 | CAACACAGAGCCC ACCAAGGGCCTTCC AGACCATCCATCCA GAAGCATGTGATA AGACCTCCTTCCAT ACTGGCCATATTTT GGAACACTGACCTA GACA (SEQ ID NO: 268) | ACATGCTTCTGGA TGGATGGTCTGG AAGGGCCCTTGGT G (SEQ ID NO: 269) | TGTCTAGGTCAG TGTTCCAAAATA TGGCCAGTATGG AAGGAGGTCTTA TC (SEQ ID NO: 270) |
| CA7 | NM_005182.2 | TCCCAGCCTGCAAC CACTGGAGCTTTCC TATGAGGCCTGCAT GTCCCTCAGCATCA CCAACAATGGCCAC TCTGTCCAGGTAGA CTTCAATGACAGCG AT (SEQ ID NO: 271) | TGAGGGACATGC AGGCCTCATAGG AAAGCTCCAGTG GTTG (SEQ ID NO: 272) | CATTGAAGTCTA CCTGGACAGAGT GGCCATTGTTGG TGATGC (SEQ ID NO: 273) |
| CACNA1D | NM_000720.2 | TATCGTGTGATTTG CAAGATGACGAGC CTGAGGAAACAAA ACGAGAAGAAGAA GATGATGTGTTCAA AAGAAATGGTGCC CTGCTTGGAAACCA TGTCAA (SEQ ID NO: 274) | TTCTTCTCGTTTT GTTTCCTCAGGCT CGTCATCTTGCAA ATCACACGATA (SEQ ID NO: 275) | TTGACATGGTTT CCAAGCAGGGC ACCATTTCTTTT GAACACATCATC TTC (SEQ ID NO: 276) |
| CALD1 | NM_033138.2 | GATTGACAGCAGA CTGGAGCAGTATAC CAGTGCAATTGAGG GAACAAAAAGCGC AAAACCTACAAAG CCGGCAGCCTCGGA TCTTCCTGTTCCTG CTGAA (SEQ ID NO: 277) | TTTTTGTTCCCTC AATTGCACTGGT ATACTGCTCCAGT CTGCTGTCAATC (SEQ ID NO: 278) | TTCAGCAGGAAC AGGAAGATCCG AGGCTGCCGGCT TTGTAGGTTTTG CGC (SEQ ID NO: 279) |
| CAMK2B | NM_001220.3 | TCACCAGAAGCTGG AGAGAGAGGCTCG GATCTGCCGCCTTC TGAAGCATTCCAAC ATCGTGCGTCTCCA CGACAGCATCTCCG AGGAGGGCTTCCAC TAC (SEQ ID NO: 280) | AATGCTTCAGAA GGCGGCAGATCC GAGCCTCTCTCT (SEQ ID NO: 281) | CTCCTCGGAGAT GCTGTCGTGGAG ACGCACGATGTT GG (SEQ ID NO: 282) |
| CAMKK1 | NM_032294.2 | GAGCCAGAAATCA GCGAGGAGCTCAA GGACCTGATCCTGA AGATGTTAGACAA GAATCCCGAGACG AGAATTGGGGTGCC AGACATCAAGTTGC ACCCTT (SEQ ID NO: 283) | TCTAACATCTTCA GGATCAGGTCCTT GAGCTCCTCGCTG ATTTCTGG (SEQ ID NO: 284) | AAGGGTGCAACT TGATGTCTGGCA CCCCAATTCTCG TCTCGGGATTCT TG (SEQ ID NO: 285) |

TABLE 1-continued

| Gene | GenBank Accession No. | Target Sequence | Capture Probe Sequence | Reporter Probe Sequence |
|---|---|---|---|---|
| CARD11 | NM_032415.2 | TTGAAAATCGGCCC AAGAAGGAGCAGG TTCTGGAACTGGAG CGGGAGAATGAAA TGCTGAAGACCAA AAACCAGGAGCTG CAGTCCATCATCCA GGCCGG (SEQ ID NO: 286) | ATTCTCCCGCTCC AGTTCCAGAACC TGCTCCTTCTTGG GCCGATTTTCAA (SEQ ID NO: 287) | CCGGCCTGGATG ATGGACTGCAGC TCCTGGTTTTTG GTCTTCAGCATT TC (SEQ ID NO: 288) |
| CAV1 | NM_001753.3 | AACCGCGACCCTAA ACACCTCAACGATG ACGTGGTCAAGATT GACTTTGAAGATGT GATTGCAGAACCA GAAGGGACACACA GTTTTGACGGCATT TGGA (SEQ ID NO: 289) | TCAAAGTCAATCT TGACCACGTCATC GTTGAGGTGTTTA GGGTCGCGGTT (SEQ ID NO: 290) | TCCAAATGCCGT CAAAACTGTGTG TCCCTTCTGGTT CTGCAATCACAT CT (SEQ ID NO: 291) |
| CAV2 | NM_198212.1 | GCCTTTTGTAAAGA CCTGCCTAATGGTT CTGCCTTCAGTGCA GACAATATGGAAG AGTGTGACAGATGT TATCATTGCTCCAT TGTGTACGAGCGTA GGA (SEQ ID NO: 292) | ATATTGTCTGCAC TGAAGGCAGAAC CATTAGGCAGGT CTTTACAAAAGG C (SEQ ID NO: 293) | TCCTACGCTCGT ACACAATGGAGC AATGATAACATC TGTCACACTCTT CC (SEQ ID NO: 294) |
| CCDC50 | NM_174908.3 | AAACACTTTCCAGA GTTCCCTGCAACCC GTGCTTATGCAGAT AGTTACTATTATGA AGATGGAGGAATG AAGCCAAGAGTGA TGAAAGAAGCTGT ATCTA (SEQ ID NO: 295) | TAGTAACTATCTG CATAAGCACGGG TTGCAGGGAACT CTGGAAAGTGTTT (SEQ ID NO: 296) | TAGATACAGCTT CTTTCATCACTC TTGGCTTCATTC CTCCATCTTCAT AA (SEQ ID NO: 297) |
| CCDC75 | NM174931.2 | ACTTGGCAAGAGTG GGGGTGGTATTGTT GAACCAATTCCTCT CAATATCAAAACA GGGAAAAGTGGCA TTGGTCATGAGGCA TCATTAAAACGGAA AGCA (SEQ ID NO: 298) | TGATATTGAGAG GAATTGGTTCAA CAATACCACCCC CACTCTTGCCAAG T (SEQ ID NO: 299) | CTTTCCGTTTTA ATGATGCCTCAT GACCAATGCCAC TTTTCCCTGTTT (SEQ ID NO: 300) |
| CCL17 | NM_002987.2 | GCCTGGAGTACTTC AAGGGAGCCATTCC CCTTAGAAAAGCTGA AGACGTGGTACCA GACATCTGAGGACT GCTCCAGGGATGCC ATCGTTTTTGTAAC TGT (SEQ ID NO: 301) | CCACGTCTTCAGC TTTCTAAGGGGA ATGGCTCCCTTGA AGTACTC (SEQ ID NO: 302) | ACAGTTACAAAA ACGATGGCATCC CTGGAGCAGTCC TCAGATGTCTGG TA (SEQ ID NO: 303) |
| CCNA2 | NM_001237.2 | CGGGACAAAGCTG GCCTGAATCATTAA TACGAAAGACTGG ATATACCCTGGAAA GTCTTAAGCCTTGT CTCATGGACCTTCA CCAGACCTACCTCA AAGC (SEQ ID NO: 304) | CAGGGTATATCC AGTCTTTCGTATT AATGATTCAGGC CAGCTTTGTCCCG (SEQ ID NO: 305) | GCTTTGAGGTAG GTCTGGTGAAGG TCCATGAGACAA GGCTTAAGACTT TC (SEQ ID NO: 306) |

TABLE 1-continued

| Gene | GenBank Accession No. | Target Sequence | Capture Probe Sequence | Reporter Probe Sequence |
| --- | --- | --- | --- | --- |
| CCNB1 | NM_031966.2 | AACTTGAGGAAGAGCAAGCAGTCAGACCAAAATACCTACTGGGTCGGGAAGTCACTGGAAACATGAGAGCCATCCTAATTGACTGGCTAGTACAGGTTCA (SEQ ID NO: 307) | TTCCCGACCCAGTAGGTATTTTGGTCTGACTGCTTGCTCTTCCTCAAGTT (SEQ ID NO: 308) | TGAACCTGTACTAGCCAGTCAATTAGGATGGCTCTCATGTTTCCAGTGAC (SEQ ID NO: 309) |
| CCNB2 | NM_004701.2 | AGGTTGATGTTGAACAGCACACTTTAGCCAAGTATTTGATGGAGCTGACTCTCATCGACTATGATATGGTGCATTATCATCCTTCTAAGGTAGCAGCAGC (SEQ ID NO: 310) | AGTCAGCTCCATCAAATACTTGGCTAAAGTGTGCTGTTCAACATCAACCT (SEQ ID NO: 311) | GCTGCTGCTACCTTAGAAGGATGATAATGCACCATATCATAGTCGATGAG (SEQ ID NO: 312) |
| CCND1 | NM_053056.2 | TTGAACACTTCCTCTCCAAAATGCCAGAGGCGGAGGAGAACAAACAGATCATCCGCAAACACGCGCAGACCTTCGTTGCCCTCTGTGCCACAGATGTGAA (SEQ ID NO: 313) | GATCTGTTTGTTCTCCTCCGCCTCTGGCATTTTGGAGAGGAAGTGTTCAA (SEQ ID NO: 314) | TTCACATCTGTGGCACAGAGGGCAACGAAGGTCTGCGCGTGTTTGCGGAT (SEQ ID NO: 315) |
| CCND2 | NM_001759.2 | AGCCTGCATCCCTTCGCCTGCAGCCTACTTTGGGGAAATAAAGTGCCTTACTGACTGTAGCCATTACAGTATCCAATGTCTTTTGACAGGTGCCTGTCCT (SEQ ID NO: 316) | TAAGGCACTTTATTTCCCCAAAGTAGGCTGCAGGCGAAGGGATGCAGGCT (SEQ ID NO: 317) | AGGACAGGCACCTGTCAAAAGACATTGGATACTGTAATGGCTACAGTCAG (SEQ ID NO: 318) |
| CCND3 | NM_001760.2 | GGCCAGCCATGTCTGCATTTCGGTGGCTAGTCAAGCTCCTCCTCCCTGCATCTGACCAGCAGCGCCTTTCCCAACTCTAGCTGGGGGTGGGCCAGGCTGA (SEQ ID NO: 319) | TGCAGGGAGGAGGAGCTTGACTAGCCACCGAAATGCAGACATGG (SEQ ID NO: 320) | CCCAGCTAGAGTTGGGAAAGGCGCTGCTGGTCAGA (SEQ ID NO: 321) |
| CCR7 | NM_001838.2 | TTCCGAAAACCAGGCCTTATCTCCAAGACCAGAGATAGTGGGGAGACTTCTTGGCTTGGTGAGGAAAAGCGGACATCAGCTGGTCAAACAAACTCTCTGA (SEQ ID NO: 322) | GAAGTCTCCCCACTATCTCTGGTCTTGGAGATAAGGCCTGGTTTTCGGAA (SEQ ID NO: 323) | TCAGAGAGTTTGTTTGACCAGCTGATGTCCGCTTTTCCTCACCAAGCCAA (SEQ ID NO: 324) |
| CD2 | NM_001767.2 | TGGGTCTCACTACAAGCAGCCTATCTGCTTAAGAGACTCTGGAGTTTCTTATGTGCCCTGGTGGACACTTGCCCACCATCCTGTGAGTAAAAGTGAAATA (SEQ ID NO: 325) | AAGAAACTCCAGAGTCTCTTAAGCAGATAGGCTGCTTGTAGTGAGACCCA (SEQ ID NO: 326) | TATTTCACTTTTACTCACAGGATGGTGGGCAAGTGTCCACCAGGGCACAT (SEQ ID NO: 327) |

TABLE 1-continued

| Gene | GenBank Accession No. | Target Sequence | Capture Probe Sequence | Reporter Probe Sequence |
|---|---|---|---|---|
| CD200 | NM_005944.5 | CCCTCGGTCAGGGATTGAAAATAGTACAGTGACTCTGTCTCACCCAAATGGGACCACGTCTGTTACCAGCATCCTCCATATCAAAGACCCTAAGAATCAG (SEQ ID NO: 328) | CATTTGGGTGAGACAGAGTCACTGTACTATTTTCAATCCCTGACCGAGG (SEQ ID NO: 329) | CTGATTCTTAGGGTCTTTGATATGGAGGATGCTGGTAACAGACGTGGTCC (SEQ ID NO: 330) |
| CD22 | NM_001771.2 | TTTTCCAGAAGATGAGGGGATTCATTACTCAGAGCTGATCCAGTTTGGGGTCGGGGAGCGGCCTCAGGCACAAGAAAATGTGGACTATGTGATCCTCAAA (SEQ ID NO: 331) | CCCCAAACTGGATCAGCTCTGAGTAATGAATCCCCTCATCTTCTGGAAAA (SEQ ID NO: 332) | TTTGAGGATCACATAGTCCACATTTTCTTGTGCCTGAGGCCGCTCCCCGA (SEQ ID NO: 333) |
| CD247 | NM_198053.1 | TGGCAGGACAGGAAAAACCCGTCAATGTACTAGGATACTGCTGCGTCATTACAGGGCACAGGCCATGGATGGAAAACGCTCTCTGCTCTGCTTTTTTTCT (SEQ ID NO: 334) | AATGACGCAGCAGTATCCTAGTACATTGACGGGTTTTTCCTGTCCTGCCA (SEQ ID NO: 335) | AGAAAAAAAGCAGAGCAGAGAGCGTTTTCCATCCATGGCCTGTGCCCTGT (SEQ ID NO: 336) |
| CD274 | NM_014143.2 | TAGGAGATTAGATCCTGAGGAAAACCATACAGCTGAATTGGTCATCCCAGAACTACCTCTGGCACATCCTCCAAATGAAAGGACTCACTTGGTAATTCTG (SEQ ID NO: 337) | CTGGGATGACCAATTCAGCTGTATGGTTTTCCTCAGGATCTAATCTCCTA (SEQ ID NO: 338) | CAGAATTACCAAGTGAGTCCTTTCATTTGGAGGATGTGCCAGAGGTAGTT (SEQ ID NO: 339) |
| CD3D | NM_000732.4 | TATCTACTGGATGAGTTCCGCTGGGAGATGGAACATAGCACGTTTCTCTCTGGCCTGGTACTGGCTACCCTTCTCTCGCAAGTGAGCCCCTTCAAGATAC (SEQ ID NO: 340) | GAGAGAAACGTGCTATGTTCCATCTCCCAGCGGAACTCATCCAGTAGATA (SEQ ID NO: 341) | TCACTTGCGAGAGAAGGGTAGCCAGTACCAGGCCA (SEQ ID NO: 342) |
| CD3E | NM_000733.2 | AAGTAACAGTCCCATGAAACAAAGATGCAGTCGGGCACTCACTGGAGAGTTCTGGGCCTCTGCCTCTTATCAGTTGGCGTTTGGGGGCAAGATGGTAATGG (SEQ ID NO: 343) | ACTCTCCAGTGAGTGCCCGACTGCATCTTTGTTTCATGGGACTGTTACTT (SEQ ID NO: 344) | CATTACCATCTTGCCCCCAAACGCCAACTGATAAGAGGCAGAGGCCCAGA (SEQ ID NO: 345) |
| CD3G | NM_000073.2 | AGAGCTTCAGACAAGCAGACTCTGTTGCCCAATGACCAGCTCTACCAGCCCCTCAAGGATCGAGAAGATGACCAGTACAGCCACCTTCAAGGAAACCAGT (SEQ ID NO: 346) | GGCTGGTAGAGCTGGTCATTGGGCAACAGAGTCTG (SEQ ID NO: 347) | ACTGGTTTCCTTGAAGGTGGCTGTACTGGTCATCTTCTCGATCCTTGAGG (SEQ ID NO: 348) |

TABLE 1-continued

| Gene | GenBank Accession No. | Target Sequence | Capture Probe Sequence | Reporter Probe Sequence |
|---|---|---|---|---|
| CD40 | NM_001250.4 | CCCAGGAAGCCATATACACAGATGCCCATTGCAGCATTGTTTGTGATAGTGAACAACTGGAAGCTGCTTAACTGTCCATCAGCAGGAGACTGGCTAAATA (SEQ ID NO: 349) | ACTATCACAAACAATGCTGCAATGGGCATCTGTGTATATGGCTTCCTGGG (SEQ ID NO: 350) | TATTTAGCCAGTCTCCTGCTGATGGACAGTTAAGCAGCTTCCAGTTGTTC (SEQ ID NO: 351) |
| CD44 | NM_000610.3 | GTGGGCAGAAGAAAAAGCTAGTGATCAACAGTGGCAATGGAGCTGTGGAGGACAGAAAGCCAAGTGGACTCAACGGAGAGGCCAGCAAGTCTCAGGAAAT (SEQ ID NO: 352) | CTCCACAGCTCCATTGCCACTGTTGATCACTAGCTTTTTCTTCTGCCCAC (SEQ ID NO: 353) | CTGGCCTCTCCGTTGAGTCCACTTGGCTTTCTGTC (SEQ ID NO: 354) |
| CD47 | NM_001777.3 | GCCATATTGGTTATTCAGGTGATAGCCTATATCCTCGCTGTGGTTGGACTGAGTCTCTGTATTGCGGCGTGTATACCAATGCATGGCCCTCTTCTGATTT (SEQ ID NO: 355) | AGTCCAACCACAGCGAGGATATAGCTATCACCTGAATAACCAATATGGC (SEQ ID NO: 356) | AAATCAGAAGAGGGCCATGCATTGGTATACACGCCGCAATACAGAGACTC (SEQ ID NO: 357) |
| CD5 | NM_014207.2 | CCAGAAGAAGCAGCGCCAGTGGATTGGCCCAACGGGAATGAACCAAAACATGTCTTTCCATCGCAACCACACGGCAACCGTCCGATCCCATGCTGAGAAC (SEQ ID NO: 358) | TGTTTTGGTTCATTCCCGTTGGGCCAATCCACTGGCGCTGCTTCTTCTGG (SEQ ID NO: 359) | GTTCTCAGCATGGGATCGGACGGTTGCCGTGTGGTTGCGATGGAAAGACA (SEQ ID NO: 360) |
| CD58 | NM_001779.2 | GTGCTTGAGTCTCTTCCATCTCCCACACTAACTTGTGCATTGACTAATGGAAGCATTGAAGTCCAATGCATGATACCAGAGCATTACAACAGCCATCGAG (SEQ ID NO: 361) | CCATTAGTCAATGCACAAGTTAGTGTGGGAGATGGAAGAGACTCAAGCAC (SEQ ID NO: 362) | CTCGATGGCTGTTGTAATGCTCTGGTATCATGCATTGGACTTCAATGCTT (SEQ ID NO: 363) |
| CD6 | NM_006725.3 | CGCTGGCAGCCAGGGTCCTCTGCTCAGCTTCCCGGAGTTTGCACAATCTGTCCACTCCCGAAGTCCCTGCAAGTGTTCAGACAGTCACTATAGAATCTTC (SEQ ID NO: 364) | CAGATTGTGCAAACTCCGGGAAGCTGAGCAGAGGACCCTGGCTGC (SEQ ID NO: 365) | GAAGATTCTATAGTGACTGTCTGAACACTTGCAGGGACTTCGGGAGTGGA (SEQ ID NO: 366) |
| CD74 | NM_001025159.1 | TTCAGCCCCCAGCCCCTCCCCCATCTCCCACCCTGTACCTCATCCCATGAGACCCTGGTGCCTGGCTCTTTCGTCACCCTTGGACAAGACAAACCAAGTC (SEQ ID NO: 367) | TCATGGGATGAGGTACAGGGTGGGAGATGGGGAG (SEQ ID NO: 368) | TTGGTTTGTCTTGTCCAAGGGTGACGAAAGAGCCAGGCACCAGGGTC (SEQ ID NO: 369) |
| CD79A | NM_001783.3 | AACGAGAAGCTCGGGTTGGATGCCGGGGATGAATATGAAGATGAAAACCTTTATGAAGGCCTGAACCTGGACGACTGCTCCATGTATGAGGACATCTCCC (SEQ ID NO: 370) | AGGTTTTCATCTTCATATTCATCCCCGGCATCCAACCCGAGCTTCTCGTT (SEQ ID NO: 371) | CTCATACATGGAGCAGTCGTCCAGGTTCAGGCCTTCATAA (SEQ ID NO: 372) |

TABLE 1-continued

| Gene | GenBank Accession No. | Target Sequence | Capture Probe Sequence | Reporter Probe Sequence |
|---|---|---|---|---|
| CD79B | NM_000626.2 | TACCGGAATCCCAAAGGTAGTGCTTGTTCGCGGATCTGGCAGAGCCCACGTTTCATAGCCAGGAAACGGGGCTTCACGGTGAAAATGCACTGCTACATGA (SEQ ID NO: 373) | CGTGGGCTCTGCCAGATCCGCGAACAAGCACTACCTTTGGGATTCCG (SEQ ID NO: 374) | TCATGTAGCAGTGCATTTTCACCGTGAAGCCCCGTTTCCTGGCTATGAAA (SEQ ID NO: 375) |
| CD8A | NM_001768.5 | GCTCAGGGCTCTTTCCTCCACACCATTCAGGTCTTTCTTTCCGAGGCCCCTGTCTCAGGGTGAGGTGCTTGAGTCTCCAACGGCAAGGGAACAAGTACTT (SEQ ID NO: 376) | GGGGCCTCGGAAAGAAAGACCTGAATGGTGTGGAGGAAAGAGCCCTGAGC (SEQ ID NO: 377) | AAGTACTTGTTCCCTTGCCGTTGGAGACTCAAGCACCTCACCCTGAGACA (SEQ ID NO: 378) |
| CD8B | NM_004931.3 | CAGCTGAGTGTGGTTGATTTCCTTCCCACCACTGCCCAGCCCACCAAGAAGTCCACCCTCAAGAAGAGAGTGTGCCGGTTACCCAGGCCAGAGACCCAGA (SEQ ID NO: 379) | TTCTTGGTGGGCTGGGCAGTGGTGGGAAGGAAATCAACCACACTCAG (SEQ ID NO: 380) | CCTGGGTAACCGGCACACTCTCTTCTTGAGGGTGGAC (SEQ ID NO: 381) |
| CDC20 | NM_001255.2 | GGAACATCAGAAAGCCTGGGCTTTGAACCTGAACGGTTTTGATGTAGAGGAAGCCAAGATCCTTCGGCTCAGTGGAAAACCACAAAATGCGCCAGAGGGT (SEQ ID NO: 382) | CCTCTACATCAAAACCGTTCAGGTTCAAAGCCCAGGCTTTCTGATGTTCC (SEQ ID NO: 383) | ACCCTCTGGCGCATTTTGTGGTTTTCCACTGAGCCGAAGGATCTTGGCT (SEQ ID NO: 384) |
| CDC25B | NM_021873.2 | CACCATACGAGCACCTCCAGCCTGAACAGAAGCTCTTACTCTTTCCTATTTCAGTGTTACCTGTGTGCTTGGTCTGTTTGACTTTACGCCCATCTCAGGA (SEQ ID NO: 385) | AATAGGAAAGAGTAAGAGCTTCTGTTCAGGCTGGAGGTGCTCGTATGGTG (SEQ ID NO: 386) | TCCTGAGATGGGCGTAAAGTCAAACAGACCAAGCACACAGGTAACACTGA (SEQ ID NO: 387) |
| CDC25C | NM_001790.2 | CTCTCTGTGTGACATTACTATCACTCAGATGCTGGAGGAAGATTCTAACCAGGGGCACCTGATTGGTGATTTTTCCAAGGTATGTGCGCTGCCAACCGTG (SEQ ID NO: 388) | GGTTAGAATCTTCCTCCAGCATCTGAGTGATAGTAATGTCACACAGAGAG (SEQ ID NO: 389) | CACGGTTGGCAGCGCACATACCTTGGAAAAATCACCAATCAGGTGCCCCT (SEQ ID NO: 390) |
| CDCA3 | NM_031299.4 | AAGGAGCCATTCTTGGAACTGGACGACTTCTGAAAACTGGAGGACGAGCATGGGAGCAAGGCCAGGACCATGACAAGGAAAATCAGCACTTTCCCTTGGT (SEQ ID NO: 391) | TGCTCGTCCTCCAGTTTTCAGAAGTCGTCCAGTTCCAAGAATGGCT (SEQ ID NO: 392) | AAGGGAAAGTGCTGATTTTCCTTGTCATGGTCCTGGCCTTGCTCCCA (SEQ ID NO: 393) |

TABLE 1-continued

| Gene | GenBank Accession No. | Target Sequence | Capture Probe Sequence | Reporter Probe Sequence |
|---|---|---|---|---|
| CDCA5 | NM_080668.3 | TGCAGTCAGAAAGCCCATCGTCTTAAAGAGGATCGTGGCCCATGCTGTAGAGGTCCCAGCTGTCCAATCACCTCGCAGGAGCCCTAGGATTCCTTTTTC (SEQ ID NO: 394) | CTACAGCATGGGCCACGATCCTCTTTAAGACGATGGGCTTTCTGAC (SEQ ID NO: 395) | GAAAAAGGAAATCCTAGGGCTCCTGCGAGGTGATTGGACAGCTGGGACCT (SEQ ID NO: 396) |
| CDCA8 | NM_018101.2 | TCCCTGTTTACTGAAGACCAAATACTGGTTTGGAGACAACTTCCATGTCTTGCTCTTCTACCTCCCTAGTTAGTGGAAATTTGGATAAGGGAACTGTAGG (SEQ ID NO: 397) | AGACATGGAAGTTGTCTCCAAACCAGTATTTGGTCTTCAGTAAACAGGGA (SEQ ID NO: 398) | CCTACAGTTCCCTTATCCAAATTTCCACTAACTAGGGAGGTAGAAGAGCA (SEQ ID NO: 399) |
| CDH11 | NM_001797.2 | CAGGAAGCCAAAGTCCCAGTGGCCATTAGGGTCCTTGATGTCAACGATAATGCTCCCAAGTTTGCTGCCCCTTATGAAGGTTTCATCTGTGAGAGTGATC (SEQ ID NO: 400) | TTATCGTTGACATCAAGGACCCTAATGGCCACTGGGACTTTGGCTTCCTG (SEQ ID NO: 401) | GATCACTCTCACAGATGAAACCTTCATAAGGGGCAGCAAACTTGGGAGCA (SEQ ID NO: 402) |
| CDK1 | NM_001786.2 | CACATGAGGTAGTAACACTCTGGTACAGATCTCCAGAAGTATTGCTGGGGTCAGCTCGTTACTCAACTCCAGTTGACATTTGGAGTATAGGCACCATATT (SEQ ID NO: 403) | CCCCAGCAATACTTCTGGAGATCTGTACCAGAGTGTTACTACCTCATGTG (SEQ ID NO: 404) | AATATGGTGCCTATACTCCAAATGTCAACTGGAGTTGAGTAACGAGCTGA (SEQ ID NO: 405) |
| CDK14 | NM_012395.2 | ATTACTCAGTGGACGGAGAAGTCTGTTTTGTTACAGAGACATGCCTCTCAGAAGGTCAGGAGGTTTTGAGTACCTATCCTTGCCACCCATACAGGAAATC (SEQ ID NO: 406) | TGAGAGGCATGTCTCTGTAACAAAACAGACTTCTCCGTCCACTGAGTAAT (SEQ ID NO: 407) | GATTTCCTGTATGGGTGGCAAGGATAGGTACTCAAAACCTCCTGACCTTC (SEQ ID NO: 408) |
| CDK4 | NM_000075.2 | ACTTTTAACCCACACAAGCGAATCTCTGCCTTTCGAGCTCTGCAGCACTCTTATCTACATAAGGATGAAGGTAATCCGGAGTGAGCAATGGAGTGGCTGC (SEQ ID NO: 409) | GAGTGCTGCAGAGCTCGAAAGGCAGAGATTCGCTTGTGTGGGTTAAAAGT (SEQ ID NO: 410) | GCAGCCACTCCATTGCTCACTCCGGATTACCTTCATCCTTATGTAGATAA (SEQ ID NO: 411) |
| CDK5RAP2 | NM_001011649.1 | AGCAACTGGAGCAGGATGTGCTTTCATATCAGAATTTGCGGAAGACCTTGGAGGAGCAGATCAGCGAAATTCGGAGGCGGGAAGAAGAATCATTTCACT (SEQ ID NO: 412) | CAAGGTCTTCCGCAAATTCTGATATGAAAGCACATCCTGCTCCAGTTGCT (SEQ ID NO: 413) | AGTGAAAATGATTCTTCTTCCCGCCTCCGAATTTCGCTGATCTGCTCCTC (SEQ ID NO: 414) |

TABLE 1-continued

| Gene | GenBank Accession No. | Target Sequence | Capture Probe Sequence | Reporter Probe Sequence |
|---|---|---|---|---|
| CDK6 | NM_001259.5 | GGGAAAGAAAAGTGCAATGATTCTGGACTGAGACGCGCTTGGGCAGAGGCTATGTAATCGTGTCTGTGTTGAGGACTTCGCTTCGAGGAGGGAAGAGGAG (SEQ ID NO: 415) | GCCTCTGCCCAAGCGCGTCTCAGTCCAGAATCATTGCACTTTTCTTTC (SEQ ID NO: 416) | CTCCTCTTCCCTCCTCGAAGCGAAGTCCTCAACACAGACACGATTACATA (SEQ ID NO: 417) |
| CDKN3 | NM_005192.3 | TACCGAAAAACCTTAATACACTGCTATGGAGGACTTGGGAGATCTTGTCTTGTAGCTGCTTGTCTCCTACTATACCTGTCTGACACAATATCACCAGAGC (SEQ ID NO: 418) | AGACAAGATCTCCCAAGTCCTCCATAGCAGTGTATTAAGGTTTTTCGGTA (SEQ ID NO: 419) | CTCTGGTGATATTGTGTCAGACAGGTATAGTAGGAGACAAGCAGCTACA (SEQ ID NO: 420) |
| CELSR1 | NM_014246.1 | CCTGGGACCTTAAAGCGTTGCAGGTTCCTGATTTGGACAGAGGTGTGGGGCCTTCCAGGCCGTTACATACCTCCTGCCAATTCTCTAACTCTCTGAGACT (SEQ ID NO: 421) | CCCCACACCTCTGTCCAAATCAGGAACCTGCAACGCTTTAAGGTCC (SEQ ID NO: 422) | AGTCTCAGAGAGTTAGAGAATTGCAGGAGGTATGTAACGGCCTGGAAGG (SEQ ID NO: 423) |
| CENPA | NM_001042426.1 | CACTTTGAGCAGTTGCCTGGAAGGCTGGGCATTTCCATCATATAGACCTCTGCCCTTCAGAGTAGCCTCACCATTAGTGGCAGCATCATGTAACTGAGTG (SEQ ID NO: 424) | GAGGTCTATATGATGGAAATGCCCAGCCTTCCAGGCAACTGCTCAAAGTG (SEQ ID NO: 425) | CACTCAGTTACATGATGCTGCCACTAATGGTGAGGCTACTCTGAAGGGCA (SEQ ID NO: 426) |
| CENPE | NM_001813.2 | GCACCAATCATCGATTCTGCCATACAAGGCTACAATGGTACTATATTTGCCTATGGACAGACTGCTTCAGGAAAAACATATACCATGATGGGTTCAGAAG (SEQ ID NO: 427) | GCAAATATAGTACCATTGTAGCCTTGTATGGCAGAATCGATGATTGGTGC (SEQ ID NO: 428) | CTTCTGAACCCATCATGGTATATGTTTTTCCTGAAGCAGTCTGTCCATAG (SEQ ID NO: 429) |
| CENPF | NM_016343.3 | AGATAATGTGGCCAAGGTGAATGACAGCTGGAAGGAGAGATTTCTTGATGTGGAAAATGAGCTGAGTAGGATCAGATCGGAGAAAGCTAGCATTGAGCAT (SEQ ID NO: 430) | CATCAAGAAATCTCTCCTTCCAGCTGTCATTCACCTTGGCCACATTATCT (SEQ ID NO: 431) | ATGCTCAATGCTAGCTTTCTCCGATCTGATCCTACTCAGCTCATTTTCCA (SEQ ID NO: 432) |
| CENPN | NM_018455.3 | CTCCCAGACTCCGTACGCCTTCACGTCCTCCTCCATGCTGAGGCGCAATACACCGCTTCTGGGTCAGGAGTTAGAAGCTACTGGGAAAATCTACCTCCGA (SEQ ID NO: 433) | TATTGCGCCTCAGCATGGAGGAGGACGTGAAGGCGTACGGAG (SEQ ID NO: 434) | TCGGAGGTAGATTTTCCCAGTAGCTTCTAACTCCTGACCCAGAAGCGGTG (SEQ ID NO: 435) |
| CENPV | NM_181716.2 | TTCATTGTTCCAGCTTCTCGCTTCAAGCTCCTGAAGGGAGCTGAGCACATAACGACTTACACGTTCAATACTCACAAAGCCCAGCATACCTTCTGTAAGA (SEQ ID NO: 436) | ATGTGCTCAGCTCCCTTCAGGAGCTTGAAGCGAGAAGCTGGAACAATGAA (SEQ ID NO: 437) | TCTTACAGAAGGTATGCTGGGCTTTGTGAGTATTGAACGTGTAAGTCGTT (SEQ ID NO: 438) |

TABLE 1-continued

| Gene | GenBank Accession No. | Target Sequence | Capture Probe Sequence | Reporter Probe Sequence |
|---|---|---|---|---|
| CEP55 | NM_018131.4 | CTGCCCGCTCTGAT AACAGTCCTTTTCC CTGGCGCTCACTTC GTGCCTGGCACCCG GCTGGGCGCCTCAA GACCGTTGTCTCTT CGATCGCTTCTTTG GA (SEQ ID NO: 439) | CCAGGCACGAAG TGAGCGCCAGGG AAAAGGACTGTT ATCAGAGCGGG (SEQ ID NO: 440) | TCCAAAGAAGCG ATCGAAGAGAC AACGGTCTTGAG GCGCCCAGCCGG GTG (SEQ ID NO: 441) |
| CFLAR | NM_003879.3 | CAAGACCCTTGTGA GCTTCCCTAGTCTA AGAGTAGGATGTCT GCTGAAGTCATCCA TCAGGTTGAAGAA GCACTTGATACAGA TGAGAAGGAGATG CTGC (SEQ ID NO: 442) | ACTTCAGCAGAC ATCCTACTCTTAG ACTAGGGAAGCT CACAAGGGTCTT G (SEQ ID NO: 443) | GCAGCATCTCCT TCTCATCTGTAT CAAGTGCTTCTT CAACCTGATGGA TG (SEQ ID NO: 444) |
| CGNL1 | NM_032866.3 | TGAACCATGGAGCT GTATTTCGGTGAAT ATCAACATGTGCAG CAGGAATATGGGG TCCATCTGAGACTC GCAAGTGATGATAC CCAAAAATCAAGG AGTT (SEQ ID NO: 445) | TATTCCTGCTGCA CATGTTGATATTC ACCGAAATACAG CTCCATGGTTCA (SEQ ID NO: 446) | CTTGATTTTTGG GTATCATCACTT GCGAGTCTCAGA TGGACCCCA (SEQ ID NO: 447) |
| CHD4 | NM_001273.2 | AGAGGCATCTGTGA AATTCCATGTGCTG CTGCATCCTATGA ATTGATCACCATTG ACATGGCTATTTTG GGCTCTATTGATTG GGCCTGCCTCATCG TG (SEQ ID NO: 448) | TGATCAATTCATA GGATGTCAGCAG CACATGGAATTTC ACAGATGCCTCT (SEQ ID NO: 449) | CACGATGAGGCA GGCCCAATCAAT AGAGCCCAAAAT AGCCATGTCAAT GG (SEQ ID NO: 450) |
| CHST5 | NM_012126.1 | TAGGAGGCTGAGG TGGGAGAATCACTT GGACTCCAAAGGT GGAGGTTGCAGTA AGCTGAAATCATGC CACTGCACCCTAGC TTGGGTGGCAAAGC AAAAC (SEQ ID NO: 451) | TGCAACCTCCACC TTTGGAGTCCAA GTGATTCTCCCAC (SEQ ID NO: 452) | CACCCAAGCTAG GGTGCAGTGGCA TGATTTCAGCTT AC (SEQ ID NO: 453) |
| CIITA | NM_000246.3 | GCCTGAGCAAGGA CATTTTCAAGCACA TAGGACCAGATGA AGTGATCGGTGAG AGTATGGAGATGCC AGCAGAAGTTGGG CAGAAAAGTCAGA AAGACC (SEQ ID NO: 454) | ACCGATCACTTCA TCTGGTCCTATGT GCTTGAAAATGT CCTTGCTCAGGC (SEQ ID NO: 455) | GGTCTTTTCTGA CTTTTCTGCCCA ACTTCTGCTGGC ATCTCCATACTC TC (SEQ ID NO: 456) |
| CKS2 | NM_001827.1 | AAACTCATCTGATG TCTGAAGAGGAGT GGAGGAGACTTGG TGTCCAACAGAGTC TAGGCTGGGTTCAT TACATGATTCATGA GCCAGAACCACAT ATTCT (SEQ ID NO: 457) | CTGTTGGACACC AAGTCTCCTCCAC TCCTCTTCAGACA TCAGATGAGTTT (SEQ ID NO: 458) | AGAATATGTGGT TCTGGCTCATGA ATCATGTAATGA ACCCAGCCTAGA CT (SEQ ID NO: 459) |
| CLIP2 | NM_003388.4 | GTCCCTGTTGGCTT TCGGTAGCTCTCGC ATGCAGTTCTATTA ACAGCCGTCTAGAA GCGATGCTTTAGTG GCCTAACCCAGGGT CAAATACAGCTCTT TC (SEQ ID NO: 460) | ACGGCTGTTAAT AGAACTGCATGC GAGAGCTACCGA AAGCCAACAGGG AC (SEQ ID NO: 461) | GAAAGAGCTGTA TTTGACCCTGGG TTAGGCCACTAA AGCATCGCTTCT AG (SEQ ID NO: 462) |

TABLE 1-continued

| Gene | GenBank Accession No. | Target Sequence | Capture Probe Sequence | Reporter Probe Sequence |
|---|---|---|---|---|
| CLMN | NM_024734.3 | TACTCAAAACTCAG GCATGCAGCTGGAT CCGTAGGTGGGGTT TTGTCCTTGTGTGC CTTGCTGGGTTGGA TAGGGAGCATTGTT AGTGATCATTAGCC CG (SEQ ID NO: 463) | AAGGACAAAACC CCACCTACGGAT CCAGCTGCATGC CTGAGTTTTGAGT A (SEQ ID NO: 464) | CGGGCTAATGAT CACTAACAATGC TCCCTATCCAAC CCAGCAAGGCAC AC (SEQ ID NO: 465) |
| CPA6 | NM_001127445.1 | GCAGACGATCACG ACTCAAAAGAGCT GTTTGGATAGACTG TGGTATTCATGCAA GAGAATGGATTGGT CCTGCCTTTTGTCA GTGGTTTGTAAAAG AAGC (SEQ ID NO: 466) | ATGAATACCACA GTCTATCCAAAC AGCTCTTTTGAGT CGTGATCGTCTGC (SEQ ID NO: 467) | GCTTCTTTTACA AACCACTGACAA AAGGCAGGACC AATCCATTCTCT TGC (SEQ ID NO: 468) |
| CPNE3 | NM_003909.2 | GACTGCTCTCTGGT CTGTGGGACTGGTC ATTCAAGATTATGA TGCTGATAAGATGT TTCCAGCTTTTGGT TTTGGCGCTCAGAT ACCTCCTCAGTGGC AG (SEQ ID NO: 469) | TATCAGCATCATA ATCTTGAATGACC AGTCCCACAGAC CAGAGAGCAGTC (SEQ ID NO: 470) | CTGCCACTGAGG AGGTATCTGAGC GCCAAAACCAA AAGCTGGAAAC ATCT (SEQ ID NO: 471) |
| CR2 | NM_001006658.1 | GGTGTCAAGCAAAT AATATGTGGGGGCC GACACGACTACCA ACCTGTGTAAGTGT TTTCCCTCTCGAGT GTCCAGCACTTCCT ATGATCCACAATGG ACA (SEQ ID NO: 472) | TACACAGGTTGG TAGTCGTGTCGGC CCCCACATATTAT TGCTTGACACC (SEQ ID NO: 473) | TGTCCATTGTGG ATCATAGGAAGT GCTGGACACTCG AGAGGGAAAAC ACT (SEQ ID NO: 474) |
| CREB3L2 | NM_194071.2 | ATGCCTGAGGGAT CAGGCTTTTCTACT CCAGGCAAACCTGC CCCATCTTGTCGCT TTTAGGACCTCCCA CAACCTGGTTCCCC ACACATCCATAGTT CT (SEQ ID NO: 475) | AAGATGGGGCAG GTTTGCCTGGAGT AGAAAAGCCTGA TCCCCT (SEQ ID NO: 476) | AGAACTATGGAT GTGTGGGGAACC AGGTTGTGGGAG GTCCTAAAAGCG AC (SEQ ID NO: 477) |
| CREBBP | NM_004380.2 | CACATTCGAGGCTC ACAGGTGATTGTCG CTCACACAGTTAGG GTCGTCAGTTGGTC TGAAACTGCATTTG GCCCACTCCTCCAT CCTCCCTGTCCGTC GT (SEQ ID NO: 478) | CTGACGACCCTA ACTGTGTGAGCG ACAATCACCTGT GAGCCTCGAATG TG (SEQ ID NO: 479) | ACGACGGACAG GGAGGATGGAG GAGTGGGCCAA ATGCAGTTTCAG ACCAA (SEQ ID NO: 480) |
| CSF2RA | NM_006140.3 | AGAAGGAGGGAGA TCCGGTGTCCTTAT TACATACAAGACTC AGGAACCCATGTG GGATGTCACCTGGA TAACCTGTCAGGAT TAACGTCTCGCAAT TACT (SEQ ID NO: 481) | TGGGTTCCTGAGT CTTGTATGTAATA AGGACACCGGAT CTCCCTCCTT (SEQ ID NO: 482) | AGTAATTGCGAG ACGTTAATCCTG ACAGGTTATCCA GGTGACATCCCA CA (SEQ ID NO: 483) |
| CSTA | NM_005213.3 | CTTCCCGGACAAAA TGAGGACTTGGTAC TTACTGGATACCAG GTTGACAAAAACA AGGATGACGAGCT GACGGGCTTTTAGC AGCATGTACCCAAA GTGT (SEQ ID NO: 484) | TTGTCAACCTGGT ATCCAGTAAGTA CCAAGTCCTTCATT TTGTCCGGGAAG (SEQ ID NO: 485) | ACACTTTGGGTA CATGCTGCTAAA AGCCCGTCAGCT CGTCATCCTTGT TT (SEQ ID NO: 486) |

TABLE 1-continued

| Gene | GenBank Accession No. | Target Sequence | Capture Probe Sequence | Reporter Probe Sequence |
|---|---|---|---|---|
| CTGF | NM_001901.2 | ACCACCCTGCCGGTGGAGTTCAAGTGCCCTGACGGCGAGGTCATGAAGAAGAACATGATGTTCATCAAGACCTGTGCCTGCCATTACAACTGTCCCGGAG (SEQ ID NO: 487) | TTCTTCATGACCTCGCCGTCAGGGCACTTGAACTCCACCGG (SEQ ID NO: 488) | CTCCGGGACAGTTGTAATGGCAGGCACAGGTCTTGATGAACATCATGTTC (SEQ ID NO: 489) |
| CTH | NM_001902.4 | CTCGCCGTCGGCTCTACCTGCGTGCTTTAGCTCCTTCTCGCCTGATCCTTCTGTCTCTCCCAACCCCGGACACCCGGCTTCGACTGGTTATATCTTCGGT (SEQ ID NO: 490) | AAGGATCAGGCGAGAAGGAGCTAAAGCACGCAGGTAGAGCCGACGGCGAG (SEQ ID NO: 491) | ACCGAAGATATAACCAGTCGAAGCCGGGTGTCCGGGGTTGGGAGAGACAG (SEQ ID NO: 492) |
| CTHRC1 | NM_138455.2 | CTGTGGAAGGACTTTGTGAAGGAATTGGTGCTGGATTAGTGGATGTTGCTATCTGGGTTGGCACTTGTTCAGATTACCCAAAAGGAGATGCTTCTACTGG (SEQ ID NO: 493) | AGCAACATCCACTAATCCAGCACCAATTCCTTCACAAAGTCCTTCCACAG (SEQ ID NO: 494) | CCAGTAGAAGCATCTCCTTTTGGGTAATCTGAACAAGTGCCAACCCAGAT (SEQ ID NO: 495) |
| CTLA4 | NM_005214.3 | AGTCTGTGCGGCAACCTACATGATGGGGAATGAGTTGACCTTCCTAGATGATTCCATCTGCACGGGCACCTCCAGTGGAAATCAAGTGAACCTCACTATC (SEQ ID NO: 496) | CATCTAGGAAGGTCAACTCATTCCCCATCATGTAGGTTGCCGC (SEQ ID NO: 497) | GATAGTGAGGTTCACTTGATTTCCACTGGAGGTGCCCGTGCAGATGGAAT (SEQ ID NO: 498) |
| CTNNA2 | NM_004389.2 | GAACCATGATTTTGCTAGAAATAGAAGGCCCAGTGGTGGAATATTAGAGGGAAGGAAACTGACAACGTGTGAAAGTTAGAGGCAAATACATAGGTGTAGC (SEQ ID NO: 499) | CCTCTAATATTCCACCACTGGGCCTTCTATTTCTAGCAAAATCATGGTTC (SEQ ID NO: 500) | CTACACCTATGTATTTGCCTCTAACTTTCACACGTTGTCAGTTTCCTTC (SEQ ID NO: 501) |
| CTPS | NM_001905.2 | CACCTTGTTTCTCAACTACCTCGCATCATTGCAGATGCTAGCGCGTTGCCTGTCGCTTTTCCCTTGGATACCTAGACCGTTATAAAGTGTGCCACATGGAC (SEQ ID NO: 502) | GGCAACGCGCTAGCATCTGCAATGATGCGAGGTAGTTGAGAAACAAGGTG (SEQ ID NO: 503) | GTCCATGTGGCACACTTTATAACGGTCTAGGTATCCAAGGGAAAGCGACA (SEQ ID NO: 504) |
| CTSH | NM_148979.2 | ACCCTGTGAGCTTTGCCTTTGAGGTGACTCAGGACTTCATGATGTATAGAACGGGCATCTACTCCAGTACTTCCTGCCATAAAACTCCAGATAAAGTAAA (SEQ ID NO: 505) | TCTATACATCATGAAGTCCTGAGTCACCTCAAAGGCAAAGCTCACAGGGT (SEQ ID NO: 506) | TTTACTTTATCTGGAGTTTTATGGCAGGAAGTACTGGAGTAGATGCCCGT (SEQ ID NO: 507) |
| CTSK | NM_000396.2 | TCTCATTCCCGCAGTAATGACACCCTTTATATCCCAGAATGGGAAGGTAGAGCCCCAGACTCTGTCGACTATCGAAAGAAAGGATATGTTACTCCTGTCA (SEQ ID NO: 508) | CTACCTTCCCATTCTGGGATATAAAGGGTGTCATTACTGCGGGAATGAGA (SEQ ID NO: 509) | TGACAGGAGTAACATATCCTTTCTTTCGATAGTCGACAGAGTCTGGGGCT (SEQ ID NO: 510) |

TABLE 1-continued

| Gene | GenBank Accession No. | Target Sequence | Capture Probe Sequence | Reporter Probe Sequence |
|---|---|---|---|---|
| CXCL10 | NM_001565.1 | GCAGAGGAACCTCCAGTCTCAGCACCATGAATCAAACTGCGATTCTGATTTGCTGCCTTATCTTTCTGACTCTAAGTGGCATTCAAGGAGTACCTCTCTC (SEQ ID NO: 511) | AATCAGAATCGCAGTTTGATTCATGGTGCTGAGACTGGAGGTTCCTCTGC (SEQ ID NO: 512) | GAGAGAGGTACTCCTTGAATGCCACTTAGAGTCAGAAAGATAAGGCAGCA (SEQ ID NO: 513) |
| CXCL12 | NM_199168.2 | GGGCCTGAGGTTTGCCAGCATTTAGACCCTGCATTTATAGCATACGGTATGATATTGCAGCTTATATTCATCCATGCCCTGTACCTGTGCACGTTGGAAC (SEQ ID NO: 514) | ATACCGTATGCTATAAATGCAGGGTCTAAATGCTGGCAAACCTCAGGCCC (SEQ ID NO: 515) | GTTCCAACGTGCACAGGTACAGGGCATGGATGAATATAAGCTGCAATATC (SEQ ID NO: 516) |
| CXCL9 | NM_002416.1 | CACCATCTCCCATGAAGAAAGGGAACGGTGAAGTACTAAGCGCTAGAGGAAGCAGCCAAGTCGGTTAGTGGAAGCATGATTGGTGCCCAGTTAGCCTCTG (SEQ ID NO: 517) | TCCTCTAGCGCTTAGTACTTCACCGTTCCCTTTCTTCATGGGAGATGGTG (SEQ ID NO: 518) | GCTAACTGGGCACCAATCATGCTTCCACTAACCGACTTGGCTGCT (SEQ ID NO: 519) |
| CYB5R2 | NM_016229.3 | CCATGTCTTAGGGCTTCCTGTAGGTAACTATGTCCAGCTCTTGGCAAAAATCGATAATGAATTGGTGGTCAGGGCTTACACCCCTGTCTCCAGTGATGAT (SEQ ID NO: 520) | TTTTTGCCAAGAGCTGGACATAGTTACCTACAGGAAGCCCTAAGACATGG (SEQ ID NO: 521) | ATCATCACTGGAGACAGGGGTGTAAGCCCTGACCACCAATTCATTATCGA (SEQ ID NO: 522) |
| CYP27A1 | NM_000784.3 | TTTGCTACATCCTGTTCGAGAAACGCATTGGCTGCCTGCAGCGATCCATCCCCGAGGACACCGTGACCTTCGTCAGATCCATCGGGTTAATGTTCCAGAA (SEQ ID NO: 523) | GATGGATCGCTGCAGGCAGCCAATGCGTTTCTCGAACAGGATGTAGCAA (SEQ ID NO: 524) | TTCTGGAACATTAACCCGATGGATCTGACGAAGGTCACGGTGTCCTCGGG (SEQ ID NO: 525) |
| CYP2J2 | NM_000775.2 | GAAAAATGGATTGATTATGTCAAGTGGCCAGGCATGGAAGGAGCAAAGAAGGTTCACTCTGACAGCACTAAGGAACTTTGGTTTAGGAAAGAAGAGCTTA (SEQ ID NO: 526) | TTCTTTGCTCCTTCCATGCCTGGCCACTTGACATAATCAATCCAT (SEQ ID NO: 527) | TAAGCTCTTCTTTCCTAAACCAAAGTTCCTTAGTGCTGTCAGAGTGAACC (SEQ ID NO: 528) |
| CYSLTR1 | NM_006639.2 | AAAGAAGCTTGCCTATAGAGCAGGCACTCTGTGAATGGACTGTGCTTTTACGACCCTACAGGGTATCAAGATACTGTGCAGCTCGCCAACAAGGATTAAT (SEQ ID NO: 529) | TAAAAGCACAGTCCATTCACAGAGTGCCTGCTCTATAGGCAAGCTTCTTT (SEQ ID NO: 530) | ATTAATCCTTGTTGGCGAGCTGCACAGTATCTTGATACCCTGTAGGGTCG (SEQ ID NO: 531) |
| DAZAP2 | NM_014764.3 | ATGCCATTACTTCTGCTTTCGTATCTCCTCAGGCAAAAGTGGAGGGTGCCTTATGGGCCCTCCTCATAGGTTGTCTCTGCATACACGAACCTAACCCAAA (SEQ ID NO: 532) | GGCACCCTCCACTTTTGCCTGAGGAGATACGAAAGCAGAAGTAATGGCAT (SEQ ID NO: 533) | TTTGGGTTAGGTTCGTGTATGCAGAGACAACCTATGAGGGAGGGCCCATAA (SEQ ID NO: 534) |

TABLE 1-continued

| Gene | GenBank Accession No. | Target Sequence | Capture Probe Sequence | Reporter Probe Sequence |
|---|---|---|---|---|
| DCBLD1 | NM_173674.1 | CTCTTGTTGAACAC AAGTGAAGTAACC GTCCGCTTTGAGAG TGGATCCCACATTT CTGGCCGGGGTTTT TTGCTGACCTATGC GAGCAGCGACCAT CCAG (SEQ ID NO: 535) | TGGGATCCACTCT CAAAGCGGACGG TTACTTCACTTGT GTTCAACAAGAG (SEQ ID NO: 536) | CTGGATGGTCGC TGCTCGCATAGG TCAGCAAAAAAC CCCGGCCAGAAA TG (SEQ ID NO: 537) |
| DCLK3 | NM_033403.1 | GAAAAAGCCATGT ATGTCTGGAGGCAG AAGGATGACTCTCA GAGATGACCAACCT GCAAAGCTAGAAA AGGAGCCCAAGAC GAGGCCAGAAGAG AACAAG (SEQ ID NO: 538) | GGTCATCTCTGAG AGTCATCCTTCTG CCTCCAGACATA CATGGCTTTTTC (SEQ ID NO: 539) | CTTGTTCTCTTCT GGCCTCGTCTTG GGCTCCTTTTCT AGCTTTGCAGGT T (SEQ ID NO: 540) |
| DCTD | NM_001012732.1 | GATCCGGCAGCCTC TCTTCACTGCTACA TGTGCTGGAAGGAC AAATAAATAATTGT GGTTGTGTTCTTAA TGGGGACGAGCAG ACACACTGATCTGA ACA (SEQ ID NO: 541) | ATTTATTTGTCCT TCCAGCACATGT AGCAGTGAAGAG AGGCTGCCGGAT C (SEQ ID NO: 542) | TGTTCAGATCAG TGTGTCTGTCG TCCCCATTAAGA ACACAACCACAA TT (SEQ ID NO: 543) |
| DDAH2 | NM_013974.1 | CGACAGGAGTGGG GGTGGCCGCTGGA GACAGGTGAAGAA ACAAGAAAACTAA GAAATCCGAGCGG TTGGAGGGGGAGT CTGTGTGGATGGGA TGGGGACG (SEQ ID NO: 544) | AGTTTTCTTGTTT CTTCACCTGTCTC CAGCGGCCACCC C (SEQ ID NO: 545) | CATCCACACAGA CTCCCCCTCCAA CCGCTCGGATTT CTT (SEQ ID NO: 546) |
| DENND4A | NM_005848.3 | TGATTTTCCCTTTCC ACTGGCCATGCCCG TATGTTCCTCTCTG CCCACTGGCTTTAG CAGATGTCTTGAGT GCACCATGTCCATT CATAGTAGGGATTG A (SEQ ID NO: 547) | CAGTGGGCAGAG AGGAACATACGG GCATGGCCAGTG GAAAGGGAAAAT CA (SEQ ID NO: 548) | TCAATCCCTACT ATGAATGGACAT GGTGCACTCAAG ACATCTGCTAAA GC (SEQ ID NO: 549) |
| DLC1 | NM_182643.1 | TGACCCACTGGATG GGACAGCCTTTAA TTCTGATGATCGTA ACACAGCATGTCAT CATGGACTAGTAGC TGACAGCTTGCAGG CAAGTATGGAAAA AGA (SEQ ID NO: 550) | TGCTGTGTTACGA TCATCAGAATTA AAAGGCTGTCCC ATCCAGTGGGTC A (SEQ ID NO: 551) | TCTTTTTCCATAC TTGCCTGCAAGC TGTCAGCTACTA GTCCATGATGAC A (SEQ ID NO: 552) |
| DLEU1 | XR_001515.1 | CATCGTGGTGCACG GCTCTCCCTTTGCT TCTTCGTTGCAGT CCTCTTGCTTCTTG CGCGTGCGTGTAGC GCTTTTGCAAAGCC GCGGAGGTGAAGT GAA (SEQ ID NO: 553) | GCAAGAGGACTG CAACCGAAGAAG CAAAGGGAGAGC CGTGCACCACGA TG (SEQ ID NO: 554) | TTCACTTCACCT CCGCGGCTTTGC AAAAGCGCTACA CGCACGCGCAAG AA (SEQ ID NO: 555) |
| DLGAP5 | NM_014750.3 | CCTGCTTCGGAGTC GGCGGTGGTCGTCC AGACCGAGTGTTCT TTACTTTTTGTTTGG TTGAGGTTTCACGC TAGAAGGTGGCTCA GGATGTCTTCATCA C (SEQ ID NO: 556) | AAAAGTAAAGAA CACTCGGTCTGG ACGACCACCGCC GACTCCGAAGCA GG (SEQ ID NO: 557) | GTGATGAAGACA TCCTGAGCCACC TTCTAGCGTGAA ACCTCAACCAAA CA (SEQ ID NO: 558) |

TABLE 1-continued

| Gene | GenBank Accession No. | Target Sequence | Capture Probe Sequence | Reporter Probe Sequence |
|---|---|---|---|---|
| DNAJA1 | NM_001539.2 | CATCATCCCAGAGGTGGTGTTCAGTGTCAGACCTCTTAATGGGCCAGTGAATAACACTCACTGCTGGCATTTAATGTGCAGTAGTGAATGAGTGAAGGAC (SEQ ID NO: 559) | TCACTGGCCCATTAAGAGGTCTGACACTGAACACCACCTCTGGGATGATG (SEQ ID NO: 560) | GTCCTTCACTCATTCACTACTGCACATTAAATGCCAGCAGTGAGTGTTAT (SEQ ID NO: 561) |
| DNAJB12 | NM_017626.4 | TTTCTTCCATGTTTTAGAAAATGAGGCCTGTTTGGGGAAGGTACCCTGGTGATGTTTTTGCTAGACATTAGCTGTAGCTGACAGCATAAGGAGAGTCGCA (SEQ ID NO: 562) | ACCAGGGTACCTTCCCCAAACAGGCCTCATTTTCTAAAACATGAAGAAA (SEQ ID NO: 563) | TGCGACTCTCCTTATGCTGTCAGCTACAGCTAATGTCTAGCAAAAACATC (SEQ ID NO: 564) |
| DNAJB9 | NM_012328.1 | GCCCGGATGCTGAAGCAAAATTCAGAGAGATTGCAGAAGCATATGAAACACTCTCAGATGCTAATAGACGAAAAGAGTATGATACACTTGGACACAGTGC (SEQ ID NO: 565) | TGTTTCATATGCTTCTGCAATCTCTGAATTTTGCTTCAGCATCCGGGC (SEQ ID NO: 566) | GCACTGTGTCCAAGTGTATCATACTCTTTTCGTCTATTAGCATCTGAGAG (SEQ ID NO: 567) |
| DNAJC10 | NM_018981.1 | AGGAGATTGTTTGACTTCACAGACACGACTCAGGCTTAGTGGCATGTTGGATGGTCTTGTTAATGTAGGATGGATGGACTGTGCCACCCAGGATAACCTT (SEQ ID NO: 568) | CCAACATGCCACTAAGCCTGAGTCGTGTCTGTGAAGTCAAACAATCTCCT (SEQ ID NO: 569) | AAGGTTATCCTGGGTGGCACAGTCCATCCATCCTACATTAACAAGACCAT (SEQ ID NO: 570) |
| DNMT3A | NM_175630.1 | TGGCAACAGCGGGCTTTCATAACGCCAACGATTGCTAGACTGGGATAATGGCGGTCCCTCCATCGCCTTCTGTGGCTGGTTGTGGGCCTTAGTTTTCTGC (SEQ ID NO: 571) | CATTATCCCAGTCTAGCAATCGTTGGCGTTATGAAAGCCCGCTGTTG (SEQ ID NO: 572) | GCAGAAAACTAAGGCCCACAACCAGCCACAGAAGGCGATGGAGGGACCGC (SEQ ID NO: 573) |
| DOCK10 | NM_014689.1 | CTGAGCTTAATCAGCTTTGCACAATGGAAGAAGTGGACATGATCAGACTGCAGCTCAAACTGCGAGGAAGTGTCAGCGTGAAGGTTAATGCTGGGCCAAT (SEQ ID NO: 574) | CAGTCTGATCATGTCCACTTCTTCCATTGTGCAAAGCTGATTAAGCTCAG (SEQ ID NO: 575) | ATTGGCCCAGCATTAACCTTCACGCTGACACTTCCTCGCAGTTTGAGCTG (SEQ ID NO: 576) |
| DPY19L1 | NM_015283.1 | TTGTGGATTGTCCTTCAGACCTTAGTCCTCAGGCATGGTTTCTGGTGCCCACTCCTGGAAGCCGCTGTTCCCTTTCTACCTTCTTACCAGAGCCCAAGGG (SEQ ID NO: 577) | GGGCACCAGAAACCATGCCTGAGGACTAAGGTCTGAAGGACAATCCACAA (SEQ ID NO: 578) | CTTGGGCTCTGGTAAGAAGGTAGAAAGGGAACAGCGGCTTCCAGGAGT (SEQ ID NO: 579) |
| DPYSL3 | NM_001387.2 | CCCTGGGCAGCCAGCATTCATTGTAAGTTCCCTCTTTGAAAACTGGTGTGTGGGTGTTCAGTTCTGTGTCTGGTGGGTATGGACAGACAGTAATCTCCTG (SEQ ID NO: 580) | CACACCAGTTTTCAAAGAGGGAACTTACAATGAATGCTGGCTGCCCAGG (SEQ ID NO: 581) | CAGGAGATTACTGTCTGTCCATACCCACCAGACACAGAACTGAACACCCA (SEQ ID NO: 582) |

TABLE 1-continued

| Gene | GenBank Accession No. | Target Sequence | Capture Probe Sequence | Reporter Probe Sequence |
|---|---|---|---|---|
| DRAM1 | NM_018370.2 | GTCTTTAGTGCTTG GATTGGTGGGATGT TTCGGAATGGGCAT TGTCGCCAATTTTC AGGAGTTAGCTGTG CCAGTGGTTCATGA CGGGGGCGCTCTTT TG (SEQ ID NO: 583) | TGGCGACAATGC CCATTCCGAAAC ATCCCACCAATCC AAGCACTAAAGA C (SEQ ID NO: 584) | CAAAAGAGCGC CCCCGTCATGAA CCACTGGCACAG CTAACTCCTGAA AAT (SEQ ID NO: 585) |
| DTX1 | NM_004416.2 | TCTTCATCTCTCTG GACTCTGATCTCCT TCTCCCTTCCCATC TCCAGGCCTTCTGT CTGTCCCAGATAAA GGCGCTGTTCTCCC ATCCTCCCTACCCC AT (SEQ ID NO: 586) | GGCCTGGAGATG GGAAGGGAGAAG GAGATCAGAGTC CAGAGAGATGAA GA (SEQ ID NO: 587) | GGTAGGGAGGA TGGGAGAACAG CGCCTTTATCTG GGACAGACAGA A (SEQ ID NO: 588) |
| E2F2 | NM_004091.2 | TCAGGGACCCTGTG TAGGATCTCGTTTG TGGTGAGTGGGCTG CTCTGAGGTCTCCA CTGGGCTGCCATTT AGCCATGTGCCATC TCTGAAGTCAGAGG TG (SEQ ID NO: 589) | CCTCAGAGCAGC CCACTCACCACA AACGAGATCCTA CACAG (SEQ ID NO: 590) | TGACTTCAGAGA TGGCACATGGCT AAATGGCAGCCC AGTGGAGA (SEQ ID NO: 591) |
| E2F8 | NM_024680.2 | CTCGTGCGCTTAGT CCGGAGCCCTGATC TGCGAACAGGATAT TAAAACTTTTAGTA CAATTGATTGGACT ACTTGAACCATCGG GATTTGGGGAGGA ACT (SEQ ID NO: 592) | AAGTTTTAATATC CTGTTCGCAGATC AGGGCTCCGGAC TAAGCGCACGAG (SEQ ID NO: 593) | AGTTCCTCCCCA AATCCCGATGGT TCAAGTAGTCCA ATCAATTGTACT AA (SEQ ID NO: 594) |
| EEPD1 | NM_030636.2 | TGCTTTTTGCAACC AAAGCTGTGGACA GAAAAGCCTCCTTA AGTGAGCTGAGGG GACAGGAAATCCA ATCAGATGACCTTT GTGTTCGTAATCGG GCTTG (SEQ ID NO: 595) | CAGCTCACTTAA GGAGGCTTTTCTG TCCACAGCTTTGG TTGCAAAAAGCA (SEQ ID NO: 596) | CAAGCCCGATTA CGAACACAAAG GTCATCTGATTG GATTTCCTGTCC CCT (SEQ ID NO: 597) |
| EFEMP2 | NM_016938.3 | GTCTACCCCGGTGC CTACAATGCCTTTC AGATCCGTGCTGGA AACTCGCAGGGGG ACTTTTACATTAGG CAAATCAACAACGT CAGCGCCATGCTGG TCC (SEQ ID NO: 598) | TGCGAGTTTCCAG CACGGATCTGAA AGGCATTGTAGG CACCGGGGTAGA C (SEQ ID NO: 599) | GGACCAGCATGG CGCTGACGTTGT TGATTTGCCTAA TGTAAAAGTCCC CC (SEQ ID NO: 600) |
| EGFL7 | NM_016215.3 | GCAGGGCCTTCCTC CTCTTCCTCCTCCC CTTCCTCGGGAGGC TCCCCAGACCCTGG CATGGGATGGGCTG GGATCTTCTCTGTG AATCCACCCCTGGC TA (SEQ ID NO: 601) | TCTGGGGAGCCT CCCGAGGAAGGG GAGGAGGAAGAG GA (SEQ ID NO: 602) | GATTCACAGAGA AGATCCCAGCCC ATCCCATGCCAG GG (SEQ ID NO: 603) |
| EHD2 | NM_014601.2 | GACGACGAGGCCG AGTGGGTGGTGACC AAGGACAAGTCCA AATACGACGAGAT CTTCTACAACCTGG CGCCTGCCGACGGC AAGCTGAGCGGCTC CAAGG (SEQ ID NO: 604) | TCGTCGTATTTGG ACTTGTCCTTGGT CACCACCCACTC GGC (SEQ ID NO: 605) | GCTTGCCGTCGG CAGGCGCCAGGT TGTAGAAGATC (SEQ ID NO: 606) |

TABLE 1-continued

| Gene | GenBank Accession No. | Target Sequence | Capture Probe Sequence | Reporter Probe Sequence |
| --- | --- | --- | --- | --- |
| EIF5AL1 | NM_001099692.1 | AGGGCCAGAAGCTGTTCTTTCCCTTAAAAGGGCAAACTCATTTCCACACTATGGGGACTCTGACAGATAGCATACCTTCCTGTCTATGGCTATTGGACCT (SEQ ID NO: 607) | AGTGTGGAAATGAGTTTGCCCTTTTAAGGGAAAGAACAGCTTCTGGCCCT (SEQ ID NO: 608) | CAATAGCCATAGACAGGAAGGTATGCTATCTGTCAGAGTCCCCAT (SEQ ID NO: 609) |
| ELL2 | NM_012081.5 | AATCCCGCAACCGAAGCACAAAAGTTATCAAACCCGGTGGACCATATGTAGGGAAAAGAGTGCAAATTCGGAAAGCACCTCAAGCTGTTTCAGATACAGT (SEQ ID NO: 610) | TACATATGGTCCACCGGGTTTGATAACTTTTGTGCTTCGGTTGCGGGATT (SEQ ID NO: 611) | ACTGTATCTGAAACAGCTTGAGGTGCTTTCCGAATTTGCACTCTTTTCCC (SEQ ID NO: 612) |
| EML1 | NM_004434.2 | CCGGAGACTACGAAATCCTCTACTGGGTTCCCTCTGCCTGTAAGCAAGTCGTAAGTGTGGAAACTACAAGAGACATTGAATGGGCTACCTATACCTGCAC (SEQ ID NO: 613) | GACTTGCTTACAGGCAGAGGGAACCCAGTAGAGGATTTCGTAGTCTCCGG (SEQ ID NO: 614) | GTGCAGGTATAGGTAGCCCATTCAATGTCTCTTGTAGTTTCCACACTTAC (SEQ ID NO: 615) |
| EMR1 | NM_001974.3 | TTCAAAGACCACCAGGCTCCCTTGACCACCTCTGAGATCAAGCTGAAGATGAATTCTCGAGTCGTTGGGGCATAATGACTGGAGAGAAGAAAGACGGCT (SEQ ID NO: 616) | ATCTTCAGCTTGATCTCAGAGGTGGTCAAGGGAGCCTG (SEQ ID NO: 617) | AGCCGTCTTTCTTCTCTCCAGTCATTATGCCCCCAACGACTCGAGAATTC (SEQ ID NO: 618) |
| ENO1 | NM_001428.2 | TTCTCGCCTCACTTTCCACCAAGTGTCTAGAGTCATGTGAGCCTCGTGTCATCTCCGGGGTGGCCACAGGCTAGATCCCCGGTGGTTTTGTGCTCAAAAT (SEQ ID NO: 619) | GACACGAGGCTCACATGACTCTAGACACTTGGTGGAAAGTGAGGCGAGAA (SEQ ID NO: 620) | ATTTTGAGCACAAAACCACCGGGGATCTAGCCTGTGGCCACCCCGGAGAT (SEQ ID NO: 621) |
| ENPP3 | NM_005021.2 | CTTTTTATGAGCCATCCCATGCAGAGGAGGTGTCAAAGTTTTCTGTTTGTGGCTTTGCTAATCCATTGCCCACAGAGTCTCTTGACTGTTTCTGCCCTCA (SEQ ID NO: 622) | ACAAACAGAAAACTTTGACACCTCCTCTGCATGGGATGGCTCATAAAAAG (SEQ ID NO: 623) | TGAGGGCAGAAACAGTCAAGAGACTCTGTGGGCAATGGATTAGCAAAGCC (SEQ ID NO: 624) |
| ENTPD1 | NM_001776.4 | TTCGAGTAACTTTAGGAAAATGAGCTGCTGGACTCCTCAGTCAATCTGTCCTTTCTAGTCAATGAAAAAGACAGGGTTTGAGGTTCCTTCCGAAACGGGG (SEQ ID NO: 625) | GACAGATTGACTGAGGAGTCCAGCAGCTCATTTTCCTAAAGTTACTCGAA (SEQ ID NO: 626) | CCCCGTTTCGGAAGGAACCTCAAACCCTGTCTTTTCATTGACTAGAAAG (SEQ ID NO: 627) |

TABLE 1-continued

| Gene | GenBank Accession No. | Target Sequence | Capture Probe Sequence | Reporter Probe Sequence |
|---|---|---|---|---|
| EP300 | NM_001429.2 | CCAGCCAGGCCCAACAGAGCAGTCCTGGATTAGGTTTGATAAATAGCATGGTCAAAAGCCCAATGACACAGGCAGGCTTGACTTCTCCCAACATGGGGAT (SEQ ID NO: 628) | CATGCTATTTATCAAACCTAATCCAGGACTGCTCTGTTGGGCCTGGCTGG (SEQ ID NO: 629) | CCCATGTTGGGAGAAGTCAAGCCTGCCTGTGTCATTGGGCTTTTGAC (SEQ ID NO: 630) |
| EPHB1 | NM_004441.3 | GCAGCGGCCGGGGTCGTGTTCGTTGTGTCCTTGGTGGCCATCTCTATCGTCTGTAGCAGGAAACGGGCTTATAGCAAAGAGGCTGTGTACAGCGATAAGC (SEQ ID NO: 631) | ACGATAGAGATGGCCACCAAGGACACAACGAACACGACCCCGGCCGCTG (SEQ ID NO: 632) | GCTTATCGCTGTACACAGCCTCTTTGCTATAAGCCCGTTTCCTGCTACAG (SEQ ID NO: 633) |
| EPSTI1 | NM_001002264.1 | AGAGAAGCATTTAGAGAGCATCAGCAATACAAAACCGCTGAGTTCTTGAGCAAACTGAACACAGAATCGCCAGACAGAAGTGCCTGTCAAAGTGCTGTTT (SEQ ID NO: 634) | CTCAAGAACTCAGCGGTTTTGTATTGCTGATGCTCTCTAAATGCTTCTCT (SEQ ID NO: 635) | AAACAGCACTTTGACAGGCACTTCTGTCTGGCGATTCTGTGTTCAGTTTG (SEQ ID NO: 636) |
| ERBB2IP | NM_018695.2 | CACAGAGACCCCTTTCTGCACGAACATACAGCATAGATGGTCCAAATGCATCAAGACCTCAGAGTGCTCGACCCTCTATTAATGAAATACCAGAGAGAAC (SEQ ID NO: 637) | TGCATTTGGACCATCTATGCTGTATGTTCGTGCAGAAAGGGGTCTCTGTG (SEQ ID NO: 638) | GTTCTCTCTGGTATTTCATTAATAGAGGGTCGAGCACTCTGAGGTCTTGA (SEQ ID NO: 639) |
| ERG | NM_182918.3 | GACCTCATCATTATGTGGGGGCTTTGTTCTCCACAGGGTCAGGTAAGAGATGGCCTTCTTGGCTGCCACAATCAGAAATCACGCAGGCATTTGGGTAGG (SEQ ID NO: 640) | TCTCTTACCTGACCCTGTGGAGAACAAAGCCCCCACATAATGATGAGGTC (SEQ ID NO: 641) | CCTACCCAAAATGCCTGCGTGATTTCTGATTGTGGCAGCCAAGAAGGCCA (SEQ ID NO: 642) |
| ERN2 | NM_033266.2 | ATCGAAGGACCAATGTACGTCACAGAAATGGCCTTTCTCTCTGACCCAGCAGATGGCAGCCTGTACATCTTGGGGACCCAAAAACAACAGGGATTAATGA (SEQ ID NO: 643) | GCTGGGTCAGAGAGAAAGGCCATTTCTGTGACGTACATTGGTCCTTCGAT (SEQ ID NO: 644) | TCATTAATCCCTGTTGTTTTGGGTCCCCAAGATGTACAGGCTGCCATCT (SEQ ID NO: 645) |
| ERP29 | NM_001034025.1 | TAACCTGCTGGCTGTGAGTCCCTTGTGGAATATAAGGGGGTAGTGGGAAAAGTGGTACTAACCCACGATTCTGAGCCCTGAGTATGCCTGGACATTGATG (SEQ ID NO: 646) | TTTCCCACTACCCCCTTATATTCCACAAGGGACTCACAGC (SEQ ID NO: 647) | CAGGCATACTCAGGGCTCAGAATCGTGGGTTAGTACCACT (SEQ ID NO: 648) |

TABLE 1-continued

| Gene | GenBank Accession No. | Target Sequence | Capture Probe Sequence | Reporter Probe Sequence |
|---|---|---|---|---|
| ERP44 | NM_015051.1 | TGAGGAAGTATTACTTAGCATTCATGCATATTGGGCTTAGGCTCTAGCCCTGCCACTATCATTGTCTTCTCTGGACTGTGAAGTCACTGAGGACAAGGAA (SEQ ID NO: 649) | GGGCTAGAGCCTAAGCCCAATATGCATGAATGCTAAGTAATACTTCCTCA (SEQ ID NO: 650) | CTTGTCCTCAGTGACTTCACAGTCCAGAGAAGACAATGATAGTGGCA (SEQ ID NO: 651) |
| ESPL1 | NM_012291.4 | CAGGGACTTCACCTCTACACTGTGGTGGTTTATGACTTTGCCCAAGGCTGTCAGATAGTTGATTTGGCTGACCTGACCCAACTAGTGGACAGTTGTAAAT (SEQ ID NO: 652) | CAGCCTTGGGCAAAGTCATAAACCACCACAGTGTAGAGGTGAAGTCC (SEQ ID NO: 653) | ATTTACAACTGTCCACTAGTTGGGTCAGGTCAGCCAAATCAACTATCTGA (SEQ ID NO: 654) |
| ETV6 | NM_001987.4 | GTATGAATATGAAATCAGAGACCAGGGCATGATGTTGCTAGGATTAGAGCCTCTCAGTCTGGCCTCTTCACCCAAGTGCAAGAACTCAGTCTCTTACTGT (SEQ ID NO: 655) | GCTCTAATCCTAGCAACATCATGCCCTGGTCTCTGATTTCATATTCATAC (SEQ ID NO: 656) | ACAGTAAGAGACTGAGTTCTTGCACTTGGGTGAAGAGGCCAGACTGAGAG (SEQ ID NO: 657) |
| EXO1 | NM_003686.3 | GCCAGAGCCAGTGGGCTGAGCAAGAAGCCGGCAAGCATCCAGAAGAGAAAGCATCATAATGCCGAGAACAAGCCGGGGTTACAGATCAAACTCAATGAGC (SEQ ID NO: 658) | TTTCTCTTCTGGATGCTTGCCGGCTTCTTGCTCAGCCCACTG (SEQ ID NO: 659) | GCTCATTGAGTTTGATCTGTAACCCCGGCTTGTTCTCGGCATTATGATGC (SEQ ID NO: 660) |
| FABP4 | NM_001442.2 | GGTGGAATGCGTCATGAAAGGCGTCACTTCCACGAGAGTTTATGAGAGAGCATAAGCCAAGGGACGTTGACCTGGACTGAAGTTCGCATTGAACTCTACA (SEQ ID NO: 661) | CTCTCTCATAAACTCTCGTGGAAGTGACGCCTTTCATGACGCATTCCACC (SEQ ID NO: 662) | TAGAGTTCAATGCGAACTTCAGTCCAGGTCAACGTCCCTTGGCTTATG (SEQ ID NO: 663) |
| FAM108C1 | NM_021214.1 | TCTGACATTCATGCAGGACTTGCCCTGTTGCCACCAATGTTCTCGGTATTTCACATGCAGCTCTCTTTCTGCCACTGGATACATGGGTTCAATCCATTTG (SEQ ID NO: 664) | AATACCGAGAACATTGGTGGCAACAGGGCAAGTCCTGCATGAATGTCAGA (SEQ ID NO: 665) | CAAATGGATTGAACCCATGTATCCAGTGGCAGAAAGAGAGCTGCATGTGA (SEQ ID NO: 666) |
| FAM159A | NM_001042693.1 | ACAGCTACATGTGGTGGCTCAGCATTGGCGCTCTCATAGGCCTGTCCGTAGCAGCAGTGGTTCTTCTCGCCTTCATTGTTACCGCCTGTGTGCTCTGCTA (SEQ ID NO: 667) | TACGGACAGGCCTATGAGAGCGCCAATGCTGAGCCACCAC (SEQ ID NO: 668) | TAGCAGAGCACACAGGCGGTAACAATGAAGGCGAGAAGAACCACTGCTGC (SEQ ID NO: 669) |
| FAM171B | NM_177454.3 | CTTTTCTCCACACCGGAACAATTACATACTGCTAAGTCAGCTACTTTGCCAAGAAAGGGACAGTTAGTCTATGGCCAATTGATGGAACCAGTAAATCGAG (SEQ ID NO: 670) | GGCAAAGTAGCTGACTTAGCAGTATGTAATTGTTCCGGTGTGGAGAAAAG (SEQ ID NO: 671) | CTCGATTTACTGGTTCCATCAATTGGCCATAGACTAACTGTCCCTTTCTT (SEQ ID NO: 672) |

TABLE 1-continued

| Gene | GenBank Accession No. | Target Sequence | Capture Probe Sequence | Reporter Probe Sequence |
|---|---|---|---|---|
| FAM189A1 | NM_015307.1 | CAGTGAACTCTCTG GTTTTATCTGGCGT GCAGCACCTTGAAC TGAGCAGTGTTGCA CAAATGTGAATACA GCAACAGGCGACA CTTACGTCACCTAA AGA (SEQ ID NO: 673) | ACTGCTCAGTTCA AGGTGCTGCACG CCAGATAAAACC AGAGAGTTCACT G (SEQ ID NO: 674) | TCTTTAGGTGAC GTAAGTGTCGCC TGTTGCTGTATT CACATTTGTGCA AC (SEQ ID NO: 675) |
| FAM46C | NM_017709.3 | TTGGAATGGGTCTA CAGTGTATCATGAG CCAACCCTCAAAGG ACCCGTATTACAGT GCCACGTTGGAAA ACGCTACAGGAAG CATGACCTATCCAC ATCT (SEQ ID NO: 676) | ATACGGGTCCTTT GAGGGTTGGCTC ATGATACACTGT AGACCCATTCCA A (SEQ ID NO: 677) | AGATGTGGATAG GTCATGCTTCCT GTAGCGTTTTCC AACGTGGCACTG TA (SEQ ID NO: 678) |
| FAM69A | NM_001006605.3 | GTGCCAGAGACAA ACCTGAAAGAACTT ATTAAGGATCGTCA CTGTGAGTCTGATT TGGACTGTGTCTAT GGCACAGATTGTAG AACTAGCTGTGATC AGA (SEQ ID NO: 679) | GACTCACAGTGA CGATCCTTAATAA GTTCTTTCAGGTT TGTCTCTGGCAC (SEQ ID NO: 680) | TCTGATCACAGC TAGTTCTACAAT CTGTGCCATAGA CACAGTCCAAAT CA (SEQ ID NO: 681) |
| FAM83D | NM_030919.2 | CACGTTGATTGATG GCATCCGCGTGGCA ACAGGCTCCTACAG TTTTACATGGACGG ATGGCAAATTAAAC AGCAGTAACTTGGT AATTCTGTCTGGCC AA (SEQ ID NO: 682) | ATGTAAAACTGT AGGAGCCTGTTG CCACGCGGATGC CATCAATCAACG TG (SEQ ID NO: 683) | TTGGCCAGACAG AATTACCAAGTT ACTGCTGTTTAA TTTGCCATCCGT CC (SEQ ID NO: 684) |
| FAP | NM_004460.2 | GCATTGGAAGCTAT CCTCCAAGCAAGA AGTGTGTTACTTGC CATCTAAGGAAAG AAAGGTGCCAATAT TACACAGCAAGTTT CAGCGACTACGCCA AGTA (SEQ ID NO: 685) | CCTTAGATGGCA AGTAACACACTT CTTGCTTGGAGG ATAGCTTCCAATG C (SEQ ID NO: 686) | TACTTGGCGTAG TCGCTGAAACTT GCTGTGTAATAT TGGCACCTTTCT TT (SEQ ID NO: 687) |
| FAR2 | NM_018099.3 | TCTTTCAGGAGCTA TAAAAGAAAGGGA GGAATCATGTCCAC AATTGCAGCTTTCT ATGGCGGCAAGTCC ATTCTCATCACGGG GGCCACAGGCTTTC TGG (SEQ ID NO: 688) | GCTGCAATTGTG GACATGATTCCTC CCTTTCTTTTATA GCTCCTGAAAGA (SEQ ID NO: 689) | CAGAAAGCCTGT GGCCCCCGTGAT GAGAATGGACTT GCCGCCATAGAA A (SEQ ID NO: 690) |
| FARP1 | NM_005766.2 | TCATGGTACGTAGT CCCCGGCACCTGTC GTTATTCCTATATC CTCCTGCAACTGTG GTTTGAAACTGCGC ATTCTCTAGTAGTA TATATCGTGCCTGT CT (SEQ ID NO: 691) | TGCAGGAGGATA TAGGAATAACGA CAGGTGCCGGGG ACTACGTACCAT GA (SEQ ID NO: 692) | AGACAGGCACG ATATATACTACT AGAGAATGCGC AGTTTCAAACCA CAGT (SEQ ID NO: 693) |
| FAS | NM_000043.3 | CACCGGGGCTTTTC GTGAGCTCGTCTCT GATCTCGCGCAAGA GTGACACACAGGT GTTCAAAGACGCTT CTGGGGAGTGAGG GAAGCGGTTTACGA GTGA (SEQ ID NO: 694) | TGTGTCACTCTTG CGCGAGATCAGA GACGAGCTCACG AAAAGCCCCGG (SEQ ID NO: 695) | TCACTCGTAAAC CGCTTCCCTCAC TCCCCAGAAGCG TCTTTGAACACC TG (SEQ ID NO: 696) |

TABLE 1-continued

| Gene | GenBank Accession No. | Target Sequence | Capture Probe Sequence | Reporter Probe Sequence |
|---|---|---|---|---|
| FBP2 | NM_003837.2 | AGATGAGGTGAAG AAACTGGATGTGCT ATCCAATTCCCTGG TGATCAACATGGTC CAATCCTCCTATAG TACCTGCGTCCTGG TCTCAGAAGAGAAT AAG (SEQ ID NO: 697) | TGTTGATCACCAG GGAATTGGATAG CACATCCAGTTTC TTCACCT (SEQ ID NO: 698) | TTATTCTCTTCTG AGACCAGGACG CAGGTACTATAG GAGGATTGGACC A (SEQ ID NO: 699) |
| FBXL13 | NM_145032.3 | ACGATGCGACTCCT GCCGAGGCACTTCC ACAACTTACAGAAT CTTAGTTTGGCTTA TTGCAGACGGTTCA CAGACAAAGGCTT ACAGTACCTGAACT TGG (SEQ ID NO: 700) | AAACTAAGATTC TGTAAGTTGTGG AAGTGCCTCGGC AGGAGTCGCATC GT (SEQ ID NO: 701) | CCAAGTTCAGGT ACTGTAAGCCTT TGTCTGTGAACC GTCTGCAATAAG CC (SEQ ID NO: 702) |
| FBXO10 | NM_012166.2 | TCAGCTCCACAGCC CATAGCAAGAAGA AAGTGGGCAATGTT TTTCAGGGAGAAG GGATAGAAGCTGG TGGGTTTCCAGTCA CTCGAAGTCTATAA AGATT (SEQ ID NO: 703) | TCCCTGAAAAAC ATTGCCCACTTTC TTCTTGCTATGGG CTGTGGAG (SEQ ID NO: 704) | AATCTTTATAGA CTTCGAGTGACT GGAAACCCACCA GCTTCTATCCCT TC (SEQ ID NO: 705) |
| FBXO11 | NM_018693.2 | TGCAGATATGGTTG CAGAAGAATCAGG TCCTGGTGCACAAA ATAGTCCATACCAA CTTCGTAGAAAAAC TCTTTTGCCGAAAA GAACAGCGTGTCCC ACA (SEQ ID NO: 706) | ATGGACTATTTTG TGCACCAGGACC TGATTCTTCTGCA ACCATATCTGCA (SEQ ID NO: 707) | TGTGGGACACGC TGTTCTTTTCGG CAAAAGAGTTTT TCTACGAAGTTG GT (SEQ ID NO: 708) |
| FBXO36 | NM_174899.4 | AGCAAAGACTATTA CCAGTTACTGGTCA CCCGGTCTCAGGTA ATCTTTAGATGGTG GAAGATCTCTCTAA GGAGTGAGTATCG ATCAACAAAACCTG GAG (SEQ ID NO: 709) | CTAAAGATTACCT GAGACCGGGTGA CCAGTAACTGGT AATAGTCTTTGCT (SEQ ID NO: 710) | CAGGTTTTGTTG ATCGATACTCAC TCCTTAGAGAGA TCTTCCACCAT (SEQ ID NO: 711) |
| FBXO41 | NM_001080410.1 | TTTGTTCTCTCCTCG GGGATGAGCTCTGC TGCTGAGTAGGGA GCTTTTGCTTGCTG GGAGGCTCTATGCA TGGATTTTTTTGGT GACCATACAGCTAG GG (SEQ ID NO: 712) | GCAAAAGCTCCC TACTCAGCAGCA GAGCTCATCCCC GAGGAGAGAACA AA (SEQ ID NO: 713) | CCCTAGCTGTAT GGTCACCAAAAA AATCCATGCATA GAGCCTCCCAGC AA (SEQ ID NO: 714) |
| FCER2 | NM_002002.4 | AACTTGGAAAGCC ACCACGGTGACCA GATGGCGCAGAAA TCCCAGTCCACGCA GATTTCACAGGAAC TGGAGGAACTTCGA GCTGAACAGCAGA GATTGA (SEQ ID NO: 715) | GTGGACTGGGAT TTCTGCGCCATCT GGTCACCGTG (SEQ ID NO: 716) | AATCTCTGCTGT TCAGCTCGAAGT TCCTCCAGTTCC TGTGAAATCTGC (SEQ ID NO: 717) |

TABLE 1-continued

| Gene | GenBank Accession No. | Target Sequence | Capture Probe Sequence | Reporter Probe Sequence |
| --- | --- | --- | --- | --- |
| FCN2 | NM_015837.2 | ACCAGGACAATGA TCTTAACACCGGAA ATTGTGCTGTGATG TTTCAGGGAGCTTG GTGGTACAAAAACT GCCATGTGTCAAAC CTGAATGGTCGCTA CCT (SEQ ID NO: 718) | TCCCTGAAACATC ACAGCACAATTT CCGGTGTTAAGA TCATTGTCCTGGT (SEQ ID NO: 719) | TAGCGACCATTC AGGTTTGACACA TGGCAGTTTTTG TACCACCAAGC (SEQ ID NO: 720) |
| FEZ1 | NM_005103.3 | TAAACGTGTATAGC TTAACCTGGATTAA ACACGAGCAAGCG CGCGGGGTCCTTTG CCGTTGGCTTCTAG TGCTAGTAATCATT GGATGCATGATGG GGCA (SEQ ID NO: 721) | GACCCCGCGCGC TTGCTCGTGTTTA ATCCAGGTTAAG CTATACACGTTTA (SEQ ID NO: 722) | TGCCCCATCATG CATCCAATGATT ACTAGCACTAGA AGCCAACGGCA AAG (SEQ ID NO: 723) |
| FGL2 | NM_006682.2 | CAATTCAGCAGGAT CGAGGAGGTGTTCA AAGAAGTCCAAAA CCTCAAGGAAATCG TAAATAGTCTAAAG AAATCTTGCCAAGA CTGCAAGCTGCAGG CTG (SEQ ID NO: 724) | TCCTTGAGGTTTT GGACTTCTTTGAA CACCTCCTCGATC CTGCTGAATTG (SEQ ID NO: 725) | CAGCCTGCAGCT TGCAGTCTTGGC AAGATTTCTTTA GACTATTTACGA TT (SEQ ID NO: 726) |
| FKBP11 | NM_016594.2 | AAAGCAGGTGATTC CAGGTCTGGAGCA GAGTCTTCTCGACA TGTGTGTGGGAGAG AAGCGAAGGGCAA TCATTCCTTCTCAC TTGGCCTATGGAAA ACGG (SEQ ID NO: 727) | CCACACACATGT CGAGAAGACTCT GCTCCAGACCTG GAATCACCTG (SEQ ID NO: 728) | TTCCATAGGCCA AGTGAGAAGGA ATGATTGCCCTT CGCTTCTCTC (SEQ ID NO: 729) |
| FKBP2 | NM_057092.2 | CCACGGCCACGGG GGCCGAGGGCAAA AGGAAGCTGCAGA TCGGGGTCAAGAA GCGGGTGGACCACT GTCCCATCAAATCG CGCAAAGGGGATG TCCTGCA (SEQ ID NO: 730) | CTTGACCCCGATC TGCAGCTTCCTTT TGCCCTCGG (SEQ ID NO: 731) | CCCTTTGCGCGA TTTGATGGGACA GTGGTCCACCCG CTT (SEQ ID NO: 732) |
| FLJ42418 | NM_001001695.1 | TCCCATTCTTACTG GCTGAAATTCAAAG CTGATAAATGGAGC TAGAGCAGATAGCT GGGAAAATGAGTT GAGGGTCTTACATT AAGACTTGCCAGCA AGA (SEQ ID NO: 733) | CTGCTCTAGCTCC ATTTATCAGCTTT GAATTTCAGCCA GTAAGAATGGGA (SEQ ID NO: 734) | TCTTGCTGGCAA GTCTTAATGTAA GACCCTCAACTC ATTTTCCCAGCT AT (SEQ ID NO: 735) |
| FLNA | NM_001456.3 | CCCTCAGGAGCCCT GGAGGAGTGCTAT GTCACAGAAATTGA CCAAGATAAGTATG CTGTGCGCTTCATC CCTCGGGAGAATG GCGTTTACCTGATT GACG (SEQ ID NO: 736) | TTATCTTGGTCAA TTTCTGTGACATA GCACTCCTCCAG GGCTCCTGAG (SEQ ID NO: 737) | CGTCAATCAGGT AAACGCCATTCT CCCGAGGGATGA AGCGCACAGCAT AC (SEQ ID NO: 738) |

TABLE 1-continued

| Gene | GenBank Accession No. | Target Sequence | Capture Probe Sequence | Reporter Probe Sequence |
|---|---|---|---|---|
| FN1 | NM_212482.1 | GGGAATGGACATGCATTGCCTACTCGCAGCTTCGAGATCAGTGCATTGTTGATGACATCACTTACAATGTGAACGACACATTCCACAAGCGTCATGAAGA (SEQ ID NO: 739) | AACAATGCACTGATCTCGAAGCTGCGAGTAGGCAATGCATGTCCATTCC (SEQ ID NO: 740) | TCTTCATGACGCTTGTGGAATGTGTCGTTCACATTGTAAGTGATGTCATC (SEQ ID NO: 741) |
| FNBP1 | NM_015033.2 | CATGACCTCCAAACCCAAAATCCACTGCTTCAGGAGCCTAAAGCGTGGGCTTTCTCTCAAGCTGGGTGCAACACCGGAGGATTTCAGCAACCTCCCACCT (SEQ ID NO: 742) | GCCCACGCTTTAGGCTCCTGAAGCAGTGGATTTTGGGTTTGGAGGTCATG (SEQ ID NO: 743) | GTGGGAGGTTGCTGAAATCCTCCGGTGTTGCACCCAGCTTGAGAGAAA (SEQ ID NO: 744) |
| FNDC1 | NM_032532.2 | GATTATAAGCAGATCGCTAACAGGCGTGTGCTGATTGAGAACCTGATTCCAGACACTGTGTATGAATTTGCAGTCCGTATTTCACAGGGTGAAAGAGATG (SEQ ID NO: 745) | GGAATCAGGTTCTCAATCAGCACACGCCTGTTAGCGATCTGCTTATAATC (SEQ ID NO: 746) | CATCTCTTTCACCCTGTGAAATACGGACTGCAAATTCATACACAGTGTCT (SEQ ID NO: 747) |
| FOXM1 | NM_021953.2 | AAGTCTTTTGTATTGGGTCAGGAGTTGAATTTGGGGTGGGAGGATGGATGCAACTGAAGCAGAGTGTGGGTGCCCAGATGTGCGCTATTAGATGTTTCTC (SEQ ID NO: 748) | CATCCATCCTCCCACCCCAAATTCAACTCCTGACCCAATACAAAAGACTT (SEQ ID NO: 749) | GAGAAACATCTAATAGCGCACATCTGGGCACCCACACTCTGCTTCAGTTG (SEQ ID NO: 750) |
| FOXO1 | NM_002015.3 | TCTCATCACCAACATCATTAACTGTTTCGACCCAGTCCTCACCTGGCACCATGATGCAGCAGACGCCGTGCTACTCGTTTGCGCCACCAAACACCAGTTT (SEQ ID NO: 751) | GGTGCCAGGTGAGGACTGGGTCGAAACAGTTAATGATGTTGGTGATGAGA (SEQ ID NO: 752) | AAACTGGTGTTTGGTGGCGCAAACGAGTAGCACGGCGTCTGCTGCATCAT (SEQ ID NO: 753) |
| FOXP1 | NM_001012505.1 | TGCTAGCCAAAAGGCTTCCCTCTGTGTGTTGCAGTCCTGTGGCATTATGCATGCCCCTCCCAGTGACCCCAGGCTTTTTATGCTGTGAGACACGTTAA (SEQ ID NO: 754) | GCATAATGCCACAGGACTGCAACACACAGAGGGAAGCCTTTTGGCTAGCA (SEQ ID NO: 755) | GCCATAAAAAGCCTGGGGTCACTGGGAGGGGGCAT (SEQ ID NO: 756) |
| FSCN1 | NM_003088.2 | CCCTGCCCTCTTGTCTGCCACGGGCGAGTCTGGCACCTCTTCTTCTGACCTCAGACGGCTCTGAGCCTTATTTCTCTGGAAGCGGCTAAGGGACGGTT (SEQ ID NO: 757) | TCAGAAGAAAGAGGTGCCAGACTCGCCCCGTGGCAGACAAGAG (SEQ ID NO: 758) | CCTTAGCCGCTTCCAGAGAAATAAGGCTCAGAGCCGTCTGAGG (SEQ ID NO: 759) |

TABLE 1-continued

| Gene | GenBank Accession No. | Target Sequence | Capture Probe Sequence | Reporter Probe Sequence |
|---|---|---|---|---|
| FUT8 | NM_004480.3 | GACATCATGAAAG GATTCTGATGGCAA TTACTGTCTCATTA GTGAACAATAAAA GAAAAATTGTTGTA TTAGCACAACCTAC TACTGTGAAGAGG AAAAG (SEQ ID NO: 760) | ATTGTTCACTAAT GAGACAGTAATT GCCATCAGAATC CTTTCATGATGTC (SEQ ID NO: 761) | CTTTTCCTCTTCA CAGTAGTAGGTT GTGCTAATACAA CAATTTTTCTTTT (SEQ ID NO: 762) |
| FYB | NM_001465.3 | ATGTAAAGTCCCTC ATGGCGAAATATA ACACGGGGGGCAA CCCGACAGAGGAT GTCTCAGTCAATAG CCGACCCTTCAGAG TCACAGGGCCAAA CTCATC (SEQ ID NO: 763) | CTCTGTCGGGTTG CCCCCCGTGTTAT ATTTCGCCATGAG GGACTTTACAT (SEQ ID NO: 764) | GATGAGTTTGGC CCTGTGACTCTG AAGGGTCGGCTA TTGACTGAGACA TC (SEQ ID NO: 765) |
| GAD2 | NM_000818.2 | TGTATGCCATGATG ATCGCACGCTTTAA GATGTTCCCAGAAG TCAAGGAGAAAGG AATGGCTGCTCTTC CCAGGCTCATTGCC TTCACGTCTGAACA TAG (SEQ ID NO: 766) | CTCCTTGACTTCT GGGAACATCTTA AAGCGTGCGATC ATCATGGCATAC A (SEQ ID NO: 767) | TTCAGACGTGAA GGCAATGAGCCT GGGAAGAGCAG CCATTCCTTT (SEQ ID NO: 768) |
| GATA1 | NM_002049.2 | TGCGGAAGGATGG TATTCAGACTCGAA ACCGCAAGGCATCT GGAAAAGGGAAAA AGAAACGGGGCTC CAGTCTGGGAGGC ACAGGAGCAGCCG AAGGACC (SEQ ID NO: 769) | CCCTTTTCCAGAT GCCTTGCGGTTTC GAGTCTGAATAC CATCCTTCCGCA (SEQ ID NO: 770) | CTCCTGTGCCTC CCAGACTGGAGC CCCGTTTCTTTTT (SEQ ID NO: 771) |
| GATA2 | NM_032638.3 | GAAGAAGGAAGGG ATCCAGACTCGGAA CCGGAAGATGTCCA ACAAGTCCAAGAA GAGCAAGAAGGG GCGGAGTGCTTCGA GGAGCTGTCAAAGT GCATG (SEQ ID NO: 772) | TGGACTTGTTGGA CATCTTCCGGTTC CGAGTCTGGATC CCTTCCTTCTTC (SEQ ID NO: 773) | CATGCACTTTGA CAGCTCCTCGAA GCACTCCGCCCC TTTCTTGCTCTTC T (SEQ ID NO: 774) |
| GBP1 | NM_002053.1 | CCAGATGACCAGC AGTAGACAAATGG ATACTGAGCAGAGT CTTAGGTAAAAGTC TTGGGAAATATTTG GGCATTGGTCTGGC CAAGTCTACAATGT CCCA (SEQ ID NO: 775) | TTTACCTAAGACT CTGCTCAGTATCC ATTTGTCTACTGC TGGTCATCTGG (SEQ ID NO: 776) | TGGGACATTGTA GACTTGGCCAGA CCAATGCCCAAA TATTTCCCAAGA CT (SEQ ID NO: 777) |
| GBP4 | NM_052941.4 | TTCTACAAGATATG CCATGGGCCTTTTC ACAGGGGACACAG GCTTCTTAAAACAA CCCGGCTTCCTCAC CCTATGTCCTTTAT TTACAAAGCTGTGC TCC (SEQ ID NO: 778) | TTAAGAAGCCTG TGTCCCCTGTGAA AAGGCCCATGGC ATATCTTGTAGAA (SEQ ID NO: 779) | GGAGCACAGCTT TGTAAATAAAGG ACATAGGGTGAG GAAGCCGGGTTG TT (SEQ ID NO: 780) |

TABLE 1-continued

| Gene | GenBank Accession No. | Target Sequence | Capture Probe Sequence | Reporter Probe Sequence |
|------|----------------------|-----------------|------------------------|-------------------------|
| GCET2 | NM_001008756.1 | GGAAAGGAGTCACCTTAACAAAGCTGCAGAAATCAACCTTATGATTTGCCATCTCTCTTGGGTATTTTAGATGCTGGGATCACCATATCGCTGAAGGGTG (SEQ ID NO: 781) | GGCAAATCATAAGGTTGATTTCTGCAGCTTTGTTAAGGTGACTCCTTTCC (SEQ ID NO: 782) | CACCCTTCAGCGATATGGTGATCCCAGCATCTAAAATACCCAAGAGAGAT (SEQ ID NO: 783) |
| GGT1 | NM_001032365.2 | CTCAGCAAGGCAAGTGAGGTGCTGCCGTCATCCAGGCTGGACAGTTCAGTGATTTGCCTGAGGCCCCACAGCAGAGTTCAACTGGAGACAGAGAAACCAG (SEQ ID NO: 784) | ACTGAACTGTCCAGCCTGGATGACGGCAGCACCTCACTTG (SEQ ID NO: 785) | TCTCCAGTTGAACTCTGCTGTGGGGCCTCAGGCAAATC (SEQ ID NO: 786) |
| GHR | NM_000163.2 | TTCATATAGTACAGTCCCCACAGGGCCTCATACTCAATGCGACTGCCTTGCCCTTGCCTGACAAAGAGTTTCTCTCATCATGTGGCTATGTGAGCACAGA (SEQ ID NO: 787) | CAAGGCAGTCGCATTGAGTATGAGGCCCTGTGGGGACTGTACTATATGA (SEQ ID NO: 788) | TCTGTGCTCACATAGCCACATGATGAGAGAAACTCTTTGTCAGGCAAGGG (SEQ ID NO: 789) |
| GIT2 | NM_057169.2 | CAGATTTTACAGGCTGAATTATTGGCAGTATATGGAGCAGACCCAGGCACACAGGATTCTAGTGGGAAAACTCCCGTTGATTATGCAAGGCAAGGAGGGC (SEQ ID NO: 790) | GTGCCTGGGTCTGCTCCATATACTGCCAATAATTCAGCCTGTAAAATCTG (SEQ ID NO: 791) | GCCCTCCTTGCCTTGCATAATCAACGGGAGTTTTCCCACTAGAATCCTGT (SEQ ID NO: 792) |
| GLDC | NM_000170.2 | AAAGCTTGGTGAGAATGATGCCTGGAAGAATGGTGGGGTAACAAGAGATGCCACTGGGAAAGAAGTGTATCGTCTTGCTCTTCAAACCAGGGAGCAACA (SEQ ID NO: 793) | ATCTCTTGTTACCCCCACCATTCTTCCAGGCATCATTCTCACCAAGCTTT (SEQ ID NO: 794) | TGTTGCTCCCTGGTTTGAAGAGCAAGACGATACACTTCTTTCCCAGTGC (SEQ ID NO: 795) |
| GLRX | NM_002064.2 | ATCCCATCCCACCTTGAAAATCACTGCCTGAACCAGTGTTCTCCACCTTGTCCTCCACAGATCTCATAGGAAATGTTCAACAATTCTGTGAAAGGTCAC (SEQ ID NO: 796) | AAGGTGGAGAACACTGGTTCAGAGCAGTGATTTTCAAGGTGGGATGGGAT (SEQ ID NO: 797) | GTGACCTTTCACAGAATTGTTGAACATTTCCTATGAGATCTGTGGAGGAC (SEQ ID NO: 798) |
| GNA13 | NM_006572.4 | TTTTCTTACAATATCTTCCTGCTATAAGAGCATTATGGGCAGACAGCGGCATACAGAATGCCTATGACCGGCGTCGAGAATTTCAACTGGGTGAATCTGT (SEQ ID NO: 799) | GCCGCTGTCTGCCCATAATGCTCTTATAGCAGGAAGATATTGTAAGAAAA (SEQ ID NO: 800) | ACAGATTCACCCAGTTGAAATTCTCGACGCCGGTCATAGGCATTCTGTAT (SEQ ID NO: 801) |
| GNB4 | NM_021629.3 | TGCCATCAGCAAGGATATCTCCTCCACTTTAATGGACAGGCCTCATTTTTGGCAGCTATGCTGTTTGAGATGTAGACTGAATATCCAAGGTTCCTCCCTA (SEQ ID NO: 802) | AAAAATGAGGCCTGTCCATTAAAGTGGAGGAGATATCCTTGCTGATGGCA (SEQ ID NO: 803) | TAGGGAGGAACCTTGGATATTCAGTCTACATCTCAAACAGCATAGCTGCC (SEQ ID NO: 804) |

TABLE 1-continued

| Gene | GenBank Accession No. | Target Sequence | Capture Probe Sequence | Reporter Probe Sequence |
|---|---|---|---|---|
| GNG10 | NM_001017998.2 | AACTTTTAGAGATATTTCAGCCCTTTCCTGTGGCCTGGTCCTATAGCCAAAATCACAGATATTCATGAGTTTCTACTTGAGTGAGAAAACTGGGTGAAGG (SEQ ID NO: 805) | TTGGCTATAGGACCAGGCCACAGGAAAGGGCTGAAATATCTCTAAAAGTT (SEQ ID NO: 806) | CCTTCACCCAGTTTTCTCACTCAAGTAGAAACTCATGAATATCTGTGATT (SEQ ID NO: 807) |
| GNG4 | NM_004485.2 | AATGAAAGAGGGCATGTCTAATAACAGCACCCACTAGCATCTCCCAAGCCAGGAAAGCTGTGGAGCAGCTAAAGATGGAAGCCTGTATGGACAGGGTCAAG (SEQ ID NO: 808) | TGGCTTGGGAGATGCTAGTGGTGCTGTTATTAGACATGCCCTCTTTCATT (SEQ ID NO: 809) | TGTCCATACAGGCTTCCATCTTTAGCTGCTCCACAGCTTTCC (SEQ ID NO: 810) |
| GNL3 | NM_014366.4 | CATTCAGAAGTGAAGTCTGCTTTGGGAAAGAGGGCCTTTGGAAACTTCTTGGAGGTTTTCAGGAAACTTGCAGCAAAGCCATTCGGGTTGGAGTAATTGG (SEQ ID NO: 811) | AAGAAGTTTCCAAAGGCCCTCTTTCCCAAAGCAGACTTCACTTCTGAATG (SEQ ID NO: 812) | CCAATTACTCCAACCCGAATGGCTTTGCTGCAAGTTTCCTGAAAACCTCC (SEQ ID NO: 813) |
| GORASP1 | NM_031899.2 | GGCCAGCTTCCCTTAACTCTGTAGCCTGGCAGTCTGACCCAAAGTTGCCCTCACCCAAAGGTTCTGGCTCTTCCCTCCCTCACTTTTACTTTCCCTTCCC (SEQ ID NO: 814) | GGGCAACTTTGGGTCAGACTGCCAGGCTACAGAGTTAAGG (SEQ ID NO: 815) | GGGAAGGGAAAGTAAAAGTGAGGGAGGGAAGAGCCAGAACCTTTGGGTGA (SEQ ID NO: 816) |
| GPR116 | NM_015234.3 | TATGTTGGGGTGGGCTTTTCCATCTTGAGCTTGGCAGCCTGTCTAGTTGTGGAAGCTGTGGTGTGGAAATCGGTGACCAAGAATCGGACTTCTTATATGC (SEQ ID NO: 817) | ACAACTAGACAGGCTGCCAAGCTCAAGATGGAAAAGCCCACCCCAACATA (SEQ ID NO: 818) | GCATATAAGAAGTCCGATTCTTGGTCACCGATTTCCACACCACAGCTTCC (SEQ ID NO: 819) |
| GPR176 | NM_007223.1 | AGTATTCTGCTCTGTGACCATCCTCAGCTTCCCTGCTATTGCTTTGGACAGGTACTACTCAGTCCTCTATCCACTGGAGAGGAAATATCTGATGCCAAG (SEQ ID NO: 820) | TGTCCAAAGCAATAGCAGGGAAGCTGAGGATGGTCACAGAGCAGAATACT (SEQ ID NO: 821) | CTTGGCATCAGATATTTTCCTCTCCAGTGGATAGAGGACTGAGTAGTACC (SEQ ID NO: 822) |
| GPR183 | NM_004951.3 | ACTGGAGAATCGGAGATGCCTTGTGTAGGATAACTGCGCTAGTGTTTTACATCAACACATATGCAGGTGTGAACTTTATGACCTGCCTGAGTATTGACCG (SEQ ID NO: 823) | GTAAAACACTAGCGCAGTTATCCTACACAAGGCATCTCCGATTCTCCAGT (SEQ ID NO: 824) | CGGTCAATACTCAGGCAGGTCATAAAGTTCACACCTGCATATGTTGAT (SEQ ID NO: 825) |
| GRAMD1B | NM_020716.1 | TTCCGCTGGGAAACTCTGCTGACAGTCCGTTTGAAAGACATCTGTTCCATGACTAAAGAAAAAACAGCTCGCCTCATTCCCAATGCCATCCAAGTTTGCA (SEQ ID NO: 826) | ATGGAACAGATGTCTTTCAAACGGACTGTCAGCGAGTTTCCCAGCGGA (SEQ ID NO: 827) | TGCAAACTTGGATGGCATTGGGAATGAGGCGAGCTGTTTTTTCTTTAGTC (SEQ ID NO: 828) |

TABLE 1-continued

| Gene | GenBank Accession No. | Target Sequence | Capture Probe Sequence | Reporter Probe Sequence |
|---|---|---|---|---|
| GRB10 | NM_005311.4 | CCTTTGCCACGTCCCCTTAGCTTAGTGATCAGGTGTGAGAGTGGCCATTTCCTTACCTTTGATCCCTGTAAAGCAGAAAGGACTCCTTTGACAGGCGACA (SEQ ID NO: 829) | AAATGGCCACTCTCACACCTGATCACTAAGCTAAGGGGACGTGGCAAAG (SEQ ID NO: 830) | TGTCGCCTGTCAAAGGAGTCCTTTCTGCTTTACAGGGATCAAAGGTAAGG (SEQ ID NO: 831) |
| GRSF1 | NM_001098477.1 | CTTTCTAAGCCTTGTGCTAAAGGCGTATAACGGTGGTGCCTATCTACTTAAGGGGGCATTCTAGTCTTAACTTAAAAGTTGTCTAAACTGTCCCTCCCTG (SEQ ID NO: 832) | TAAGTAGATAGGCACCACCGTTATACGCCTTTAGCACAAGGCTTAGAAAG (SEQ ID NO: 833) | CAGGGAGGGACAGTTTAGACAACTTTTAAGTTAAGACTAGAATGCCCCCT (SEQ ID NO: 834) |
| GSK3B | NM_002093.2 | ACTGATTATACCTCTAGTATAGATGTATGGTCTGCTGGCTGTGTGTTGGCTGAGCTGTTACTAGGACAACCAATATTTCCAGGGGATAGTGGTGTGGATC (SEQ ID NO: 835) | GCCAACACACAGCCAGCAGACCATACATCTATACTAGAGGTATAATCAGT (SEQ ID NO: 836) | GATCCACACCACTATCCCCTGGAAATATTGGTTGTCCTAGTAACAGCTCA (SEQ ID NO: 837) |
| GTSE1 | NM_016426.5 | GATGAAGTCTTCTTCGGACCCTTTGGACATAAAGAAAGATGTATTGCTGCCAGCTTGGAATTAAATAATCCGGTTCCCGAACAGCCTCCGTTGCCCACAT (SEQ ID NO: 838) | GCAGCAATACATCTTTCTTTATGTCCAAAGGGTCCGAAGAAGACTTCATC (SEQ ID NO: 839) | ATGTGGGCAACGGAGGCTTTCGGGAACGGATTATTTAATTCCAAGCTG (SEQ ID NO: 840) |
| GXYLT2 | NM_001080393.1 | GTCATGCTCAAATCAGCTGTGCTTTTTAGCCACAGGAAGATCCAATTCCACATCTTCACTGAAGACTCTCTGAAGCCCGAGTTTGATAAGCAGTTACGCC (SEQ ID NO: 841) | TGGAATTGGATCTTCCTGTGGCTAAAAAGCACAGCTGATTTGAGCATGAC (SEQ ID NO: 842) | GGCGTAACTGCTTATCAAAACTCGGGCTTCAGAGAGTCTTCAGTGAAGATG (SEQ ID NO: 843) |
| GYG2 | NM_001184704.1 | CTCTTGGCTTGGTCTCTACCCTCACTACCTCAGTTCTCAATAACTTAGTGAATCACTGCCCTCCTCAAAGCCATTTCCACTCAGCTCTTTCCAGAGAATT (SEQ ID NO: 844) | CACTAAGTTATTGAGAACTGAGGTAGTGAGGGTAGAGACCAAGCCAAGAG (SEQ ID NO: 845) | AATTCTCTGGAAAGAGCTGAGTGGAAATGGCTTTGAGGAGGGCAGTGATT (SEQ ID NO: 846) |
| GYPC | NM_016815.2 | AGTACTTTATTTGAGGGACAACAGACTTCACTTCCCTGAATGCCTCCCCCATCTCCATCAGGAAAAATACACCCCATCGCCCAGCACCCCTGCTGATACC (SEQ ID NO: 847) | GGGGGAGGCATTCAGGGAAGTGAAGTCTGTTGTCCCTCAAATAAAGTACT (SEQ ID NO: 848) | CAGGGGTGCTGGGCGATGGGGTGTATTTTTCCTGATGGAGAT (SEQ ID NO: 849) |
| H1FOO | NM_153833.1 | GGCTCCTGGGAGCGTCACCAGCGACATCTCACCCTCCTCGACTTCCACAGCAGGATCATCCAGGTCTCCTGAATCTGAAAAGCCAGGGCCCGAGCCACGGC (SEQ ID NO: 850) | CTGTGGAAGTCGAGGAGGGTGAGATGTCGCTGGTGACGCT (SEQ ID NO: 851) | GCCTGGCTTTTCAGATTCAGGAGACCTGGATGATCCTG (SEQ ID NO: 852) |

TABLE 1-continued

| Gene | GenBank Accession No. | Target Sequence | Capture Probe Sequence | Reporter Probe Sequence |
|---|---|---|---|---|
| H2AFV | NM_138635.3 | ATGGCTTGTGTTACAAGTAGAGAGCAGTGGAGAGTTGGGCTTTGTAATTCTTTCAAGGGTGATTGTAGTTCTGGAGTCCTATCTACCTGGGTTCAGATCT (SEQ ID NO: 853) | GAATTACAAAGCCCAACTCTCCACTGCTCTCTACTTGTAACACAAGCCAT (SEQ ID NO: 854) | AGATCTGAACCCAGGTAGATAGGACTCCAGAACTACAATCACCCTTGAAA (SEQ ID NO: 855) |
| II2AFX | NM_002105.2 | CCGCCCCATTTCCCTTCCAGCAAACTCAACTCGGCAATCCAAGCACCTAGATACCAGCACAAGTCGGTTAATCCCTGTCTGGACTGAGCCTCCGTTGGCT (SEQ ID NO: 856) | CTAGGTGCTTGGATTGCCGAGTTGAGTTTGCTGGAAGGGAAATGGGGCGG (SEQ ID NO: 857) | CAACGGAGGCTCAGTCCAGACAGGGATTAACCGACTTGTGCTGGTAT (SEQ ID NO: 858) |
| HARBI1 | NM_173811.3 | TGCAGCAGTCTTCCCTCAGTAGTCAGTTTGAAGCGGGTATGCACAAAGATAGCTGGCTTCTGGGTGACAGTTCCTTCTTTCTTCGAACCTGGCTCATGAC (SEQ ID NO: 859) | ATCTTTGTGCATACCCGCTTCAAACTGACTACTGAGGGAAGACTGCTGCA (SEQ ID NO: 860) | GTCATGAGCCAGGTTCGAAGAAAGAAGGAACTGTCACCCAGAAGCCAGCT (SEQ ID NO: 861) |
| HCK | NM_002110.2 | CCAGGTCGGAGGCAATACATTCTCAAAACTGAAACCAGCGCCAGCCCACACTGTCCTGTGTACGTGCCGGATCCCACATCCACCATCAAGCCGGGGCCT (SEQ ID NO: 862) | GTGGGCTGGCGCTGGTTTCAGTTTTGTGAGAATGTATTGCCTCCGACCTG (SEQ ID NO: 863) | CTTGATGGTGGATGTGGGATCCGGCACGTACACAGGACAGT (SEQ ID NO: 864) |
| HDAC1 | NM_004964.2 | CAAGCCGGTCATGTCCAAAGTAATGGAGATGTTCCAGCCTAGTGCGGTGGTCTTACAGTGTGGCTCAGACTCCCTATCTGGGGATCGGTTAGGTTGCTTC (SEQ ID NO: 865) | CCACCGCACTAGGCTGGAACATCTCCATTACTTTGGACATGACCGGCTTG (SEQ ID NO: 866) | AACCTAACCGATCCCCAGATAGGGAGTCTGAGCCACACTGTAAGA (SEQ ID NO: 867) |
| HDAC2 | NM_001527.1 | AAGCCTATTATCTCAAAGGTGATGGAGATGTATCAACCTAGTGCTGTGGTATTACAGTGTGGTGCAGACTCATTATCTGGTGATAGACTGGGTTGTTTCA (SEQ ID NO: 868) | ACCACAGCACTAGGTTGATACATCTCCATCACCTTTGAGATAATAGGCTT (SEQ ID NO: 869) | TGAAACAACCCAGTCTATCACCAGATAATGAGTCTGCACCACACTGTAAT (SEQ ID NO: 870) |
| HDGF | NM_004494.2 | TCATCAAGAGAATTTGGGGCTTCCAAGTTGTTCGGGCCAAGGACCTGAGACCTGAAGGGTTGACTTTACCCATTTGGGTGGGAGTGTTGAGCATCTGTCC (SEQ ID NO: 871) | TCTCAGGTCCTTGGCCCGAACAACTTGGAAGCCCCAAATTCTCTTGATGA (SEQ ID NO: 872) | GGACAGATGCTCAACACTCCCACCCAAATGGGTAAAGTCAACCCTTCAGG (SEQ ID NO: 873) |
| HEG1 | NM_020733.1 | GAAGTAACATCTCATCCTATGACGGGGAATATGCTCAGCCTTCTACTGAGTCGCCAGTTCTGCATACATCCAACCTTCCGTCCTACACACCCACCATTAA (SEQ ID NO: 874) | CTCAGTAGAAGGCTGAGCATATTCCCGTCATAGGATGAGATGTTACTTC (SEQ ID NO: 875) | TTAATGGTGGGTGTGTAGGACGGAGGTTGGGATGTATGCAGAACTGGCGA (SEQ ID NO: 876) |

TABLE 1-continued

| Gene | GenBank Accession No. | Target Sequence | Capture Probe Sequence | Reporter Probe Sequence |
|---|---|---|---|---|
| HHIP | NM_022475.1 | GATTTGTATACCGGGGCTGCCAGTCAGAAAGATTGTATGGAAGCTACGTGTTTGGAGATCGTAATGGGAATTTCCTAACTCTCCAGCAAAGTCCTGTGAC (SEQ ID NO: 877) | CACGTAGCTTCCATACAATCTTTCTGACTGGCAGCCCCGGTATACAAATC (SEQ ID NO: 878) | GTCACAGGACTTTGCTGGAGAGTTAGGAAATTCCCATTACGATCTCCAAA (SEQ ID NO: 879) |
| HJURP | NM_018410.3 | AACAATACGACAGGGCCATGGAGAGAACCGTCAGAGGGAGATTGAAATCCGATTTGATCAGCTTCATCGGGAATATTGCCTGAGTCCCAGGAACCAGCCT (SEQ ID NO: 880) | GGATTTCAATCTCCCTCTGACGGTTCTCTCCATGGCC (SEQ ID NO: 881) | AGGCTGGTTCCTGGGACTCAGGCAATATTCCCGATGAAGCTGATCAAATC (SEQ ID NO: 882) |
| HLA-A | NM_002116.5 | GGAAGAGCTCAGATAGAAAAGGAGGGAGTTACACTCAGGCTGCAAGCAGTGACAGTGCCCAGGGCTCTGATGTGTCCCTCACAGCTTGTAAAGTGTGAGA (SEQ ID NO: 883) | ACTGCTTGCAGCCTGAGTGTAACTCCTCCTTTTCTATCTGAGCTCTTCC (SEQ ID NO: 884) | TCTCACACTTTACAAGCTGTGAGGGACACATCAGAGCCCTGGGCACTGTC (SEQ ID NO: 885) |
| HLA-B | NM_005514.6 | TGAATGTGTCTGCGTCCCTGTTAGCATAATGTGAGGAGGTGGAGAGACAGCCCACCCTTGTGTCCACTGTGACCCCTGTTCCCATGCTGACCTGTGTTTC (SEQ ID NO: 886) | CTGTCTCTCCACCTCCTCACATTATGCTAACAGGGACGCAGACACATT (SEQ ID NO: 887) | GAAACACAGGTCAGCATGGGAACAGGGGTCACAGTGGACACAAGGGTGGG (SEQ ID NO: 888) |
| HLA-C | NM_002117.4 | AGCTGGGAGCCATCTTCCCAGCCCACCATCCCCATCATGGGCATCGTTGCTGGCCTGGCTGTCCTGGTTGTCCTAGCTGTCCTTGGAGCTGTGGTCACCG (SEQ ID NO: 889) | GCAACGATGCCCATGATGGGGATGGTGGGCTGGGAAGATGGCTC (SEQ ID NO: 890) | CACAGCTCCAAGGACAGCTAGGACAACCAGGACAGCCAGGCCA (SEQ ID NO: 891) |
| HLA-DMA | NM_006120.3 | TTATTTGACAAAGAGTTCTGCGAGTGGATGATCCAGCAAATAGGGCCAAAACTTGATGGGAAAATCCCGGTGTCCAGAGGGTTCCTATCGCTGAAGTGT (SEQ ID NO: 892) | TTTGGCCCTATTTGCTGGATCATCCACTCGCAGAACTCTTTGTCAAATAA (SEQ ID NO: 893) | ACACTTCAGCGATAGGAAACCCTCTGGACACCGGGATTTTCCCATCAAGT (SEQ ID NO: 894) |
| HLA-DPA1 | NM_033554.2 | GGAGAGATCTGAACTCCAGCTGCCCTACAAACTCCATCTCAGCTTTTCTTCTCACTTCATGTGAAAACTACTCCAGTGGCTGACTGAATTGCTGACCCTT (SEQ ID NO: 895) | AAGAAAAGCTGAGATGGAGTTTGTAGGGCAGCTGGAGTTCAGATCTCTC (SEQ ID NO: 896) | AAGGGTCAGCAATTCAGTCAGCCACTGGAGTAGTTTTCACATGAAGTGAG (SEQ ID NO: 897) |
| HLA-DPB1 | NM_002121.4 | TCCAAATTGGATACTGCTGCCAAGAAGTTGCTCTGAAGTCAGTTTCTATCATTCTGCTCTTTGATTCAAAGCACTGTTTCTCTCACTGGGCCTCCAACCA (SEQ ID NO: 898) | GATAGAAACTGACTTCAGAGCAACTTCTTGGCAGCAGTATCCAATTTGGA (SEQ ID NO: 899) | TGGTTGGAGGCCCAGTGAGAGAAACAGTGCTTTGAATCAAAGAGCAGAAT (SEQ ID NO: 900) |

TABLE 1-continued

| Gene | GenBank Accession No. | Target Sequence | Capture Probe Sequence | Reporter Probe Sequence |
|---|---|---|---|---|
| HLA-DRA | NM_019111.3 | GGCCAACATAGCTGTGGACAAAGCCAACCTGGAAATCATGACAAAGCGCTCCAACTATACTCCGATCACCAATGTACCTCCAGAGGTAACTGTGCTCACG (SEQ ID NO: 901) | AGCGCTTTGTCATGATTTCCAGGTTGGCTTTGTCCACAGCTATGTTGGCC (SEQ ID NO: 902) | CGTGAGCACAGTTACCTCTGGAGGTACATTGGTGATCGGAGTATAGTTGG (SEQ ID NO: 903) |
| HLA-E | NM_005516.4 | TGTCTTAGGGGACTCTGGCTTCTCTTTTTGCAAGGGCCTCTGAATCTGTCTGTGTCCCTGTTAGCACAATGTGAGGAGGTAGAGAAACAGTCCACCTCTG (SEQ ID NO: 904) | GACAGATTCAGAGGCCCTTGCAAAAAGAGAAGCCAGAGTCCCCTAAGACA (SEQ ID NO: 905) | TGGACTGTTTCTCTACCTCCTCACATTGTGCTAACAGGGACACA (SEQ ID NO: 906) |
| HLA-F | NM_001098479.1 | CCATTGGGCGTCGCGTTTCTAGAGAAGCCAATCAGTGTCGCCGCAGTTCCCAGGTTCTAAAGTCCCACGCACCCCGCGGGACTCATATTTTTCCCAGACG (SEQ ID NO: 907) | GGAACTGCGGCGACACTGATTGGCTTCTCTAGAAACGCGACGCCCAATGG (SEQ ID NO: 908) | CGTCTGGGAAAAATATGAGTCCCGCGGGGTGCGTGGGACTTTAGAACCTG (SEQ ID NO: 909) |
| HOMER2 | NM_004839.2 | TGGAAGACAAAGTGCGTTCCTTAAAGACAGACATTGAGGAGAGCAAATACCGACAGCGCCACCTGAAGGTGGAGTTGAAGAGCTTCCTGGAGGTGCTGGA (SEQ ID NO: 910) | GTATTTGCTCTCCTCAATGTCTGTCTTTAAGGAACGCACTTTGTCTTCCA (SEQ ID NO: 911) | AGGAAGCTCTTCAACTCCACCTTCAGGTGGCGCTGTCG (SEQ ID NO: 912) |
| HOPX | NM_001145460.1 | AACAATAGGAAGCTATGTGTATCTTCTGTGTAAAGCAGTGGCTTCACTGGAAAAATGGTGTGGCTAGCATTTCCCTTTGAGTCATGATGACAGATGGTGT (SEQ ID NO: 913) | CCAGTGAAGCCACTGCTTTACACAGAAGATACACATAGCTTCCTATTGTT (SEQ ID NO: 914) | ACACCATCTGTCATCATGACTCAAAGGGAAATGCTAGCCACACCATTTTT (SEQ ID NO: 915) |
| HPCAL1 | NM_134421.1 | CTGTTTCTAAGGAAATGCATGTGTGCCCTGAGCCGTGATGATCCTCCCATCCGTGTTGTGAGCACAGGCATTTGTGTCTGGTCTGTCCTCCCTGTTGATT (SEQ ID NO: 916) | ATGGGAGGATCATCACGGCTCAGGGCACACATGCATTTCCTTAGAAACAG (SEQ ID NO: 917) | AATCAACAGGGAGGACAGACCAGACACAAATGCCTGTGCTCACAACACGG (SEQ ID NO: 918) |
| HSP90AA1 | NM_005348.3 | GGTGGCGCGTCAGTTGCTTCAGCGTCCCGGTGTGGCTGTGCCGTTGGTCCTGTGCGGTCACTTAGCCAAGATGCCTGAGGAAACCCAGACCCAAGACCAA (SEQ ID NO: 919) | GGACCAACGGCACAGCCACACCGGGACGCTGAAGCAACTGACG (SEQ ID NO: 920) | TCTGGGTTTCCTCAGGCATCTTGGCTAAGTGACCGCACA (SEQ ID NO: 921) |
| HSP90B1 | NM_003299.1 | TCAGAGCTGACGATGAAGTTGATGTGGATGGTACAGTAGAAGAGGATCTGGGTAAAAGTAGAGAAGGATCAAGGACGGATGATGAAGTAGTACAGAGAGA (SEQ ID NO: 922) | CAGATCCTCTTCTACTGTACCATCCACATCAACTTCATCGTCAGCT (SEQ ID NO: 923) | TCTCTCTGTACTACTTCATCATCCGTCCTTGATCCTTCTCTACTTTTAC C (SEQ ID NO: 924) |

TABLE 1-continued

| Gene | GenBank Accession No. | Target Sequence | Capture Probe Sequence | Reporter Probe Sequence |
|---|---|---|---|---|
| HSPA12B | NM_052970.4 | GAAAGGGCAGTAGATCTCTAATGTGGAGGTGGGAACATTATTGTGGTGGAGGCAATTATGAGGGTAGCATTTCTTTCGAGACAAAACACCCGTCTGGGAA (SEQ ID NO: 925) | TCCACCACAATAATGTTCCCACCTCCACATTAGAGATCTACTGCC (SEQ ID NO: 926) | TTCCCAGACGGGTGTTTTGTCTCGAAAGAAATGCTACCCTCATAATTGCC (SEQ ID NO: 927) |
| HSPA9 | NM_004134.4 | TTCAAGAGAGAGACAGGGGTTGATTTGACTAAAGACAACATGGCACTTCAGAGGGTACGGGAAGCTGCTGAAAAGGCTAAATGTGAACTCTCCTCATCTG (SEQ ID NO: 928) | TGAAGTGCCATGTTGTCTTTAGTCAAATCAACCCCTGTCTCTCTCTTGAA (SEQ ID NO: 929) | CAGATGAGGAGAGTTCACATTTAGCCTTTTCAGCAGCTTCCCGTACCCTC (SEQ ID NO: 930) |
| HSPB8 | NM_014365.2 | CAGATTTAGTGCAAGTAAAATGTTAGAGGGTGCGGGGGTGAGGACTGACCACAGATTCCCTGGATAGTGTAGTGGTAGATTTCTCCACAGGATAGCGCAA (SEQ ID NO: 931) | GGTCAGTCCTCACCCCCGCACCCTCTAACATTTTACTTGCACTAAATCTG (SEQ ID NO: 932) | TTGCGCTATCCTGTGGAGAAATCTACCACTACACTATCCAGGGAATCTGT (SEQ ID NO: 933) |
| HTRA1 | NM_002775.4 | TTGCAATCCCATCTGATAAGATTAAAAAGTTCCTCACGGAGTCCCATGACCGACAGGCCAAAGGAAAAGCCATCACCAAGAAGAAGTATATTGGTATCCG (SEQ ID NO: 934) | GTCATGGGACTCCGTGAGGAACTTTTTAATCTTATCAGATGGGATTGCAA (SEQ ID NO: 935) | ATACCAATATACTTCTTCTTGGTGATGGCTTTTCCTTTGGCCTGTCG (SEQ ID NO: 936) |
| HYOU1 | NM_006389.3 | CAGGTTGCTGGGGAGTTTCCACTCTTCTCTGGTGATTGTTCCTTCCCTCCCTTCCTCTCCCACCATGCGATGAGCATCCTTTCAGGCCAGTGTCTGCAGA (SEQ ID NO: 937) | GGAGGGAAGGAACAATCACCAGAGAAGAGTGGAAACTCCCCAGCAACCTG (SEQ ID NO: 938) | CAGACACTGGCCTGAAAGGATGCTCATCGCATGGTGGGAGAGGAAG (SEQ ID NO: 939) |
| ICAM1 | NM_000201.1 | GAAATACTGAAACTTGCTGCCTATTGGGTATGCTGAGGCCCACAGACTTACAGAAGAAGTGGCCCTCCATAGACATGTGTAGCATCAAAACACAAAGGCC (SEQ ID NO: 940) | TAAGTCTGTGGGCCTCAGCATACCCAATAGGCAGCAAGTTTCAGTATTTC (SEQ ID NO: 941) | GGCCTTTGTGTTTTGATGCTACACATGTCTATGGAGGCCACTTCTTCTG (SEQ ID NO: 942) |
| ID1 | NM_002165.2 | CTGCCCCAGAACCGCAAGGTGAGCAAGGTGGAGATTCTCCAGCACGTCATCGACTACATCAGGGACCTTCAGTTGGAGCTGAACTCGGAATCCGAAGTTG (SEQ ID NO: 943) | ATGACGTGCTGGAGAATCTCCACCTTGCTCACCTTGCGGTTCTG (SEQ ID NO: 944) | CAACTTCGGATTCCGAGTTCAGCTCCAACTGAAGGTCCCTGATGTAGTCG (SEQ ID NO: 945) |

TABLE 1-continued

| Gene | GenBank Accession No. | Target Sequence | Capture Probe Sequence | Reporter Probe Sequence |
|---|---|---|---|---|
| ID2 | NM_002166.4 | CGGATATCAGCATCCTGTCCTTGCAGGCTTCTGAATTCCCTTCTGAGTTAATGTCAAATGACAGCAAAGCACTGTGTGGCTGAATAAGCGGTGTTCATGA (SEQ ID NO: 946) | TAACTCAGAAGGGAATTCAGAAGCCTGCAAGGACAGGATGCTGATATCCG (SEQ ID NO: 947) | TCATGAACACCGCTTATTCAGCCACACAGTGCTTTGCTGTCATTTGACAT (SEQ ID NO: 948) |
| ID3 | NM_002167.3 | AGGAAGCCTGTTTGCAATTTAAGCGGGCTGTGAACGCCCAGGGCCGGCGGGGGCAGGGCCGAGGCGGGCCATTTTGAATAAAGAGGCGTGCCTTCCAGGC (SEQ ID NO: 949) | CCGCCGGCCCTGGGCGTTCACAGCCCGCTTAAATTGCAAACAG (SEQ ID NO: 950) | CCTCTTTATTCAAAATGGCCCGCCTCGGCCCTGCCC (SEQ ID NO: 951) |
| IDS | NM_000202.4 | GGGAAGACGTCCAAGCCTTAAACATCAGTGTGCCGTATGGTCCAATTCCTGTGGACTTTCAGCGGAAAATCCGCCAGAGCTACTTTGCCTCTGTGTCATA (SEQ ID NO: 952) | AGGAATTGGACCATACGGCACACTGATGTTTAAGGCTTGGACGTCTTCCC (SEQ ID NO: 953) | TATGACACAGAGGCAAAGTAGCTCTGGCGGATTTTCCGCTGAAAGTCCAC (SEQ ID NO: 954) |
| IER3 | NM_003897.2 | TCAACTCCGTCTGTCTACTGTGTGAGACTTCGGCGGACCATTAGGAATGAGATCCGTGAGATCCTTCCATCTTCTTGAAGTCGCCTTTAGGGTGGCTACG (SEQ ID NO: 955) | TCATTCCTAATGGTCCGCCGAAGTCTCACACAGTAGACAGACGGAGTTGA (SEQ ID NO: 956) | CGTAGCCACCCTAAAGGCGACTTCAAGAAGATGGAAGGATCTCACGGATC (SEQ ID NO: 957) |
| IFI35 | NM_005533.3 | TGCCCTCTGCTTGCGGGCTCTGCTCTGATCACCTTTGATGACCCCAAAGTGGCTGAGCAGGTGCTGCAACAAAAGGAGCACACGATCAACATGGAGGAGT (SEQ ID NO: 958) | ACTTTGGGGTCATCAAAGGTGATCAGAGCAGAGCCCGCAAGCAGAG (SEQ ID NO: 959) | TTGATCGTGTGCTCCTTTTGTTGCAGCACCTGCTCAGCC (SEQ ID NO: 960) |
| IFI44L | NM_006820.2 | ATCTCTGCCATTTATGTTGTGTGACACTATGGGGCTAGATGGGGCAGAAGGAGCAGGACTGTGCATGGATGACATTCCCACATCTTAAAAGGTTGTATG (SEQ ID NO: 961) | CTTCTGCCCCATCTAGCCCCATAGTGTCACACAACATAAATGGCAGAGAT (SEQ ID NO: 962) | CATACAACCTTTTAAGATGTGGGGAATGTCATCCATGCACAGTCCTGCTC (SEQ ID NO: 963) |
| IFI6 | NM_002038.3 | GGGGTGGAGGCAGGTAAGAAAAAGTGCTCGGAGAGCTCGGACAGCGGCTCCGGGTTCTGGAAGGCCCTGACCTTCATGGCCGTCGGAGGAGGACTCGCAG (SEQ ID NO: 964) | GAGCCGCTGTCCGAGCTCTCCGAGCACTTTTTCTTACCTG (SEQ ID NO: 965) | CGACGGCCATGAAGGTCAGGGCCTTCCAGAACCCG (SEQ ID NO: 966) |

TABLE 1-continued

| Gene | GenBank Accession No. | Target Sequence | Capture Probe Sequence | Reporter Probe Sequence |
|---|---|---|---|---|
| IFIH1 | NM_022168.2 | GCTTGGGAGAACCC TCTCCCTTCTCTGA GAAAGAAAGATGT CGAATGGGTATTCC ACAGACGAGAATTT CCGCTATCTCATCT CGTGCTTCAGGGCC AGG (SEQ ID NO: 967) | ACCCATTCGACAT CTTTCTTTCTCAG AGAAGGGAGAGG GTTCTCCCAAGC (SEQ ID NO: 968) | CCTGGCCCTGAA GCACGAGATGA GATAGCGGAAAT TCTCGTCTGTGG AAT (SEQ ID NO: 969) |
| IFIT1 | NM_001548.3 | GAGAAAGGCATTA GATCTGGAAAGCTT GAGCCTCCTTGGGT TCGTCTACAAATTG GAAGGAAATATGA ATGAAGCCCTGGA GTACTATGAGCGGG CCCTG (SEQ ID NO: 970) | TGTAGACGAACC CAAGGAGGCTCA AGCTTTCCAGATC TAATGCCTTTCTC (SEQ ID NO: 971) | CAGGGCCCGCTC ATAGTACTCCAG GCTTCATTCAT ATTTCCTTCCAA TT (SEQ ID NO: 972) |
| IFIT2 | NM_001547.4 | TGCATCCCATAGAG GTTAGTCCTGCATA GCCAGTAATGTGCT AAGTTCATCCAAAA GCTGGCGGACCAA AGTCTAAATAGGGC TCAGTATCCCCCAT CGC (SEQ ID NO: 973) | ATGAACTTAGCA CATTACTGGCTAT GCAGGACTAACC TCTATGGGATGC A (SEQ ID NO: 974) | GCGATGGGGGAT ACTGAGCCCTAT TTAGACTTTGGT CCGCCAGCTTTT GG (SEQ ID NO: 975) |
| IFIT3 | NM_001549.4 | GAAGAACAAATCA GCCTGGTCACCAGC TTTTCGGAACAGCA GAGACACAGAGGG CAGTCATGAGTGAG GTCACCAAGAATTC CCTGGAGAAAATCC TTCC (SEQ ID NO: 976) | CTGTGTCTCTGCT GTTCCGAAAAGC TGGTGACCAGGC TGATTTGT (SEQ ID NO: 977) | GATTTTCTCCAG GGAATTCTTGGT GACCTCACTCAT GACTGCCCT (SEQ ID NO: 978) |
| IFITM1 | NM_003641.3 | CCTGTTACTGGTAT TCGGCTCTGTGACA GTCTACCATATTAT GTTACAGATAATAC AGGAAAAACGGGG TTACTAGTAGCCGC CCATAGCCTGCAAC CTT (SEQ ID NO: 979) | TCTGTAACATAAT ATGGTAGACTGT CACAGAGCCGAA TACCAGTAACAG G (SEQ ID NO: 980) | AAGGTTGCAGGC TATGGGCGGCTA CTAGTAACCCCG TTTTTCCTGTATT A (SEQ ID NO: 981) |
| IGFBP5 | NM_000599.3 | AATGGGTTGCAAA ATAGAAATGAGCTT AATCCAGGCCGCA GAGCCAGGGAAGG TGAGTAACTTTAGG AGGGTGCTAGACTT TAGAAGCCAGATA GGAAGA (SEQ ID NO: 982) | TCCCTGGCTCTGC GGCCTGGATTAA GCTCATTTCTATT TTGCAACCCATT (SEQ ID NO: 983) | TCTTCCTATCTG GCTTCTAAAGTC TAGCACCCTCCT AAAGTTACTCAC CT (SEQ ID NO: 984) |
| IGSF3 | NM_001542.2 | AGTGGCTGTGAGAC CTCATTGCGCATTG TCTACTGGAGCTTT AGTCTTCTGAGACG GAGGAAAACTGCT GAATACTCTGGATT CATCTATGTCTACA ATG (SEQ ID NO: 985) | AGAAGACTAAAG CTCCAGTAGACA ATGCGCAATGAG GTCTCACAGCCA CT (SEQ ID NO: 986) | CATTGTAGACAT AGATGAATCCAG AGTATTCAGCAG TTTTCCTCCGTCT C (SEQ ID NO: 987) |

TABLE 1-continued

| Gene | GenBank Accession No. | Target Sequence | Capture Probe Sequence | Reporter Probe Sequence |
|---|---|---|---|---|
| IK | NM_006083.3 | GTCCAAATTCTTGGGTGGTGACATGGAACACACCCATTTGGTGAAAGGCTTGGATTTTGCTCTGCTTCAAAAGGTACGAGCTGAGATTGCCAGCAAAGAG (SEQ ID NO: 988) | AGCCTTTCACCAATGGGTGTGTTCCATGTCACCACCCAAGAATTTGGAC (SEQ ID NO: 989) | CTCTTTGCTGGCAATCTCAGCTCGTACCTTTTGAAGCAGAGCAAAATCCA (SEQ ID NO: 990) |
| IL10 | NM_000572.2 | AAGGATCAGCTGGACAACTTGTTGTTAAAGGAGTCCTTGCTGGAGGACTTTAAGGGTTACCTGGGTTGCCAAGCCTTGTCTGAGATGATCCAGTTTTACC (SEQ ID NO: 991) | AAGTCCTCCAGCAAGGACTCCTTTAACAACAAGTTGTCCAGCTGATCCTT (SEQ ID NO: 992) | GGTAAAACTGGATCATCTCAGACAAGGCTTGGCAACCCAGGTAACCCTTA (SEQ ID NO: 993) |
| IL12A | NM_000882.2 | CTTTCTAGATCAAAACATGCTGGCAGTTATTGATGAGCTGATGCAGGCCCTGAATTTCAACAGTGAGACTGTGCCACAAAAATCCTCCCTTGAAGAACCG (SEQ ID NO: 994) | GGGCCTGCATCAGCTCATCAATAACTGCCAGCATGTTTTGATCTAGAAAG (SEQ ID NO: 995) | CGGTTCTTCAAGGGAGGATTTTTGTGGCACAGTCTCACTGTTGAAATTCA (SEQ ID NO: 996) |
| IL13RA1 | NM_001560.2 | TCTGCACTGGAAGAAGTACGACATCTATGAGAAGCAAACCAAGGAGGAAACCGACTCTGTAGTGCTGATAGAAAACCTGAAGAAAGCCTCTCAGTGATGG (SEQ ID NO: 997) | TTTCCTCCTTGGTTTGCTTCTCATAGATGTCGTACTTCTTCCAGTGCAGA (SEQ ID NO: 998) | CCATCACTGAGAGGCTTTCTTCAGGTTTTCTATCGCACTACAGAGTCGG (SEQ ID NO: 999) |
| IL16 | NM_004513.4 | GGCATCTCCAACATCATCATCCAACGAAGACTCAGCTGCAAATGGTTCTGCTGAAACATCTGCCTTGGACACAGGGTTCTCGCTCAACCTTTCAGAGCTG (SEQ ID NO: 1000) | CAGAACCATTTGCAGCTGAGTCTTCGTTGGATGATGATGTTGGAGATGCC (SEQ ID NO: 1001) | CAGCTCTGAAAGGTTGAGCGAGAACCCTGTGTCCAAGGCAGATGTTTCAG (SEQ ID NO: 1002) |
| IL17RB | NM_018725.3 | TCAATTTTGATGAATGTAAGCTGGGTACTCCGGGCAGATGCCAGCATCCGCTTGTTGAAGGCCACCAAGATTTGTGTGACGGGCAAAAGCAACTTCCAGT (SEQ ID NO: 1003) | CGGATGCTGGCATCTGCCCGGAGTACCCAGCTTACATTCATCAAAATTGA (SEQ ID NO: 1004) | ACTGGAAGTTGCTTTTGCCCGTCACACAAATCTTGGTGGCCTTCAACAAG (SEQ ID NO: 1005) |
| IL4I1 | NM_172374.1 | CAAGGGCACCACTAACAAGGACAAAGCCACCATCATTCACCTTGATTCCGCACATGCCCAACGATGACTTCTGTCCTGGGCTAACCATAAAGGCCATGGG (SEQ ID NO: 1006) | CGGAATCAAGGTGAATGATGGTGGCTTTGTCCTTGTTAGTGGTGC (SEQ ID NO: 1007) | CTTTATGGTTAGCCCAGGACAGAAGTCATCGTTGGGCATGTG (SEQ ID NO: 1008) |

TABLE 1-continued

| Gene | GenBank Accession No. | Target Sequence | Capture Probe Sequence | Reporter Probe Sequence |
|---|---|---|---|---|
| IL6 | NM_000600.1 | TGACAAACAAATTCGGTACATCCTCGACGGCATCTCAGCCCTGAGAAAGGAGACATGTAACAAGAGTAACATGTGTGAAAGCAGCAAAGAGGCACTGGCA (SEQ ID NO: 1009) | CCTTTCTCAGGGCTGAGATGCCGTCGAGGATGTACCGAATTTGTTTGTCA (SEQ ID NO: 1010) | TGCCAGTGCCTCTTTGCTGCTTTCACACATGTTACTCTTGTTACATGTCT (SEQ ID NO: 1011) |
| ING1 | NM_198219.1 | TTGGAAGTGCAGTCAGCAGATGCTGTTGTGAAGCTAATGTCACAATTATGTGCAAAGGTGTGCTTCCTGCTGTATGTGAGCTGTAAAAATGTTACGTGAA (SEQ ID NO: 1012) | CATAATTGTGACATTAGCTTCACAACAGCATCTGCTGACTGCACTTCCAA (SEQ ID NO: 1013) | TTCACGTAACATTTTTACAGCTCACATACAGCAGGAAGCACACCTTTGCA (SEQ ID NO: 1014) |
| INPP5D | NM_005541.3 | ATAATGGCCACATGGATCGAACACTCATGATGTGCCAAGTGCTGTGCTAAGTGCTTTACGAACATTCGTCATATCAGGATGACCTCGAGAGCTGAGGCTC (SEQ ID NO: 1015) | TTAGCACAGCACTTGGCACATCATGAGTGTTCGATCCATGTGGCCATTAT (SEQ ID NO: 1016) | GAGCCTCAGCTCTCGAGGTCATCCTGATATGACGAATGTTCGTAAAGCAC (SEQ ID NO: 1017) |
| IRAK1 | NM_001569.3 | CACAGCCGTGGAAGGACTGGCCCTTGGCAGCTCTGCATCATCGTCGTCAGAGCCACCGCAGATTATCATCAACCCTGCCCGACAGAAGATGGTCCAGAAG (SEQ ID NO: 1018) | CTGACGACGATGATGCAGAGCTGCCAAGGGCCAGTC (SEQ ID NO: 1019) | CATCTTCTGTCGGGCAGGGTTGATGATAATCTGCGGTGGCT (SEQ ID NO: 1020) |
| IRAK2 | NM_001570.3 | GTGTTGGCCGAGGTCCTCACGGGCATCCCTGCAATGGATAACAACCGAAGCCCGGTTTACCTGAAGGACTTACTCCTCAGTGATATTCCAAGCAGCACCG (SEQ ID NO: 1021) | CTTCGGTTGTTATCCATTGCAGGGATGCCCGTGAGGACCTCGG (SEQ ID NO: 1022) | CGGTGCTGCTTGGAATATCACTGAGGAGTAAGTCCTTCAGGTAAACCGGG (SEQ ID NO: 1023) |
| IRAK3 | NM_007199.1 | AGGTAAATATAGATCCTTCTTCAGAAGCTCCAGGGCATTCTTGCAGGAGCAGGCCAGTGGAGAGCAGCTGTTCCTCCAAATTTTCCTGGGATGAATATGA (SEQ ID NO: 1024) | GCTCCTGCAAGAATGCCCTGGAGCTTCTGAAGAAGGATCTATATTTACCT (SEQ ID NO: 1025) | TCATATTCATCCCAGGAAAATTTGGAGGAACAGCTGCTCTCCACTGGCCT (SEQ ID NO: 1026) |
| IRAK4 | NM_016123.1 | GAATTCTCCTTGTAAGCCTTGAAGAAGTATGTGAGAGGGCCACATTGGCTAAAACCTAAAGGTGGCCTCTAGGAGATGAGACCTACCTTCCAGTTGTCAG (SEQ ID NO: 1027) | AGCCAATGTGGCCCTCTCACATACTTCTTCAAGGCTTACAAGGAGAATTC (SEQ ID NO: 1028) | CTGACAACTGGAAGGTAGGTCTCATCTCCTAGAGGCCACCTTTAGGTTTT (SEQ ID NO: 1029) |

TABLE 1-continued

| Gene | GenBank Accession No. | Target Sequence | Capture Probe Sequence | Reporter Probe Sequence |
|---|---|---|---|---|
| IRF1 | NM_002198.1 | CTGTGCGAGTGTAC CGGATGCTTCCACC TCTCACCAAGAACC AGAGAAAAGAAAG AAAGTCGAAGTCC AGCCGAGATGCTA AGAGCAAGGCCAA GAGGAA (SEQ ID NO: 1030) | TTTTCTCTGGTTC TTGGTGAGAGGT GGAAGCATCCGG TACACTCGCACA G (SEQ ID NO: 1031) | TTCCTCTTGGCC TTGCTCTTAGCA TCTCGGCTGGAC TTCGACTTTCTTT C (SEQ ID NO: 1032) |
| IRF4 | NM_002460.1 | GGGCACTGTTTAAA GGAAAGTTCCGAG AAGGCATCGACAA GCCGGACCCTCCCA CCTGGAAGACGCG CCTGCGGTGCGCTT TGAACAAGAGCAA TGACTT (SEQ ID NO: 1033) | AGGGTCCGGCTT GTCGATGCCTTCT CGGAACTTTCCTT TAAACAGTGCCC (SEQ ID NO: 1034) | TTGTTCAAAGCG CACCGCAGGCGC GTCTTCCAGGTG GG (SEQ ID NO: 1035) |
| ISG15 | NM_005101.3 | CCCGGCAGCACGGT CCTGCTGGTGGTGG ACAAATGCGACGA ACCTCTGAGCATCC TGGTGAGGAATAA CAAGGGCCGCAGC AGCACCTACGAGGT ACGGC (SEQ ID NO: 1036) | CTCAGAGGTTCGT CGCATTTGTCCAC CACCAGCAGGAC (SEQ ID NO: 1037) | TGCTGCTGCGGC CCTTGTTATTCCT CACCAGGATG (SEQ ID NO: 1038) |
| ISY1 | NM_020701.2 | GGCAAAACATCAG TGTCTGTGGGTAGT TGGAATCTTCAGTT CCTGTGAGCGTCGG CGTCTTCTGGGCCT GTGGAGTTTCTTGG ACAGGGGCCGCGG GGCT (SEQ ID NO: 1039) | GCTCACAGGAAC TGAAGATTCCAA CTACCCACAGAC ACTGATGTTTTGC C (SEQ ID NO: 1040) | CCCCTGTCCAAG AAACTCCACAGG CCCAGAAGACGC CGAC (SEQ ID NO: 1041) |
| ITGA9 | NM_002207.2 | CATGTCTCCAACCT CCTTTGTATATGGC GAGTCCGTGGACGC AGCCAACTTCATTC AGCTGGATGACCTG GAGTGTCACTTTCA GCCCATCAATATCA CC (SEQ ID NO: 1042) | AGTTGGCTGCGTC CACGGACTCGCC ATATACAAAGGA GGTTGGAGACAT G (SEQ ID NO: 1043) | GGTGATATTGAT GGGCTGAAAGTG ACACTCCAGGTC ATCCAGCTGAAT GA (SEQ ID NO: 1044) |
| ITGAV | NM_002210.2 | TTTCTTCCGATTCC AAACTGGGAGCAC AAGGAGAACCCTG AGACTGAAGAAGA TGTTGGGCCAGTTG TTCAGCACATCTAT GAGCTGAGAAACA ATGGTC (SEQ ID NO: 1045) | TCTTCAGTCTCAG GGTTCTCCTTGTG CTCCCAGTTTGGA ATCGGAAGAAA (SEQ ID NO: 1046) | GACCATTGTTTC TCAGCTCATAGA TGTGCTGAACAA CTGGCCCAACAT CT (SEQ ID NO: 1047) |
| ITGAX | NM_000887.3 | CCCCTCAGCCTGTT GGCTTCTGTTCACC AGCTGCAAGGGTTT ACATACACGGCCAC CGCCATCCAAAATG TCGTGCACCGATTG TTCCATGCCTCATA TG (SEQ ID NO: 1048) | GTGTATGTAAAC CCTTGCAGCTGGT GAACAGAAGCCA ACAGGCTGAGGG (SEQ ID NO: 1049) | CATATGAGGCAT GGAACAATCGGT GCACGACATTTT GGATGGCGGTGG CC (SEQ ID NO: 1050) |

TABLE 1-continued

| Gene | GenBank Accession No. | Target Sequence | Capture Probe Sequence | Reporter Probe Sequence |
|---|---|---|---|---|
| ITGB2 | NM_000211.2 | CATCGACCTGTACTATCTGATGGACCTCTCCTACTCCATGCTTGATGACCTCAGGAATGTCAAGAAGCTAGGTGGCGACCTGCTCCGGGCCCTCAACGAG (SEQ ID NO: 1051) | GGTCATCAAGCATGGAGTAGGAGAGGTCCATCAGATAGTAC (SEQ ID NO: 1052) | CGGAGCAGGTCGCCACCTAGCTTCTTGACATTCCTGA (SEQ ID NO: 1053) |
| ITPKB | NM_002221.3 | GTGGCCTCCTGGCATCATTTGTTATTGCCTCTGAAACAAGCCTTACTGCCTGGAGGGCTTAGATTCCTGCTTCTCCAATGTAGTGTGGGTATCTTGTAGG (SEQ ID NO: 1054) | GGCAGTAAGGCTTGTTTCAGAGGCAATAACAAATGATGCCAGGAGGCCAC (SEQ ID NO: 1055) | CCTACAAGATACCCACACTACATTGGAGAAGCAGGAATCTAAGCCCTCCA (SEQ ID NO: 1056) |
| JAK1 | NM_002227.1 | GAGAACACCAAGCTCTGGTATGCTCCAAATCGCACCATCACCGTTGATGACAAGATGTCCCTCCGGCTCCACTACCGGATGAGGTTCTATTTCACCAATT (SEQ ID NO: 1057) | TCATCAACGGTGATGGTGCGATTTGGAGCATACCAGAGCTTGGTGTTCTC (SEQ ID NO: 1058) | AATTGGTGAAATAGAACCTCATCCGGTAGTGGAGCCGGAGGGACATCTTG (SEQ ID NO: 1059) |
| JAK2 | NM_004972.2 | CTCCTCCCGCGACGGCAAATGTTCTGAAAAAGACTCTGCATGGGAATGGCCTGCCTTACGATGACAGAAATGGAGGGAACATCCACCTCTTCTATATATC (SEQ ID NO: 1060) | GCCATTCCCATGCAGAGTCTTTTTCAGAACATTTGCCGTCGCGGGAGGAG (SEQ ID NO: 1061) | GATATATAGAAGAGGTGGATGTTCCCTCCATTTCTGTCATCGTAAGGCAG (SEQ ID NO: 1062) |
| JAK3 | NM_000215.2 | GTGCTGCTGAAGGTCATGGATGCCAAGCACAAGAACTGCATGGAGTCATTCCTGGAAGCAGCGAGCTTGATGAGCCAAGTGTCGTACCGGCATCTCGTGC (SEQ ID NO: 1063) | AATGACTCCATGCAGTTCTTGTGCTTGGCATCCATGACCTTCAGCAG (SEQ ID NO: 1064) | CGGTACGACACTTGGCTCATCAAGCTCGCTGCTTCCAGG (SEQ ID NO: 1065) |
| KCNJ1 | NM_153766.1 | GGAGGTGCTTTGGGGCTACCGTTTTGCTCCCATAGTATCCAAGACAAAGGAAGGGAAATACCGAGTGGATTTCCATAACTTTAGCAAGACAGTGGAAGTG (SEQ ID NO: 1066) | CCTTTGTCTTGGATACTATGGGAGCAAAACGGTAGCCCCAAAGCACCTC (SEQ ID NO: 1067) | CACTTCCACTGTCTTGCTAAAGTTATGGAAATCCACTCGGTATTTCCCTT (SEQ ID NO: 1068) |
| KCNK12 | NM_022055.1 | CCAGGGGCTCTACCGCCTGGGCAACTTCCTCTTCATCCTGCTCGGCGTGTGCTGCATTTACTCGCTCTTCAACGTCATCTCCATCCTCATCAAGCAGGTG (SEQ ID NO: 1069) | ACACGCCGAGCAGGATGAAGAGGAAGTTGCCCAGGCGGTA (SEQ ID NO: 1070) | CACCTGCTTGATGAGGATGGAGATGACGTTGAAGAGCGAGTAAATGCAGC (SEQ ID NO: 1071) |

TABLE 1-continued

| Gene | GenBank Accession No. | Target Sequence | Capture Probe Sequence | Reporter Probe Sequence |
|---|---|---|---|---|
| KCNMA1 | NM_001014797.1 | TATTGAGTACCTCAAGCGGGAATGGGAGACGCTTCATAACTTCCCCAAAGTGTCCATATTGCCTGGTACGCCATTAAGTCGGGCTGATTTAAGGGCTGTC (SEQ ID NO: 1072) | CTTTGGGGAAGTTATGAAGCGTCTCCCATTCCCGCTTGAGGTACTCAATA (SEQ ID NO: 1073) | GACAGCCCTTAAATCAGCCCGACTTAATGGCGTACCAGGCAATATGGACA (SEQ ID NO: 1074) |
| KCNQ3 | NM_004519.2 | GTATGAGACTGTCTCGGGAGACTGGCTTCTGTTACTGGAGACATTTGCTATTTTCATCTTTTGGAGCCGAGTTTGCTTTGAGGATCTGGGCTGCTGGATGT (SEQ ID NO: 1075) | TAGCAAATGTCTCCAGTAACAGAAGCCAGTCTCCCGAGACAGTCTCATAC (SEQ ID NO: 1076) | ACATCCAGCAGCCCAGATCCTCAAAGCAAACTCGGCTCCAAAGATGAAAA (SEQ ID NO: 1077) |
| KCP | NM_001135914.1 | TATGCCAATGGGCAGAACTTCACGGATGCAGACAGCCCTTGCCATGCCTGCCACTGTCAGGATGGAACTGTGACATGCTCCTTGGTTGACTGCCCTCCCA (SEQ ID NO: 1078) | CAGGCATGGCAAGGGCTGTCTGCATCCGTGAAGTTCTG (SEQ ID NO: 1079) | CAGTCAACCAAGGAGCATGTCACAGTTCCATCCTGACAGTGG (SEQ ID NO: 1080) |
| KDM4C | NM_015061.2 | ATTCTCCACCCAATGCCTTCCTTGAAGAGGATGGAACAAGTCTCCTTATTTCCTGTGCAAAGTGCTGCGTACGGGTTCATGCAAGTTGTTATGGTATTCC (SEQ ID NO: 1081) | AATAAGGAGACTTGTTCCATCCTCTTCAAGGAAGGCATTTGGGTGGAGAAT (SEQ ID NO: 1082) | GGAATACCATAACAACTTGCATGAACCCGTACGCAGCACTTTGCACAGGA (SEQ ID NO: 1083) |
| KDR | NM_002253.2 | CAATCACACAATTAAAGCGGGGCATGTACTGACGATTATGGAAGTGAGTGAAAGAGACACAGGAAATTACACTGTCATCCTTACCAATCCCATTTCAAAG (SEQ ID NO: 1084) | CACTCACTTCCATAATCGTCAGTACATGCCCCGCTTTAATTGTGTGATTG (SEQ ID NO: 1085) | CTTTGAAATGGGATTGGTAAGGATGACAGTGTAATTTCCTGTGTCTCTTT (SEQ ID NO: 1086) |
| KIAA1147 | NM_001080392.1 | CCAGGTGGGAGTGGAATTCAGGTTTGGGGCTCGTTGGTATCCATGCAAAATATGACAAAGGCCTGTTCAAGAGGGCATTTCAATTCTGTAGGCTCAGCA (SEQ ID NO: 1087) | TTTTGCATGGATACCAACGAGCCCCAAACCTGAATTCCACTCCCACCTGG (SEQ ID NO: 1088) | TGCTGAGCCTACAGAATTGAAATGCCCTCTTGAACAGGCCTTTGTCATA (SEQ ID NO: 1089) |
| KIAA1274 | NM_014431.2 | AGGAAAGCCTGTCTTTGGTTAGGCTCGTGTACTTCTGCAGGAAAAAAAAAAAGGATGTGTCATTGGTCATGATATTTGAAAAGGGGAGGAGGCCGAAGT (SEQ ID NO: 1090) | TTTTTTTTTCCTGCAGAAGTACACGAGCCTAACCAAAGACAGGCTTTCCT (SEQ ID NO: 1091) | ACTTCGGCCTCCTCCCCTTTTCAAATATCATGACCAATGCACACATCCTTT (SEQ ID NO: 1092) |

TABLE 1-continued

| Gene | GenBank Accession No. | Target Sequence | Capture Probe Sequence | Reporter Probe Sequence |
|---|---|---|---|---|
| KIF11 | NM_004523.3 | CAGACCATTTAATTTGGCAGAGCGGAAAGCTAGCGCCCATTCAATAGTAGAATGTGATCCTGTACGAAAAGAAGTTAGTGTACGAACTGGAGGATTGGCT (SEQ ID NO: 1093) | CTACTATTGAATGGGCGCTAGCTTTCCGCTCTGCCAAATTAAATGGTCTG (SEQ ID NO: 1094) | AGCCAATCCTCCAGTTCGTACACTAACTTCTTTTCGTACAGGATCACATT (SEQ ID NO: 1095) |
| KIF14 | NM_014875.2 | TGATCGAGCAATCCAGTCACTTACTATTCAGACTGCATGTGCTTTTGAGCAGCTAGTAGTGCTAATGAAACACTGGCTGAGTGATTTACTGCCTTGTACC (SEQ ID NO: 1096) | GCTCAAAAGCACATGCAGTCTGAATAGTAAGTGACTGGATTGCTCGATCA (SEQ ID NO: 1097) | GGTACAAGGCAGTAAATCACTCAGCCAGTGTTTCATTAGCACTACTAGCT (SEQ ID NO: 1098) |
| KIF15 | NM_020242.2 | AACCACCTCAAGTTTCTGATGAACATTCTGCATCCATATACACCCTGTGACAGTCAGCAGTCTGCTATTAAGTGGCCTACTTCAAGGCTTTGAATCAACT (SEQ ID NO: 1099) | TCACAGGGTGTATATGGATGCAGAATGTTCATCAGAAACTTGAGGTGGTT (SEQ ID NO: 1100) | AGTTGATTCAAAGCCTTGAAGTAGGCCACTTAATAGCAGACTGCTGACTG (SEQ ID NO: 1101) |
| KIF18A | NM_031217.3 | CATAGACTTGCAATGTTGAAAACTCGTCGCTCCTACCTGGAGAAAAGGAGGGAGGAGGAATTGAAGCAATTTGATGAGAATACTAATTGGCTCCATCGTG (SEQ ID NO: 1102) | CTCCTTTTCTCCAGGTAGGAGCGACGAGTTTTCAACATTGCAAGTCTATG (SEQ ID NO: 1103) | CACGATGGAGCCAATTAGTATTCTCATCAAATTGCTTCAATTCCTCCTCC (SEQ ID NO: 1104) |
| KIF18B | NM_001080443.1 | TCCAAGCAGCCAACCTCCTGACGCCCGACATGATCACAGAGTTTGAGACCCTACAGCAGCTGGTGCAAGAGGAAAAAATTGAGCCTGGGGCAGAGGCCTT (SEQ ID NO: 1105) | GGTCTCAAACTCTGTGATCATGTCGGGCGTCAGGAGGTTGG (SEQ ID NO: 1106) | CCAGGCTCAATTTTTTCCTCTTGCACCAGCTGCTGTAG (SEQ ID NO: 1107) |
| KIF20A | NM_005733.2 | GCAGGCTTCCCTATCTGATTGGCCGAACGAACGCAGCGCGTAATTTAAAATATTGTATCTGTAACAAAGCTGCACCTCGTGGGCGGAGTTGTGCTCTGCG (SEQ ID NO: 1108) | TTTTAAAATTACGCGCTGCGTTCGTTCGGCCAATCAGATAGGGAAGCCTGC (SEQ ID NO: 1109) | CGCAGAGCACAACTCCGCCCACGAGGTGCAGCTTTGTTACAGATACAATA (SEQ ID NO: 1110) |
| KIF23 | NM_138555.1 | TGTGTGGATGATTTCTCGAAAGCCATGCCAGAAGCAGTCTTCCAGGTCATCTTGTAGAACTCCAGCTTTGTTGAAAATCACGGACCTCAGCTACATCATA (SEQ ID NO: 1111) | ATGACCTGGAAGACTGCTTCTGGCATGGCTTTCGAGAAATCATCCACACA (SEQ ID NO: 1112) | TATGATGTAGCTGAGGTCCGTGATTTTCAACAAAGCTGGAGTTCTACAAG (SEQ ID NO: 1113) |

TABLE 1-continued

| Gene | GenBank Accession No. | Target Sequence | Capture Probe Sequence | Reporter Probe Sequence |
|---|---|---|---|---|
| KIF2C | NM_006845.3 | CCTGCTCTAACGGG GCGCTGATTCCAGG CAATTTATCCAAGG AAGAGGAGGAACT GTCTTCCCAGATGT CCAGCTTTAACGAA GCCATGACTCAGAT CAG (SEQ ID NO: 1114) | CTCCTCTTCCTTG GATAAATTGCCT GGAATCAGCGCC CCGTTAGAGCAG G (SEQ ID NO: 1115) | CTGATCTGAGTC ATGGCTTCGTTA AAGCTGGACATC TGGGAAGACAGT TC (SEQ ID NO: 1116) |
| KIF4A | NM_012310.3 | GGAGCAAAGCATG GACATCGAGGATCT AAAATATTGTTCAG AGCATTCTGTGAAT GAGCATGAGGATG GTGATGGTGATGAT GATGAGGGGGATG ACGAG (SEQ ID NO: 1117) | CAGAATGCTCTG AACAATATTTTAG ATCCTCGATGTCC ATGCTTTGCTCC (SEQ ID NO: 1118) | CCCTCATCATCA TCACCATCACCA TCCTCATGCTCA TTCA (SEQ ID NO: 1119) |
| KIF6 | NM_145027.4 | GGACTTCAGCATTT TGGGGAAAAGATC CAGTTTGCTCCACA AGAAAATAGGAAT GAGAGAGGAAATG TCATTAGGATGCCA GGAGGCTTTTGAAA TCTTC (SEQ ID NO: 1120) | CTATTTTCTTGTG GAGCAAACTGGA TCTTTTCCCCAAA ATGCTGAAGTCC (SEQ ID NO: 1121) | GAAGATTTCAAA AGCCTCCTGGCA TCCTAATGACAT TCCTCTCTCATT C (SEQ ID NO: 1122) |
| KLHL5 | NM_015990.4 | GTGGGGAGAGATT GCTAAAAAGGAGT TTCCTTCTAGGGTG ATGAAAATGTTCTG GAACTACTTATTGG GGATGATTGCACAA CATGGTGAAGGTAC TCAA (SEQ ID NO: 1123) | ACATTTTCATCAC CCTAGAAGGAAA CTCCTTTTTAGCA ATCTCTCCCCAC (SEQ ID NO: 1124) | TTGAGTACCTTC ACCATGTTGTGC AATCATCCCCAA TAAGTAGTTCCA GA (SEQ ID NO: 1125) |
| KPNA2 | NM_002266.2 | TGATGATCCAGAAG TATTAGCAGATACC TGCTGGGCTATTTC CTACCTTACTGATG GTCCAAATGAACG AATTGGCATGGTGG TGAAAACAGGAGT TGTG (SEQ ID NO: 1126) | TAAGGTAGGAAA TAGCCCAGCAGG TATCTGCTAATAC TTCTGGATCATCA (SEQ ID NO: 1127) | CACAACTCCTGT TTTCACCACCAT GCCAATTCGTTC ATTTGGACCATC AG (SEQ ID NO: 1128) |
| KRAS | NM_033360.2 | CATGGACTGTGTCC CCACGGTCATCCAG TGTTGTCATGCATT GGTTAGTCAAAATG GGGAGGGACTAGG GCAGTTTGGATAGC TCAACAAGATACA ATCT (SEQ ID NO: 1129) | GACTAACCAATG CATGACAACACT GGATGACCGTGG GGACACAGTCCA TG (SEQ ID NO: 1130) | AGATTGTATCTT GTTGAGCTATCC AAACTGCCCTAG TCCCTCCCCATT TT (SEQ ID NO: 1131) |
| KYNU | NM_003937.2 | TAAGTGGGCCAAA ATAGCAGCCTATGG TCATGAAGTGGGG AAGCGTCCTTGGAT TACAGGAGATGAG AGTATTGTAGGCCT TATGAAGGACATTG TAGGA (SEQ ID NO: 1132) | AAGGACGCTTCC CCACTTCATGACC ATAGGCTGCTATT TTGGCCCACTTA (SEQ ID NO: 1133) | TCCTACAATGTC CTTCATAAGGCC TACAATACTCTC ATCTCCTGTAAT CC (SEQ ID NO: 1134) |

TABLE 1-continued

| Gene | GenBank Accession No. | Target Sequence | Capture Probe Sequence | Reporter Probe Sequence |
|---|---|---|---|---|
| LAMB1 | NM_002291.2 | TTGCCAGGAGCTGCTACCAAGATCCTGTTACTTTACAGCTTGCCTGTGTTTGTGATCCTGGATACATTGGTTCCAGATGTGACGACTGTGCCTCAGGATA (SEQ ID NO: 1135) | AACACAGGCAAGCTGTAAAGTAACAGGATCTTGGTAGCAGCTCCTGGCAA (SEQ ID NO: 1136) | TATCCTGAGGCACAGTCGTCACATCTGGAACCAATGTATCCAGGATCACA (SEQ ID NO: 1137) |
| LAMP3 | NM_014398.3 | GGTCTCTGCCTTATGGGTATGGGTGTCTATAAAATCCGCCTAAGGTGTCAATCATCTGGATACCAGAGAATCTAATTGTTGCCCGGGGGGAATGAAAATA (SEQ ID NO: 1138) | TGACACCTTAGGCGGATTTTATAGACACCCATACCCATAAGGCAGAGACC (SEQ ID NO: 1139) | TATTTTCATTCCCCCCGGGCAACAATTAGATTCTCTGGTATCCAGATGAT (SEQ ID NO: 1140) |
| LANCL1 | NM_006055.1 | AATGCCTATGCCTTCCTGACACTCTACAACCTCACACAGGACATGAAGTACCTGTATAGGGCCTGTAAGTTTGCTGAATGGTGCTTAGAGTATGGAGAAC (SEQ ID NO: 1141) | TACTTCATGTCCTGTGTGAGGTTGTAGAGTGTCAGGAAGGCATAG (SEQ ID NO: 1142) | GTTCTCCATACTCTAAGCACCATTCAGCAAACTTACAGGCCCTATACAGG (SEQ ID NO: 1143) |
| LAT | NM_001014987.1 | TGTGTAATAGAATAAAGGCCTGCGTGTGTCTGTGTTGAGCGTGCGTCTGTGTGTGCCTGTGTGCGAGTCTGAGTCAGAGATTTGGAGATGTCTCTGTGTG (SEQ ID NO: 1144) | ACAGACGCACGCTCAACACAGACACACGCAGGCCTTTATTCTATTACACA (SEQ ID NO: 1145) | CACACAGAGACATCTCCAAATCTCTGACTCAGACTCGCACACAGGCACAC (SEQ ID NO: 1146) |
| LAT2 | NM_014146.3 | TGCAGAGCTGATTAACAGTGTTGTGACTGTCTCATGGGAAGAGCTGGGGCCCAGAGGGACCTTGAGTCAGAAATGTTGCCAGAAAAAGTATCTCCTCCA (SEQ ID NO: 1147) | CCCCAGCTCTTCCCATGAGACAGTCACAACACTGTTTAATCAG (SEQ ID NO: 1148) | GAGATACTTTTTCTGGCAACATTTCTGACTCAAGGTCCCTCTGGG (SEQ ID NO: 1149) |
| LDHA | NM_005566.1 | CAGAATGGAATCTCAGACCTTGTGAAGGTGACTCTGACTTCTGAGGAAGAGGCCCGTTTGAAGAAGAGTGCAGATACACTTTGGGGGATCCAAAAGGAGC (SEQ ID NO: 1150) | TCTTCCTCAGAAGTCAGAGTCACCTTCACAAGGTCTGAGATTCCATTCTG (SEQ ID NO: 1151) | GCTCCTTTTGGATCCCCCAAAGTGTATCTGCACTCTTCTTCAAACGGGCC (SEQ ID NO: 1152) |
| LHFPL3 | NM_199000.2 | TGTGCTTGGCTGTATGATTTTCCCTGATGGCTGGGACTCAGATGAAGTAAAACGGATGTGTGGAGAAAAGACAGACAAGTACACTCTTGGGGCTTGCTCA (SEQ ID NO: 1153) | TTACTTCATCTGAGTCCCAGCCATCAGGGAAAATCATACAGCCAAGCACA (SEQ ID NO: 1154) | CCAAGAGTGTACTTGTCTGTCTTTTCTCCACACATCCGTT (SEQ ID NO: 1155) |

TABLE 1-continued

| Gene | GenBank Accession No. | Target Sequence | Capture Probe Sequence | Reporter Probe Sequence |
|---|---|---|---|---|
| LHX2 | NM_004789.3 | TAGAGGCTTTGAGC AACTAACTAACCAC ATTTTAGGATCTCG CCTGGAAACAGAG GTAAAAAAAGAA GTGTGCGCCCGGCT AATGCAGCGGTGTG GACC (SEQ ID NO: 1156) | TTTCCAGGCGAG ATCCTAAAATGT GGTTAGTTAGTTG CTCAAAGCCTCTA (SEQ ID NO: 1157) | ACACCGCTGCAT TAGCCGGGCGCA CACTTCTTTTTTT TACCTCTG (SEQ ID NO: 1158) |
| LIMA1 | NM_001113547.1 | AACTACATCCTGAA CTCGACGTCCTGAG GTATAATACAACAG AGCACTTTTTGAGG CAATTGAAAAACC AACCTACACTCTTC GGTGCTTAGAGAG ATCT (SEQ ID NO: 1159) | AAAGTGCTCTGTT GTATTATACCTCA GGACGTCGAGTT CAGGATGTAGTT (SEQ ID NO: 1160) | AGATCTCTCTAA GCACCGAAGAGT GTAGGTTGGTTT TTCAATTGCCTC AA (SEQ ID NO: 1161) |
| LIMD1 | NM_014240.2 | AAGGCAAGTCTCA GGAACCCATGCAG GTACATCGCTTGCA CCTGTTTTTAGCTT ATTTAATGACGGGC TTTTGGGAAGAGCT GCCCGCATACTGAG AGAC (SEQ ID NO: 1162) | TAAAACAGGTG CAAGCGATGTAC CTGCATGGGTTCC TGAGACTTGCCTT (SEQ ID NO: 1163) | TCTCTCAGTATG CGGGCAGCTCTT CCCAAAAGCCCG TCATTAAATAAG C (SEQ ID NO: 1164) |
| LMAN2 | NM_006816.2 | CTTTTGTTGTTGGG GTCTGTGACTGCGG ATATAACTGACGGC AACAGTGAACATCT CAAGCGGGAGCAT TCGCTCATTAAGCC CTACCAAGGGGTCG GTT (SEQ ID NO: 1165) | TCACTGTTGCCGT CAGTTATATCCGC AGTCACAGACCC CAACAACAAAAG (SEQ ID NO: 1166) | CCTTGGTAGGGC TTAATGAGCGAA TGCTCCCGCTTG AGATGT (SEQ ID NO: 1167) |
| LMO2 | NM_005574.3 | AAGCATTTCTGTGT AGGTGACAGATAC CTCCTCATCAACTC TGACATAGTGTGCG AACAGGACATCTAC GAGTGGACTAAGA TCAATGGGATGATA TAGG (SEQ ID NO: 1168) | ACTATGTCAGAG TTGATGAGGAGG TATCTGTCACCTA CACAGAAATGCT T (SEQ ID NO: 1169) | CCTATATCATCC CATTGATCTTAG TCCACTCGTAGA TGTCCTGTTCGC AC (SEQ ID NO: 1170) |
| LOC643529 | XR_041961.1 | CCATTATGTCTCCA TATCAGACTCTGTT GGGTACAAGTGAC ACAGAAAGTCATCT CAAACTAGCTGAA ACACAAAAGCGCA GGAAGGCGGAAGG GAAGGC (SEQ ID NO: 1171) | ACTTTCTGTGTCA CTTGTACCCAACA GAGTCTGATATG GAGACATAATGG (SEQ ID NO: 1172) | CGCCTTCCTGCG CTTTTGTGTTTCA GCTAGTTTGAGA TG (SEQ ID NO: 1173) |
| LOXL2 | NM_002318.2 | GGTTTGCCATCCTC CTCTAGTTAAAAGT AAGGGGGAAAAGA GTAAACGCGCGACT CCAGCGCGCGGCTA CCTACGCTTGGTGC TTGCTTTCTCCAGC CAT (SEQ ID NO: 1174) | CGCGTTTACTCTT TTCCCCCTTACTT TTAACTAGAGGA GGATGGCAAACC (SEQ ID NO: 1175) | TGGAGAAAGCA AGCACCAAGCGT AGGTAGCCGCGC GCTGGAGTCG (SEQ ID NO: 1176) |

TABLE 1-continued

| Gene | GenBank Accession No. | Target Sequence | Capture Probe Sequence | Reporter Probe Sequence |
|---|---|---|---|---|
| LPCAT3 | NM_005768.5 | TGCCACCGGCAACTACGATATCAAGTGGACAATGCCACATTGTGTTCTGACTTTGAAGCTGATTGGTTTGGCTGTTGACTACTTTGACGGAGGGAAAGAT (SEQ ID NO: 1177) | TCAGAACACAATGTGGCATTGTCCACTTGATATCGTAGTTGCCGGTGGCA (SEQ ID NO: 1178) | ATCTTTCCCTCCGTCAAAGTAGTCAACAGCCAAACCAATCAGCTTCAAAG (SEQ ID NO: 1179) |
| LRMP | NM_006152.2 | TCCATCAGAAAGGCTAATAAGGCCCTCTGGCTCTCTATTGCATTCATTGTACTGTTTGCAGCTTTGATGAGCTTCCTCACAGGCCAATTATTCCAGAAGT (SEQ ID NO: 1180) | ACAATGAATGCAATAGAGAGCCAGAGGGCCTTATTAGCCTTTCTGATGGA (SEQ ID NO: 1181) | ACTTCTGGAATAATTGGCCTGTGAGGAAGCTCATCAAAGCTGCAAACAGT (SEQ ID NO: 1182) |
| LRP3 | NM_002333.3 | GCCAGGAGGCCTTCCGCCTCTGTGGCTCCGCCATCCCACCTGCCTTCATCTCTGCCCGCGACCATGTCTGGATTTTCTTCCACTCAGACGCCTCCAGCTC (SEQ ID NO: 1183) | GATGAAGGCAGGTGGGATGGCGGAGCCACAGAGGCGGAAG (SEQ ID NO: 1184) | CTGGAGGCGTCTGAGTGGAAGAAAATCCAGACATGGTCGCGGGCAGA (SEQ ID NO: 1185) |
| LRPPRC | NM_133259.3 | AAAATGTGAGTGTGGTACAGAGGAAATAGGTAAGACCCCCTTATCTAGCCCTCTCGGCAGCAGCGGGGGGGTGTTACAAAGGACTAGCTGTTCAAATATC (SEQ ID NO: 1186) | GGCTAGATAAGGGGGTCTTACCTATTTCCTCTGTACCACACTCACATTTT (SEQ ID NO: 1187) | GATATTTGAACAGCTAGTCCTTTGTAACACCCCCCGCTGCTGCCGAGAG (SEQ ID NO: 1188) |
| LRRC15 | NM_001135057.2 | CTGCCTTCTCTGGCTTTTCCTGCTATACACATATTCACATGGCGCTCAAGAAGTTAGGCTCATGGCAACGTGTGTCTTTCTCTGGACAACTGGCCCAGTTT (SEQ ID NO: 1189) | TCTTGAGCGCCATGTGAATATGTGTATAGCAGGAAAGCCAGAGAAGGCAG (SEQ ID NO: 1190) | AAACTGGGCCAGTTGTCCAGAGAAAGACACACGTTGCCATGAGCCTAACT (SEQ ID NO: 1191) |
| LRRC33 | NM_198565.1 | GTGTGCCAAGACTCGAAATTCGGTCCGCACACAACAGGACACTTTCTCTGCCAGCTTTCAAGATGTGATGCAGAGGCCAAGTCTGACGAATTGAAGTTTC (SEQ ID NO: 1192) | CAGAGAAAGTGTCCTGTTGTGTGCGGACCGAATTTCGAGTCTTGGCACAC (SEQ ID NO: 1193) | GAAACTTCAATTCGTCAGACTTGGCCTCTGCATCACATCTTGAAAGCTGG (SEQ ID NO: 1194) |
| LTBP2 | NM_000428.2 | CATCTCTCCCAGCTTAGCCTCTGGCTGTAAGCTTCGGTCATTGCCTCCATGCCCTTGCTTGGCTCAAGCACCACCAATCGCTTTAATGCTTCAGCCACCG (SEQ ID NO: 1195) | ATGGAGGCAATGACCGAAGCTTACAGCCAGAGGCTAAGCTGGGAGAGATG (SEQ ID NO: 1196) | CGGTGGCTGAAGCATTAAAGCGATTGGTGGTGCTTGAGCCAAGCAAGGGC (SEQ ID NO: 1197) |

TABLE 1-continued

| Gene | GenBank Accession No. | Target Sequence | Capture Probe Sequence | Reporter Probe Sequence |
|---|---|---|---|---|
| LYPD6B | NM_177964.3 | AAACTGTGTGAACGGTGAACTTTGGAGTGAAGATCAATCTTGCACTTGGTGAAGAGTGCACATTGGACCTCAAGGCGAAAGCCAGTGGTTTGCTTGGATA (SEQ ID NO: 1198) | ACCAAGTGCAAGATTGATCTTCACTCCAAAGTTCACCGTTCACACAGTTT (SEQ ID NO: 1199) | AAGCAAACCACTGGCTTTCGCCTTGAGGTCCAATGTGCACTCTTC (SEQ ID NO: 1200) |
| LYZ | NM_000239.2 | ATGATGGCAAAACCCCAGGAGCAGTTAATGCCTGTCATTTATCCTGCAGTGCTTTGCTGCAAGATAACATCGCTGATGCTGTAGCTTGTGCAAAGAGGGT (SEQ ID NO: 1201) | ACTGCAGGATAAATGACAGGCATTAACTGCTCCTGGGGTTTTGCCATCAT (SEQ ID NO: 1202) | ACCCTCTTTGCACAAGCTACAGCATCAGCGATGTTACTTGCAGCAAAGC (SEQ ID NO: 1203) |
| MACROD2 | NM_080676.5 | CTATAGAGGTGACATCACATTGCTAGAGGTAGATGCTATAGTCAATGCCGCAAATGCCAGTCTTCTTGGAGGAGGAGGTGTGGATGGCTGTATTCATAGA (SEQ ID NO: 1204) | CGGCATTGACTATAGCATCTACCTCTAGCAATGTGATGTCACCTCTATAG (SEQ ID NO: 1205) | TCTATGAATACAGCCATCCACACCTCCTCCTCCAAGAAGACTGGCATTTG (SEQ ID NO: 1206) |
| MAL | NM_002371.2 | GCCTTCGCGTCCGGGTTGGGAGCTTGCTGTGTCTAACCTCCAACTGCTGTGCTGTCTGCTAGGGTCACCTCCTGTTTGTGAAAGGGGACCTTCTTGTTCG (SEQ ID NO: 1207) | ACAGCAGTTGGAGGTTAGACACAGCAAGCTCCCAACCCGGACGCGAAG (SEQ ID NO: 1208) | CGAACAAGAAGGTCCCCTTTCACAAACAGGAGGTGACCCTAGCAGACAGC (SEQ ID NO: 1209) |
| MALT1 | NM_006785.2 | AGTGTTGATGGCGTCTCTGAATCCAAGTTGCAAATCTGTGTTGAACCAACTTCCCAAAAGCTGATGCCAGGCAGCACATTGGTTTTACAGTGTGTTGCTG (SEQ ID NO: 1210) | GTTGGTTCAACACAGATTTGCAACTTGGATTCAGAGACGCCATCAACACT (SEQ ID NO: 1211) | CAGCAACACACTGTAAAACCAATGTGCTGCCTGGCATCAGCTTTTGGGAA (SEQ ID NO: 1212) |
| MAML3 | NM_018717.4 | TGGAAGCCATCAACAATTTGCCCAGTAACATGCCACTGCCTTCAGCTTCTCCTCTTCACCAACTTGACCTGAAACCTTCTTTGCCCTTGCAGAACAGTGG (SEQ ID NO: 1213) | AGAAGCTGAAGGCAGTGGCATGTTACTGGGCAAATTGTTGATGGCTTCCA (SEQ ID NO: 1214) | CCACTGTTCTGCAAGGGCAAAGAAGGTTTCAGGTCAAGTTGGTGAAGAGG (SEQ ID NO: 1215) |
| MAP3K1 | NM_005921.1 | ACTTCAGAGACTTCTCCAGCCAGTTGTAGACACCATCCTAGTCAAATGTGCAGATGCCAATAGCCGCACAAGTCAGCTGTCCATATCAACACTGTTGGAA (SEQ ID NO: 1216) | CACATTTGACTAGGATGGTGTCTACAACTGGCTGGAGAAGTCTCTGAAGT (SEQ ID NO: 1217) | TTCCAACAGTGTTGATATGGACAGCTGACTTGTGCGGCTATTGGCATCTG (SEQ ID NO: 1218) |

TABLE 1-continued

| Gene | GenBank Accession No. | Target Sequence | Capture Probe Sequence | Reporter Probe Sequence |
|---|---|---|---|---|
| MAP3K8 | NM_005204.2 | CTGGCTACTTCAATCTTGTTCGGGGACCACCAACGCTTGAATATGGCTGAAGGATGCCATGTTTGCTCTAAATTAAGACAGCATTGATCTCCTGGAGGCT (SEQ ID NO: 1219) | TCAGCCATATTCAAGCGTTGGTGGTCCCCGAACAAGATTGAAGTAGCCAG (SEQ ID NO: 1220) | AGCCTCCAGGAGATCAATGCTGTCTTAATTTAGAGCAAACATGGCATCCT (SEQ ID NO: 1221) |
| MAP4K4 | NM_004834.3 | GATGCCTACATCAGTAGCATATATTCGATCCAATCAGACAATGGGCTGGGGAGAGAAGGCCATAGAGATCCGATCTGTGGAAACTGGTCACTTGGATGGT (SEQ ID NO: 1222) | CCCAGCCCATTGTCTGATTGGATCGAATATATGCTACTGATGTAGGCATC (SEQ ID NO: 1223) | CAAGTGACCAGTTTCCACAGATCGGATCTCTATGGCCTTCTCTC (SEQ ID NO: 1224) |
| MAPK10 | NM_002753.2 | GTATTCATACAGCACTACTTACTTAGAGATGCTACTGTCAGTGTCCTCAGGGCTCTACCAAGACATAATGCACTGGGGTACCACATGGTCCATTTCATGT (SEQ ID NO: 1225) | CTGAGGACACTGACAGTAGCATCTCTAAGTAAGTAGTGCTGTATGAATAC (SEQ ID NO: 1226) | ACATGAAATGGACCATGTGGTACCCCAGTGCATTATGTCTTGGTAGAGCC (SEQ ID NO: 1227) |
| MAPKAPK5 | NM_003668.2 | GCGAAGAAAGATCATGACAGGCAGTTTTGAGTTCCCAGAGGAAGAGTGGAGTCAGATCTCAGAGATGGCCAAAGATGTTGTGAGGAAGCTCCTGAAGGTC (SEQ ID NO: 1228) | TCCACTCTTCCTCTGGGAACTCAAAACTGCCTGTCATGATCTTTCTTCGC (SEQ ID NO: 1229) | GACCTTCAGGAGCTTCCTCACAACATCTTTGGCCATCTCTGAGATCTGAC (SEQ ID NO: 1230) |
| MARCKS | NM_002356.5 | CCACCACCCCCACCCCCCTCCCTCCGGTGTGTGTGCCGCTGCCGCTGTTGCCGCCGCCGCTGCTGCTGCTCGCCCCGTCGTTACACCAACCCGAGGCTCT (SEQ ID NO: 1231) | CAACAGCGGCAGCGGCACACACACCGGAGGGAGGG (SEQ ID NO: 1232) | TGTAACGACGGGGCGAGCAGCAGCAGCGGCGGCG (SEQ ID NO: 1233) |
| MARCKSL1 | NM_023009.5 | CAGCTTCCCAAGTTAGGTTAGTGATGTGAAATGCTCCTGTCCCTGGCCCTACCTCCTTCCCTGTCCCCACCCCTGCATAAGGCAGTTGTTGGTTTTCTTC (SEQ ID NO: 1234) | AGGGCCAGGGACAGGAGCATTTCACATCACTAACCTAACTTGGGAAGCTG (SEQ ID NO: 1235) | GAAGAAAACCAACAACTGCCTTATGCAGGGGTGGGACAGGGAAGGAGGT (SEQ ID NO: 1236) |
| MAST2 | NM_015112.1 | ATGCTCCTCACAGGAAAAGCTGCATCAGTTGCCTTTCCAGCCTACAGCTGATGAGCTGCACTTTTTGACGAAGCATTTCAGCACAGAGAGCGTACCAGAT (SEQ ID NO: 1237) | CAGCTGTAGGCTGGAAAGGCAACTGATGCAGCTTTTCCTGTGAGGAGCAT (SEQ ID NO: 1238) | ATCTGGTACGCTCTCTGTGCTGAAATGCTTCGTCAAAAAGTGCAGCTCAT (SEQ ID NO: 1239) |

TABLE 1-continued

| Gene | GenBank Accession No. | Target Sequence | Capture Probe Sequence | Reporter Probe Sequence |
|---|---|---|---|---|
| MATR3 | NM_001194954.1 | AAGGAGTGGAGTCAACATATCAATGGAGCAAGTCACAGTCGTCGATGCCAGCTTCTTCTTGAAATCTACCCAGAATGGAATCCTGACAATGATACAGGAC (SEQ ID NO: 1240) | TGGCATCGACGACTGTGACTTGCTCCATTGATATGTTGACTCCACTC (SEQ ID NO: 1241) | GTCCTGTATCATTGTCAGGATTCCATTCTGGGTAGATTTCAAGAAGAAGC (SEQ ID NO: 1242) |
| MCL1 | NM_021960.3 | GCTGTAACTTCCTAGAGTTGCACCCTAGCAACCTAGCCAGAAAAGCAAGTGGCAAGAGGATTATGGCTAACAAGAATAAATACATGGGAAGAGTGCTCCC (SEQ ID NO: 1243) | ACTTGCTTTTCTGGCTAGGTTGCTAGGGTGCAACTCTAGGAAGTTACAGC (SEQ ID NO: 1244) | GGGAGCACTCTTCCCATGTATTTATTCTTGTTAGCCATAATCCTCTTGCC (SEQ ID NO: 1245) |
| MCM10 | NM_018518.3 | AATAACTTCTTGACGCGGGAAAATGGCGAGCCCGACGCATTTGATGAGCTCTTTGATGCCGACGGCGACGGTGAATCTTATACAGAAGAGGCTGATGATG (SEQ ID NO: 1246) | AGCTCATCAAATGCGTCGGGCTCGCCATTTTCCCGCGTCAAGAAGTTATT (SEQ ID NO: 1247) | CATCATCAGCCTCTTCTGTATAAGATTCACCGTCGCCGTCGGCATCAAAG (SEQ ID NO: 1248) |
| MCM7 | NM_182776.1 | TGGGAAATATCCCTCGTAGTATCACGGTGCTGGTAGAAGGAGAGAACACAAGGATTGCCCAGCCTGGAGACCACGTCAGCGTCACTGGTATTTTCTTGCC (SEQ ID NO: 1249) | TGTGTTCTCTCCTTCTACCAGCACCGTGATACTACGAGGGATATT (SEQ ID NO: 1250) | CAAGAAAATACCAGTGACGCTGACGTGGTCTCCAGGCTGGGCAATCCT (SEQ ID NO: 1251) |
| MDFIC | NM_199072.2 | CAATAGCCACTTCACACATGGAGAGATGCAAGACCAGTCCATTTGGGGAAATCCTTCGGATGGTGAACTCATTAGAACCCAACCTCAGCGCTTGCCTCAG (SEQ ID NO: 1252) | TTCCCCAAATGGACTGGTCTTGCATCTCTCCATGTGTGAAGTGGCTATTG (SEQ ID NO: 1253) | CTGAGGCAAGCGCTGAGGTTGGGTTCTAATGAGTTCACCATCCGAAGGAT (SEQ ID NO: 1254) |
| MDM2 | NM_002392.2 | GATCTACAGGAACTTGGTAGTAGTCAATCAGCAGGAATCATCGGACTCAGGTACATCTGTGAGTGAGAACAGGTGTCACCTTGAAGGTGGGAGTGATCAA (SEQ ID NO: 1255) | CTGAGTCCGATGATTCCTGCTGATTGACTACTACCAAGTTCCTGTAGATC (SEQ ID NO: 1256) | TTGATCACTCCCACCTTCAAGGTGACACCTGTTCTCACTCACAGATGTAC (SEQ ID NO: 1257) |
| MFAP5 | NM_003480.2 | CTCATCTCATTGTTTCAGCGGAGGCAAATCTGAAGTCCTTTCCAGGGAGTGGCTCTGTTCATCTTATTCGCCAGCCAAAGTAGGAACAGCGTAAGAGGA (SEQ ID NO: 1258) | CTCCCTGGAAAGGACTTCAGATTTGGCCTCCGCTGAAACAATGAGATGAG (SEQ ID NO: 1259) | TCCTCTTACGCTGTTCCTACTTTGGCTGGCGAATAAGATGAACAGAGCCA (SEQ ID NO: 1260) |

TABLE 1-continued

| Gene | GenBank Accession No. | Target Sequence | Capture Probe Sequence | Reporter Probe Sequence |
|---|---|---|---|---|
| MFNG | NM_002405.2 | CGAACAGGACCAGATTTTGTTGGAGCCTCAGCATGCCGGGGCCCAGATGATGGAGCATAACGGGTCCCAGCCAATTGTGATGATCCTTTTGCTCATTT (SEQ ID NO: 1261) | CATCTGGGCCCCGGCATGCTGAGGCTCCAAACAAAATCTGGTCCT (SEQ ID NO: 1262) | AAATGAGCAAAAAGGATCATCACAATTGGCTGGGACCCGTTATGCTCCAT (SEQ ID NO: 1263) |
| MFSD2A | NM_001136493.1 | GTTGGGATCTCATCAGCAGTGCCATTTCTCATCTTGGTGGCCCTCATGGAGAGTAACCTCATCATTACATATGCGGTAGCTGTGGCAGCTGGCATCAGTG (SEQ ID NO: 1264) | TCCATGAGGGCCACCAAGATGAGAAATGGCACTGCTGATGAGATCCCAAC (SEQ ID NO: 1265) | CACTGATGCCAGCTGCCACAGCTACCGCATATGTAATGATGAGGTTACTC (SEQ ID NO: 1266) |
| MGC87042 | NM_001164460.1 | CAGGCTATACTGACTGGAAGCCTGGTAGCTTTGTGCAACTTTCAGGCCACTAAACTGGCCAAGACACAACTGGTAGGCACACCAAATTTCTGGCAGGAGC (SEQ ID NO: 1267) | GTGGCCTGAAAGTTGCACAAAGCTACCAGGCTTCCAGTCA (SEQ ID NO: 1268) | GAAATTTGGTGTGCCTACCAGTTGTGTCTTGGCCAGTTTA (SEQ ID NO: 1269) |
| MIR17HG | NR_027349.1 | TGGACCTAACTGCACCAGTAGCTTTTCTGAGAATACTTGCTGAAAAGGAAGTTTTCTGGAATGGTATTTGCTAAGTGGAAGCCAGAAGAGGAGGAAAATG (SEQ ID NO: 1270) | TTCCTTTTCAGCAAGTATTCTCAGAAAAGCTACTGGTGCAGTTAGGTCCA (SEQ ID NO: 1271) | CATTTTCCTCCTCTTCTGGCTTCCACTTAGCAAATACCATTCCAGAAAAC (SEQ ID NO: 1272) |
| MKI67 | NM_002417.2 | AGCAGATGTAGAGGGAGAACTCTTAGCGTGCAGGAATCTAATGCCATCAGCAGGCAAAGCCATGCACACGCCTAAACCATCAGTAGGTGAAGAGAAAGAC (SEQ ID NO: 1273) | CTGATGGCATTAGATTCCTGCACGCTAAGAGTTCTCCCTCTACATCTG (SEQ ID NO: 1274) | GTCTTTCTCTTCACCTACTGATGGTTTAGGCGTGTGCATGGCTTTGCCTG (SEQ ID NO: 1275) |
| MLL2 | NM_003482.3 | CCAACATTAATTTTCCTAATCTCAAGCAAGACTACCCAGACTGGTCAAGCCGTTGCAAACAAATCATGAAGCTCTGGAGAAAGGTTCCAGCAGCTGACAA (SEQ ID NO: 1276) | GCTTGACCAGTCTGGGTAGTCTTGCTTGAGATTAGGAAAATTAATGTTGG (SEQ ID NO: 1277) | CAGCTGCTGGAACCTTTCTCCAGAGCTTCATGATTTGTTTGCAACG (SEQ ID NO: 1278) |
| MLLT10 | NM_004641.2 | CTGAGCGGCAAAGCCCGAATGGTCTCTAGCGACCGGCCCGTGTCACTGGAGGACGAGGTCTCCCATAGTATGAAGGAGATGATTGGAGGCTGTTGCGTTT (SEQ ID NO: 1279) | TCCAGTGACACGGGCCGGTCGCTAGAGACCATTCG (SEQ ID NO: 1280) | AAACGCAACAGCCTCCAATCATCTCCTTCATACTATGGGAGACCTCGTCC (SEQ ID NO: 1281) |

TABLE 1-continued

| Gene | GenBank Accession No. | Target Sequence | Capture Probe Sequence | Reporter Probe Sequence |
|---|---|---|---|---|
| MME | NM_000902.2 | GGATTGTAGGTGCAAGCTGTCCAGAGAAAAGAGTCCTTGTTCCAGCCCTATTCTGCCACTCCTGACAGGGTGACCTTGGGTATTTGCAATATTCCTTTGG (SEQ ID NO: 1282) | TAGGGCTGGAACAAGGACTCTTTTCTCTGGACAGCTTGCACCTACAATCC (SEQ ID NO: 1283) | CCAAAGGAATATTGCAAATACCCAAGGTCACCCTGTCAGGAGTGGCAGAA (SEQ ID NO: 1284) |
| MMP1 | NM_002421.2 | CAACTTACATCGTGTTGCGGCTCATGAACTCGGCCATTCTCTTGGACTCTCCCATTCTACTGATATCGGGGCTTTGATGTACCCTAGCTACACCTTCAGT (SEQ ID NO: 1285) | AGAGTCCAAGAGAATGGCCGAGTTCATGAGCCGCAACACGATGTAAGTTG (SEQ ID NO: 1286) | ACTGAAGGTGTAGCTAGGGTACATCAAAGCCCCGATATCAGTAGAATGGG (SEQ ID NO: 1287) |
| MMP2 | NM_004530.2 | CCCGGAGGGGCCTGGCAGCCGTGCCTTCAGCTCTACAGCTAATCAGCATTCTCACTCCTACCTGGTAATTTAAGATTCCAGAGAGTGGCTCCTCCCGGTG (SEQ ID NO: 1288) | AATGCTGATTAGCTGTAGAGCTGAAGGCACGGCTGCCAGG (SEQ ID NO: 1289) | CACCGGGAGGAGCCCACTCTCTGGAATCTTAAATTACCAGGTAGGAGTGAG (SEQ ID NO: 1290) |
| MMP9 | NM_004994.2 | CACTACTGTGCCTTTGAGTCCGGTGGACGATGCCTGCAACGTGAACATCTTCGACGCCATCGCGGAGATTGGGAACCAGCTGTATTTGTTCAAGGATGGG (SEQ ID NO: 1291) | AGATGTTCACGTTGCAGGCATCGTCCACCGGACTCAAAGGCACAG (SEQ ID NO: 1292) | CCCATCCTTGAACAAATACAGCTGGTTCCCAATCTCCGCGATGGCGTCGA (SEQ ID NO: 1293) |
| MMRN2 | NM_024756.2 | GCCAAGGATGGGCTGGAGGTCATTCAGTTGGTCTGTCTCTTCCCTGGAAACCTTCTGCAAAGATGGTGTGGTGTACGTGGCTTCCCTGTAACCACATGGG (SEQ ID NO: 1294) | TTTCCAGGGAAGAGACAGACCAACTGAATGACCTCCAGCCCATCC (SEQ ID NO: 1295) | CATGTGGTTACAGGGAAGCCACGTACACCACACCATCTTTGCAGAAGG (SEQ ID NO: 1296) |
| MNDA | NM_002432.1 | CCAACGGCAGGTGGATGCAAGAAGAAATGTTCCCCAAAACGACCCAGTGACAGTGGTGGTACTGAAAGCAACAGCGCCATTTAAATACGAGTCCCCAGAA (SEQ ID NO: 1297) | TCACTGGGTCGTTTTGGGGAACATTTCTTCTTGCATCCACCTGCCGTTGG (SEQ ID NO: 1298) | TTCTGGGGACTCGTATTTAAATGGCGCTGTTGCTTTCAGTACCACCACTG (SEQ ID NO: 1299) |
| MOBKL2C | NM_145279.4 | TTCTCTTACCCAGAGATGCCCATGAGCTGACATTTTACTCATCCCTCTGCCTCCAAGAAGGCCTGTATTATACGTGTCCTCCTGGGGGTTGGAGATGATC (SEQ ID NO: 1300) | GCAGAGGGATGAGTAAAATGTCAGCTCATGGGCATCTCTGGGTAAGAGAA (SEQ ID NO: 1301) | TCTCCAACCCCCAGGAGGACACGTATAATACAGGCCTTCTTGGAG (SEQ ID NO: 1302) |

TABLE 1-continued

| Gene | GenBank Accession No. | Target Sequence | Capture Probe Sequence | Reporter Probe Sequence |
|---|---|---|---|---|
| MPEG1 | XM_937323.1 | GCTGTGAAGCGCTATTATACATTCAACACCTACCCTGGCTGCACAGATCTCAATTCTCCCAACTTCAATTTTCAGGCCAACACGGATGATGGCTCCTGCG (SEQ ID NO: 1303) | AGATCTGTGCAGCCAGGGTAGGTGTTGAATGTATAATAGCGCTTCA (SEQ ID NO: 1304) | CGCAGGAGCCATCATCCGTGTTGGCCTGAAAATTGAAGTTGGGAGAATTG (SEQ ID NO: 1305) |
| MS4A1 | NM_152866.2 | CTTCTGATGATCCCAGCAGGGATCTATGCACCCATCTGTGTGACTGTGTGGTACCCTCTCTGGGGAGGCATTATGTATATTATTTCCGGATCACTCCTGG (SEQ ID NO: 1306) | CACACAGTCACACAGATGGGTGCATAGATCCCTGC (SEQ ID NO: 1307) | CCAGGAGTGATCCGGAAATAATATACATAATGCCTCCCCAGAGAGGGTAC (SEQ ID NO: 1308) |
| MST1R | NM_002447.1 | CCACTTTGGAGTTGTCTACCACGGAGAATACATAGACCAGGCCCAGAATCGAATCCAATGTGCCATCAAGTCACTAAGTCGCATCACAGAGATGCAGCAG (SEQ ID NO: 1309) | GATTCTGGGCCTGGTCTATGTATTCTCCGTGGTAGACAACTCCAAAGTG (SEQ ID NO: 1310) | CTGCTGCATCTCTGTGATGCGACTTAGTGACTTGATGGCACATTGGATTC (SEQ ID NO: 1311) |
| MSX2 | NM_002449.4 | GCCGCTGCCGGGTTGCCAGCGGAGTCGCGCGTCGGGAGCTACGTAGGGCAGAGAAGTCATGGCTTCTCCGTCCAAAGGCAATGACTTGTTTTCGCCCGAC (SEQ ID NO: 1312) | TGCCCTACGTAGCTCCCGACGCGCGACTCCGCTGGCAACCCG (SEQ ID NO: 1313) | GTCGGGCGAAAACAAGTCATTGCCTTTGGACGGAGAAGCCATGACTTCTC (SEQ ID NO: 1314) |
| MTHFD2 | NM_006636.3 | TGGAGGTGTTGGCCCCATGACAGTGGCAATGCTAATGAAGAATACCATTATTGCTGCAAAAAAGGTGCTGAGGCTTGAAGAGCGAGAAGTGCTGAAGTCT (SEQ ID NO: 1315) | TAATGGTATTCTTCATTAGCATTGCCACTGTCATGGGGCCAACACCTCCA (SEQ ID NO: 1316) | AGACTTCAGCACTTCTCGCTCTTCAAGCCTCAGCACCTTTTTTGCAGCAA (SEQ ID NO: 1317) |
| MTUS2 | NM_001033602.2 | AACCTGCAAACACAAATTCAGTTACAGCTTAGCTGTCCGAATTAGGAACCGCTTACATAGCCGCACCTGCTAAATGCAGTTACACAGCAATACTGACTTC (SEQ ID NO: 1318) | GGTTCCTAATTCGGACAGCTAAGCTGTAACTGAATTTGTGTTTGCAGGTT (SEQ ID NO: 1319) | GAAGTCAGTATTGCTGTGTAACTGCATTTAGCAGGTGCGGCTATGTAAGC (SEQ ID NO: 1320) |
| MUC16 | NM_024690.2 | TCTTCTAGACACAGGTTTTCCCAGGTCAAATGCGGGGACCCCAGCCATATCTCCCACCCTGAGAAATTTTGGAGTTTCAGGGAGCTCAGAAGCTCTGCAG (SEQ ID NO: 1321) | ATATGGCTGGGGTCCCCGCATTTGACCTGGGAAAACCTGTGTCTAGAAGA (SEQ ID NO: 1322) | CTGCAGAGCTTCTGAGCTCCCTGAAACTCCAAAATTTCTCAGGGTGGGAG (SEQ ID NO: 1323) |

TABLE 1-continued

| Gene | GenBank Accession No. | Target Sequence | Capture Probe Sequence | Reporter Probe Sequence |
|---|---|---|---|---|
| MYB | NM_005375.2 | AACTGTTGCATGGATCCTGTGTTTGCAACTGGGGAGACAGAAACTGTGGTTGATAGCCAGTCACTGCCTTAAGAACATTTGATGCAAGATGGCCAGCACT (SEQ ID NO: 1324) | ACCACAGTTTCTGTCTCCCCAGTTGCAAACACAGGATCCATGCAACAGTT (SEQ ID NO: 1325) | AGTGCTGGCCATCTTGCATCAAATGTTCTTAAGGCAGTGACTGGCTATCA (SEQ ID NO: 1326) |
| MYBL1 | XM_034274.14 | GGCAAACGCTGTGTTATCCTCTTTGCAGACCATCCCAGAATTTGCAGAGACTCTAGAACTTATTGAATCTGATCCTGTAGCATGGAGTGACGTTACCAGT (SEQ ID NO: 1327) | TCTCTGCAAATTCTGGGATGGTCTGCAAAGAGGATAACACAGCGTTTGCC (SEQ ID NO: 1328) | ACTGGTAACGTCACTCCATGCTACAGGATCAGATTCAATAAGTTCTAGAG (SEQ ID NO: 1329) |
| MYC | NM_002467.3 | TCGGACACCGAGGAGAATGTCAAGAGGCGAACACACAACGTCTTGGAGCGCCAGAGGAGGAACGAGCTAAAACGGAGCTTTTTTGCCCTGCGTGACCAGA (SEQ ID NO: 1330) | CGCTCCAAGACGTTGTGTGTTCGCCTCTTGACATTCTCCTCGGTG (SEQ ID NO: 1331) | TCTGGTCACGCAGGGCAAAAAAGCTCCGTTTTAGCTCGTTCCTCCTCTGG (SEQ ID NO: 1332) |
| MYD88 | NM_002468.3 | ACGTTTTTCTAGGTACAGCTCCCAGGAACAGCTAGGTGGGAAAGTCCCATCACTGAGGGAGCCTAACCATGTCCCTGAACAAAAATTGGGCACTCATCTA (SEQ ID NO: 1333) | ATGGGACTTTCCCACCTAGCTGTTCCTGGGAGCTGTACCTAGAAAAACGT (SEQ ID NO: 1334) | TAGATGAGTGCCCAATTTTGTTCAGGGACATGGTTAGGCTCCCTCAGTG (SEQ ID NO: 1335) |
| MYO7A | NM_001127180.1 | CGACGCCTTCGTAAAGGGGATCTACGGGCGGCTGTTCGTGTGGATTGTGGACAAGATCAACGCAGCAATTTACAAGCCTCCCTCCCAGGATGTGAAGAAC (SEQ ID NO: 1336) | CCACAATCCACACGAACAGCCGCCCGTAGATCCCCTTTACGAAGG (SEQ ID NO: 1337) | TCACATCCTGGGAGGGAGGCTTGTAAATTGCTGCGTTGATCTTGT (SEQ ID NO: 1338) |
| MZT2B | NM_025029.3 | TTGAAAGAGGCATTTACCGAGCGCCCAATGTATGCCTGGCACTGGGCTGGGTGCTGCCACCTAAGCGAGCACGACCAATGCAGTCTATCAGGGAGGCCA (SEQ ID NO: 1339) | CCAGCCCAGTGCCAGGCATACATTGGGCGCTCGGTAAATG (SEQ ID NO: 1340) | TGATAGACTGCATTGGTCGTGCTCGCTTAGGTGGCAGCAC (SEQ ID NO: 1341) |
| NAIF1 | NM_197956.3 | GATTGGCCTTGGCCTTAGACCGGCCACGTGCACAGCTCCCTCTTTAATAAACGCTTAGGGGTTGCACTGTTTTTGAGAAGAGGAATTTGTTGGGCTCCTG (SEQ ID NO: 1342) | TTATTAAAGAGGGAGCTGTGCACGTGGCCGGTCTAAGGCCAAGG (SEQ ID NO: 1343) | CAGGAGCCCAACAAATTCCTCTTCTCAAAAACAGTGCAACCCCTAAGCGT (SEQ ID NO: 1344) |

TABLE 1-continued

| Gene | GenBank Accession No. | Target Sequence | Capture Probe Sequence | Reporter Probe Sequence |
|---|---|---|---|---|
| NANS | NM_018946.3 | TTCCTTATCTGGAAAAGACAGCCAAAAAAGGTCGCCCAATGGTGATCTCCAGTGGGATGCAGTCAATGGACACCATGAAGCAAGTTTATCAGATCGTGAA (SEQ ID NO: 1345) | GGAGATCACCATTGGGCGACCTTTTTTGGCTGTCTTTTCCAGATAAGGAA (SEQ ID NO: 1346) | TTCACGATCTGATAAACTTGCTTCATGGTGTCCATTGACTGCATCCCACT (SEQ ID NO: 1347) |
| NASP | NM_172164.1 | TTTGGCTGTGAGCCAGGCCTAGGATGGTTCTTGTCCTATATCCACCTAGTCTTCACCTGGGGCTATAATTCTGTCCTGGAAAAAGAACTCTGAAAACCTG (SEQ ID NO: 1348) | ACTAGGTGGATATAGGACAAGAACCATCCTAGGCCTGGCTCACAGCCAAA (SEQ ID NO: 1349) | CAGGTTTTCAGAGTTCTTTTTCCAGGACAGAATTATAGCCCCAGGTGAAG (SEQ ID NO: 1350) |
| NBN | NM_002485.4 | GACTACAAAGAATTACTGTGATCCTCAGGGCCATCCCAGTACAGGATTAAAGACAACAACTCCAGGACCAAGCCTTTCACAAGGCGTGTCAGTTGATGAA (SEQ ID NO: 1351) | TTAATCCTGTACTGGGATGGCCCTGAGGATCACAGTAATTCTTTGTAGTC (SEQ ID NO: 1352) | TTCATCAACTGACACGCCTTGTGAAAGGCTTGGTCCTGGAGTTGTTGTCT (SEQ ID NO: 1353) |
| NCAPG | NM_022346.3 | GTATTGCACCATCAGCAAAGACTTTGCCAAAAATTGTAGGGCGCACCAAGGATGTGAAAGAGGCTGTCAGAAAGCTGGCTTATCAGGTTTTAGCTGAAAA (SEQ ID NO: 1354) | CTTGGTGCGCCCTACAATTTTTGGCAAAGTCTTTGCTGATGGTGCAATAC (SEQ ID NO: 1355) | TTTTCAGCTAAAACCTGATAAGCCAGCTTTCTGACAGCCTCTTTCACATC (SEQ ID NO: 1356) |
| NCAPH | NM_015341.3 | TGCTACTATTCTGACCAAGTCCACTTTGGAGAACCAGAATTGGAGAGCTACCACCCTTCCTACAGATTTCAACTACAATGTTGACACTCTGGTCCAGCTT (SEQ ID NO: 1357) | TAGCTCTCCAATTCTGGTTCTCCAAAGTGGACTTGGTCAGAATAGTAGCA (SEQ ID NO: 1358) | AAGCTGGACCAGAGTGTCAACATTGTAGTTGAAATCTGTAGGAAGGGTGG (SEQ ID NO: 1359) |
| NCF2 | NM_000433.2 | GCCACTAAGGCAGCCCTGCTAGGGGAGACGCTCCAACCTGTCTTCTCTCTGTCTCCTGGCAGCTCTCTTGGCCTCCTAGTTTCTACCTAATCATGTCCCT (SEQ ID NO: 1360) | AGAGAGAAGACAGGTTGGAGCGTCTCCCCTAGCAG (SEQ ID NO: 1361) | AGGGACATGATTAGGTAGAAACTAGGAGGCCAAGAGAGCTGCCAGGAGAC (SEQ ID NO: 1362) |
| NCRNA00158 | NR_024027.2 | AGTAGGATCCAGAGCCATTTTGGAACTTTACCAAGGATTAAGGATGAGCACAGATCACATCAAGAGTCTAAATATCACTTTGGAGGCCATGTGCAGATCA (SEQ ID NO: 1363) | TGCTCATCCTTAATCCTTGGTAAAGTTCCAAAATGGCTCTGGATCCTACT (SEQ ID NO: 1364) | TGATCTGCACATGGCCTCCAAAGTGATATTTAGACTCTTGATGTGATCTG (SEQ ID NO: 1365) |

TABLE 1-continued

| Gene | GenBank Accession No. | Target Sequence | Capture Probe Sequence | Reporter Probe Sequence |
|---|---|---|---|---|
| NDST4 | NM_022569.1 | GGCTCCATCTGACT TAAAAACTTTGCAG AGAAGATGCCTAGT ACCTGGATGGTATG CAGTCCACATAGAA AGATGGCTAACTTA CTTTGCTACTTCTC AG (SEQ ID NO: 1366) | ATCCAGGTACTA GGCATCTTCTCTG CAAAGTTTTTAAG TCAGATGGAGC (SEQ ID NO: 1367) | CTGAGAAGTAGC AAAGTAAGTTAG CCATCTTTCTAT GTGGACTGCATA CC (SEQ ID NO: 1368) |
| NEBL | NM_006393.1 | GGGGTGGCATTCAC TTAGGGTCTGACTT CACAGCTATGACAA AACCGAAAAAGCA AAACTGCGAGGAA GTGCTAAGATGTAC GGGTCTTGGGGATA TCTG (SEQ ID NO: 1369) | TTTCGGTTTTGTC ATAGCTGTGAAG TCAGACCCTAAG TGAATGCCACCC C (SEQ ID NO: 1370) | CAGATATCCCCA AGACCCGTACAT CTTAGCACTTCC TCGCAGTTTTGC TT (SEQ ID NO: 1371) |
| NECAP2 | NM_018090.1 | CTCTCCTCTCCTCCT TGTCTGGCTCTGTT GACAAACCGGGCA TGTTTGGCAGTAAA TTGGCACCGTGTCA CACTGTTTCCTGGG ATTCAAGTATGCAA CC (SEQ ID NO: 1372) | GCCAAACATGCC CGGTTTGTCAACA GAGCCAGACAAG GAGGAGAGGAGA G (SEQ ID NO: 1373) | GGTTGCATACTT GAATCCCAGGAA ACAGTGTGACAC GGTGCCAATTTA CT (SEQ ID NO: 1374) |
| NEIL1 | NM_024608.2 | TTAGCAGGAGGCTC TCCTTGCTTGCACT CACCCTTTCTTATT GTCTTGCCCTGCAT CTGGGGGTCTGAAT TTTTGGGAGCAGGC AATATCTGAAGGTG CA (SEQ ID NO: 1375) | GGCAAGACAATA AGAAAGGGTGAG TGCAAGCAAGGA GAGCCTCCTGCTA A (SEQ ID NO: 1376) | TGCACCTTCAGA TATTGCCTGCTC CCAAAAATTCAG ACCCCCAGATGC AG (SEQ ID NO: 1377) |
| NEK6 | NM_014397.3 | GCATCGGGAAGCA GGAGCATCTTCTTG GCAGCCAGGCTGG GCCATCTTCTCCTG GACACCTGCTGTGT ACCAGGAACTTCGT CACCTCCTTGAATG CTGG (SEQ ID NO: 1378) | AGAAGATGGCCC AGCCTGGCTGCC AAGAAGATGCT (SEQ ID NO: 1379) | ATTCAAGGAGGT GACGAAGTTCCT GGTACACAGCAG GTGTCCAGG (SEQ ID NO: 1380) |
| NEU3 | NM_006656.5 | TGGTTCTAAGATTT CTCATCTTCTCATC CCTAGGACAAGCAT AGTGCCTGCATGCT TCATGATCAGTAAG TCCTGGCTGCATAA AGGACTCTGATGTC AA (SEQ ID NO: 1381) | CAGGCACTATGC TTGTCCTAGGGAT GAGAAGATGAGA AATCTTAGAACC A (SEQ ID NO: 1382) | TTGACATCAGAG TCCTTTATGCAG CCAGGACTTACT GATCATGAAGCA TG (SEQ ID NO: 1383) |
| NFATC1 | NM_172390.1 | CCAGTACCAGCGTT TCACCTACCTTCCC GCCAACGGTAACG CCATCTTTCTAACC GTAAGCCGTGAAC ATGAGCGCGTGGG GTGCTTTTTCTAAA GACGC (SEQ ID NO: 1384) | GAAAGATGGCGT TACCGTTGGCGG GAAGGTAGGTGA AACGCTGGTACT GG (SEQ ID NO: 1385) | GCGTCTTTAGAA AAAGCACCCCAC GCGCTCATGTTC ACGGCTTACGGT TA (SEQ ID NO: 1386) |

TABLE 1-continued

| Gene | GenBank Accession No. | Target Sequence | Capture Probe Sequence | Reporter Probe Sequence |
|---|---|---|---|---|
| NFIL3 | NM_005381.2 | CCTTTCTTTCTCCTCGCCGGCCCGAGAGCAGGAACACGATAACGAAGGAGGCCCAACTTCATTCAATAAGGAGCCTGACGGATTTATCCCAGACGGTAGA (SEQ ID NO: 1387) | CTCCTTCGTTATCGTGTTCCTGCTCTCGGGCCGGCCGAGGAGAAAGAAAGG (SEQ ID NO: 1388) | TCTACCGTCTGGGATAAATCCGTCAGGCTCCTTATTGAATGAAGTTGGGC (SEQ ID NO: 1389) |
| NFKBIA | NM_020529.1 | GGATGAGGAGAGCTATGACACAGAGTCAGAGTTCACGGAGTTCACAGAGGACGAGCTGCCCTATGATGACTGTGTGTTTGGAGGCCAGCGTCTGACGTTA (SEQ ID NO: 1390) | CCTCTGTGAACTCCGTGAACTCTGACTCTGTGTCATAGC (SEQ ID NO: 1391) | GCCTCCAAACACACAGTCATCATAGGGCAGCTCGT (SEQ ID NO: 1392) |
| NFKBIZ | NM_001005474.1 | ATTTGGTTCCCGATGGCCCTGTGGGAGAACAGATCCGACGTATCCTGAAGGGAAAGTCCATTCAGCAGAGAGCTCCACCGTATTAGCTCCATTAGCTTGG (SEQ ID NO: 1393) | CTTCAGGATACGTCGGATCTGTTCTCCCACAGGGCCATCGGGAACCAAAT (SEQ ID NO: 1394) | CCAAGCTAATGGAGCTAATACGGTGGGAGCTCTCTGCTGAATGGACTTTCC (SEQ ID NO: 1395) |
| NHLH2 | NM_005599.3 | CTCTGGCTCTCCCACCCTCTTCCCGTCTTTCTCTGCTTCCTTGTCACTGTTACTCCAGGAGACGTTCACTTTTCACCAACCTTTCTCCAAGCATCTCCAA (SEQ ID NO: 1396) | ACAGTGACAAGGAAGCAGAGAAAGACGGGAAGAGGGTGGGAGAGCCAGAG (SEQ ID NO: 1397) | TTGGAGATGCTTGGAGAAAGGTTGGTGAAAAGTGAACGTCTCCTGGAGTA (SEQ ID NO: 1398) |
| NIPA2 | NM_001008860.1 | AACGATTTCTCAGGTTGAGATGATCACCGTGAATCCGGCTTCCTCTGAGCATTCGATGGCCTTAGCACCTCATCAAGCCAGCACATCCTGCCTGCTGTTG (SEQ ID NO: 1399) | GCTCAGAGGAAGCCGGATTCACGGTGATCATCTCAACCTGAGAAATCGTT (SEQ ID NO: 1400) | GCAGGATGTGCTGGCTTGATGAGGTGCTAAGGCCATCGAAT (SEQ ID NO: 1401) |
| NOC3L | NM_022451.9 | GTTGAGATTGTACTCCAGTGCCTTGATGTCATGCTAACTAAGCGCAGAAAGCAAGTTTCTCAGCAGCGAGCTCTTGCCTTCATCAAACGCCTTTGTACCC (SEQ ID NO: 1402) | TTTCTGCGCTTAGTTAGCATGACATCAAGGCACTGGAGTACAATCTCAAC (SEQ ID NO: 1403) | GGGTACAAAGGCGTTTGATGAAGGCAAGAGCTCGCTGCTGAGAAACTTGC (SEQ ID NO: 1404) |
| NOP14 | NM_003703.1 | CTGATCCACAAACACAAGCGTGAATTTAAAGGGGCCGTTCGAGAAATCCGCAAGGACAATCAGTTCCTGGCGAGGATGCAACTCTCAGAAATCATGGAAC (SEQ ID NO: 1405) | CGGATTTCTCGAACGGCCCCTTTAAATTCACGCTTGTGTTTGTGGATCAG (SEQ ID NO: 1406) | TTCCATGATTTCTGAGAGTTGCATCCTCGCCAGGAACTGATTGTCCTTG (SEQ ID NO: 1407) |

TABLE 1-continued

| Gene | GenBank Accession No. | Target Sequence | Capture Probe Sequence | Reporter Probe Sequence |
|---|---|---|---|---|
| NOP56 | NM_006392.2 | TTCTCTATGCGTGTCAGGGAGTGGTACGGGTATCACTTTCCGGAGCTGGTGAAGATCATCAACGACAATGCCACATACTGCCGTCTTGCCCAGTTTATTG (SEQ ID NO: 1408) | ACCAGCTCCGGAAAGTGATACCCGTACCACTCCCTGACACGCATAGAGAA (SEQ ID NO: 1409) | CAATAAACTGGGCAAGACGGCAGTATGTGGCATTGTCGTTGATGATCTTC (SEQ ID NO: 1410) |
| NOTCH1 | NM_017617.3 | CTGCCAGGCTTCACCGGCCAGAACTGTGAGGAAAATATCGACGATTGTCCAGGAAACAACTGCAAGAACGGGGGTGCCTGTGTGGACGGCGTGAACACCT (SEQ ID NO: 1411) | GGACAATCGTCGATATTTTCCTCACAGTTCTGGCCGGTGAAGCCTGGCAG (SEQ ID NO: 1412) | TCCACACAGGCACCCCCGTTCTTGCAGTTGTTTCCT (SEQ ID NO: 1413) |
| NOTCH2 | NM_024408.2 | TCCTGGTGAACAAGAACAGGAGGTGGCTGGCTCTAAAGTCTTTCTGGAAATTGACAACCGCCAGTGTGTTCAAGACTCAGACCACTGCTTCAAGAACACG (SEQ ID NO: 1414) | TTTCCAGAAAGACTTTAGAGCCAGCCACCTCCTGTTCTTGTTCACCAGGA (SEQ ID NO: 1415) | CGTGTTCTTGAAGCAGTGGTCTGAGTCTTGAACACACTGGCGGTTGTCAA (SEQ ID NO: 1416) |
| NRG1 | NM_004495.2 | TACATCTACATCCACCACTGGGACAAGCCATCTTGTAAAATGTGCGGAGAAGGAGAAAACTTTCTGTGTGAATGAGGGGAGTGCTTCATGGTGAAAGAC (SEQ ID NO: 1417) | TCTCCGCACATTTTACAAGATGGCTTGTCCCAGTGGTGGATGTAGATGTA (SEQ ID NO: 1418) | GTCTTTCACCATGAAGCACTCCCCTCCATTCACACAGAAAGTTTTCTCT (SEQ ID NO: 1419) |
| NUF2 | NM_145697.2 | GACTTCCAGTAGGAGGCGGCAAGTTTGAAAAGTGATGACGGTTGACGTTTGCTGATTTTTGACTTTGCTTGTAGCTGCTCCCCGAACTCGCCGTCTTCCT (SEQ ID NO: 1420) | AAACGTCAACCGTCATCACTTTTCAAACTTGCCGCCTCCTACTGGAAGTC (SEQ ID NO: 1421) | AGGAAGACGGCGAGTTCGGGGAGCAGCTACAAGCAAAGTCAAAAATCAGC (SEQ ID NO: 1422) |
| NUP62 | NM_016553.3 | GGCACTGCAAAGACGGCAACAACCACACCTGCTACAGGGTTTTCTTTCTCCACCTCTGGCACTGGAGGGTTTAATTTTGGGGCTCCCTTCCAACCAGCCA (SEQ ID NO: 1423) | GAGAAAGAAAACCCTGTAGCAGGTGTGGTTGTTGCCGTCTTTGCAGTGCC (SEQ ID NO: 1424) | CTGGTTGGAAGGGAGCCCCAAAATTAAACCCTCCAGTGCCAGAGGTG (SEQ ID NO: 1425) |
| NUSAP1 | NM_018454.6 | TCAAGCGCTCTGCTATCTCTGCAGCTAAAACGGGTGTCAGGTTTTCAGCTGCTACTAAAGATAATGAGCATAAGCGTTCACTGACCAAGACTCCAGCCAG (SEQ ID NO: 1426) | AGCTGAAAACCTGACACCCGTTTTAGCTGCAGAGATAGCAGAGCGCTTGA (SEQ ID NO: 1427) | CTGGCTGGAGTCTTGGTCAGTGAACGCTTATGCTCATTATCTTTAGTAGC (SEQ ID NO: 1428) |

TABLE 1-continued

| Gene | GenBank Accession No. | Target Sequence | Capture Probe Sequence | Reporter Probe Sequence |
|---|---|---|---|---|
| OAS2 | NM_016817.2 | AAGCAAAGGAATGGTTATCCTCTCCCTGCTTCAAGGATGGGACTGGAAACCCAATACCACCTTGGAAAGTGCCGACAATGCAGACACCAGGAAGTTGTGG (SEQ ID NO: 1429) | GTTTCCAGTCCCATCCTTGAAGCAGGGAGAGGATAACCATTCCTTTGCTT (SEQ ID NO: 1430) | CCACAACTTCCTGGTGTCTGCATTGTCGGCACTTTCCAAGGTGGTATTGG (SEQ ID NO: 1431) |
| OAS3 | NM_006187.2 | GAGTGCCTTAGACAGCCTGACTCTCCACAAACCACTGTTAAAACTTACCTGCTAGGAATGCTAGATTGAATGGGATGGGAAGAGCCTTCCCTCATTATTG (SEQ ID NO: 1432) | AGGTAAGTTTTAACAGTGGTTTGTGGAGAGTCAGGCTGTCTAAGGCACTC (SEQ ID NO: 1433) | CAATAATGAGGGAAGGCTCTTCCCATCCCATTCAATCTAGCATTCCTAGC (SEQ ID NO: 1434) |
| OPA1 | NM_130837.1 | CTGAGACCATATCCTTAAATGTAAAAGGCCCTGGACTACAGAGGATGGTGCTTGTTGACTTACCAGGTGTGATTAATACTGTGACATCAGGCATGGCTCC (SEQ ID NO: 1435) | CACCATCCTCTGTAGTCCAGGGCCTTTTACATTTAAGGATATGGTCTCAG (SEQ ID NO: 1436) | GGAGCCATGCCTGATGTCACAGTATTAATCACACCTGGTAAGTCAACAAG (SEQ ID NO: 1437) |
| OPN3 | NM_014322.2 | ACTCACCTCCTCCTGGTCAACATCAGCCTCAGCGACCTGCTGGTGTCCCTCTTCGGGGTCACCTTTACCTTCGTGTCCTGCCTGAGGAACGGCTGGGTGT (SEQ ID NO: 1438) | AGGGACACCAGCAGGTCGCTGAGGCTGATGTTGAC (SEQ ID NO: 1439) | CAGCCGTTCCTCAGGCAGGACACGAAGGTAAAGGTGACCCCGAAG (SEQ ID NO: 1440) |
| OSBPL3 | NM_145320.1 | AGAGGATTGAACAACTGCAGAGAGAAAGGCGGCGGGTCTTAGAAGAAAATCATGTGGAGCACCAGCCTCGGTTTTTCAGGAAATCCGACGATGACTCTTG (SEQ ID NO: 1441) | ATTTTCTTCTAAGACCCGCCGCCTTTCTCTCTGCAGTTGTTCAATCCTCT (SEQ ID NO: 1442) | CAAGAGTCATCGTCGGATTTCCTGAAAAACCGAGGCTGGTGCTCCACATG (SEQ ID NO: 1443) |
| PA2G4 | NM_006191.2 | TGGATTGCTGGGGGTTTGTAGAGAAAGGTGACAAATTTCAGTACCTCTGGCATGCTGTCCCAGGAAACTAGGGCTCCCACTAACTTATGAGGTTTTTAAA (SEQ ID NO: 1444) | CCAGAGGTACTGAAATTTGTCACCTTTCTCTACAAACCCCCAGCAATCCA (SEQ ID NO: 1445) | TTTAAAAACCTCATAAGTTAGTGGGAGCCCTAGTTTCCTGGGACAGCATG (SEQ ID NO: 1446) |
| PAG1 | NM_018440.3 | TCACATGATGGGGTTCTTTAGTACATGGTAACAGCCATGTCATCTTACACACCTAGCATTGTGAATGCTGTAGTGACATCCTTTATAGGCACCTTACAGC (SEQ ID NO: 1447) | GTGTAAGATGACATGGCTGTTACCATGTACTAAAGAACCCCATCATGTGA (SEQ ID NO: 1448) | GCTGTAAGGTGCCTATAAAGGATGTCACTACAGCATTCACAATGCTAGGT (SEQ ID NO: 1449) |

TABLE 1-continued

| Gene | GenBank Accession No. | Target Sequence | Capture Probe Sequence | Reporter Probe Sequence |
|---|---|---|---|---|
| PARM1 | NM_015393.3 | GACCATGCCTGGTG CCACAGCCATGGTT TCCATTTCTAGATG AAAGGATGGCCTA GGACATAGGTCTCA AAGACTCTTGGATC AGAATCAGGAGAT TAGG (SEQ ID NO: 1450) | CATCCTTTCATCT AGAAATGGAAAC CATGGCTGTGGC ACCAGGCATGGT C (SEQ ID NO: 1451) | TAATCTCCTGAT TCTGATCCAAGA GTCTTTGAGACC TATGTCCTAGGC (SEQ ID NO: 1452) |
| PAX6 | NM_001604.4 | CTTTAACTAGGGGC GCGCAGATGTGTGA GGCCTTTTATTGTG AGAGTGGACAGAC ATCCGAGATTTCAG AGCCCCATATTCGA GCCCCGTGGAATCC CGC (SEQ ID NO: 1453) | TCCACTCTCACAA TAAAAGGCCTCA CACATCTGCGCG CCCCTAGTTAAA G (SEQ ID NO: 1454) | GGATTCCACGGG GCTCGAATATGG GGCTCTGAAATC TCGGATGTCTG (SEQ ID NO: 1455) |
| PCNA | NM_002592.2 | GGTGTTGGAGGCAC TCAAGGACCTCATC AACGAGGCCTGCTG GGATATTAGCTCCA GCGGTGTAAACCTG CAGAGCATGGACTC GTCCCACGTCTCTT TG (SEQ ID NO: 1456) | TAATATCCCAGC AGGCCTCGTTGAT GAGGTCCTTGAG TG (SEQ ID NO: 1457) | CGAGTCCATGCT CTGCAGGTTTAC ACCGCTGGAGC (SEQ ID NO: 1458) |
| PDCD1LG2 | NM_025239.3 | TGTGGAGCTGTGGC AAGTCCTCATATCA AATACAGAACATG ATCTTCCTCCTGCT AATGTTGAGCCTGG AATTGCAGCTTCAC CAGATAGCAGCTTT ATT (SEQ ID NO: 1459) | GAGGAAGATCAT GTTCTGTATTTGA TATGAGGACTTG CCACAGCTCCAC A (SEQ ID NO: 1460) | AATAAAGCTGCT ATCTGGTGAAGC TGCAATTCCAGG CTCAACATTAGC AG (SEQ ID NO: 1461) |
| PDE4DIP | NM_001002810.2 | AGGAGAACTTCAG CCTCAAGCTGCGCA TCTACTTCCTGGAG GAGCGCATGCAAC AGAAGTATGAGGC CAGCCGGGAGGAC ATCTACAAGCGGA ACATTGA (SEQ ID NO: 1462) | CATGCGCTCCTCC AGGAAGTAGATG CGCAGCTTGAG (SEQ ID NO: 1463) | TAGATGTCCTCC CGGCTGGCCTCA TACTTCTGTTG (SEQ ID NO: 1464) |
| PDE9A | NM_001001567.1 | CAGCAGGACCAAC TGCCCCTGTAAGTA CAGTTTTTTGGATA ACCACAAGAAGTT GACTCCTCGACGCG ATGTTCCCACTTAC CCCAAGTACCTGCT CTCT (SEQ ID NO: 1465) | TCTTGTGGTTATC CAAAAAACTGTA CTTACAGGGGCA GTTGGTCCTGCTG (SEQ ID NO: 1466) | GCAGGTACTTGG GGTAAGTGGGA ACATCGCGTCGA GGAGTCAACT (SEQ ID NO: 1467) |
| PDGFRA | NM_006206.3 | TAGTGCTTGGTCGG GTCTTGGGGTCTGG AGCGTTTGGGAAG GTGGTTGAAGGAA CAGCCTATGGATTA AGCCGGTCCCAACC TGTCATGAAAGTTG CAGT (SEQ ID NO: 1468) | TTCAACCACCTTC CCAAACGCTCCA GACCCCAAGACC CGACCAAGCACT A (SEQ ID NO: 1469) | ACTGCAACTTTC ATGACAGGTTGG GACCGGCTTAAT CCATAGGCTGTT CC (SEQ ID NO: 1470) |

TABLE 1-continued

| Gene | GenBank Accession No. | Target Sequence | Capture Probe Sequence | Reporter Probe Sequence |
|---|---|---|---|---|
| PDIA4 | NM_004911.4 | TGAAGCCAGTCATC AAATCCCAGCCAGT GCCCAAGAACAAC AAGGGACCCGTCA AGGTCGTGGTGGG AAAGACCTTTGACT CCATTGTGATGGAC CCCAA (SEQ ID NO: 1471) | GGGTCCCTTGTTG TTCTTGGGCACTG GCTGGGATTTGAT GACTGG (SEQ ID NO: 1472) | TTGGGGTCCATC ACAATGGAGTCA AAGGTCTTTCCC ACCACGACCTTG AC (SEQ ID NO: 1473) |
| PDIA5 | NM_006810.2 | GCTACCCCACTTTC CACTACTACCACTA TGGGAAGTTCGCAG AAAAGTATGACAG CGACCGCACAGAA TTGGGATTTACCAA TTATATTCGAGCCC TCCG (SEQ ID NO: 1474) | ATACTTTTCTGCG AACTTCCCATAGT GGTAGTAGTGGA AAGTGGGGTAGC (SEQ ID NO: 1475) | CGGAGGGCTCGA ATATAATTGGTA AATCCCAATTCT GTGCGGTCGCTG TC (SEQ ID NO: 1476) |
| PDK4 | NM_002612.3 | AATCAGAACACTG ATCCAATGAGGAAT GGAGCTTGTTTCTG TGACCCAGGAGAA CTTAGTGCAAGACT ACAGGAGTTAACA GATGGCCAGCTCCT TATTT (SEQ ID NO: 1477) | CCTGGGTCACAG AAACAAGCTCCA TTCCTCATTGGAT CAGTGTTCTGATT (SEQ ID NO: 1478) | AAATAAGGAGCT GGCCATCTGTTA ACTCCTGTAGTC TTGCACTAAGTT CT (SEQ ID NO: 1479) |
| PDLIM1 | NM_020992.2 | GGATCCCAACAAG CCCTCAGGATTCAG AAGTGTTAAAGCTC CTGTCACTAAAGTG GCTGCGTCGATTGG AAATGCTCAGAAGT TGCCTATGTGTGAC AAA (SEQ ID NO: 1480) | TAGTGACAGGAG CTTTAACACTTCT GAATCCTGAGGG CTTGTTGGGATC (SEQ ID NO: 1481) | TTTGTCACACAT AGGCAACTTCTG AGCATTTCCAAT CGACGCAGCCAC TT (SEQ ID NO: 1482) |
| PDLIM3 | NM_001114107.2 | CTTTGGGACAGAGT CCATGACTCATGCT GATGCGCAGGACA GGATTAAAGCAGC AGCTCACCAGCTGT GTCTCAAAATTGAC AGGGGAGAAACTC ACTTA (SEQ ID NO: 1483) | CTTTAATCCTGTC CTGCGCATCAGC ATGAGTCATGGA CTCTG (SEQ ID NO: 1484) | TAAGTGAGTTTC TCCCCTGTCAAT TTTGAGACACAG CTGGTGAGCTGC TG (SEQ ID NO: 1485) |
| PDPN | NM_006474.4 | CTCCAGGAACCAGC GAAGACCGCTATA AGTCTGGCTTGACA ACTCTGGTGGCAAC AAGTGTCAACAGTG TAACAGGCATTCGC ATCGAGGATCTGCC AAC (SEQ ID NO: 1486) | CACCAGAGTTGT CAAGCCAGACTT ATAGCGGTCTTCG CTGGTTCC (SEQ ID NO: 1487) | GTTGGCAGATCC TCGATGCGAATG CCTGTTACACTG TTGACACTTGTT GC (SEQ ID NO: 1488) |
| PECAM1 | NM_000442.3 | ATCTGCACTGCAGG TATTGACAAAGTGG TCAAGAAAAGCAA CACAGTCCAGATAG TCGTATGTGAAATG CTCTCCCAGCCCAG GATTTCTTATGATG CCC (SEQ ID NO: 1489) | TGGACTGTGTTGC TTTTCTTGACCAC TTTGTCAATACCT GCAGTG (SEQ ID NO: 1490) | GGGCATCATAAG AAATCCTGGGCT GGGAGAGCATTT CACATACGACTA TC (SEQ ID NO: 1491) |

TABLE 1-continued

| Gene | GenBank Accession No. | Target Sequence | Capture Probe Sequence | Reporter Probe Sequence |
|---|---|---|---|---|
| PECR | NM_018441.5 | CATTGTCCCTACTAAAGCTGGATTTCCATTAGCTGTGCATTCTGGAGCTGCAAGAGCAGGTGTTTACAACCTCACCAAATCTTTAGCTTTGGAATGGGCC (SEQ ID NO: 1492) | CAGCTCCAGAATGCACAGCTAATGGAAATCCAGCTTTAGTAGGGACAATG (SEQ ID NO: 1493) | GGCCCATTCCAAAGCTAAAGATTTGGTGAGGTTGTAAACACCTGCTCTTG (SEQ ID NO: 1494) |
| PGAM1 | NM_002629.2 | ATGGAAAAGCTCCCCTTATCCAACAGAGTTTAAAAGTAGTGACTTGGGTTTTTGCGAGTGCTTTGTTTACTAAGGACTTTGGGGAGGAACCATGCTAAGC (SEQ ID NO: 1495) | AACCCAAGTCACTACTTTTAAACTCTGTTGGATAAGGGGAGCTTTTCCAT (SEQ ID NO: 1496) | GCTTAGCATGGTTCCTCCCCAAAGTCCTTAGTAAACAAAGCACTCGCAAA (SEQ ID NO: 1497) |
| PHAX | NM_032177.3 | GAAAAAAACATTCCCAGTGGCAGCCTGCCTAAGACTGTCTTACCTTATGTTAAGGAAGTCAGGTATTTAAAATGTTACATATGCCGGCGCAGTGGCTCAT (SEQ ID NO: 1498) | ACATAAGGTAAGACAGTCTTAGGCAGGCTGCCACTGGGAATGTTTTTTTC (SEQ ID NO: 1499) | ATGAGCCACTGCGCCGGCATATGTAACATTTTAAATACCTGACTTCCTTA (SEQ ID NO: 1500) |
| PHC3 | NM_024947.3 | CTACATCTCCCACAGGAAGTGTCACACAGCAGTCAAGTATGTCCCAAACGTCTATCAACCTCTCCACTTCTCCTACACCTGCACAGTTAATAAGCCGTTC (SEQ ID NO: 1501) | CGTTTGGGACATACTTGACTGCTGTGTGACACTTCCTGTGGGAGA (SEQ ID NO: 1502) | GAACGGCTTATTAACTGTGCAGGTGTAGGAGAAGTGGAGAGGTTGATAGA (SEQ ID NO: 1503) |
| PHF16 | NM_014735.3 | GTAGCCTTTGTCCCTTCATGCCTTTCAATTCTGAGTGGGAGGAAAAGCAAACATCAAAACAGTGCTTCAGCCAAATTCCATATGTAATGCCATTGGGAGA (SEQ ID NO: 1504) | TTGCTTTTCCTCCCACTCAGAATTGAAAGGCATGAAGGGACAAAGGCTAC (SEQ ID NO: 1505) | TCTCCCAATGGCATTACATATGGAATTTGGCTGAAGCACTGTTTTGATGT (SEQ ID NO: 1506) |
| PHF23 | NM_024297.2 | CTGTCTGTGTCCCGACACATAATCTCTGTCTCTTGGACCTGCCACCATCACTTTCTGGGTCAGGATTGGAATTGGGATGGAATGGGACAGTTGTCTATAA (SEQ ID NO: 1507) | TGATGGTGGCAGGTCCAAGAGACAGAGATTATGTGTCGGGACACAGACAG (SEQ ID NO: 1508) | TTATAGACAACTGTCCCATTCCATCCCAATTCCAATCCTGACCCAGAAAG (SEQ ID NO: 1509) |
| PIK3CA | NM_006218.2 | CCTCAGGCTTGAAGAGTGTCGAATTATGTCCTCTGCAAAAGGCCACTGTGGTTGAATTGGGAGAACCCAGACATCATGTCAGAGTTACTGTTTCAGAAC (SEQ ID NO: 1510) | ACAGTGGCCTTTTTGCAGAGGACATAATTCGACACTCTTCAAGCCTGAGG (SEQ ID NO: 1511) | GTTCTGAAACAGTAACTCTGACATGATGTCTGGGTTCTCCCAATTCAACC (SEQ ID NO: 1512) |

TABLE 1-continued

| Gene | GenBank Accession No. | Target Sequence | Capture Probe Sequence | Reporter Probe Sequence |
|---|---|---|---|---|
| PIK3CD | NM_005026.3 | TGACACTCATTGAT TCTAAAGCATCTT AATCTGCCAGGCGG AGGGGGCTTTGCTG GTCTTTCTTGGACT ATTCCAGAGAGGA CAACTGTCATCTGG GAA (SEQ ID NO: 1513) | AGCCCCCTCCGCC TGGCAGATTAAA GATGCTTTAGAAT CAATGAGTG (SEQ ID NO: 1514) | TTCCCAGATGAC AGTTGTCCTCTC TGGAATAGTCCA AGAAAGACCAG CAA (SEQ ID NO: 1515) |
| PIM1 | NM_002648.2 | CTTCATCATGAGTT CTGCTGAATGCCGC GATGGGTCAGGTA GGGGGGAAACAGG TTGGGATGGGATAG GACTAGCACCATTT TAAGTCCCTGTCAC CTCT (SEQ ID NO: 1516) | TTTCCCCCCTACC TGACCCATCGCG GCATTCAGCAGA ACTCATGATGAA G (SEQ ID NO: 1517) | AGAGGTGACAG GGACTTAAAATG GTGCTAGTCCTA TCCCATCCCAAC CTG (SEQ ID NO: 1518) |
| PIM2 | NM_006875.2 | GCCATCCAGCACTG CCATTCCCGTGGAG TTGTCCATCGTGAC ATCAAGGATGAGA ACATCCTGATAGAC CTACGCCGTGGCTG TGCCAAACTCATTG ATT (SEQ ID NO: 1519) | TCCTTGATGTCAC GATGGACAACTC CACGGGAATGGC AGTGCTGGATG (SEQ ID NO: 1520) | AATCAATGAGTT TGGCACAGCCAC GGCGTAGGTCTA TCAGGATGTTCT CA (SEQ ID NO: 1521) |
| PLAU | NM_002658.2 | TTCATTGATTACCC AAAGAAGGAGGAC TACATCGTCTACCT GGGTCGCTCAAGGC TTAACTCCAACACG CAAGGGAGATGA AGTTTGAGGTGGAA AACC (SEQ ID NO: 1522) | GAGCGACCCAGG TAGACGATGTAG TCCTCCTTCTTTG GGTAATCAATGA A (SEQ ID NO: 1523) | GGTTTTCCACCT CAAACTTCATCT CCCCTTGCGTGT TGGAGTTAAGCC TT (SEQ ID NO: 1524) |
| PLEK | NM_002664.2 | AAATGATATTGCGT TCGTGCCTCAGCTT TAAGCACAAGTAG CAGCAGCTCCTGCT TGAGTTCTGAGGGC ATCATGGCCCTATG ATTAACCAGAGTGA TCT (SEQ ID NO: 1525) | GAGCTGCTGCTA CTTGTGCTTAAAG CTGAGGCACGAA CGCAATATCATTT (SEQ ID NO: 1526) | AGATCACTCTGG TTAATCATAGGG CCATGATGCCCT CAGAACTCAAGC AG (SEQ ID NO: 1527) |
| PLEKHF2 | NM_024613.2 | ATCGTCGCCACCAT TGCCGCAAATGTGG TTTTGTTGTCTGTG GGCCCTGCTCTGAA AAGAGATTTCTTCT TCCCAGCCAGTCCT CTAAGCCTGTGCGG AT (SEQ ID NO: 1528) | GCAGGGCCCACA GACAACAAAACC ACATTTGCGGCA ATGGTGGCGACG AT (SEQ ID NO: 1529) | ATCCGCACAGGC TTAGAGGACTGG CTGGGAAGAAG AAATCTCTTTTC AGA (SEQ ID NO: 1530) |
| PLEKHG4B | NM_052909.3 | CGGTTTCAGCAGGT CCCATGTAGTTAGC AGGACAGCACTTG AGTTAGGTCTGAGA AAGAACGCCTGTTT GTCATGGCATTTCC TGTAAGGAGCCCA GAGC (SEQ ID NO: 1531) | GACCTAACTCAA GTGCTGTCCTGCT AACTACATGGGA CCTGCTGAAACC G (SEQ ID NO: 1532) | CTCTGGGCTCCT TACAGGAAATGC CATGACAAACAG GCGTTCTTTCTC A (SEQ ID NO: 1533) |

TABLE 1-continued

| Gene | GenBank Accession No. | Target Sequence | Capture Probe Sequence | Reporter Probe Sequence |
|---|---|---|---|---|
| PLXNB1 | NM_001130082.1 | CCAACAGCTTGCCT CTGAGGTTCTGGAT CAATATAATAAAA AACCCGCAGTTTGT GTTCGACGTGCAAA CATCTGATAACATG GATGCGGTGCTCCT TGT (SEQ ID NO: 1534) | CTGCGGGTTTTTT ATTATATTGATCC AGAACCTCAGAG GCAAGCTGTTGG (SEQ ID NO: 1535) | ACAAGGAGCAC CGCATCCATGTT ATCAGATGTTTG CACGTCGAACAC AAA (SEQ ID NO: 1536) |
| PMCHL1 | NM_031887.2 | CGGGGGAAAGCCC ATCCGTACTACCAG GAGACTGGATCCGC AAAGTAGACACTTG GTCTCATGAAGCCA CTGCTGGGCTCCAG AGAGAAGGGAAAA CTAA (SEQ ID NO: 1537) | GTCTACTTTGCGG ATCCAGTCTCCTG GTAGTACGGATG GG (SEQ ID NO: 1538) | TCTCTGGAGCCC AGCAGTGGCTTC ATGAGACCAAGT (SEQ ID NO: 1539) |
| PMEPA1 | NM_020182.3 | GCTGAGACAGTCCT CATATCCTCTTGAG CCAAACTGTTTGGG TCTCGTTGCTTCAT GGTATGGTCTGGAT TTGTGGGAATGGCT TTGCGTGAGAAAG GGG (SEQ ID NO: 1540) | CAACGAGACCCA AACAGTTTGGCTC AAGAGGATATGA GGACTGTCTCAG C (SEQ ID NO: 1541) | CCCCTTTCTCAC GCAAAGCCATTC CCACAAATCCAG ACCATACCATGA AG (SEQ ID NO: 1542) |
| PMP22 | NM_000304.2 | GTCTAGGCTGTTCT GTGCCTCCAAGGAC TGTCTGGCAATGAC TTGTATTGGCCACC AACTGTAGATGTAT ATATGGTGCCCTTC TGATGCTAAGACTC CA (SEQ ID NO: 1543) | CAATACAAGTCA TTGCCAGACAGT CCTTGGAGGCAC AGAACAGCCTAG AC (SEQ ID NO: 1544) | AGTCTTAGCATC AGAAGGGCACC ATATATACATCT ACAGTTGGTGGC (SEQ ID NO: 1545) |
| PNLIP | NM_000936.2 | GAAAACAGTTCAA CTTCTGTAGTCCAG AAACCGTCAGGGA GGAAGTTCTGCTCA CCCTCACACCGTGT TAGGAGACTACTGT TATTTGACCAATGA ATTG (SEQ ID NO: 1546) | CAGAACTTCCTCC CTGACGGTTTCTG GACTACAGAAGT TGAACTGTTTTC (SEQ ID NO: 1547) | CAATTCATTGGT CAAATAACAGTA GTCTCCTAACAC GGTGTGAGGGTG AG (SEQ ID NO: 1548) |
| PNP | NM_000270.3 | CGCTGTTGGCATGA GTACAGTACCAGA AGTTATCGTTGCAC GGCACTGTGGACTT CGAGTCTTTGGCTT CTCACTCATCACTA ACAAGGTCATCATG GAT (SEQ ID NO: 1549) | CACAGTGCCGTG CAACGATAACTT CTGGTACTGTACT CATGCCAACAGC G (SEQ ID NO: 1550) | ATCCATGATGAC CTTGTTAGTGAT GAGTGAGAAGC CAAAGACTCGAA GTC (SEQ ID NO: 1551) |
| POU2AF1 | NM_006235.2 | CCCTGATGCCAGAG TCCTTGAGCTGTCA GTTCCCACAGTTGC TCCTTTGTTTGCTCT TCTCAGCCTCGGCC AGATTTACAGTCCA GGCAGCAAAATCTC A (SEQ ID NO: 1552) | ACAAAGGAGCAA CTGTGGGAACTG ACAGCTCAAGGA CTCTGGCATCAG GG (SEQ ID NO: 1553) | TGAGATTTTGCT GCCTGGACTGTA AATCTGGCCGAG GCTGAGAAGAG CAA (SEQ ID NO: 1554) |

TABLE 1-continued

| Gene | GenBank Accession No. | Target Sequence | Capture Probe Sequence | Reporter Probe Sequence |
| --- | --- | --- | --- | --- |
| POU2F1 | NM_002697.2 | GCTATGGGGAAACT ATATGGAAATGACT TCAGCCAAACTACC ATCTCTCGATTTGA AGCCTTGAACCTCA GCTTTAAGAACATG TGCAAGTTGAAGCC AC (SEQ ID NO: 1555) | CGAGAGATGGTA GTTTGGCTGAAGT CATTTCCATATAG TTTCCCCATAGC (SEQ ID NO: 1556) | GTGGCTTCAACT TGCACATGTTCT TAAAGCTGAGGT TCAAGGCTTCAA AT (SEQ ID NO: 1557) |
| POU2F2 | NM_002698.2 | ATGGGGCCTGGCAC CTCGTCTACCCAAC CTCACCGGAATGTA AGCATCTCCGCTGA ACGACTCCCTGCCC TTACCCTACCTCTG AGTTTGTCCATGTT TA (SEQ ID NO: 1558) | GAGATGCTTACA TTCCGGTGAGGTT GGGTAGACGAGG TGCCAGG (SEQ ID NO: 1559) | TAAACATGGACA AACTCAGAGGTA GGGTAAGGGCA GGGAGTCGTTCA GCG (SEQ ID NO: 1560) |
| PPA1 | NM_021129.3 | ATACTGGCTGTTGT GGTGACAATGACCC AATTGATGTGTGTG AAATTGGAAGCAA GGTATGTGCAAGA GGTGAAATAATTGG CGTGAAAGTTCTAG GCAT (SEQ ID NO: 1561) | TCCAATTTCACAC ACATCAATTGGG TCATTGTCACCAC AACAGCCAGTAT (SEQ ID NO: 1562) | ATGCCTAGAACT TTCACGCCAATT ATTTCACCTCTT GCACATACCTTG CT (SEQ ID NO: 1563) |
| PPP2R3B | NM_199326.1 | CCCTGACATGCATC TTCGTCTCTCCATC CTGGCTTTCGATCT AGAGGCAGAAAAG TGCAGAAGGAAGG GAAGATCAGCTATG CCGACTTTGTCTGG TTTT (SEQ ID NO: 1564) | CTGCCTCTAGATC GAAAGCCAGGAT GGAGAGACGAAG ATGCATGTCAGG G (SEQ ID NO: 1565) | AAAACCAGACA AAGTCGGCATAG CTGATCTTCCCT TCCTTCTGCACT TTT (SEQ ID NO: 1566) |
| PPP3CC | NM_005605.3 | AGCAGAAGGAAGC ACTACAGTTCGTAA GGAGATCATCAGG AATAAGATCAGAG CCATTGGGAAGATG GCACGGGTCTTTTC AATTCTTCGGCAAG AAAGT (SEQ ID NO: 1567) | TGATCTTATTCCT GATGATCTCCTTA CGAACTGTAGTG CTTCCTTCTG (SEQ ID NO: 1568) | ACTTTCTTGCCG AAGAATTGAAA AGACCCGTGCCA TCTTCCCAATGG CTC (SEQ ID NO: 1569) |
| PPPDE2 | NM_015704.2 | CAAGACCCACTGAT TTGCCAGTGTGCAT GGAAATAATAGATT AGAGCAGAAACTA GCAGGGACTGTTGT ATAATCGTGATCTA CTAGCAGAATTGGG CCC (SEQ ID NO: 1570) | TCTGCTCTAATCT ATTATTTCCATGC ACACTGGCAAAT CAGTGGGTCTTG (SEQ ID NO: 1571) | GCCCAATTCTGC TAGTAGATCACG ATTATACAACAG TCCCTGCTAGTT (SEQ ID NO: 1572) |
| PRDM1 | NM_182907.1 | CATCCCTGCCAACC AGGAACTTCTTGTG TGGTATTGTCGGGA CTTTGCAGAAAGGC TTCACTACCCTTAT CCCGGAGAGCTGA CAATGATGAATCTC ACA (SEQ ID NO: 1573) | CTGCAAAGTCCC GACAATACCACA CAAGAAGTTCCT GGTTGGCAGGGA TG (SEQ ID NO: 1574) | TGTGAGATTCAT CATTGTCAGCTC TCCGGGATAAGG GTAGTGAAGCCT TT (SEQ ID NO: 1575) |

TABLE 1-continued

| Gene | GenBank Accession No. | Target Sequence | Capture Probe Sequence | Reporter Probe Sequence |
|---|---|---|---|---|
| PRDM12 | NM_021619.2 | CCACACTTCCCTCG GTCCCTGCCCGTTT CCTCAAATTCGGGC CGTGCGCGCCCTCT GGTGTCGCCTCTCA CACTTTGCAGTCAT TTACCAGGATTCCC GT (SEQ ID NO: 1576) | CGCGCACGGCCC GAATTTGAGGAA ACGGGCAGGGAC CGAGGGAAGTG (SEQ ID NO: 1577) | ACGGGAATCCTG GTAAATGACTGC AAAGTGTGAGA GGCGACACCAG AGGG (SEQ ID NO: 1578) |
| PRDX2 | NM_005809.4 | GCATGGGGAAGTTT GTCCCGCTGGCTGG AAGCCTGGCAGTG ACACGATTAAGCCC AACGTGGATGACA GCAAGGAATATTTC TCCAAACACAATTA GGCT (SEQ ID NO: 1579) | TAATCGTGTCACT GCCAGGCTTCCA GCCAGCGGGACA AAC (SEQ ID NO: 1580) | AGCCTAATTGTG TTTGGAGAAATA TTCCTTGCTGTC ATCCACGTTGGG CT (SEQ ID NO: 1581) |
| PRDX4 | NM_006406.1 | AGGAGGACTTGGG CCAATAAGGATTCC ACTTCTTTCAGATT TGACCCATCAGATC TCAAAGGACTATGG TGTATACCTAGAGG ACTCAGGCCACACT CTT (SEQ ID NO: 1582) | GATGGGTCAAAT CTGAAAGAAGTG GAATCCTTATTGG CCCAAGTCCTCCT (SEQ ID NO: 1583) | CCTGAGTCCTCT AGGTATACACCA TAGTCCTTTGAG ATCT (SEQ ID NO: 1584) |
| PRICKLE1 | NM_153026.1 | AGTTTCCTGGCCTC TCAGGCAATGCTGA TGACACCCTTTCTC GAAAATTGGATGAT CTGAGTCTCTCCAG ACAAGGAACAAGT TTTGCCAGTGAAGA ATT (SEQ ID NO: 1585) | CAATTTTCGAGA AAGGGTGTCATC AGCATTGCCTGA GAGGCCAGGAAA CT (SEQ ID NO: 1586) | AATTCTTCACTG GCAAAACTTGTT CCTTGTCTGGAG AGACTCAGATCA TC (SEQ ID NO: 1587) |
| PRKCB | NM_212535.1 | GCATTTGGAGTCCT GCTGTATGAAATGT TGGCTGGGCAGGC ACCCTTTGAAGGGG AGGATGAAGATGA ACTCTTCCAATCCA TCATGGAACACAAC GTAG (SEQ ID NO: 1588) | TCAAAGGGTGCC TGCCCAGCCAAC ATTTCATACAGCA GGACTCCAAATG C (SEQ ID NO: 1589) | CTACGTTGTGTT CCATGATGGATT GGAAGAGTTCAT CTTCATCCTCCC CT (SEQ ID NO: 1590) |
| PRMT1 | NM_198319.2 | ACTGCATCATGGAG AATTTTGTAGCCAC CTTGGCTAATGGGA TGAGCCTCCAGCCG CCTCTTGAAGAAGT AACCCCCCTTTGCC CTTCCCTGTGTCTG CC (SEQ ID NO: 1591) | GAGGCTCATCCC ATTAGCCAAGGT GGCTACAAAATT CTCCATGATGCA GT (SEQ ID NO: 1592) | GCAGACACAGG GAAGGGCAAAG GGGGGTTACTTC TTCAAGAGGCGG CTG (SEQ ID NO: 1593) |
| PRPSAP2 | NM_002767.2 | AGACCTCTTGTGCC AAGAGCATCATTGG CGTGATACCCTACT TTCCTTACAGCAAG CAGTGCAAGATGA GAAAAAGAGGCTC CATTGTCTCTAAAT TGCT (SEQ ID NO: 1594) | GTAAGGAAAGTA GGGTATCACGCC AATGATGCTCTTG GCACAAGAGGTC T (SEQ ID NO: 1595) | AGCAATTTAGAG ACAATGGAGCCT CTTTTTCTCATCT TGCACTGCTTGC T (SEQ ID NO: 1596) |

TABLE 1-continued

| Gene | GenBank Accession No. | Target Sequence | Capture Probe Sequence | Reporter Probe Sequence |
|---|---|---|---|---|
| PRSS1 | NM_002769.3 | GTAATCAACGCCCGCGTGTCCACCATCTCTCTGCCCACCGCCCCTCCAGCCACTGGCACGAAGTGCCTCATCTCTGGCTGGGGCAACACTGCGAGCTCTG (SEQ ID NO: 1597) | GCTGGAGGGGCGGTGGGCAGAGAGATGGTGGACACGCGG (SEQ ID NO: 1598) | TTGCCCCAGCCAGAGATGAGGCACTTCGTGCCAGTG (SEQ ID NO: 1599) |
| PSMG1 | NM_003720.2 | AAAATCCAATCCCTCGGTTTTTCTCTGTCAGTGCAGTTGCTATGTTGCAGAAGATCAACAGTATCAGTGGCTGGAAAAGGTTTTTGGCTCTTGTCCAAGG (SEQ ID NO: 1600) | CTGCAACATAGCAACTGCACTGACAGAGAAAAACCGAGGGATTGGATTTT (SEQ ID NO: 1601) | CCTTGGACAAGAGCCAAAAACCTTTTCCAGCCACTGATACTGTTGATCTT (SEQ ID NO: 1602) |
| PTEN | NM_000314.3 | TGTGGTCTGCCAGCTAAAGGTGAAGATATATTCCTCCAATTCAGGACCCACACGACGGGAAGACAAGTTCATGTACTTTGAGTTCCCTCAGCCGTTACCT (SEQ ID NO: 1603) | TGGGTCCTGAATTGGAGGAATATATCTTCACCTTTAGCTGGCAGACCACA (SEQ ID NO: 1604) | AGGTAACGGCTGAGGGAACTCAAAGTACATGAACTTGTCTTCCCGTCGTG (SEQ ID NO: 1605) |
| PTENP1 | NR_023917.1 | ACCACAATGAGATGACACTACACATTTGCCAGAATGATGATTATTAAAAAGACCAAGTATTGGAGAGGATGTGAAAAAACTGGAACCTCACACATTGAC (SEQ ID NO: 1606) | TTTTTAATAATCATCATTCTGGCAAATGTGTAGTGTCATCTCATTGTGGT (SEQ ID NO: 1607) | TCAATGTGTGAGGTTCCAGTTTTTTCACATCCTCTCCAATACTTGGTCT (SEQ ID NO: 1608) |
| PTGER4 | NM_000958.2 | CGCGGGCGCCGAGATCCAGATGGTCATCTTACTCATTGCCACCTCCCTGGTGGTGCTCATCTGCTCCATCCCGCTCGTGGTGCGAGTATTCGTCAACCAG (SEQ ID NO: 1609) | CCAGGGAGGTGGCAATGAGTAAGATGACCATCTGGATCTCGG (SEQ ID NO: 1610) | CTGGTTGACGAATACTCGCACCACGAGCGGGATGGAGCAGATGAGCACCA (SEQ ID NO: 1611) |
| PTGIR | NM_000960.3 | CTGACATTTCAAGCTGACCCTGTGATCTCTGCCCTGTCTTCGGGCGACAGGAGCCAGAAAATCAGGGACATGGCTGATGGCTGCGGATGCTGGAACCTTG (SEQ ID NO: 1612) | CTGTCGCCCGAAGACAGGGCAGAGATCACAGGGTCAGCTTGAAATG (SEQ ID NO: 1613) | CGCAGCCATCAGCCATGTCCCTGATTTTCTGGCTC (SEQ ID NO: 1614) |
| PTK2 | NM_005607.3 | GGTTCAAGCTGGATTATTTCAGTGGAACTGGCAATCGGCCCAGAAGAAGGAATCAGTTACCTAACGGACAAGGGCTGCAATCCCACACATCTTGCTGACT (SEQ ID NO: 1615) | CCTTCTTCTGGGCCGATTGCCAGTTCCACTGAAATAATCCAGCTTGAACC (SEQ ID NO: 1616) | AGTCAGCAAGATGTGTGGGATTGCAGCCCTTGTCCGTTAGGTAACTGATT (SEQ ID NO: 1617) |

TABLE 1-continued

| Gene | GenBank Accession No. | Target Sequence | Capture Probe Sequence | Reporter Probe Sequence |
|---|---|---|---|---|
| PTPN1 | NM_002827.2 | AGTGACTTCCCATGTAGAGTGGCCAAGCTTCCTAAGAACAAAAACCGAAATAGGTACAGAGACGTCAGTCCCTTTGACCATAGTCGGATTAAACTACATC (SEQ ID NO: 1618) | TTTCGGTTTTTGTTCTTAGGAAGCTTGGCCACTCTACATGGGAAGT (SEQ ID NO: 1619) | GATGTAGTTTAATCCGACTATGGTCAAAGGGACTGACGTCTCTGTACCTA (SEQ ID NO: 1620) |
| PTPN21 | NM_007039.3 | ATTGGAGCGTGTCTTGAAGGTATCTTTGTGAAACACAAGAATGGAAGGCATCCTGTGGTATTTAGGTGGCATGACATTGCCAACATGTCCCACAACAAGT (SEQ ID NO: 1621) | TGCCTTCCATTCTTGTGTTTCACAAAGATACCTTCAAGACACGCTCCAAT (SEQ ID NO: 1622) | ACTTGTTGTGGGACATGTTGGCAATGTCATGCCACCTAAATACCACAGGA (SEQ ID NO: 1623) |
| PTPRB | NM_002837.3 | CTTGTAAATACCGCAACCGAGTATCGATTTACTTCCCTAACACCAGGCCGCCAATACAAAATTCTTGTCTTGACGATTAGCGGGGATGTACAGCAGTCAG (SEQ ID NO: 1624) | CGGCCTGGTGTTAGGGAAGTAAATCGATACTCGGTTGCGGTATTTACAAG (SEQ ID NO: 1625) | CTGACTGCTGTACATCCCCGCTAATCGTCAAGACAAGAATTTTGTATTGG (SEQ ID NO: 1626) |
| PTRH1 | NM_001002913.1 | CCCGGCGCACCCTGAGGCGGTTCAGGCCCATGTGCTGGGCTGCTTCTCCCCTGCTGAGCAGGAGCTGCTGCCTCTGTTGCTGGATCGAGCCACCGACCTG (SEQ ID NO: 1627) | GGGAGAAGCAGCCCAGCACATGGGCCTGAACCGCC (SEQ ID NO: 1628) | ATCCAGCAACAGAGGCAGCAGCTCCTGCTCAGCAG (SEQ ID NO: 1629) |
| PVRL1 | NM_002855.4 | GTTAAGCGGGGCCTTGGGCAGTGTTTTCCTGCTGAGGGTGGTTTTACATTTTTTTTCCTCATTGGCCCACAGAGAGTGGAGTTGGCCTAGCTCTGACGCG (SEQ ID NO: 1630) | AATGTAAAACCACCCTCAGCAGGAAAACACTGCCCAAGGCCCCGCTTAAC (SEQ ID NO: 1631) | CGCGTCAGAGCTAGGCCAACTCCACTCTCTGTGGGCCAATGAGGAAAAAA (SEQ ID NO: 1632) |
| PXDN | NM_012293.1 | GCGACTGTTGACAGAGCTATAAACTCAACCCGAACACATTTGTTTGACAGCCGTCCTCGTTCTCCAAATGATTTGCTGGCCTTGTTCCGGTATCCGAGGG (SEQ ID NO: 1633) | CTGTCAAACAAATGTGTTCGGGTTGAGTTTATAGCTCTGTCAACAGTCGC (SEQ ID NO: 1634) | CCCTCGGATACCGGAACAAGGCCAGCAAATCATTTGGAGAACGAGGACGG (SEQ ID NO: 1635) |
| QSOX1 | NM_002826.4 | TAGGGCAGCTCAGTCCCTGGCCTCTTAGCACCACATTCCTGTTTTTCAGCTTATTTGAAGTCCTGCCTCATTCTCACTGGAGCCTCAGTCTCTCCTGCTT (SEQ ID NO: 1636) | GCTGAAAAACAGGAATGTGGTGCTAAGAGGCCAGGGACTGAGCTGCCCTA (SEQ ID NO: 1637) | AAGCAGGAGAGACTGAGGCTCCAGTGAGAATGAGGCAGGACTTCAAATAA (SEQ ID NO: 1638) |

TABLE 1-continued

| Gene | GenBank Accession No. | Target Sequence | Capture Probe Sequence | Reporter Probe Sequence |
|---|---|---|---|---|
| R3HDM1 | NM_015361.2 | CCTGTGTTCCCAAG AGAATTACATTATT GACAAAAGACTCC AAGACGAGGATGC CAGTAGTACCCAGC AGAGGCGCCAGAT ATTTAGAGTTAATA AAGAT (SEQ ID NO: 1639) | CCTCGTCTTGGAG TCTTTTGTCAATA ATGTAATTCTCTT GGGAACACAGG (SEQ ID NO: 1640) | ATCTTTATTAAC TCTAAATATCTG GCGCCTCTGCTG GGTACTACTGGC AT (SEQ ID NO: 1641) |
| RAB20 | NM_017817.1 | AGACCGGCTACAAT GTGGACCTCCTGTT TGAGACCCTCTTTG ACCTGGTGGTGCCA ATGATCTTACAGCA GAGAGCTGAGAGG CCGTCACACACAGT GGA (SEQ ID NO: 1642) | CACCAGGTCAAA GAGGGTCTCAAA CAGGAGGTCCAC ATTGTAGCCGG (SEQ ID NO: 1643) | GACGGCCTCTCA GCTCTCTGCTGT AAGATCATTGGC AC (SEQ ID NO: 1644) |
| RAB31 | NM_006868.3 | TTTTGTAAAGAGCT TCCATCTGGGCTGG ACCCAGTTCTTGCA CATACAAGACACC GCTGCAGTCAGCTA GGACCTTTCCGCCA TGTATTCTATTCTG TAG (SEQ ID NO: 1645) | CTTGTATGTGCAA GAACTGGGTCCA GCCCAGATGGAA GCTCTTTACAAAA (SEQ ID NO: 1646) | CTACAGAATAGA ATACATGGCGGA AAGGTCCTAGCT GACTGCAGCGGT GT (SEQ ID NO: 1647) |
| RAB33A | NM_004794.2 | GGGAGAAGACCGT GGAAATCGAGGGC GAGAAGATCAAGG TTCAGGTGTGGGAC ACAGCAGGTCAGG AACGTTTCCGCAAA AGCATGGTCGAGC ATTACTA (SEQ ID NO: 1648) | CCACACCTGAAC CTTGATCTTCTCG CCCTCGATTTCCA CG (SEQ ID NO: 1649) | TAGTAATGCTCG ACCATGCTTTTG CGGAAACGTTCC TGACCTGCTGTG TC (SEQ ID NO: 1650) |
| RAB3A | NM_002866.4 | CGCCACAGACTCGC GCTATGGGCAGAA GGAGTCCTCGGATC AGAACTTCGACTAC ATGTTCAAGATTCT CATCATCGGCAACA GCAGCGTGGGCAA GACG (SEQ ID NO: 1651) | CGAAGTTCTGATC CGAGGACTCCTTC TGCCCATAGCGC GA (SEQ ID NO: 1652) | CGTCTTGCCCAC GCTGCTGTTGCC GATGATGAGAAT CTTGAACATGTA GT (SEQ ID NO: 1653) |
| RAB7L1 | NM_001135664.1 | CATTTGAATTGTCT CCTGACTACTGTCC AGTAAGGAGGCCC ATTGTCACTTAGAA AAGACACCTGGAA CCCATGTGCATTTC TGCATCTCCTGGAT TAGC (SEQ ID NO: 1654) | AGTGACAATGGG CCTCCTTACTGGA CAGTAGTCAGGA GACAATTCAAAT G (SEQ ID NO: 1655) | CTAATCCAGGAG ATGCAGAAATGC ACATGGGTTCCA GGTGTCTTTTCT A (SEQ ID NO: 1656) |
| RANBP9 | NM_005493.2 | TTGAAGGATGCATT CAGTCTACTAGCAT ATTCAGATCCCTGG AACAGCCCAGTTGG AAATCAGCTTGACC CGATTCAGAGAGA ACCTGTGTGCTCAG CTC (SEQ ID NO: 1657) | GGGCTGTTCCAG GGATCTGAATAT GCTAGTAGACTG AATGCATCCTTCA A (SEQ ID NO: 1658) | TGAGCACACAGG TTCTCTCTGAAT CGGGTCAAGCTG ATTTCCAACT (SEQ ID NO: 1659) |

TABLE 1-continued

| Gene | GenBank Accession No. | Target Sequence | Capture Probe Sequence | Reporter Probe Sequence |
|---|---|---|---|---|
| RAPGEF5 | NM_012294.3 | GCATTTTGCGTACCTCATACAGGCTCCTTGCCCACACTATGGAATGACAGCAGCCAGTGCAGGGAGGTTAAGTGACATTTAATGAGTGAAGCACTTAGCA (SEQ ID NO: 1660) | CTGTCATTCCATAGTGTGGGCAAGGAGCCTGTATGAGGTACGCAAAATGC (SEQ ID NO: 1661) | TGCTAAGTGCTTCACTCATTAAATGTCACTTAACCTCCCTGCACTGGCTG (SEQ ID NO: 1662) |
| RARRES2 | NM_002889.3 | GAAACCCGAGTGCAAAGTCAGGCCCAATGGGAGGAAACGGAAATGCCTGGCCTGCATCAAACTGGGCTCTGAGGACAAAGTTCTGGGCCGGTTGGTCCAC (SEQ ID NO: 1663) | CCAGGCATTTCCGTTTCCTCCCATTGGGCCTGACTTTGCACTCGGGTTTC (SEQ ID NO: 1664) | CAACCGGCCCAGAACTTTGTCCTCAGAGCCCAGTTTGATGCAGG (SEQ ID NO: 1665) |
| RASGRP3 | NM015376.2 | GCTGACTTGCATGATTATGGAGATGGTCTATCTGATGCTGAAAATGTCTCTAGTTTTTTGACAACGGCTAAATAACCATGGATCAAGTGGCCTTGGGAA (SEQ ID NO: 1666) | GAGACATTTTCAGCATCAGATAGACCATCTCCATAATCATGCAAGTCAGC (SEQ ID NO: 1667) | TTCCCAAGGCCACTTGATCCCATGGTTATTTAGCCGTTGTCAAAAAACTA (SEQ ID NO: 1668) |
| RASSF4 | NM_032023.3 | TGAAGGAAGACTGTCTGCCGAGTTCTCACGTGCCCATCAGTGACAGCAAGTCCATTCAGAAGTCGGAGCTCTTAGGCCTGCTGAAAACCTACAACTGCTA (SEQ ID NO: 1669) | CTTGCTGTCACTGATGGGCACGTGAGAACTCGGCAGACAGTCTT (SEQ ID NO: 1670) | TAGCAGTTGTAGGTTTTCAGCAGGCCTAAGAGCTCCGACTTCTGAATGGA (SEQ ID NO: 1671) |
| RC3H2 | NM_018835.2 | AGATCCAATAATTCCCTTTAGTGATGGACCCATCATCTCAAAATGGGGTGCGATTTCCAGATCTTCCCGTACAGGTTACCATACCACAGATCCTGTCCAG (SEQ ID NO: 1672) | CACCCCATTTTGAGATGATGGGTCCATCACTAAAGGGAATTATTGGATCT (SEQ ID NO: 1673) | CTGGACAGGATCTGTGGTATGGTAACCTGTACGGGAAGATCTGGAAATCG (SEQ ID NO: 1674) |
| RCL1 | NM_005772.3 | TGGTGAATCATTTGAACTGAAGATTGTGCGACGGGGAATGCCTCCCGGAGGAGGAGGCGAAGTGGTTTTCTCATGTCCTGTGAGGAAGGTCTTGAAGCCC (SEQ ID NO: 1675) | CTCCGGGAGGCATTCCCCGTCGCACAATCTTCAGTTCAAATGATTCACCA (SEQ ID NO: 1676) | GGGCTTCAAGACCTTCCTCACAGGACATGAGAAAACCACTTCGCCTCCTC (SEQ ID NO: 1677) |
| REL | NM_002908.2 | TGGCCTCCGGTGCGTATAACCCGTATATAGAGATAATTGAACAACCCAGGCAGAGGGGAATGCGTTTTAGATACAAATGTGAAGGGCGATCAGCAGGCAG (SEQ ID NO: 1678) | CCTGGGTTGTTCAATTATCTCTATATACGGGTTATACGCACCGGAGGCCA (SEQ ID NO: 1679) | CTGCCTGCTGATCGCCCTTCACATTTGTATCTAAAACGCATTCCCCTCTG (SEQ ID NO: 1680) |

TABLE 1-continued

| Gene | GenBank Accession No. | Target Sequence | Capture Probe Sequence | Reporter Probe Sequence |
|---|---|---|---|---|
| RETNLB | NM_032579.2 | TGACCTGACAGGG AGGAGGCTGAGAA CTCAGTTTTGTGAC CATGACAGTAATGA AACCAGGGTCCCA ACCAAGAAATCTA ACTCAAACGTCCCA CTTCAT (SEQ ID NO: 1681) | TACTGTCATGGTC ACAAAACTGAGT TCTCAGCCTCCTC CC (SEQ ID NO: 1682) | ATGAAGTGGGAC GTTTGAGTTAGA TTTCTTGGTTGG GACCCTGGTTTC AT (SEQ ID NO: 1683) |
| RFTN1 | NM_015150.1 | AGAGCCATCCTGAT CAAGAAAACCGAC AGATCTCAGAAAA CTGATCTTCACAAT GAAGGCTACATCTT GGAATTAGATTGCT GTTCCTCCTTAGAC CACC (SEQ ID NO: 1684) | TGAAGATCAGTTT TCTGAGATCTGTC GGTTTTCTTGATC AGGATGGCTCT (SEQ ID NO: 1685) | GGTGGTCTAAGG AGGAACAGCAA TCTAATTCCAAG ATGTAGCCTTCA TTG (SEQ ID NO: 1686) |
| RGL1 | NM_015149.3 | AGCCATGTGAATTC CACAAGAAGCACC AGGGAAAGTTTAG AGATTTGCGGCAAT GGACCGAAGAACG GGCCAGGAAGTCCT CCAATTTCCTTTGG TCTTT (SEQ ID NO: 1687) | CCGCAAATCTCTA AACTTTCCCTGGT GCTTCTTGTGGAA TTCACATGGCT (SEQ ID NO: 1688) | AAAGACCAAAG GAAATTGGAGG ACTTCCTGGCCC GTTCTTCGGTCC ATTG (SEQ ID NO: 1689) |
| RGS9 | NM_003835.1 | GGATCACCGATGAC ACCCAGTTCTGGGA CTTAAATGCCAAAT TGGTGGAAATCCCA ACCAAGATGCGAG TGGAACGATGGGC CTTCAACTTCAGCG AATT (SEQ ID NO: 1690) | TTCCACCAATTTG GCATTTAAGTCCC AGAACTGGGTGT CATCGGTGATCC (SEQ ID NO: 1691) | AATTCGCTGAAG TTGAAGGCCCAT CGTTCCACTCGC ATCTTGGTTGGG AT (SEQ ID NO: 1692) |
| RHCE | NM_020485.4 | GACAACTTCCTCTC ACTGTTGCCTGCAT TTGTACGTGAGAAA CGCTCATGACAGCA AAGTCTCCTTATGT ATAATGAAACAAG GTCAGAGACAGATT TGA (SEQ ID NO: 1693) | CATGAGCGTTTCT CACGTACAAATG CAGGCAACAGTG AGAGGAAGTTGT C (SEQ ID NO: 1694) | TCAAATCTGTCT CTGACCTTGTTT CATTATACATAA GGAGACTTTGCT GT (SEQ ID NO: 1695) |
| RHEBL1 | NM_144593.1 | GAAGACATCTTTGG CACATCAATTTGTG GAAGGCGAGTTCTC GGAAGGCTACGAT CCTACAGTGGAGA ATACTTACAGCAAG ATAGTGACTCTTGG CAAA (SEQ ID NO: 1696) | AGCCTTCCGAGA ACTCGCCTTCCAC AAATTGATGTGC CAAAGATGTCTTC (SEQ ID NO: 1697) | TTTGCCAAGAGT CACTATCTTGCT GTAAGTATTCTC CACTGTAGGATC GT (SEQ ID NO: 1698) |
| RHOF | NM_019034.2 | CTGCGGCAAGACCT CGCTGCTCATGGTG TACAGCCAGGGCTC CTTCCCCGAGCACT ACGCCCCATCGGTG TTCGAGAAGTACAC GGCCAGCGTGACC GTT (SEQ ID NO: 1699) | CGGGGAAGGAGC CCTGGCTGTACAC CATGAGCAGCGA G (SEQ ID NO: 1700) | TGGCCGTGTACT TCTCGAACACCG ATGGGGCGTAGT GCT (SEQ ID NO: 1701) |

TABLE 1-continued

| Gene | GenBank Accession No. | Target Sequence | Capture Probe Sequence | Reporter Probe Sequence |
|---|---|---|---|---|
| RHOXF1 | NM_139282.1 | CGCCAATGAACTACGTGCTGACCCAGACGACTGTGTCTACATCGTCGTGGACTAGCCCTAGAATGCCATCCTTCTTCAGGAGCTAGTTTGGAGATGGGTT (SEQ ID NO: 1702) | CCACGACGATGTAGACACAGTCGTCTGGGTCAGCACGTAGTTCAT (SEQ ID NO: 1703) | AACCCATCTCCAAACTAGCTCCTGAAGAAGGATGGCATTCTAGGGCTAGT (SEQ ID NO: 1704) |
| RNASEH2B | NM_001142279.1 | CAGTTCCCGGGTACAGTCAACTGCATTTTTCTCTGGTGACCAAGCTTCCACTGACAAGGAAGAGGATTATATTCGTTATGCCCATGGTCTGATATCTGAC (SEQ ID NO: 1705) | TGGAAGCTTGGTCACCAGAGAAAAATGCAGTTGACTGTACCCGGGAACTG (SEQ ID NO: 1706) | GTCAGATATCAGACCATGGGCATAACGAATATAATCCTCTTCCTTGTCAG (SEQ ID NO: 1707) |
| RNF214 | NM_207343.2 | AAGCTTGGATTTCCGACCTGTAGTGTCTCCAGCAAATGGGGTTGAAGGAGTCCGAGTGGATCAGGATGATGATCAAGATAGCTCTTCCCTGAAGCTTTCT (SEQ ID NO: 1708) | CTCCTTCAACCCCATTTGCTGGAGACACTACAGGTCGGAAATCCAAGCTT (SEQ ID NO: 1709) | AGAAAGCTTCAGGGAAGAGCTATCTTGATCATCATCCTGATCCACTCGGA (SEQ ID NO: 1710) |
| RNGTT | NM_003800.3 | CCTTTTTGGTGGAGAAAATGGATTGGAGTATCGAAGCAGCAGTTGCTACTTTTGCCCAAGCCAGACCACCAGGAATCTACAAGGGTGATTATTTGAAGGA (SEQ ID NO: 1711) | AGTAGCAACTGCTGCTTCGATACTCCAATCCATTTTCTCCACCAAAAAGG (SEQ ID NO: 1712) | TCCTTCAAATAATCACCCTTGTAGATTCCTGGTGGTCTGGCTTGGGCAAA (SEQ ID NO: 1713) |
| ROBO1 | NM_902941.2 | TGAACCACAAAAAAAAAGGCTGGTGTTCACCAAAACCAAACTTGTTCATTTAGATAATTTGAAAAAGTTCCATAGAAAAGGCGTGCAGTACTAAGGGAAC (SEQ ID NO: 1714) | AATGAACAAGTTTGGTTTTGGTGAACACCAGCCTTTTTTTTTGTGGTTCA (SEQ ID NO: 1715) | GTTCCCTTAGTACTGCACGCCTTTTCTATGGAACTTTTTCAAATTATCTA (SEQ ID NO: 1716) |
| ROBO4 | NM_019055.5 | CCTGACTCTCAGATCTCTTCCCAGAGAAGTCAGCTCCACTGTCGTATGCCCAAGGCTGGTGCTTCTCCTGTAGATTACTCCTGAACCGTGTCCCTGAGAC (SEQ ID NO: 1717) | GGCATACGACAGTGGAGCTGACTTCTCTGGGAAGAGATCTGAGAG (SEQ ID NO: 1718) | CAGGGACACGGTTCAGGAGTAATCTACAGGAGAAGCACCAGCCTTG (SEQ ID NO: 1719) |
| RPN2 | NM_001135771.1 | AGATGCCACTTTGAAGAACCCAATCCTCTGGAATGTGGCTGATGTGGTCATCAAGTTCCCTGAGGAAGAAGCTCCCTCGACTGTCTTGTCCCAGAACCTT (SEQ ID NO: 1720) | TGACCACATCAGCCACATTCCAGAGGATTGGGTTCTTCAAAGTGGCATCT (SEQ ID NO: 1721) | AAGGTTCTGGGACAAGACAGTCGAGGGAGCTTCTTCCTCAGGGAACTTGA (SEQ ID NO: 1722) |

TABLE 1-continued

| Gene | GenBank Accession No. | Target Sequence | Capture Probe Sequence | Reporter Probe Sequence |
|---|---|---|---|---|
| RPS6KA5 | NM_004755.2 | GTGGAACTATTGAATACATGGCACCAGATATTGTCAGAGGGGGAGATTCAGGACATGACAAGGCAGTTGACTGGTGGAGTTTGGGTGTTCTAATGTATGA (SEQ ID NO: 1723) | TGAATCTCCCCCTCTGACAATATCTGGTGCCATGTATTCAATAGTTCCAC (SEQ ID NO: 1724) | TCATACATTAGAACACCCAAACTCCACCAGTCAACTGCCTTGTCATGTCC (SEQ ID NO: 1725) |
| RRP1B | NM_015056.2 | CAACAGGAAGCGCCTCTCCAAACTCATCAAGAAATTCCAAGACCTTTCTGAAGGAAGCAGTATATCTCAACTCAGTTTTGCGGAGGACATTTCTGCTGAT (SEQ ID NO: 1726) | CAGAAAGGTCTTGGAATTTCTTGATGAGTTTGGAGAGGCGCTTCCTGTTG (SEQ ID NO: 1727) | ATCAGCAGAAATGTCCTCCGCAAAACTGAGTTGAGATATACTGCTTCCTT (SEQ ID NO: 1728) |
| RSAD2 | NM_080657.4 | AGGAAGCTGGTATGGAGAAGATCAACTTTTCAGGTGGAGAGCCATTTCTTCAAGACCGGGGAGAATACCTGGGCAAGTTGGTGAGGTTCTGCAAAGTAGA (SEQ ID NO: 1729) | AAGAAATGGCTCTCCACCTGAAAAGTTGATCTTCTCCATACCAGCTTCCT (SEQ ID NO: 1730) | TCTACTTTGCAGAACCTCACCAACTTGCCCAGGTATTCTCCCCGGTCTTG (SEQ ID NO: 1731) |
| RTCD1 | NM_001130841.1 | AGCGTGGCTGTGTGACTAAGATATATGGAAGAGCTTTCGTTGCTGGTGTTTTGCCATTTAAAGTAGCAAAAGATATGGCAGCGGCAGCAGTTAGATGCAT (SEQ ID NO: 1732) | AACACCAGCAACGAAAGCTCTTCCATATATCTTAGTCACACAGCCACGCT (SEQ ID NO: 1733) | ATGCATCTAACTGCTGCCGCTGCCATATCTTTTGCTACTTTAAATGGCAA (SEQ ID NO: 1734) |
| RUNDC2B | XM_001714307.1 | CCTGCGTGCCCGGGCCTGTCCCTCCTGACCCCAGGATTATAGTGGCGAGGCAGGGTGTTAGCCAAGCGGATTGAGCCAGGACACAGCACCGCGGAGCCCT (SEQ ID NO: 1735) | CCTCGCCACTATAATCCTGGGGTCAGGAGGGACAGGC (SEQ ID NO: 1736) | TGCTGTGTCCTGGCTCAATCCGCTTGGCTAACACCCTG (SEQ ID NO: 1737) |
| RXRA | NM_002957.4 | TACAAATGTAATTTTATCCCTCATGTATACTTGGATATGGCGGGGGGAGGGCTGGGACTGTTTCGTTTCTGCTTCTAGAGATTGAGGTGAAAGCTTCGTC (SEQ ID NO: 1738) | CCTCCCCCCGCCATATCCAAGTATACATGAGGGATAAAATTACATTTGTA (SEQ ID NO: 1739) | GACGAAGCTTTCACCTCAATCTCTAGAAGCAGAAACGAAACAGTCCCAGC (SEQ ID NO: 1740) |
| S100Z | NM_130772.3 | GGGGTCTGCCTGGAATAGCACTGAATGTGTTTAGTAGTGCCTTTGGCTTGGGGGCTTTGGAGAAAGCTGCTTGAGCCCTTCCCATGCTCATAAATTAGGT (SEQ ID NO: 1741) | CAAGCCAAAGGCACTACTAAACACATTCAGTGCTATTCCAGGCAGACCCC (SEQ ID NO: 1742) | ACCTAATTTATGAGCATGGGAAGGGCTCAAGCAGCTTTCTCCAAAGCCCC (SEQ ID NO: 1743) |

TABLE 1-continued

| Gene | GenBank Accession No. | Target Sequence | Capture Probe Sequence | Reporter Probe Sequence |
|---|---|---|---|---|
| S1PR2 | NM_004230.2 | TCCCGCCAGGTGGC CTCGGCCTTCATCG TCATCCTCTGTTGC GCCATTGTGGTGGA AAACCTTCTGGTGC TCATTGCGGTGGCC CGAAACAGCAAGT TCC (SEQ ID NO: 1744) | ACAATGGCGCAA CAGAGGATGACG ATGAAGGCCGAG GCCACCTGG (SEQ ID NO: 1745) | GGAACTTGCTGT TTCGGGCCACCG CAATGAGCACCA GAAGGTTTTCCA CC (SEQ ID NO: 1746) |
| SAA1 | NM_199161.1 | AGCTTCTTTTCGTT CCTTGGCGAGGCTT TTGATGGGGCTCGG GACATGTGGAGAG CCTACTCTGACATG AGAGAAGCCAATT ACATCGGCTCAGAC AAAT (SEQ ID NO: 1747) | CACATGTCCCGA GCCCCATCAAAA GCCTCGCCAAGG AACGAAAAGAAG CT (SEQ ID NO: 1748) | ATTTGTCTGAGC CGATGTAATTGG CTTCTCTCATGT CAGAGTAGGCTC TC (SEQ ID NO: 1749) |
| SACS | NM_014363.4 | TTGAGTCTTTTAGG GCAGATGCAGACA CAGTGCTGCTCTTT CTGAAAAGTGTGCA GGATGTTTCCTTAT ATGTCCGAGAGGCT GACGGAACAGAGA AACT (SEQ ID NO: 1750) | ACTTTTCAGAAA GAGCAGCACTGT GTCTGCATCTGCC CTAAAAGACTCA A (SEQ ID NO: 1751) | TTTCTCTGTTCCG TCAGCCTCTCGG ACATATAAGGAA ACATCCTGCAC (SEQ ID NO: 1752) |
| SAE1 | NM_005500.2 | CTACCAGTTGCCTT TTCAGACCTGAGGC TCTAACTCAAGAGA TTCCTCCTCTCCCTC ACCATTCCTGCCAC CATTTTTTCTGGGT GATGCAGCAAGAG TT (SEQ ID NO: 1753) | AGGAGGAATCTC TTGAGTTAGAGC CTCAGGTCTGAA AAGGCAACTGGT AG (SEQ ID NO: 1754) | AACTCTTGCTGC ATCACCCAGAAA AAATGGTGGCAG GAATGGTGAGG GAG (SEQ ID NO: 1755) |
| SAMSN1 | NM_022136.3 | ATTCAGGACCATTC TGTGGCCGTGCCAG AGTGCATACGGATT TCACGCCAAGTCCC TATGACACTGACTC CCTCAAAATCAAGA AAGGAGACATCAT AGA (SEQ ID NO: 1756) | TGGCGTGAAATC CGTATGCACTCTG GCACGGCCACAG AATGGTCCTGAA T (SEQ ID NO: 1757) | TCTATGATGTCT CCTTTCTTGATTT TGAGGGAGTCAG TGTCATAGGGAC T (SEQ ID NO: 1758) |
| SAP30 | NM_003864.3 | ACAAGTAAATACA CTTAGGAGATACAA AAGACACTTCAAGC TACCAACCAGACCA GGACTTAATAAAGC ACAACTTGTTGAGA TAGTTGGTTGCCAC TTT (SEQ ID NO: 1759) | TGGTTGGTAGCTT GAAGTGTCTTTTG TATCTCCTAAGTG TATTTACTTGT (SEQ ID NO: 1760) | AAAGTGGCAACC AACTATCTCAAC AAGTTGTGCTTT ATTAAGTCCTGG TC (SEQ ID NO: 1761) |
| SCARA5 | NM_173833.4 | CAGCCTTACCTCCA GGTAGCACTTAATT GGTCCATTCACCTA GACTGCAAGTAAG AAGACAAAATGAC TGAGACCGTGTGCC CACCTGAACTTATT GTCT (SEQ ID NO: 1762) | TTGCAGTCTAGGT GAATGGACCAAT TAAGTGCTACCTG GAGGTAAGGCTG (SEQ ID NO: 1763) | AGACAATAAGTT CAGGTGGGCACA CGGTCTCAGTCA TTTTGTCTTCTTA C (SEQ ID NO: 1764) |

TABLE 1-continued

| Gene | GenBank Accession No. | Target Sequence | Capture Probe Sequence | Reporter Probe Sequence |
|---|---|---|---|---|
| SDC1 | NM_002997.4 | TGAAATTCTCCTGG AGGTCGGTAGGTTC AGCCAAGGTTTTAT AAGGCTGATGTCAA TTTCTGTGTTGCCA AGCTCCAAGCCCCA TCTTCTAAATGGCA AA (SEQ ID NO: 1765) | TCAGCCTTATAAA ACCTTGGCTGAA CCTACCGACCTCC AGGAGAATTTCA (SEQ ID NO: 1766) | TTTGCCATTTAG AAGATGGGGCTT GGAGCTTGGCAA CACAGAAATTGA CA (SEQ ID NO: 1767) |
| SDCCAG8 | NM_006642.2 | CCGGAAACATGCA CAATTCTTGGATTA CAACAGGTGAAGA TTCTGGGGTGGGCG AAACCTCCAAAAG ACCATTTTCCCATG ACAATGCAGATTTT GGCAA (SEQ ID NO: 1768) | CACCCCAGAATC TTCACCTGTTGTA ATCCAAGAATTG TGCATGTTTCCGG (SEQ ID NO: 1769) | TTGCCAAAATCT GCATTGTCATGG GAAAATGGTCTT TTGGAGGTTTCG CC (SEQ ID NO: 1770) |
| SEL1L3 | NM015187.3 | TACTCCATTATTGC AAGGCCAACCTCTG TGGGATTCTGTACT TTGTTGACTCTAAT GAGATGTACGGCA CACCTTCTGTATTT CTTACGGAAGAGG GCTA (SEQ ID NO: 1771) | GTCAACAAAGTA CAGAATCCCACA GAGGTTGGCCTT GCAATAATGGAG TA (SEQ ID NO: 1772) | TAGCCCTCTTCC GTAAGAAATACA GAAGGTGTGCCG TACATCTCATTA GA (SEQ ID NO: 1773) |
| SEMA7A | NM_001146029.1 | CCCACAGTTCATCA AGCCACCATCGTG CACCAAGACCAGG CTTACGATGACAAG ATCTACTACTTCTT CCGAGAGGACAAT CCTGACAAGAATCC TGAG (SEQ ID NO: 1774) | CATCGTAAGCCT GGTCTTGGTGCAC GATGGTGGCTTTG ATGAACTG (SEQ ID NO: 1775) | TCAGGATTCTTG TCAGGATTGTCC TCTCGGAAGAAG TAGTAGATCTTG T (SEQ ID NO: 1776) |
| SEPHS1 | NM_001195602.1 | TGCCCATCTTCGTG AGAGAAAAAGCAG CACATCCTGCCCAT TTCTGGTGCTTTCT GCTCACAGGCACCA AAGCTGCACATGTA AACTGACTTCTTGC CAA (SEQ ID NO: 1777) | GCACCAGAAATG GGCAGGATGTGC TGCTTTTTCTCTC ACGAAGATGG (SEQ ID NO: 1778) | TTGGCAAGAAGT CAGTTTACATGT GCAGCTTTGGTG CCTGTGAGCAGA AA (SEQ ID NO: 1779) |
| SERBP1 | NM_001018068.1 | CCAAAGGGCGCTG GTTGGTAGGGTGAG GTGGGGGAGTATTT TAATTTTTGGAATT TGGGAAGCAGACA GCTTTACTTTGTAA GGTTGGAACAGCA GCACT (SEQ ID NO: 1780) | CAAAAATTAAAA TACTCCCCCACCT CACCCTACCAAC CAGCGCCCTTTGG (SEQ ID NO: 1781) | AGTGCTGCTGTT CCAACCTTACAA AGTAAAGCTGTC TGCTTCCCAAAT TC (SEQ ID NO: 1782) |
| SERPINA9 | NM_001042518.1 | CCACTAAATCCTAG GTGGGAAATGGCCT GTTAACTGATGGCA CATTGCTAATGCAC AAGAAATAACAAA CCACATCCCTCTTT CTGTTCTGAGGGTG CAT (SEQ ID NO: 1783) | TAGCAATGTGCC ATCAGTTAACAG GCCATTTCCCACC TAGGATTTAG (SEQ ID NO: 1784) | ATGCACCCTCAG AACAGAAAGAG GGATGTGGTTTG TTATTTCTTGTGC AT (SEQ ID NO: 1785) |

TABLE 1-continued

| Gene | GenBank Accession No. | Target Sequence | Capture Probe Sequence | Reporter Probe Sequence |
| --- | --- | --- | --- | --- |
| SERPINB1 | NM_030666.2 | TTACACTCTCAACTCCGACCTCGCCCGCCTAGGTGTGCAGGATCTCTTTAACAGTAGCAAGGCTGATCTGTCTGGCATGTCAGGAGCCAGAGATATTTTT (SEQ ID NO: 1786) | TAAAGAGATCCTGCACACCTAGGCGGGCGAGGTCGGAGTTGAG (SEQ ID NO: 1787) | AAAAATATCTCTGGCTCCTGACATGCCAGACAGATCAGCCTTGCTACTGT (SEQ ID NO: 1788) |
| SFN | NM_006142.3 | TGGGCCTGGCCCTGAACTTTTCCGTCTTCCACTACGAGATCGCCAACAGCCCCGAGGAGGCCATCTCTCTGGCCAAGACCACTTTCGACGAGGCCATGGC (SEQ ID NO: 1789) | GCTGTTGGCGATCTCGTAGTGGAAGACGGAAAAGTTCAGGGCCAGGC (SEQ ID NO: 1790) | TCGAAAGTGGTCTTGGCCAGAGAGATGGCCTCCTCGGG (SEQ ID NO: 1791) |
| SFPQ | NM_005066.2 | GGAGGTGGTGGTGGCATAGGTTATGAAGCTAATCCTGGCGTTCCACCAGCAACCATGAGTGGTTCCATGATGGGAAGTGACATGCGTACTGAGCGCTTTG (SEQ ID NO: 1792) | GCTGGTGGAACGCCAGGATTAGCTTCATAACCTATGCCACCACC (SEQ ID NO: 1793) | CAAAGCGCTCAGTACGCATGTCACTTCCCATCATGGAACCACTCATGGTT (SEQ ID NO: 1794) |
| SGK1 | NM_005627.2 | GTGTGAACCGTCGTGTGAGTGTGGTATGCCTGATCACAGATGGATTTTGTTATAAGCATCAATGTGACACTTGCAGGACACTACAACGTGGGACATTGTT (SEQ ID NO: 1795) | ACAAAATCCATCTGTGATCAGGCATACCACACTCACACGACGGTTCAC (SEQ ID NO: 1796) | AACAATGTCCCACGTTGTAGTGTCCTGCAAGTGTCACATTGATGCTTA (SEQ ID NO: 1797) |
| SGOL2 | NM_152524.5 | AGACCTCCATAGATCCTTCTCCAGAGAGCCATGAAGTAATGGAAAGAATACTTGACAGCGTTCAGGGAAAGTCTACTGTATCTGAACAAGCTGATAAGGA (SEQ ID NO: 1798) | TATTCTTTCCATTACTTCATGGCTCTCTGGAGAAGGATCTATGGAGGT (SEQ ID NO: 1799) | TCCTTATCAGCTTGTTCAGATACAGTAGACTTTCCCTGAACGCTGTCAAG (SEQ ID NO: 1800) |
| SH2D1A | NM_002351.4 | GCTGTATACACGGTTACATTTATACATACCGAGTGTCCCAGACAGAAACAGGTTCTTGGAGTGCTGAGACAGCACCTGGGGTACATAAAAGATATTTCGG (SEQ ID NO: 1801) | CTGTTTCTGTCTGGGACACTCGGTATGTATAAATGTAACCGTGATACAGC (SEQ ID NO: 1802) | CCGGAAATATCTTTTATGTACCCCAGGTGCTGTCTCAGCACTCCAAGAAC (SEQ ID NO: 1803) |
| SH3BP5 | NM_001018009.2 | AGCTCTTGGGCTGGTTTTTCAGAGCAGAGTTCTTGTTGTGGGTAGACTGTGACTAGGTTCACAGCCTTTGTGGAACATTCCGTATAACGGCATTGTGGAA (SEQ ID NO: 1804) | ACAGTCTACCCACAACAAGAACTCTGCTCTGAAAAACCAGCCCAAGAGCT (SEQ ID NO: 1805) | TTCCACAATGCCGTTATACGGAATGTTCCACAAAGGCTGTGAACCTAGTC (SEQ ID NO: 1806) |

TABLE 1-continued

| Gene | GenBank Accession No. | Target Sequence | Capture Probe Sequence | Reporter Probe Sequence |
|---|---|---|---|---|
| SIDT1 | NM_017699.2 | GGTCATCATGGTCACCGTCCTTGGAGTGGTGTTTGGAAAAAATGACGTATGGTTCTGGGTCATCTTCTCTGCAATCCACGTTCTGGCCTCGCTAGCCCTC (SEQ ID NO: 1807) | ATACGTCATTTTTTCCAAACACCACTCCAAGGACGGTGACCATGATGAC C (SEQ ID NO: 1808) | GGCTAGCGAGGCCAGAACGTGGATTGCAGAGAAGATGACCCAGAACC (SEQ ID NO: 1809) |
| SIRPA | NM_080792.2 | CCAGGGCAAGCAGATGTCGCAAGCCCTATTTATTCAGTCTTCACTATAACTCTTAGAGTTGAGACGCTAATGTTCATGACTCCTGGCCTTGGGATGCCCA (SEQ ID NO: 1810) | GTTATAGTGAAGACTGAATAAATAGGGCTTGCGACATCTGCTTGCCCTG G (SEQ ID NO: 1811) | GCATCCCAAGGCCAGGAGTCATGAACATTAGCGTCTCAACTCTAAGA (SEQ ID NO: 1812) |
| SIRPB1 | NM_006065.2 | ACAATTGGTTTTCAGGGCCCAGTCCAAGCCTGCTGCTGGAAACCTCAGAGTTAAATCCCTATTCTCCACACCTCTCACCTCCACCACCCCTCCCTGTCCC (SEQ ID NO: 1813) | CTCTGAGGTTTCCAGCAGCAGGCTTGGACTGGGCCCTGAAAACCAATTG T (SEQ ID NO: 1814) | GACAGGGAGGGGTGGTGGAGGTGAGAGGTGTGGAGAATAGGGATTTAA (SEQ ID NO: 1815) |
| SLA | NM_001045556.2 | GTGTGATTTCTGATGAAGGGGGCTGGTGGAAAGCTATTTCTCTTAGCACTGGTCGAGAGAGTTACATCCCTGGAATATGTGTGCCAGAGTTTACCATGG (SEQ ID NO: 1816) | AGTGCTAAGAGAAATAGCTTTCCACCAGCCCCCTTCATCAGAAATCACAC (SEQ ID NO: 1817) | CCATGGTAAACTCTGGCCACACATATTCCAGGGATGTAACTCTCTCGACC (SEQ ID NO: 1818) |
| SLAMF1 | NM_003037.2 | GTGTCTCTTGATCCATCCGAAGCAGGCCCTCCACGTTATCTAGGAGATCGCTACAAGTTTTATCTGGAGAATCTCACCCTGGGGATACGGGAAAGCAGGA (SEQ ID NO: 1819) | CGATCTCCTAGATAACGTGGAGGGCCTGCTTCGGATGGATCAAGAGACAC (SEQ ID NO: 1820) | TCCTGCTTTCCCGTATCCCCAGGGTGAGATTCTCCAGATAAAACTTGTAG (SEQ ID NO: 1821) |
| SLC12A8 | NM_024628.5 | GAACAACACGCTGCCCGATTACAGCCCGGGGGAATCTTTTTTCACTGTCTTTGGGGTTTTCTTCCCAGCGGCTACAGGAGTCATGGCCGGCTTCAACATG (SEQ ID NO: 1822) | AGACAGTGAAAAAAGATTCCCCCGGGCTGTAATCGGGCAGCGTGTTGTT C (SEQ ID NO: 1823) | CATGTTGAAGCCGGCCATGACTCCTGTAGCCGCTGGGAAGAAAACCCCAA (SEQ ID NO: 1824) |
| SLC16A9 | NM_194298.2 | TTACCTCACTGAAGTACTCGCATGTTGTTTGGTACCCACTGAGCAACTGTTTCAGTTCCTAAGGTATTTGCTGAGATGTGGGTGAACTCCAAATGGAGAA (SEQ ID NO: 1825) | ACAGTTGCTCAGTGGGTACCAAACAACATGCGAGTACTTCAGTGAGGTA A (SEQ ID NO: 1826) | TTCTCCATTTGGAGTTCACCCACATCTCAGCAAATACCTTAGGAACTGAA (SEQ ID NO: 1827) |

TABLE 1-continued

| Gene | GenBank Accession No. | Target Sequence | Capture Probe Sequence | Reporter Probe Sequence |
|---|---|---|---|---|
| SLC1A4 | NM_003038.4 | TTTTTCCAATTACCTGCTGACACGGTTCTAAGCTAAGTGAAGGGGAAGATCTGAGAGCGTGCTGTTTGTGGCTGTTGATGCATATTCGTGATGTAACAGG (SEQ ID NO: 1828) | ATCTTCCCCTTCACTTAGCTTAGAACCGTGTCAGCAGGTAATTGGAAAAA (SEQ ID NO: 1829) | CCTGTTACATCACGAATATGCATCAACAGCCACAAACAGCACGCTCTCAG (SEQ ID NO: 1830) |
| SLC31A1 | NM_001859.3 | TTGACATCAAACTCTATGGCGTGGCCTTATCGATTGCAGTGGGAAGTTGTTGAAGACTTGAAGACGTGATTCCTGCTCCAATCATCCCTTCTTGCTCCTC (SEQ ID NO: 1831) | ACAACTTCCCACTGCAATCGATAAGGCCACGCCATAGAGTTTGATGTCAA (SEQ ID NO: 1832) | GAGGAGCAAGAAGGGATGATTGGAGCAGGAATCACGTCTTCAAGTCTTCA (SEQ ID NO: 1833) |
| SLC35E2B | NM_001110781.1 | CGGTGACTTTCAGCGTCGCCAGCACCGTGAAACATGCCTTGTCCATCTGGCTCAGCGTAATCGTTTTCGGCAACAAGATCACCAGCTTGTCGGCCGTTGG (SEQ ID NO: 1834) | CCAGATGGACAAGGCATGTTTCACGGTGCTGGCGACGCTGAAAGTCACCG (SEQ ID NO: 1835) | CCAACGGCCGACAAGCTGGTGATCTTGTTGCCGAAAACGATTACGCTGAG (SEQ ID NO: 1836) |
| SLC38A5 | NM_033518.2 | ACGACATGTGGCCATAGCTCTGATCCTGCTTGTTTTGGTCAATGTCCTTGTCATCTGTGTGCCAACCATCCGGGATATCTTTGGAGTTATCGGGTCCACC (SEQ ID NO: 1837) | CAAGGACATTGACCAAAACAAGCAGGATCAGAGCTATGGCCACATGTCGT (SEQ ID NO: 1838) | GGTGGACCCGATAACTCCAAAGATATCCCCGATGGTTGGCACACAGATGA (SEQ ID NO: 1839) |
| SMAD1 | NM_005900.2 | CCTTGCATGTACTTGAAGGATGGATGAGTCAGACACGATTGAGAACTGACAAAGGAGCCTTGATAATACTTGACCTCTGTGACCAACTGTTGGATTCAGA (SEQ ID NO: 1840) | GTCAGTTCTCAATCGTGTCTGACTCATCCATCCTTCAAGTACATG (SEQ ID NO: 1841) | TCTGAATCCAACAGTTGGTCACAGAGGTCAAGTATTATCAAGGCTCCTTT (SEQ ID NO: 1842) |
| SMAD7 | NM_005904.2 | AGCAGAAATCCAAGCACCACCAAACACAGTGTATGAAGGGGGGCGGTCATCATTTCACTTGTCAGGAGTGTGTGTGAGTGTGAGTGTGCGGCTGTGTGTG (SEQ ID NO: 1843) | ATGACCGCCCCCCTTCATACACTGTGTTTGGTGGTGCTTGGATTTCTG (SEQ ID NO: 1844) | CACACACAGCCGCACACTCACACTCACACACACTCCTGACAAGTGAAATG (SEQ ID NO: 1845) |
| SMARCA4 | NM_003072.3 | GCCCTGTCCTGGCATCAGTAGCATCTGTAACAGCATTAACTGTCTTAAAGAGAGAGAGAGAGAATTCCGAATTGGGGAACACACGATACCTGTTTTTCTT (SEQ ID NO: 1846) | CTTTAAGACAGTTAATGCTGTTACAGATGCTACTGATGCCAGGACAGGGC (SEQ ID NO: 1847) | AAGAAAAACAGGTATCGTGTGTTCCCCAATTCGGAATTCTCTCTCTCT (SEQ ID NO: 1848) |

TABLE 1-continued

| Gene | GenBank Accession No. | Target Sequence | Capture Probe Sequence | Reporter Probe Sequence |
|------|----------------------|-----------------|------------------------|-------------------------|
| SNAP23 | NM_003825.2 | GTTGAGGGAAGGA CAAGAGATAAGAG GTTGTTACCTCAGT AAAAACCTTCAGGC CACAAAGCAAAAA GTTGCATAGCCACA ACGAAGATCTAGTT GGATA (SEQ ID NO: 1849) | GAAGGTTTTTACT GAGGTAACAACC TCTTATCTCTTGT CCTTCCCTCAAC (SEQ ID NO: 1850) | CAACTAGATCTT CGTTGTGGCTAT GCAACTTTTTGC TTTGTGGCCT (SEQ ID NO: 1851) |
| SNN | NM_003498.4 | GGCAGGGGTCTCTC ATGTGTGTCCATCT GCGTGTATGTCAAG GAAGTGAGATGCC AATTTGGGGTCTTG AGGCTGACCAGTTG GGGTGCTTGGGTGA TCT (SEQ ID NO: 1852) | CTCACTTCCTTGA CATACACGCAGA TGGACACACATG AGAGACCCCTGC C (SEQ ID NO: 1853) | CAAGCACCCCAA CTGGTCAGCCTC AAGACCCCAAAT TGGCAT (SEQ ID NO: 1854) |
| SNX11 | NM_152244.1 | TGGGAGGAGATCA TGCTGTGCCTTTGG ACCCTGGTCAGTTA GAAACAGTTTTGGA AAAGTGAGCTCTGG GTTCTGCTCTGAGA TGGTCAGAGAAGA TGCG (SEQ ID NO: 1855) | AACTGTTTCTAAC TGACCAGGGTCC AAAGGCACAGCA TGATCTCCTCC (SEQ ID NO: 1856) | CGCATCTTCTCT GACCATCTCAGA GCAGAACCCAG AGCTCACTTTTC CAA (SEQ ID NO: 1857) |
| SNX22 | NM_024798.2 | AGGACTTAATTACC CAGTGCCCAGTTGT GCCACATTCCCACT CAAGGCTCAGAACT TGGCTCGCATTGGT AGCTGGAGGTGGT AGAATTTGTATGCT CTT (SEQ ID NO: 1858) | GAGCCTTGAGTG GGAATGTGGCAC AACTGGGCACTG GGTAATTAAGT (SEQ ID NO: 1859) | AAGAGCATACA AATTCTACCACC TCCAGCTACCAA TGCGAGCCAAGT TCT (SEQ ID NO: 1860) |
| SNX29 | NM_001080530.2 | ACTGCATTTTCCAC CAACAGTCATTAGA CACCTGGCACTGTC ACAGCTCACTTTTC CAGAGGGATATTCC TGTGGCTTTGGCAA GGAGCCATTAGTGA TG (SEQ ID NO: 1861) | TGAGCTGTGACA GTGCCAGGTGTCT AATGACTGTTGGT GGAAAATGCAGT (SEQ ID NO: 1862) | CATCACTAATGG CTCCTTGCCAAA GCCACAGGAATA TCCCTCTGGAAA AG (SEQ ID NO: 1863) |
| SOCS1 | NM_003745.1 | TTAACTGTATCTGG AGCCAGGACCTGA ACTCGCACCTCCTA CCTCTTCATGTTTA CATATACCCAGTAT CTTTGCACAAACCA GGGGTTGGGGGAG GGTC (SEQ ID NO: 1864) | ATGAAGAGGTAG GAGGTGCGAGTT CAGGTCCTGGC (SEQ ID NO: 1865) | GACCCTCCCCCA ACCCCTGGTTTG TGCAAAGATACT GGGTATATGTAA AC (SEQ ID NO: 1866) |
| SOCS2 | NM_003877.3 | GGAACGGCACTGTT CACCTTTATCTGAC CAAACCGCTCTACA CGTCAGCACCATCT CTGCAGCATCTCTG TAGGCTCACCATTA ACAAATGTACCGGT GC (SEQ ID NO: 1867) | TGCTGACGTGTA GAGCGGTTTGGT CAGATAAAGGTG AACAGTGCCGTT CC (SEQ ID NO: 1868) | GCACCGGTACAT TTGTTAATGGTG AGCCTACAGAGA TGCTGCAGAGAT GG (SEQ ID NO: 1869) |

TABLE 1-continued

| Gene | GenBank Accession No. | Target Sequence | Capture Probe Sequence | Reporter Probe Sequence |
|---|---|---|---|---|
| SOCS3 | NM_003955.3 | GGAGGATGGAGGAGACGGGACATCTTTCACCTCAGGCTCCTGGTAGAGAAGACAGGGGATTCTACTCTGTGCCTCCTGACTATGTCTGGCTAAGAGATTC (SEQ ID NO: 1870) | TTCTCTACCAGGAGCCTGAGGTGAAAGATGTCCCGTC (SEQ ID NO: 1871) | ACATAGTCAGGAGGCACAGAGTAGAATCCCCTGTC (SEQ ID NO: 1872) |
| SORBS1 | NM_001034956.1 | CCTCTCTTAGATCCTGAGTGAGACAAATACAGAAATGACCCATTCCCTGCCCACCAGAAACTCAGAGGTGATTGGGGAGACTGACACAGGAAAATGAACT (SEQ ID NO: 1873) | GCAGGGAATGGGTCATTTCTGTATTTGTCTCACTCAGGATCTAAGAGAGG (SEQ ID NO: 1874) | TTCATTTTCCTGTGTCAGTCTCCCCAATCACCTCTGAGTTTCTGGTGG (SEQ ID NO: 1875) |
| SOX11 | NM_003108.3 | CTAAGCATTGACAGAATATCTTAAAATGGTAACCTGGGGGTGGCGGGTGGGTGCTGTGTGCACGGCAGCCTAGCCAGTGGGGATCCTGCTGTTTATTATA (SEQ ID NO: 1876) | CCACCCGCCACCCCCAGGTTACCATTTTAAGATATTCTGTCAATGCTTAG (SEQ ID NO: 1877) | TATAATAAACAGCAGGATCCCCACTGGCTAGGCTGCCGTGCACACAGCAC (SEQ ID NO: 1878) |
| SOX5 | NM_152989.2 | TAGCCATGCAATGATGGATTTCAATCTGAGTGGAGATTCTGATGGAAGTGCTGGAGTCTCAGAGTCAAGAATTTATAGGGAATCCCGAGGGCGTGGTAGC (SEQ ID NO: 1879) | CACTTCCATCAGAATCTCCACTCAGATTGAAATCCATCATTGCATGGCTA (SEQ ID NO: 1880) | TACCACGCCCTCGGGATTCCCTATAAATTCTTGACTCTGAGACTCCAG (SEQ ID NO: 1881) |
| SPAG5 | NM_006461.3 | AACAAGACATGATATTTGAGGCCCGTTTAGATACCATGGCAGAGACAAACAGCATATCTTTAAATGGACCTTTGAGAACAGACGATCTGGTGAGAGAGGA (SEQ ID NO: 1882) | GTTTGTCTCTGCCATGGTATCTAAACGGGCCTCAAATATCATGTCTTGTT (SEQ ID NO: 1883) | TCCTCTCTCACCAGATCGTCTGTTCTCAAAGGTCCATTTAAAGATATGCT (SEQ ID NO: 1884) |
| SPARC | NM_003118.2 | TTTTCGAGACCTGTGACCTGGACAATGACAAGTACATCGCCCTGGATGAGTGGGCCGGCTGCTTCGGCATCAAGCAGAAGGATATCGACAAGGATCTTGT (SEQ ID NO: 1885) | CTCATCCAGGGCGATGTACTTGTCATTGTCCAGGTCACAGGTCTCGAAAA (SEQ ID NO: 1886) | CGATATCCTTCTGCTTGATGCCGAAGCAGCCGGCCCA (SEQ ID NO: 1887) |
| SPARCL1 | NM_004684.4 | TTGACCAACACCCTATGGATAGAGTCTTGACACATTCTGAACTTGCTCCTCTGCGAGCATCTCTGGTGCCCATGGAACACTGCATAACCCGTTTCTTTGA (SEQ ID NO: 1888) | AGGAGCAAGTTCAGAATGTGTCAAGACTCTATCCATAGGGTGTTGGTCAA (SEQ ID NO: 1889) | TCAAAGAAACGGGTTATGCAGTGTTCCATGGGCACCAGAGATGCTCGCAG (SEQ ID NO: 1890) |

TABLE 1-continued

| Gene | GenBank Accession No. | Target Sequence | Capture Probe Sequence | Reporter Probe Sequence |
|---|---|---|---|---|
| SPATA6 | NM_019073.2 | GTCCAAACCAAATG TCTGGACACCATGA TTCAAACCGCCAGG TTACCATGAGGAGG ATTTCTGGCCTTCG AGGAAATGCTCCA AGGCTGGAATTTTC TAC (SEQ ID NO: 1891) | CATGGTAACCTG GCGGTTTGAATC ATGGTGTCCAGA CATTTGGTTTGGA C (SEQ ID NO: 1892) | GTAGAAAATTCC AGCCTTGGAGCA TTTCCTCGAAGG CCAGAAATCCTC CT (SEQ ID NO: 1893) |
| SPATS1 | NM_145026.3 | CCACTTGAGCCTCT TCCACAAATTCCCA ACTTGCCTTTCTGG GTGAAGGAGAAGG CCAACAGTTTGAAA AATGAGATACAAG AGGTTGAGGAGCTT GACA (SEQ ID NO: 1894) | TCCTTCACCCAGA AAGGCAAGTTGG GAATTTGTGGAA GAGGCTCAAGTG G (SEQ ID NO: 1895) | TCAAGCTCCTCA ACCTCTTGTATC TCATTTTTCAAA CTGTTGGCCTTC (SEQ ID NO: 1896) |
| SPIB | NM_003121.3 | CTTTGTCATGTACA GACTCCCTGGGATC CTCATGTTTTGGGT GACAGGACCTATG GACCACTATACTCG GGGAGGCAGGGTA GCAGTTCTTCCAGA ATCC (SEQ ID NO: 1897) | GTCCTGTCACCCA AAACATGAGGAT CCCAGGGAGTCT GTACATGACAAA G (SEQ ID NO: 1898) | AAGAACTGCTAC CCTGCCTCCCCG AGTATAGTGGTC CATAG (SEQ ID NO: 1899) |
| SPINK2 | NM_021114.2 | CCTGGCAGTCACCT TCGCAGCCTCTCTG ATCCCTCAATTTGG TCTGTTTTCAAAAT ATAGAACGCCAAA CTGCTCTCAGTATA GATTACCAGGATGT CCC (SEQ ID NO: 1900) | AAAACAGACCAA ATTGAGGGATCA GAGAGGCTGCGA AGGTGACTGCCA GG (SEQ ID NO: 1901) | GGGACATCCTGG TAATCTATACTG AGAGCAGTTTGG CGTTCTATATTTT G (SEQ ID NO: 1902) |
| SPINT2 | NM_021102.2 | CAGATGCCGGGCCT CCATGCCTAGGTGG TGGTACAATGTCAC TGACGGATCCTGCC AGCTGTTTGTGTAT GGGGGCTGTGACG GAAACAGCAATAA TTAC (SEQ ID NO: 1903) | ATCCGTCAGTGA CATTGTACCACCA CCTAGGCATGGA GGC (SEQ ID NO: 1904) | GTAATTATTGCT GTTTCCGTCACA GCCCCCATACAC AAACAGCTGGCA GG (SEQ ID NO: 1905) |
| SPON1 | NM_006108.2 | GATTCCACATTTGA TGGGGTGACTGACA AACCCATCTTAGAC TGCTGTGCCTGCGG AACTGCCAAGTACA GACTCACATTTTAT GGGAATTGGTCCGA GA (SEQ ID NO: 1906) | GCACAGCAGTCT AAGATGGGTTTG TCAGTCACCCCAT CAAATGTGGAAT C (SEQ ID NO: 1907) | TCTCGGACCAAT TCCCATAAAATG TGAGTCTGTACT TGGCAGTTCCGC AG (SEQ ID NO: 1908) |
| SPRED2 | NM_181784.2 | TGTCGCTAGCAAGC ATCTGGTTCAGCGG AAATGGGATGTGA GAATGATGAAACC CGACAGAAGTATCT CAGCCTGCAGTCAG TTATTATGTATAGG AGGT (SEQ ID NO: 1909) | TCATCATTCTCAC ATCCCATTTCCGC TGAACCAGATGC TTGCTAGCGACA (SEQ ID NO: 1910) | ACCTCCTATACA TAATAACTGACT GCAGGCTGAGAT ACTTCTGTCGGG TT (SEQ ID NO: 1911) |

TABLE 1-continued

| Gene | GenBank Accession No. | Target Sequence | Capture Probe Sequence | Reporter Probe Sequence |
|---|---|---|---|---|
| SPRY1 | NM_005841.1 | GGATGACTTGAAG GGTTCCTTGAAAGA GGACCTGACACAG CACAAGTTCATTTG TGAACAGTGTGGG AAGTGCAAGTGTG GAGAATGCACTGCT CCCAGG (SEQ ID NO: 1912) | TGAACTTGTGCTG TGTCAGGTCCTCT TTCAAGGAACCC TTCAAGTCATCC (SEQ ID NO: 1913) | CTGGGAGCAGTG CATTCTCCACAC TTGCACTTCCCA CACTGTTCACAA A (SEQ ID NO: 1914) |
| SRPK1 | NM_003137.3 | GGGCCTTTTTGAGG TTCTAGTGGAGAAG TATGAGTGGTCGCA GGAAGAGGCAGCT GGCTTCACAGATTT CTTACTGCCCATGT TGGAGCTGATCCCT GAG (SEQ ID NO: 1915) | CCTCTTCCTGCGA CCACTCATACTTC TCCACTAGAACCT CAAAAAGGCCC (SEQ ID NO: 1916) | CAGGGATCAGCT CCAACATGGCA GTAAGAAATCTG TGAAGCCAGCTG (SEQ ID NO: 1917) |
| SRPX | NM_006307.2 | GTATGGTGCTAGTG GATAAGCATGGCAT GGACAAAGAGCGC TATGTCTCCCTGGT GATGCCTGTGGCCC TGTTCAACCTGATT GACACTTTTCCCTT GAG (SEQ ID NO: 1918) | GGAGACATAGCG CTCTTTGTCCATG CCATGCTTATCCA CTAG (SEQ ID NO: 1919) | CTCAAGGGAAA AGTGTCAATCAG GTTGAACAGGGC CACAGGCATCAC CAG (SEQ ID NO: 1920) |
| SRSF1 | NM_006924.4 | GAGAGGGCTCACT GGATCCCAATCCTT GGAGCTGGATCATT GGATTCAAATCATA ATGTGGATAGGATA GGGAGGATGAATT ACCAGGATTCATGG AGCG (SEQ ID NO: 1921) | TTTGAATCCAATG ATCCAGCTCCAA GGATTGGGATCC AGTGAGCCCTCTC (SEQ ID NO: 1922) | CGCTCCATGAAT CCTGGTAATTCA TCCTCCCTATCC TATCCACATTAT GA (SEQ ID NO: 1923) |
| SSBP2 | NM_012446.2 | GGATCCAACTCGAC AACAAGGACATCC AAATATGGGTGGG CCAATGCAGAGAA TGACTCCTCCAAGA GGAATGGTGCCCTT AGGACCACAGAAC TATGGA (SEQ ID NO: 1924) | TCTGCATTGGCCC ACCCATATTTGGA TGTCCTTGTTGTC GAGTTGGATCC (SEQ ID NO: 1925) | TGGTCCTAAGGG CACCATTCCTCT TGGAGGAGTCAT TC (SEQ ID NO: 1926) |
| SSPN | NM_005086.4 | TCTCCTCTAAACCA CGAAAGAGTAAGA TTTGTGCAACCCTC CTCCTCTTCCACCT CCTTCAGGAGAATT AAATGAATCAAGA CTTTGGAAAGACGG GGAA (SEQ ID NO: 1927) | GAAGAGGAGGAG GGTTGCACAAAT CTTACTCTTTCGT GGTTTAGAGGAG A (SEQ ID NO: 1928) | TTCCCCGTCTTTC CAAAGTCTTGAT TCATTTAATTCT CCTGAAGGAGGT G (SEQ ID NO: 1929) |
| STAG3 | NM_012447.2 | AGGGACTCAAACC ATACCTCAGAGGG GAATGGCGACTCTT TGTTAGCTGATGAA GACACTGACTTTGA AGACAGCTTGAATC GCAATGTGAAGAA GAGAG (SEQ ID NO: 1930) | TCAGCTAACAAA GAGTCGCCATTCC CCTCTGAGGTATG GTTTGAG (SEQ ID NO: 1931) | CTCTTCTTCACA TTGCGATTCAAG CTGTCTTCAAAG TCAGTGTCTTCA (SEQ ID NO: 1932) |

TABLE 1-continued

| Gene | GenBank Accession No. | Target Sequence | Capture Probe Sequence | Reporter Probe Sequence |
|---|---|---|---|---|
| STAMBPL1 | NM_020799.2 | ATGCTGGCATGCTT GAGGTTTCTGCTTG TAAAAAAAGGGC TTTCATCCACACAC CAAGGAGCCCAGG CTGTTCAGTATATG CAAACATGTGTTGG TAAA (SEQ ID NO: 1933) | TGGATGAAAGCC CTTTTTTTTACAA GCAGAAACCTCA AGCATGCCAGCA T (SEQ ID NO: 1934) | TTTACCAACACA TGTTTGCATATA CTGAACAGCCTG GGCTCCTTGGTG TG (SEQ ID NO: 1935) |
| STAP1 | NM_012108.2 | GAACCCTTCTTTGG GAAATATGATCCTG AGGCCTGGTAGTGA CAGTAGAAACTACT CCATCACTATTCGG CAGGAGATAGACA TTCCAAGAATCAAG CAC (SEQ ID NO: 1936) | TTCTACTGTCACT ACCAGGCCTCAG GATCATATTTCCC AAAGAAGGGTTC (SEQ ID NO: 1937) | GTGCTTGATTCT TGGAATGTCTAT CTCCTGCCGAAT AGTGATGGAGTA GT (SEQ ID NO: 1938) |
| STAT1 | NM_007315.2 | TTTGCTGTATGCCA TCCTCGAGAGCTGT CTAGGTTAACGTTC GCACTCTGTGTATA TAACCTCGACAGTC TTGGCACCTAACGT GCTGTGCGTAGCTG CT (SEQ ID NO: 1939) | CAGAGTGCGAAC GTTAACCTAGAC AGCTCTCGAGGA TGGCATACAGCA AA (SEQ ID NO: 1940) | AGCAGCTACGCA CAGCACGTTAGG TGCCAAGACTGT CGAGGTTATATA CA (SEQ ID NO: 1941) |
| STAT3 | NM_139276.2 | AGACTTGGGCTTAC CATTGGGTTTAAAT CATAGGGACCTAG GGCGAGGGTTCAG GGCTTCTCTGGAGC AGATATTGTCAAGT TCATGGCCTTAGGT AGCA (SEQ ID NO: 1942) | ACCCTCGCCCTAG GTCCCTATGATTT AAACCCAATGGT AAGCCCAAG (SEQ ID NO: 1943) | TGCTACCTAAGG CCATGAACTTGA CAATATCTGCTC CAGAGAAGCCCT GA (SEQ ID NO: 1944) |
| STEAP1 | NM_012449.2 | GATGCCTGGATTGA GCATGATGTTTGGA GAATGGAGATTTAT GTGTCTCTGGGAAT TGTGGGATTGGCAA TACTGGCTCTGTTG GCTGTGACATCTAT TC (SEQ ID NO: 1945) | AGAGACACATAA ATCTCCATTCTCC AAACATCATGCT CAATCCAGGCAT C (SEQ ID NO: 1946) | GAATAGATGTCA CAGCCAACAGA GCCAGTATTGCC AATCCCACAATT CCC (SEQ ID NO: 1947) |
| STK17A | NM_004760.1 | CTTTCAGGATGGAA AAGGCACTAGAAG AAGCAAATGCCCTC CAAGAAGGTCATTC TGTGCCTGAAATTA ATTCGGATACCGAC AAATCAGAAACCG AGGA (SEQ ID NO: 1948) | ACCTTCTTGGAGG GCATTTGCTTCTT CTAGTGCCTTTTC CATCCTGAAAG (SEQ ID NO: 1949) | TCCTCGGTTTCT GATTTGTCGGTA TCCGAATTAATT TCAGGCACAGAA TG (SEQ ID NO: 1950) |
| STK38L | NM_015000.1 | CCAGACTTGGCTTG GATGACTTTGAGTC TCTGAAAGTTATAG GAAGAGGAGCTTTT GGGAGAGGTGCGGT TGGTCCAGAAGAA AGATACAGGCCAT ATCTA (SEQ ID NO: 1951) | TCCTCTTCCTATA ACTTTCAGAGACT CAAAGTCATCCA AGCCAAGTCTGG (SEQ ID NO: 1952) | TAGATATGGCCT GTATCTTTCTTCT GGACCAACCGCA CCTCTCCAAAAG C (SEQ ID NO: 1953) |

TABLE 1-continued

| Gene | GenBank Accession No. | Target Sequence | Capture Probe Sequence | Reporter Probe Sequence |
|---|---|---|---|---|
| STMN1 | NM_203401.1 | CGTGGGTGGCGGC AGGACTTTCCTTAT CCCAGTTGATTGIG CAGAATACACTGCC TGTCGCTTGTCTTC TATTCACCATGGCT TCTTCTGATATCCA GGT (SEQ ID NO: 1954) | TGTATTCTGCACA ATCAACTGGGAT AAGGAAAGTCCT GCCGCCACCCAC G (SEQ ID NO: 1955) | ACCTGGATATCA GAAGAAGCCAT GGTGAATAGAA GACAAGCGACA GGCAG (SEQ ID NO: 1956) |
| STS | NM_000351.4 | GACCCAGCTGTAGT GAGGTTGCAGTGAT TGAGTAGGATTGGC CTGCTTCAAAGCAG AGGTTTCTCATGGG AATATGCTTATTAA ACTCCCACTGGTGC AG (SEQ ID NO: 1957) | TGAAGCAGGCCA ATCCTACTCAATC ACTGCAACCTCA CTACAGCTGG (SEQ ID NO: 1958) | CTGCACCAGTGG GAGTTTAATAAG CATATTCCCATG AGAAACCTCTGC TT (SEQ ID NO: 1959) |
| STX11 | NM_003764.3 | TGACACCTTGCACT CTTACCGTCTTGAC AGAAGCCAAGTAA GGAACTGAAGTTGT ATCTGACTGTAGGG TGAATGTCTGAGGC CTGCCTCCTAATAA AGA (SEQ ID NO: 1960) | TTCAGTTCCTTAC TTGGCTTCTGTCA AGACGGTAAGAG TGCAAGGTG (SEQ ID NO: 1961) | TTTATTAGGAGG CAGGCCTCAGAC ATTCACCCTACA GTCAGATACAAC (SEQ ID NO: 1962) |
| SUFU | NM_016169.2 | GGTGCCTCTTCCTG CCCGTATCTTTCTC TTCCAAGGGCAGTG CTCCAAGGCAGGG ACTGGAGAAGCCA AGGGGAGAGTCTA AAAGGGCTAGAGC ATTTTT (SEQ ID NO: 1963) | CCTTGGAGCACT GCCCTTGGAAGA GAAAGATACGGG CAGGAAGAGGCA CC (SEQ ID NO: 1964) | AAAAATGCTCTA GCCCTTTTAGAC TCTCCCCTTGGC TTCTCCAGTCCC TG (SEQ ID NO: 1965) |
| SULF1 | NM_015170.2 | TCCAGAAATCAGG AGACGGAGACATTT TGTCAGTTTTGCAA CATTGGACCAAATA CAATGAAGTATTCT TGCTGTGCTCTGGT TTTGGCTGTCCTGG GCA (SEQ ID NO: 1966) | GGTCCAATGTTGC AAAACTGACAAA ATGTCTCCGTCTC CTGATTTCTGGA (SEQ ID NO: 1967) | TGCCCAGGACAG CCAAAACCAGA GCACAGCAAGA ATACTTCATTGT ATTT (SEQ ID NO: 1968) |
| SUN5 | NM_080675.3 | GATGGAAGCCATGT CCGATGAGCAAAA AATGGCCCAGAAA ATAATGAAGATGAT ACACGGAGATTAC ATCGAAAAGCCAG ACTTTGCCCTGAAG TCTATA (SEQ ID NO: 1969) | TCTTCATTATTTT CTGGGCCATTTTT TGCTCATCGGAC ATGGCTT (SEQ ID NO: 1970) | TATAGACTTCAG GGCAAAGTCTGG CTTTTCGATGTA ATCTCCGTGTAT CA (SEQ ID NO: 1971) |
| SYCP1 | NM_003176.2 | GCATTGTTCGTACC ACCGAGATCAAGC AGCAGTCAGGTGTC TGCGGTGAAACCTC AGACCCTGGGAGG CGATTCCACTTTCT TCAAGAGTTTCAAC AAAT (SEQ ID NO: 1972) | TTCACCGCAGAC ACCTGACTGCTGC TTGATCTCGGTGG TACGAACAATG (SEQ ID NO: 1973) | ATTTGTTGAAAC TCTTGAAGAAAG TGGAATCGCCTC CCAGGGTCTGAG GT (SEQ ID NO: 1974) |

TABLE 1-continued

| Gene | GenBank Accession No. | Target Sequence | Capture Probe Sequence | Reporter Probe Sequence |
|---|---|---|---|---|
| SYK | NM_003177.3 | CGGACTCTCCAAAGCACTGCGTGCTGATGAAAACTACTACAAGGCCCAGACCCATGGAAAGTGGCCTGTCAAGTGGTACGCTCCGGAATGCATCAACTAC (SEQ ID NO: 1975) | TCTGGGCCTTGTAGTAGTTTTCATCAGCACGCAGTGCTTTGGAGAGTCCG (SEQ ID NO: 1976) | GTAGTTGATGCATTCCGGAGCGTACCACTTGACAGGCCACTTTCCATGGG (SEQ ID NO: 1977) |
| SYPL1 | NM_182715.1 | GGTCCTCGAGTGGATTGCTTCTATCTTTGCTTTTGCCACCTGTGGAGGTTTTAAGGGCCAAACAGAAATTCAAGTGAATTGTCCTCCTGCAGTTACTGAG (SEQ ID NO: 1978) | AACCTCCACAGGTGGCAAAAGCAAAGATAGAAGCAATCCACTCGAGGACC (SEQ ID NO: 1979) | CTCAGTAACTGCAGGAGGACAATTCACTTGAATTTCTGTTTGGCCCTTAA (SEQ ID NO: 1980) |
| SYT17 | NM_016524.2 | CTGCTCCTGACCGTGGTGGATTTTGATAAGTTCTCCCGCCACTGTGTCATTGGGAAAGTTTCTGTGCCTTTGTGTGAAGTTGACCTGGTCAAGGGCGGGC (SEQ ID NO: 1981) | ATGACACAGTGGCGGGAGAACTTATCAAAATCCACCACGGTCAGGAGCAG (SEQ ID NO: 1982) | CCGCCCTTGACCAGGTCAACTTCACACAAAGGCACAGAAACTTTCCCA (SEQ ID NO: 1983) |
| SYTL4 | NM_001129896.1 | GCCGGAGCTGGGTTGCGATCTTCCCGGAGCCGGAGACCCTCCCTTGAAAACCGGCACTGGGACTTCTCGATCTCTGGAGGCACCTGTTGCAAGTGACAGAG (SEQ ID NO: 1984) | GTTTCAAGGGAGGGTCTCCGGCTCCGGGAAGATCGCAAC (SEQ ID NO: 1985) | CAACAGGTGCCTCCAGAGATCGAGAAGTCCCAGTGCCG (SEQ ID NO: 1986) |
| TARS | NM_152295.3 | CCCTCGCCAGGTAATGGTAGTTCCAGTGGGACCAACCTGTGATGAATATGCCCAAAAGGTACGACAACAATTCCACGATGCCAAATTCATGGCAGACATT (SEQ ID NO: 1987) | CATATTCATCACAGGTTGGTCCCACTGGAACTACCATTACCTGGCG (SEQ ID NO: 1988) | AATGTCTGCCATGAATTTGGCATCGTGGAATTGTTGTCGTACCTTTTGGG (SEQ ID NO: 1989) |
| TAX1BP1 | NM_006024.4 | AAAAAACCACACCTAAAATAGACCACTGAGGAGACCATAGAGCGGATGCTTTCATGCACCCTTTACTGCACTTTCTGACCAGGAGCTACTTTGAGTTTGG (SEQ ID NO: 1990) | AGCATCCGCTCTATGGTCTCCTCAGTGGTCTATTTTAGGTGTGGTTTTTT (SEQ ID NO: 1991) | CCAAACTCAAAGTAGCTCCTGGTCAGAAAGTGCAGTAAAGGGTGCATGAA (SEQ ID NO: 1992) |
| TBC1D27 | XM_002343481.2 | TGAGCTGCATTTTTTGGAGAGGCGGCCCCTGTCCCCAAAGCTGGTGCAAGCCCTGGGTGTAGCAGGCCAGTGCCTTGCAGTGCAATTGTACCTGAGGACC (SEQ ID NO: 1993) | CTTGCACCAGCTTTGGGGACAGGGGCCGCCTCTCCAAAAATGCAG (SEQ ID NO: 1994) | TACAATTGCACTGCAAGGCACTGGCCTGCTACACCCAGGG (SEQ ID NO: 1995) |

TABLE 1-continued

| Gene | GenBank Accession No. | Target Sequence | Capture Probe Sequence | Reporter Probe Sequence |
| --- | --- | --- | --- | --- |
| TBC1D9 | NM_015130.2 | ACCAATAAAGACAGCACACTGCCTCCCATTCCTCACCTCCACTCCTTGCTCAGCGATGATGTGGAACCTTACCCTGAGGTAGACATCTTTAGACTCATCA (SEQ ID NO: 1996) | AGCAAGGAGTGGAGGTGAGGAATGGGAGGCAGTGTGCTGTCTTTATTG (SEQ ID NO: 1997) | TGATGAGTCTAAAGATGTCTACCTCAGGGTAAGGTTCCACATCATCGCTG (SEQ ID NO: 1998) |
| TCF3 | NM_003200.2 | ATACGTGTCAACACAGCTGGCTGGATGATTGGGACTTTAAAACGACCCTCTTTCAGGTGGATTCAGAGACCTGTCCTGTATATAACAGCACTGTAGCAAT (SEQ ID NO: 1999) | GAGGGTCGTTTTAAAGTCCCAATCATCCAGCCAGCTGTGTTGACACGTAT (SEQ ID NO: 2000) | ATTGCTACAGTGCTGTTATATACAGGACAGGTCTCTGAATCCACCTGAAA (SEQ ID NO: 2001) |
| TCF4 | NM_001083962.1 | TTAGGGGAAGCTCGGCTGCCCTAGTAACAAAACCAGCAAACGTCCTGATGACAACGAAGTGATGACATTAGCCATTCCTTAGGGTAGGAGGAACAGATGG (SEQ ID NO: 2002) | CATCAGGACGTTTGCTGGTTTTGTTACTAGGGCAGCCGAGCTTCCCCTAA (SEQ ID NO: 2003) | CCATCTGTTCCTCCTACCCTAAGGAATGGCTAATGTCATCACTTCGTTGT (SEQ ID NO: 2004) |
| TCTN3 | NM_015631.5 | AGGTATTGTGGGCATATGTAGGTCTCCTGTCCAACCCGCAAGCTCATGTATCAGGAGTTCGATTCCTATACCAGTGCCAGTCTATACAGGATTCTCAGCA (SEQ ID NO: 2005) | TACATGAGCTTGCGGGTTGGACAGGAGACCTACATATGCCCACAATACCT (SEQ ID NO: 2006) | TGCTGAGAATCCTGTATAGACTGGCACTGGTATAGGAATCGAACTCCTGA (SEQ ID NO: 2007) |
| TEAD1 | NM_021961.5 | CCAGAAGAGGGCTAAGATACGTTTTCTGTCTTGAGCTGAAAGCACAGTCTACTCTCCTTCGTTTTGTCGATGAGAAAGTTGAGGCCAGAGGGGAGGTGAC (SEQ ID NO: 2008) | AGACTGTGCTTTCAGCTCAAGACAGAAAACGTATCTTAGCCCTCTTCTGG (SEQ ID NO: 2009) | TCACCTCCCCTCTGGCCTCAACTTTCTCATCGACAAAACGAAGGAGAGT (SEQ ID NO: 2010) |
| TEK | NM_000459.2 | CGAGTTCGAGGAGAGGCAATCAGGATACGAACCATGAAGATGCGTCAACAAGCTTCCTTCCTACCAGCTACTTTAACTATGACTGTGGACAAGGGAGATA (SEQ ID NO: 2011) | TGTTGACGCATCTTCATGGTTCGTATCCTGATTGCCTCTCCTCGAACTCG (SEQ ID NO: 2012) | TATCTCCCTTGTCCACAGTCATAGTTAAAGTAGCTGGTAGGAAGGAAGCT (SEQ ID NO: 2013) |
| TERT | NM_198253.1 | GGCTTCAAGGCTGGGAGGAACATGCGTCGCAAACTCTTTGGGGTCTTGCGGCTGAAGTGTCACAGCCTGTTTCTGGATTTGCAGGTGAACAGCCTCCAGA (SEQ ID NO: 2014) | CGCAAGACCCCAAAGAGTTTGCGACGCATGTTCCTCCAGCCTTGAAGC (SEQ ID NO: 2015) | TCTGGAGGCTGTTCACCTGCAAATCCAGAAACAGGCTGTGACACTTCAGC (SEQ ID NO: 2016) |

TABLE 1-continued

| Gene | GenBank Accession No. | Target Sequence | Capture Probe Sequence | Reporter Probe Sequence |
|---|---|---|---|---|
| TEX9 | NM_198524.1 | ACCTGGACCCGACCTCCTCGCCTTGGAGGAAGAATATAAGCGTTTAAATGCAGAATTGCAGGCAAAAACAGCTGACGTGGTTCAACAAGCTAAGGAAATA (SEQ ID NO: 2017) | CATTTAAACGCTTATATTCTTCCTCCAAGGCGAGGAGGTCGGGTCCAG (SEQ ID NO: 2018) | TATTTCCTTAGCTTGTTGAACCACGTCAGCTGTTTTTGCCTGCAATTCTG (SEQ ID NO: 2019) |
| TFDP2 | NM_006286.3 | GACCTTCTTGGTTAAATCAGGGACTACTTCTGAACTCTACCCAATCAGTTTCAAATTTAGACCTGACCACTGGTGCCACCTTACCCCAGTCAAGTGTAAA (SEQ ID NO: 2020) | AACTGATTGGGTAGAGTTCAGAAGTAGTCCCTGATTTAACCAAGAAGGTC (SEQ ID NO: 2021) | TTTACACTTGACTGGGGTAAGGTGGCACCAGTGGTCAGGTCTAAATTTGA (SEQ ID NO: 2022) |
| TFPI2 | NM_006528.2 | TTTAATCCAAGATACAGAACCTGTGATGCTTTCACCTATACTGGCTGTGGAGGGAATGACAATAACTTTGTTAGCAGGGAGGATTGCAAACGTGCATGTG (SEQ ID NO: 2023) | CCACAGCCAGTATAGGTGAAAGCATCACAGGTTCTGTATCTTGGATTAAA (SEQ ID NO: 2024) | CACATGCACGTTTGCAATCCTCCCTGCTAACAAAGTTATTGTCATTCCCT (SEQ ID NO: 2025) |
| TGFBR1 | NM_004612.2 | GGGGAAATACGACTTAGTGAGGCATAGACATCCCTGGTCCATCCTTTCTGTCTCCAGCTGTTTCTTGGAACCTGCTCTCCTGCTTGCTGGTCCCTGACGC (SEQ ID NO: 2026) | CAGAAAGGATGGACCAGGGATGTCTATGCCTCACTAAGTCGTATTTCCCC (SEQ ID NO: 2027) | AGGGACCAGCAAGCAGGAGAGCAGGTTCCAAGAAACAGCTGGAGA (SEQ ID NO: 2028) |
| THBS2 | NM_003247.2 | AAACATCCTTGCAAATGGGTGTGACGCGGTTCCAGATGTGGATTTGGCAAAACCTCATTTAAGTAAAAGGTTAGCAGAGCAAAGTGCGGTGCTTTAGCTG (SEQ ID NO: 2029) | TTGCCAAATCCACATCTGGAACCGCGTCACACCCATTTGCAAGGATGTTT (SEQ ID NO: 2030) | CAGCTAAAGCACCGCACTTTGCTCTGCTAACCTTTTACTTAAATGAGGTT (SEQ ID NO: 2031) |
| THOC5 | NM_001002878.1 | CCTGGGGATCATGGAAAGAAAACTCCGAATCCAGCCAATCAGTATCAGTTTGATAAAGTTGGCATCCTGACTTTGAGCGACTATGTACTTGAGCTAGGTC (SEQ ID NO: 2032) | AACTGATACTGATTGGCTGGATTCGGAGTTTTCTTTCCATGATCCCCAGG (SEQ ID NO: 2033) | GACCTAGCTCAAGTACATAGTCGCTCAAAGTCAGGATGCCAACTTTATCA (SEQ ID NO: 2034) |
| THY1 | NM_006288.2 | CCTGCCTAGTGGACCAGAGCCTTCGTCTGGACTGCCGCCATGAGAATACCAGCAGTTCACCCATCCAGTACGAGTTCAGCCTGACCCGTGAGACAAAGAA (SEQ ID NO: 2035) | GGTATTCTCATGGCGGCAGTCCAGACGAAGGCTCT (SEQ ID NO: 2036) | TTCTTTGTCTCACGGGTCAGGCTGAACTCGTACTGGATGGGTGAACTGCT (SEQ ID NO: 2037) |

TABLE 1-continued

| Gene | GenBank Accession No. | Target Sequence | Capture Probe Sequence | Reporter Probe Sequence |
|---|---|---|---|---|
| TIAM2 | NM_001010927.2 | TTGCCTGGGGATGAGAGGGAGAGACAACGTGTGTCTTACACATCTCCCAACAGCCGACTTAGATGTGATCCGTTCTCCCAGAGGGAGCAGGTTTCTTTGA (SEQ ID NO: 2038) | TTGGGAGATGTGTAAGACACACGTTGTCTCTCCCTCTCATCC (SEQ ID NO: 2039) | TCAAAGAAACCTGCTCCCTCTGGGAGAACGGATCACATCTAAGTCGGCTG (SEQ ID NO: 2040) |
| TICAM2 | NM_021649.4 | TATTCCCCACTTGTATATCCCCTACCAGTACCGGGATCTGCACACATCTTTTTGCAGTTACCTCTTCATAGCCATGAACCAAAACGTTCTATGAGGAGCA (SEQ ID NO: 2041) | AAGATGTGTGCAGATCCCGGTACTGGTAGGGGATATACAAGTGGGGAATA (SEQ ID NO: 2042) | TGCTCCTCATAGAACGTTTTGGTTCATGGCTATGAAGAGGTAACTGCAAA (SEQ ID NO: 2043) |
| TJP2 | NM_004817.2 | AGCCAATGATAGCTGGTTTGGCAGCTTAAAGGACACTATTCAGCATCAGCAAGGAGAAGCGGTTTGGGTCTCTGAAGGAAAGATGGAAGGGATGGATGAT (SEQ ID NO: 2044) | GCTGATGCTGAATAGTGTCCTTTAAGCTGCCAAACCAGCTATCATTGGCT (SEQ ID NO: 2045) | ATCATCCATCCCTTCCATCTTTCCTTCAGAGACCCAAACCGCTTCTCCTT (SEQ ID NO: 2046) |
| TK1 | NM_003258.1 | GGATGGCCTGGATTCACGCCCTCTTGTTTCCTTTTGGGCTCAAAGCCCTTCCTACCTCTGGTGATGGTTTCCACAGGAACAACAGCATCTTTCACCAAGA (SEQ ID NO: 2047) | AAGGGCTTTGAGCCCAAAAGGAAACAAGAGGGCGTGAATCCAGGCCATCC (SEQ ID NO: 2048) | TCTTGGTGAAAGATGCTGTTGTTCCTGTGGAAACCATCACCAGAGGTAGG (SEQ ID NO: 2049) |
| TLE4 | NM_007005.3 | AAAACAAGGACAGCAGAGGAGGGTTTGCAGAGACCTCCCTCTGAAAAACACAAAGAATGGACTCTCTCCTGGGATGAGGACTTGCTTTCTTTACCTCCGG (SEQ ID NO: 2050) | TGTTTTTCAGAGGGAGGTCTCTGCAAACCCTCCTCTGCTGTCCTTGTTTT (SEQ ID NO: 2051) | CCGGAGGTAAAGAAAGCAAGTCCTCATCCCAGGAGAGAGTCCATTCTTTG (SEQ ID NO: 2052) |
| TLK1 | NM_012290.3 | CCACGCGTCCGCGGGTTCCCAGAAAGTAGCTTGATGAGTGTCCAAAGTAGCAGTGGAAGTTTGGAGGGGCCGCCATCTTGGTCCCAGCTCTCCACGTCTC (SEQ ID NO: 2053) | CTACTTTGGACACTCATCAAGCTACTTTCTGGGAACCCGCGGACGCGTGG (SEQ ID NO: 2054) | TGGGACCAAGATGGCGGCCCCTCCAAACTTCCACTG (SEQ ID NO: 2055) |
| TLR7 | NM_016562.3 | TGTGGGCACCACACAGGTGGTTGCTGCTTCAGTGCTTCCTGCTCTTTTTCCTTGGGCCTGCTTCTGGGTTCCATAGGGAAACAGTAAGAAAGAAAGACAC (SEQ ID NO: 2056) | GAAAAAGAGCAGGAAGCACTGAAGCAGCAACCACCTGTGTGGTGCCCACA (SEQ ID NO: 2057) | GTGTCTTTCTTTCTTACTGTTTCCCTATGGAACCCAGAAGCAGGCCCAAG (SEQ ID NO: 2058) |

TABLE 1-continued

| Gene | GenBank Accession No. | Target Sequence | Capture Probe Sequence | Reporter Probe Sequence |
|---|---|---|---|---|
| TM4SF1 | NM_014220.2 | AATCGCAGTATTTA AGAGGTAGCAGGA ATGGGCTGAGAGT GGTGTTTGCTTTCT CCACCAGAAGGGC ACACTTTCATCTAA TTTGGGGTATCACT GAGCT (SEQ ID NO: 2059) | AGCAAACACCAC TCTCAGCCCATTC CTGCTACCTCTTA AATACTGCGATT (SEQ ID NO: 2060) | AGCTCAGTGATA CCCCAAATTAGA TGAAAGTGTGCC CTTCTGGTGGAG AA (SEQ ID NO: 2061) |
| TMBIM6 | NM_003217.2 | GGCCCTTCCTTCCT CATTGTTGTTTGGT ATGCGCACAGTTCC TGTGGGACTGGGCC GTGAGTTTTCCATT GGAAAGAAGTTCA GTGGTCCCATTGTT AAC (SEQ ID NO: 2062) | GTCCCACAGGAA CTGTGCGCATACC AAACAACAATGA GGAAGGAAGGGC C (SEQ ID NO: 2063) | GTTAACAATGGG ACCACTGAACTT CTTTCCAATGGA AAACTCACGGCC CA (SEQ ID NO: 2064) |
| TMEM109 | NM_024092.2 | TAGGGGCCACTTTT CCTTTGAGGCTCTA GTGGAGGTGGATGT CCTTCTCTGCCAGG CTTGGCACATGATG TGAAGAATAAATG CCCAATTCTTACTG TTC (SEQ ID NO: 2065) | AGAGAAGGACAT CCACCTCCACTAG AGCCTCAAAGGA AAAGTGGCCCCT A (SEQ ID NO: 2066) | GAACAGTAAGA ATTGGGCATTTA TTCTTCACATCA TGTGCCAAGCCT GGC (SEQ ID NO: 2067) |
| TMEM119 | NM_181724.2 | GTCACAGGTCATTT GTGGGGCAAACAT CACTGCTTTTCCAT CAAGGGAGCAAAG AATAAGTGGGAGTT TTGGAAGAGTTTGG ATGAGAGACGCCA AGGTG (SEQ ID NO: 2068) | GCTCCCTTGATGG AAAAGCAGTGAT GTTTGCCCCACAA ATGACCTGTGAC (SEQ ID NO: 2069) | CACCTTGGCGTC TCTCATCCAAAC TCTTCCAAAACT CCCACTTATTCT TT (SEQ ID NO: 2070) |
| TMOD1 | NM_003275.2 | AGATGCTCAAGGA GAACAAGGTGTTG AAGACACTGAATGT GGAATCCAACTTCA TTTCTGGAGCTGGG ATTCTGCGCCTGGT AGAAGCCCTCCCAT ACAA (SEQ ID NO: 2071) | GTTGGATTCCACA TTCAGTGTCTTCA ACACCTTGTTCTC CTTGAGCATCT (SEQ ID NO: 2072) | TTGTATGGGAGG GCTTCTACCAGG CGCAGAATCCCA GCTCCAGAAATG AA (SEQ ID NO: 2073) |
| TMPRSS6 | NM_153609.2 | CCCGAGGGCCTAGT GATCCTGGAAGCCA GTGTGAAAGACAT AGCTGCATTGAATT CCACGCTGGGTTGT TACCGCTACAGCTA CGTGGGCCAGGGC CAGG (SEQ ID NO: 2074) | AATGCAGCTATG TCTTTCACACTGG CTTCCAGGATCAC TAGG (SEQ ID NO: 2075) | GCCCACGTAGCT GTAGCGGTAACA ACCCAGCGTGGA ATTC (SEQ ID NO: 2076) |
| TNF | NM_000594.2 | AGCAACAAGACCA CCACTTCGAAACCT GGGATTCAGGAAT GTGTGGCCTGCACA GTGAAGTGCTGGCA ACCACTAAGAATTC AAACTGGGGCCTCC AGAA (SEQ ID NO: 2077) | CAGGCCACACAT TCCTGAATCCCAG GTTTCGAAGTGGT GGTCTTGTTGCT (SEQ ID NO: 2078) | TTCTGGAGGCCC CAGTTTGAATTC TTAGTGGTTGCC AGCACTTCACTG TG (SEQ ID NO: 2079) |

TABLE 1-continued

| Gene | GenBank Accession No. | Target Sequence | Capture Probe Sequence | Reporter Probe Sequence |
|---|---|---|---|---|
| TNFAIP2 | NM_006291.2 | GTCACTGTACCCGG CCTGCTCTACCGCT TTTAAGGACGCTTA TGATCACATTGCGC CTACCCAGAGAACC CAGGTCGTCTTTCT ATTTTCAGGTCAGC TG (SEQ ID NO: 2080) | TGTGATCATAAG CGTCCTTAAAAG CGGTAGAGCAGG CCGGGTACAGTG AC (SEQ ID NO: 2081) | CAGCTGACCTGA AAATAGAAAGA CGACCTGGGTTC TCTGGGTAGGCG CAA (SEQ ID NO: 2082) |
| TNFAIP3 | NM_006290.2 | CAAAGCCCTCATCG ACAGAAACATCCA GGCCACCCTGGAA AGCCAGAAGAAAC TCAACTGGTGTCGA GAAGTCCGGAAGC TTGTGGCGCTGAAA ACGAAC (SEQ ID NO: 2083) | TCTTCTGGCTTTC CAGGGTGGCCTG GATGTTTCTGTCG ATGAG (SEQ ID NO: 2084) | GTTCGTTTTCAG CGCCACAAGCTT CCGGACTTCTCG ACACCAGTTGAG TT (SEQ ID NO: 2085) |
| TNFRSF13B | NM_012452.2 | TGCAAAACCATTTG CAACCATCAGAGCC AGCGCACCTGTGCA GCCTTCTGCAGGTC ACTCAGCTGCCGCA AGGAGCAAGGCAA GTTCTATGACCATC TCC (SEQ ID NO: 2086) | CAGAAGGCTGCA CAGGTGCGCTGG CTCTGATGGTTGC AAATGGTTTTGCA (SEQ ID NO: 2087) | TCATAGAACTTG CCTTGCTCCTTG CGGCAGCTGAGT GACCTG (SEQ ID NO: 2088) |
| TNFRSF14 | NM_003820.2 | CTCAGGGAGCCTCG TCATCGTCATTGTT TGCTCCACAGTTGG CCTAATCATATGTG TGAAAAGAAGAAA GCCAAGGGGTGAT GTAGTCAAGGTGAT CGTC (SEQ ID NO: 2089) | TGATTAGGCCAA CTGTGGAGCAAA CAATGACGATGA CGAGGCTCCCTG AG (SEQ ID NO: 2090) | GACGATCACCTT GACTACATCACC CCTTGGCTTTCTT CTTTTCACACAT A (SEQ ID NO: 2091) |
| TNFRSF17 | NM001192.2 | TCTGACCATTGCTT TCCACTCCCAGCTA TGGAGGAAGGCGC AACCATTCTTGTCA CCACGAAAACGAA TGACTATTGCAAGA GCCTGCCAGCTGCT TTGA (SEQ ID NO: 2092) | AGAATGGTTGCG CCTTCCTCCATAG CTGGGAGTGGAA AGCAATGGT (SEQ ID NO: 2093) | TCAAAGCAGCTG GCAGGCTCTTGC AATAGTCATTCG TTTTCGTGGTGA CA (SEQ ID NO: 2094) |
| TNFRSF19 | NM_018647.2 | TGAATCAGGAGACT GTAGACAGCAAGA ATTCAGGGATCGGT CTGGAAACTGTGTT CCCTGCAACCAGTG TGGGCCAGGCATG GAGTTGTCTAAGGA ATGT (SEQ ID NO: 2095) | AGTTTCCAGACC GATCCCTGAATTC TTGCTGTCTACAG TCTCCTGATTCA (SEQ ID NO: 2096) | TTAGACAACTCC ATGCCTGGCCCA CACTGGTTGCAG GGAACAC (SEQ ID NO: 2097) |
| TNFSF10 | NM_003810.2 | GGGGGGACCCAGC CTGGGACAGACCTG CGTGCTGATCGTGA TCTTCACAGTGCTC CTGCAGTCTCTCTG TGTGGCTGTAACTT ACGTGTACTTTACC AAC (SEQ ID NO: 2098) | CTGTGAAGATCA CGATCAGCACGC AGGTCTGTCCC (SEQ ID NO: 2099) | GTTGGTAAAGTA CACGTAAGTTAC AGCCACACAGA GAGACTGCAGG AGCA (SEQ ID NO: 2100) |

TABLE 1-continued

| Gene | GenBank Accession No. | Target Sequence | Capture Probe Sequence | Reporter Probe Sequence |
|---|---|---|---|---|
| TNFSF4 | NM_003326.2 | GAAGGTCAGGTCTG TCAACTCCTTGATG GTGGCCTCTCTGAC TTACAAAGACAAA GTCTACTTGAATGT GACCACTGACAATA CCTCCCTGGATGAC TTC (SEQ ID NO: 2101) | CTTTGTAAGTCAG AGAGGCCACCAT CAAGGAGTTGAC AGACCTGACCTTC (SEQ ID NO: 2102) | GAAGTCATCCAG GGAGGTATTGTC AGTGGTCACATT CAAGTAGACTTT GT (SEQ ID NO: 2103) |
| TNXB | NM_019105.5 | CAGGTGGTACCTGT GGAAGGGCCCGAG CGTTCATTTGTTGT CTCCTCACTGGACC CTGACCACAAGTAC AGATTCACTCTGTT TGGAATTGCGAACA AGA (SEQ ID NO: 2104) | AGTGAGGAGACA ACAAATGAACGC TCGGGCCCTTCCA CAGGTACCACCT G (SEQ ID NO: 2105) | TCTTGTTCGCAA TTCCAAACAGAG TGAATCTGTACT TGTGGTCAGGGT CC (SEQ ID NO: 2106) |
| TOP2A | NM_001067.2 | TTTCAGCTCTTGAC CTGTCCCCTCTGGC TGCCTCTGAGTCTG AATCTCCCAAAGAG AGAAACCAATTTCT AAGAGGACTGGAT TGCAGAAGACTCG GGGA (SEQ ID NO: 2107) | GGGAGATTCAGA CTCAGAGGCAGC CAGAGGGGACA (SEQ ID NO: 2108) | TCCCCGAGTCTT CTGCAATCCAGT CCTCTTAGAAAT TGGTTTCTCTCTT T (SEQ ID NO: 2109) |
| TOX | NM_014729.2 | AATGAGCAGCTTTG ACTTTGACAGGCGG TTTGTGCAGGAAAG CACAGTGCCGTGTT GTTTACAGCTTTTC TAGAGCAGCTGTGC GACCAGGGTAGAG AGT (SEQ ID NO: 2110) | GCACTGTGCTTTC CTGCACAAACCG CCTGTCAAAGTC AAAGCTGC (SEQ ID NO: 2111) | ACTCTCTACCCT GGTCGCACAGCT GCTCTAGAAAAG CTGTAAACAACA CG (SEQ ID NO: 2112) |
| TP53 | NM_000546.2 | GGGGAGCAGGGCT CACTCCAGCCACCT GAAGTCCAAAAAG GGTCAGTCTACCTC CCGCCATAAAAAA CTCATGTTCAAGAC AGAAGGGCCTGAC TCAGAC (SEQ ID NO: 2113) | TAGACTGACCCTT TTTGGACTTCAGG TGGCTGGAGTGA GCCCTG (SEQ ID NO: 2114) | GTCTGAGTCAGG CCCTTCTGTCTT GAACATGAGTTT TTTATGGCGGGA GG (SEQ ID NO: 2115) |
| TP73 | NM_005427.1 | CAAGCCGGGGGAA TAATGAGGTGGTGG GCGGAACGGATTCC AGCATGGACGTCTT CCACCTGGAGGGC ATGACTACATCTGT CATGGCCCAGTTCA ATCT (SEQ ID NO: 2116) | GTCCATGCTGGA ATCCGTTCCGCCC ACCACCTCATTAT T (SEQ ID NO: 2117) | CATGACAGATGT AGTCATGCCCTC CAGGTGGAAGA C (SEQ ID NO: 2118) |
| TPM1 | NM_000366.5 | CCTCTCTGAGCTCT GCATTTGTCTATTC TCCAGCTGACCCTG GTTCTCTCTCTTAG CATCCTGCCTTAGA GCCAGGCACACACT GTGCTTTCTATTGT AC (SEQ ID NO: 2119) | GAGAGAACCAGG GTCAGCTGGAGA ATAGACAAATGC AGAGCTCAGAGA GG (SEQ ID NO: 2120) | GTACAATAGAAA GCACAGTGTGTG CCTGGCTCTAAG GCAGGATGCTAA GA (SEQ ID NO: 2121) |

TABLE 1-continued

| Gene | GenBank Accession No. | Target Sequence | Capture Probe Sequence | Reporter Probe Sequence |
|---|---|---|---|---|
| TPX2 | NM_012112.4 | TGGGACCTGCTCTTAACCTCAAACCTAGGACCGTCTTGCTTTGTCATTGGGCATGGAGAGAACCCATTTCTCCAGACTTTTACCTACCCGTGCCTGAGAA (SEQ ID NO: 2122) | CCAATGACAAAGCAAGACGGTCCTAGGTTTGAGGTTAAGAGCAGGTCCCA (SEQ ID NO: 2123) | TTCTCAGGCACGGGTAGGTAAAAGTCTGGGAGAAATGGGTTCTCTCCATGC (SEQ ID NO: 2124) |
| TRAF1 | NM_005658.3 | CGAGTGATGGGTCTAGGCCCTGAAACTGATGTCCTAGCAATAACCTCTTGATCCCTACTCACCGAGTGTTGAGCCCAAGGGGGGATTTGTAGAACAAGCC (SEQ ID NO: 2125) | CAAGAGGTTATTGCTAGGACATCAGTTTCAGGGCCTAGACCCATCACTCG (SEQ ID NO: 2126) | TTGTTCTACAAATCCCCCCTTGGGCTCAACACTCGGTGAGTAGGGAT (SEQ ID NO: 2127) |
| TRAF3 | NM_145725.1 | ATATGATGCCCTGCTTCCTTGGCCGTTTAAGCAGAAAGTGACACTCATGCTGATGGATCAGGGGTCCTCTCGACGTCATTTGGGAGATGCATTCAAGCCC (SEQ ID NO: 2128) | GCATGAGTGTCACTTTCTGCTTAAACGGCCAAGGAAGCAGGGCATCATAT (SEQ ID NO: 2129) | GCTTGAATGCATCTCCCAAATGACGTCGAGAGGACCCCTGATCCATCA (SEQ ID NO: 2130) |
| TRIM56 | NM_030961.1 | GTGGAGGCCGAGGACATTTTCCTGAAGGGCAGGGGTTGGCAACTTTTCAACATGGAGTGCCAAACTGCTAACCCGTCTTCTAGTGTGTGAGAATAGGGAC (SEQ ID NO: 2131) | TTGAAAAGTTGCCAACCCCTGCCCTTCAGGAAAATGTCCTCGGCCT (SEQ ID NO: 2132) | CCTATTCTCACACACTAGAAGACGGGTTAGCAGTTTGGCACTCCATG (SEQ ID NO: 2133) |
| TRIM6-TRIM34 | NM_001003819.3 | AAGGATGCTGCGAGTGTGTAGAGAGCTGACAGATGTCCAAAGCTACTGGGCCATCCAGGGGTCTTTAACCAGAAGAGAGAGGAGAGCCTCAGGAGTTAGG (SEQ ID NO: 2134) | CCCAGTAGCTTTGGACATCTGTCAGCTCTCTACACAC (SEQ ID NO: 2135) | CTCTCCTCTCTCTTCTGGTTAAAGACCCCTGGATGG (SEQ ID NO: 2136) |
| TRIM62 | NM_018207.2 | GATTTACTACCTGGCCCCTGGTGGCTTGCAAAATTGTTGAAGAGCTGGAGAAGCAGACTCTGCTGAATTTCCAGGAACTCCCAGCGCCAGATTCATCAT (SEQ ID NO: 2137) | TCCAGCTCTTCCAACAATTTTGCAAGCCACCAGGGGCCAGGTAGTAAATC (SEQ ID NO: 2138) | ATGATGAATCTGGCGCTGGGAGTTCCTGGAAATTCAGCAGAGTCTGCTTC (SEQ ID NO: 2139) |
| TRIP13 | NM_004237.2 | AAGAGACAGAAAACATAATTGCAGCAAATCACTGGGTTCTACCTGCAGCTGAATTCCATGGGCTTTGGGACAGCTTGGTATACGATGTGGAAGTCAAATC (SEQ ID NO: 2140) | AGCTGCAGGTAGAACCCAGTGATTTGCTGCAATTATGTTTTCTGT (SEQ ID NO: 2141) | GATTTGACTTCCACATCGTATACCAAGCTGTCCCAAAGCCCATGGAATTC (SEQ ID NO: 2142) |

TABLE 1-continued

| Gene | GenBank Accession No. | Target Sequence | Capture Probe Sequence | Reporter Probe Sequence |
| --- | --- | --- | --- | --- |
| TTC9 | NM_015351.1 | AGCATCGTATAGGC TAGGGGATTGAACT GTGGACTGATTCAG TGTAAATAAAAAC AAATTAACAGGTA GTAGTTCCTGTCAG TTCTGTTGGAAGCA GCCC (SEQ ID NO: 2143) | TATTTACACTGAA TCAGTCCACAGTT CAATCCCCTAGCC TATACGATGCT (SEQ ID NO: 2144) | GGGCTGCTTCCA ACAGAACTGACA GGAACTACTACC TGTTAATTTGTTT T (SEQ ID NO: 2145) |
| TUBB2C | NM_006088.5 | TGGCGGAGCGTCG GTTGTAGCACTCTG CGCGCCCGCTCTTC TGCTGCTGTTTGTC TACTTCCTCCTGCT TCCCCGCCGCCGCC GCCGCCATCATGAG GGA (SEQ ID NO: 2146) | ACAGCAGCAGAA GAGCGGGCGCGC AGAGTGCTACAA (SEQ ID NO: 2147) | GCGGCGGCGGC GGGGAAGCAGG AGGAAGTAGAC AA (SEQ ID NO: 2148) |
| TUBG1 | NM_001070.4 | CCCCTCAGAGCACA GATCAGGGACCTCA CGCATCTCTTTCTC ATATACATGGACTC TCTGTTGGCCTGCA AACACATTTACTTC TCCTCTTATGAGAC TA (SEQ ID NO: 2149) | ATGTATATGAGA AAGAGATGCGTG AGGTCCCTGATCT GTGCTCTGAGGG G (SEQ ID NO: 2150) | TAGTCTCATAAG AGGAGAAGTAA ATGTGTTTGCAG GCCAACAGAGA GTCC (SEQ ID NO: 2151) |
| TXN | NM_003329.2 | CAGCCAAGATGGT GAAGCAGATCGAG AGCAAGACTGCTTT TCAGGAAGCCTTGG ACGCTGCAGGTGAT AAACTTGTAGTAGT TGACTTCTCAGCCA CGTG (SEQ ID NO: 2152) | GGCTTCCTGAAA AGCAGTCTTGCTC TCGATCTGCTTCA CCATCTTGG (SEQ ID NO: 2153) | CACGTGGCTGAG AAGTCAACTACT ACAAGTTTATCA CCTGCAGCGTCC AA (SEQ ID NO: 2154) |
| TXNDC5 | NM_030810.2 | AGCAGATTGAAAT GCAAAAACCCACA CCTCTGGAAGATAC CTTCACGGCCGCTG CTGGAGCTTCTGTT GCTGTGAATACTTC TCTCAGTGTGAGAG GTTA (SEQ ID NO: 2155) | GGCCGTGAAGGT ATCTTCCAGAGGT GTGGGTTTTTGCA TTTCAATCTGCT (SEQ ID NO: 2156) | TAACCTCTCACA CTGAGAGAAGTA TTCACAGCAACA GAAGCTCCAGCA GC (SEQ ID NO: 2157) |
| TYK2 | NM_003331.3 | TCATCGCTGACAGC TGAGGAAGTCTGCA TCCACATTGCACAT AAAGTTGGTATCAC TCCTCCTTGCTTCA ATCTCTTTGCCCTC TTCGATGCTCAGGC CC (SEQ ID NO: 2158) | CCAACTTTATGTG CAATGTGGATGC AGACTTCCTCAGC TGTCAGCGATGA (SEQ ID NO: 2159) | GGGCCTGAGCAT CGAAGAGGGCA AAGAGATTGAA GCAAGGAGGAG TGATA (SEQ ID NO: 2160) |
| TYMS | NM_001071.1 | TCAGATTATTCAGG ACAGGGAGTTGAC CAACTGCAAAGAG TGATTGACACCATC AAAACCAACCCTG ACGACAGAAGAAT CATCATGTGCGCTT GGAATC (SEQ ID NO: 2161) | GTGTCAATCACTC TTTGCAGTTGGTC AACTCCCTGTCCT GAATAATCTGA (SEQ ID NO: 2162) | GATTCCAAGCGC ACATGATGATTC TTCTGTCGTCAG GGTTGGTTTTGA TG (SEQ ID NO: 2163) |

TABLE 1-continued

| Gene | GenBank Accession No. | Target Sequence | Capture Probe Sequence | Reporter Probe Sequence |
|------|----------------------|-----------------|------------------------|-------------------------|
| UBE2I | NM_003345.3 | CGGCCGCCCGAGG GACTTTGAACATGT CGGGGATCGCCCTC AGCAGACTCGCCCA GGGAGAGGAAAGCA TGGAGGAAAGACC ACCCATTTGGTTTC GTGGC (SEQ ID NO: 2164) | GAGTCTGCTGAG GGCGATCCCCGA CATGTTCAAAGTC (SEQ ID NO: 2165) | CACGAAACCAA ATGGGTGGTCTT TCCTCCATGCTT TCCTCTCCTGGG C (SEQ ID NO: 2166) |
| UBE2S | NM_014501.2 | CCTCTCCGCCACTT CCCTCGCTTCTGAC CATAGTTTGCGGGG AAGGGAGCGAGCG CGTCGAAACCAA GGAACGTGCGCGCT GACGTCACGGTTGA GGCT (SEQ ID NO: 2167) | GCTCCCTTCCCCG CAAACTATGGTC AGAAGCGAGGGA AGTGG (SEQ ID NO: 2168) | GACGTCAGCGCG CACGTTCCTTGG TTTTCGACGCGC TC (SEQ ID NO: 2169) |
| UBXN4 | NM_014607.3 | CATCGCGACGGCCA AAAGGAGCGGCGC GGTCTTCGTGGTGT TCGTGGCAGGTGAT GATGAACAGTCTAC ACAGATGGCTGCA AGTTGGGAAGATG ATAAA (SEQ ID NO: 2170) | CTGCCACGAACA CCACGAAGACCG CGCCGCTCCTTTT GGCCG (SEQ ID NO: 2171) | TTTATCATCTTCC CAACTTGCAGCC ATCTGTGTAGAC TGTTCATCATCA C (SEQ ID NO: 2172) |
| USP12 | NM_182488.3 | GTTCTTGCGTATAA GAGTCAACCTAGG AAAAAGGAGAGCC TTCTTACATGCTTA GCAGATCTCTTCCA TAGCATAGCCACTC AGAAGAAAAAGGT TGGAG (SEQ ID NO: 2173) | CATGTAAGAAGG CTCTCCTTTTTCC TAGGTTGACTCTT ATACGCAAGAAC (SEQ ID NO: 2174) | CTCCAACCTTTT TCTTCTGAGTGG CTATGCTATGGA AGAGATCTGCTA AG (SEQ ID NO: 2175) |
| USP18 | NM_017414.3 | GGAAATGCC ACCTTCAGAGATTG ACACGCTGTCATTT TCCATTTCCGTTCC TGGATCTACGGAGT CTTCTAAGAGATTT TGCAATGAGGAGA AGCA (SEQ ID NO: 2176) | CAAAGGAAATGGAAAA TGACAGCGTGTC AATCTCTGAAGG TTTTGGGCATTTC C (SEQ ID NO: 2177) | TGCTTCTCCTCA TTGCAAAATCTC TTAGAAGACTCC GTAGATCCAGGA AC (SEQ ID NO: 2178) |
| USP46 | NM_022832.2 | AATACCAGAGTTAG CTGGGTATAGAGGT GGCTCAAAGGAAG TGTCCGTGGGCAGG GGGAGGAATGAAC AAAATGGCGCTGTT TCTTTGGCTCAGAC TCCT (SEQ ID NO: 2179) | CCACGGACACTT CCTTTGAGCCACC TCTATACCCAGCT AACTCTGGTATT (SEQ ID NO: 2180) | AGGAGTCTGAGC CAAAGAAACAG CGCCATTTTGTT CATTCCTCCCCC TGC (SEQ ID NO: 2181) |
| VAC14 | NM_018052.3 | CCACCTCAGTGACA CGGCCATTGGGATG ATGACCAGGATTGC AGTTCTCAAGTGGC TCTACCACCTCTAC ATCAAAACTCCTCG GAAGATGTTCCGGC AC (SEQ ID NO: 2182) | TGAGAACTGCAA TCCTGGTCATCAT CCCAATGGCCGT GTCACTGA (SEQ ID NO: 2183) | CGGAACATCTTC CGAGGAGTTTTG ATGTAGAGGTGG TAGAGCCACT (SEQ ID NO: 2184) |

TABLE 1-continued

| Gene | GenBank Accession No. | Target Sequence | Capture Probe Sequence | Reporter Probe Sequence |
|---|---|---|---|---|
| VASH2 | NM_024749.3 | TCAAATCCGAATTT AGCCAAGCCATACC GGCCAGCAAGAGG GTTTCTGTGGTGCT TCTCTCTGCACTTT ACCCAGCATCTTCA GGAGGAACTGCAA CTAT (SEQ ID NO: 2185) | CACAGAAACCCT CTTGCTGGCCGGT ATGGCTTGGCTA AATTCGGATTTGA (SEQ ID NO: 2186) | ATAGTTGCAGTT CCTCCTGAAGAT GCTGGGTAAAGT GCAGAGAGAAG CAC (SEQ ID NO: 2187) |
| VGLL4 | NM_001128220.1 | GCGCTTTCTCAGTC ACAAGCCATGATG AATTGGTGACTCAG ACGCTTTGTGCTTT TTCCTTTGCTTCTTG AGACCGGGGTGTGT GTGGCTCAGCTTCC AC (SEQ ID NO: 2188) | ACAAAGCGTCTG AGTCACCAATTC ATCATGGCTTGTG ACTGAGAAAGCG C (SEQ ID NO: 2189) | GTGGAAGCTGAG CCACACACACCC CGGTCTCAAGAA GCAAAGGAAAA AGC (SEQ ID NO: 2190) |
| VMP1 | NM_030938.3 | GATGATGAAGAGT ATCAGGAATTTGAA GAGATGCTGGAAC ATGCAGAGTCTGCA CAAGACTTTGCCTC CCGGGCCAAACTG GCAGTTCAAAAACT AGTAC (SEQ ID NO: 2191) | GACTCTGCATGTT CCAGCATCTCTTC AAATTCCTGATAC TCTTCATCATC (SEQ ID NO: 2192) | GTACTAGTTTTT GAACTGCCAGTT TGGCCCGGGAGG CAAAGTCTTGTG CA (SEQ ID NO: 2193) |
| VRK3 | NM_016440.3 | ACAGACAAGAGTG GGCGACAGTGGAA GCTGAAGTCCTTCC AGACCAGGGACAA CCAGGGCATTCTCT ATGAAGCTGCACCC ACCTCCACCCTCAC CTGTG (SEQ ID NO: 2194) | TCCCTGGTCTGGA AGGACTTCAGCTT CCACTGTCG (SEQ ID NO: 2195) | TGGAGGTGGGTG CAGCTTCATAGA GAATGCCCTGGT TG (SEQ ID NO: 2196) |
| VWF | NM_000552.3 | CACCTGCAACCCCT GCCCCCTGGGTTAC AAGGAAGAAAATA ACACAGGTGAATGT TGTGGGAGATGTTT GCCTACGGCTTGCA CCATTCAGCTAAGA GGA (SEQ ID NO: 2197) | CACCTGTGTTATT TTCTTCCTTGTAA CCCAGGGGGCAG GGGTTGCAGGTG (SEQ ID NO: 2198) | TCCTCTTAGCTG AATGGTGCAAGC CGTAGGCAAACA TCTCCCACAACA TT (SEQ ID NO: 2199) |
| WAC | NM_100486.2 | CCTCTGGACTGAAC CCACATCTGCACC TCCAACATCTGCTT CAGCGGTCCCTGTT TCTCCTGTTCCACA GTCGCCAATACCTC CCTTACTTCAGGAC CC (SEQ ID NO: 2200) | GACCGCTGAAGC AGATGTTGGAGG TGCAGATGTGGG GTT (SEQ ID NO: 2201) | GGGTCCTGAAGT AAGGGAGGTATT GGCGACTGTGGA ACAGGAGAAAC AGG (SEQ ID NO: 2202) |
| WASF1 | NM_001024934.1 | TGGCCCAGCCTCTC ATTTTGAAACAAGA CCTCAGACATACGT GGATCATATGGATG GATCTTACTCACTT TCTGCCTTGCCATT TAGTCAGATGAGTG AG (SEQ ID NO: 2203) | TATGATCCACGTA TGTCTGAGGTCTT GTTTCAAAATGA GAGGCTGGGCCA (SEQ ID NO: 2204) | CTCACTCATCTG ACTAAATGGCAA GGCAGAAAGTG AGTAAGATCCAT CCA (SEQ ID NO: 2205) |

TABLE 1-continued

| Gene | GenBank Accession No. | Target Sequence | Capture Probe Sequence | Reporter Probe Sequence |
|---|---|---|---|---|
| WDR25 | NM_024515.4 | GCATCCTCAGTGGT GGCTTTGACTTCGC GCTGCACCTAACAG ACCTTGAAACAGG AACCCAGCTATTTA GTGGTCGAAGTGAC TTTAGAATCACTAC CTT (SEQ ID NO: 2206) | TTCAAGGTCTGTT AGGTGCAGCGCG AAGTCAAAGCCA CCACTGAG (SEQ ID NO: 2207) | AAGGTAGTGATT CTAAAGTCACTT CGACCACTAAAT AGCTGGGTTCCT GT (SEQ ID NO: 2208) |
| WDR55 | NM_017706.4 | CTACCTCTTCAATT GGAATGGCTTTGGG GCCACAAGTGACC GCTTTGCCCTGAGA GCTGAATCTATCGA CTGCATGGTTCCAG TCACCGAGAGTCTG CTG (SEQ ID NO: 2209) | GGGCAAAGCGGT CACTTGTGGCCCC AAAGCCATTCCA ATTGAAGAG (SEQ ID NO: 2210) | GACTCTCGGTGA CTGGAACCATGC AGTCGATAGATT CAGCTCTCA (SEQ ID NO: 2211) |
| WFDC9 | NM_147198.2 | CAGAGTATTGGGA AAAGACTTGCCTTC TGCCAGAACTTAAC CCAAATACACACA GAGAGCACCATGA AGCCCTGGATTCTT CTACTCGTCATGTT CATCT (SEQ ID NO: 2212) | TGTATTTGGGTTA AGTTCTGGCAGA AGGCAAGTCTTTT CCCAATACTCTG (SEQ ID NO: 2213) | AGATGAACATGA CGAGTAGAAGA ATCCAGGGCTTC ATGGTGCTCTCT GTG (SEQ ID NO: 2214) |
| WHSC1 | NM_007331.1 | AAAAGAGTGCACG CCAGTATCACGTAC AGTTCTTTGGTGAC GCCCCAGAAAGAG CTTGGATATTTGAG AAGAGCCTCGTAGC TTTTGAAGGAGAAG GACA (SEQ ID NO: 2215) | TTCTGGGGCGTCA CCAAAGAACTGT ACGTGATACTGG CGTGCACTCTTTT (SEQ ID NO: 2216) | TGTCCTTCTCCTT CAAAAGCTACGA GGCTCTTCTCAA ATATCCAAGCTC T (SEQ ID NO: 2217) |
| WNT3 | NM_030753.3 | CCAACTCGCCTGTG GACGGGGAGGCTC TCCCTCTCTCTCAT CTTACATTTCTCAC CCTACTCTGGATGG TGTGTGGTTTTAA AGAAGGGGCTTTC TTT (SEQ ID NO: 2218) | ATGTAAGATGAG AGAGAGGGAGAG CCTCCCCGTCCAC AGGCGAGTTGG (SEQ ID NO: 2219) | AAAGAAAGCCC CCTTCTTTAAAA ACCACACACCAT CCAGAGTAGGGT GAGAA (SEQ ID NO: 2220) |
| XAF1 | NM_017523.2 | TGGTTTGCCCAAGG ACTACAAATAAACC AACGGGAAAAAAG AAAGGTTCCAGTTT TGTCTGAAAATTCT GATTAAGCCTCTGG GCCCTACAGCCTGG AGA (SEQ ID NO: 2221) | GGAACCTTTCTTT TTTCCCGTTGGTT TATTTGTAGTCCT TGGGCAAAC (SEQ ID NO: 2222) | TCTCCAGGCTGT AGGGCCCAGAG GCTTAATCAGAA TTTTCAGACAAA ACT (SEQ ID NO: 2223) |
| XBP1 | NM_005080.2 | GGAGTTAAGACAG CGCTTGGGGATGGA TGCCCTGGTTGCTG AAGAGGAGGCGGA AGCCAAGGGGAAT GAAGTGAGGCCAG TGGCCGGGTCTGCT GAGTCC (SEQ ID NO: 2224) | CCTCCTCTTCAGC AACCAGGGCATC CATCCCCAAG (SEQ ID NO: 2225) | CGGCCACTGGCC TCACTTCATTCC CCTTGGCTTCCG (SEQ ID NO: 2226) |

TABLE 1-continued

| Gene | GenBank Accession No. | Target Sequence | Capture Probe Sequence | Reporter Probe Sequence |
|---|---|---|---|---|
| YPEL1 | NM_013313.3 | ATAGAGGGGCCTGTGCAATCTCCTAAGGCCTGTGTTTCTGCCATATATTTTATTATAAATTACAATCCACTCATCCACCTGCCCTCCACCAGGAGTGGGC (SEQ ID NO: 2227) | AAATATATGGCAGAAACACAGGCCTTAGGAGATTGCACAGGCCCTCTAT (SEQ ID NO: 2228) | CCCACTCCTGGTGGAGGGCAGGTGGATGAGTGGATTGTAATTTATAATA (SEQ ID NO: 2229) |
| ZAP70 | NM_001079.3 | GGAGCTCAAGGACAAGAAGCTCTTCCTGAAGCGCGATAACCTCCTCATAGCTGACATTGAACTTGGCTGCGGCAACTTTGGCTCAGTGCGCCAGGGCGTG (SEQ ID NO: 2230) | CTATGAGGAGGTTATCGCGCTTCAGGAAGAGCTTCTTGTCCTTGAGCTCC (SEQ ID NO: 2231) | CTGGCGCACTGAGCCAAAGTTGCCGCAGCCAAGTTCAATGTCAG (SEQ ID NO: 2232) |
| ZBTB32 | NM_014383.1 | AGGCCGTCTCGGCCCTCGACCTCTCCCTGTTGTCCTTCTTCCTCCACCACCTGACGGGGTGTCGGTAGCGTCTTAGCCAAGAGTCCAATTAAAGAACGAA (SEQ ID NO: 2233) | GTGGTGGAGGAAGAAGGACAACAGGGAGAGGTCGAGGGCCGAGACG (SEQ ID NO: 2234) | TTCGTTCTTTAATTGGACTCTTGGCTAAGACGCTACCGACACCCCGTCAG (SEQ ID NO: 2235) |
| ZBTB37 | NM_001122770.1 | GAACATACAATTGGAGATTCCTGACTTCAGCAACTCTGTCCTGAGCCATCTAAACCAGTTGCGCATGCAGGGCCGTCTCTGTGATATTGTGGTCAATGTG (SEQ ID NO: 2236) | GATGGCTCAGGACAGAGTTGCTGAAGTCAGGAATCTCCAATTGTATGTTC (SEQ ID NO: 2237) | CACATTGACCACAATATCACAGAGACGGCCCTGCATGCGCAACTGGTTTA (SEQ ID NO: 2238) |
| ZBTB38 | XM_929657.1 | CAAGACCTGCGGACGGTGCTTTTCGGTGCAAGGAAACTTACAGAAACATGAACGCATCCACCTGGGCTTGAAGGAGTTCGTCTGTCAGTATTGCAACAAG (SEQ ID NO: 2239) | CATGTTTCTGTAAGTTTCCTTGCACCGAAAAGCACCGTCCGCAGGTCTTG (SEQ ID NO: 2240) | CTTGTTGCAATACTGACAGACGAACTCCTTCAAGCCCAGGTGGATGCGTT (SEQ ID NO: 2241) |
| ZBTB8A | NM_001040441.1 | TGGAGATAAGGATTCCAGATGGCACTTGAGTGAAGATGAGAATAGATCCTATGTGGAGATTGTAGAAGATGGGTCTGGTGATCTGGTCATCCAACAGGTT (SEQ ID NO: 2242) | AGGATCTATTCTCATCTTCACTCAAGTGCCATCTGGAATCCTTATCTCCA (SEQ ID NO: 2243) | AACCTGTTGGATGACCAGATCACCAGACCCATCTTCTACAATCTCCACAT (SEQ ID NO: 2244) |
| ZCCHC2 | NM_017742.4 | GGCCAACAGCTTGCACTGGAGAATCGGAAAAGCACCTTGAGTTACTGGCTTCCCCTTTACCTATTCCATCAACCTTCCTTCCACACAGTAGTACTCCCGC (SEQ ID NO: 2245) | AGCCAGTAACTCAAGGTGCTTTTCCGATTCTCCAGTGCAAGCTGTTGGC (SEQ ID NO: 2246) | GCGGGAGTACTACTGTGTGGAAGGAAGGTTGATGGAATAGGTAAAGGGGA (SEQ ID NO: 2247) |

TABLE 1-continued

| Gene | GenBank Accession No. | Target Sequence | Capture Probe Sequence | Reporter Probe Sequence |
|---|---|---|---|---|
| ZCCHC7 | NM_032226.2 | CTGCTGAAGCTGTT GTCAGAATCTTCCT TTGGACAAAACATC ACTAGCTGACTATA AAAACAAAGTGT CATCATTGAAGCCC TGAAGAGGCAGGG AATT (SEQ ID NO: 2248) | CAGCTAGTGATG TTTTGTCCAAAGG AAGATTCTGACA ACAGCTTCAGCA G (SEQ ID NO: 2249) | AATTCCCTGCCT CTTCAGGGCTTC AATGATGACACT TTTGTTTTTATAG T (SEQ ID NO: 2250) |
| ZFP36L1 | NM_004926.2 | CCACGTGCCCATCT CAAGACATTCCACT CACAGATTTGAGGT TCTGGATTCCAGGT CTGGAGTTTTCCAA TGTTAATGTAAACA GAACTGGCACACA CAC (SEQ ID NO: 2251) | AATCCAGAACCT CAAATCTGTGAG TGGAATGTCTTGA GATGGGCACGTG G (SEQ ID NO: 2252) | GTGTGTGTGCCA GTTCTGTTTACA TTAACATTGGAA AACTCCAGACCT GG (SEQ ID NO: 2253) |
| ZFP42 | NM_174900.3 | AAAGAATATGACA GTCTGAGCGCAATC GCTTGTCCTCAGAG TGGATGCACTAGGA AGTTGAGGAATAG AGCTGCCCTGAGAA AGCATCTCCTCATT CATG (SEQ ID NO: 2254) | GTGCATCCACTCT GAGGACAAGCGA TTGCGCTCAGACT GTCATATTCTTT (SEQ ID NO: 2255) | CATGAATGAGGA GATGCTTTCTCA GGGCAGCTCTAT TCCTCAACTTCC TA (SEQ ID NO: 2256) |
| ZMYND8 | NM_183047.1 | GTTGGGATCGGGA GTTTCGGCACAGAC TATCCCATCAAGCC GTTGGCTCCTTTCA GCTACTACGTTACC ACGTTCCTAAAACG CAAGCTCTCCGGAC CAG (SEQ ID NO: 2257) | GGAGCCAACGGC TTGATGGGATAG TCTGTGCCGAAA CTCCCGATC (SEQ ID NO: 2258) | CTGGTCCGGAGA GCTTGCGTTTTA GGAACGTGGTAA CGTAGTAGCTGA AA (SEQ ID NO: 2259) |
| ZNF135 | NM_003436.2 | ACTAGACCCAAAGT CAAACTGTCAGTTC TAAAGCAAGGCAT CTCTGAAGAAATAT CCAACAGTGTCATC TTGGTAGAAAGATT CCTGTGGGATGGTC TGT (SEQ ID NO: 2260) | TCTTCAGAGATGC CTTGCTTTAGAAC TGACAGTTTGACT TTGGGTCTAGT (SEQ ID NO: 2261) | ACAGACCATCCC ACAGGAATCTTT CTACCAAGATGA CACTGTTGGATA TT (SEQ ID NO: 2262) |
| ZNF238 | NM_006352.3 | GGGACTGGAGCGC TGAAAAGTTGTTCC TGACCAGGCTCTAA TGAGAAATTCCTCT CTCCCCAGGTTATG AAGACAGTATGGA GTTTCCAGACCATA GTAG (SEQ ID NO: 2263) | AATTTCTCATTAG AGCCTGGTCAGG AACAACTTTTCAG CGCTCCAGTCCC (SEQ ID NO: 2264) | CTACTATGGTCT GGAAACTCCATA CTGTCTTCATAA CCTGGGGAGAG AGG (SEQ ID NO: 2265) |
| ZNF281 | NM_012482.3 | AGCGTTTGGTTCTC AGTTTAAGTCGGGC AGCAGGGTGCCAA TGACCTTTATCACT AACTCTAATGGAGA AGTGGACCATAGA GTAAGGACTTCAGT GTCA (SEQ ID NO: 2266) | TAAAGGTCATTG GCACCCTGCTGCC CGACTTAAACTG AGAACCAAACGC T (SEQ ID NO: 2267) | TGACACTGAAGT CCTTACTCTATG GTCCACTTCTCC ATTAGAGTTAGT GA (SEQ ID NO: 2268) |

TABLE 1-continued

| Gene | GenBank Accession No. | Target Sequence | Capture Probe Sequence | Reporter Probe Sequence |
|---|---|---|---|---|
| ZNF318 | NM014345.2 | TCCGACCCAACCTGCCTATTCCATCCACAGTACTCCGCAAGTCATGTTCAGCCACAATGAGCAAGCCAGCTCCTCTTAACACCTTTCTGTCTATTAAGTC (SEQ ID NO: 2269) | TGAACATGACTTGCGGAGTACTGTGGATGGAATAGGCAGGTTGGGTCGGA (SEQ ID NO: 2270) | GACTTAATAGACAGAAAGGTGTTAAGAGGAGCTGGCTTGCTCATTGTGGC (SEQ ID NO: 2271) |
| ZNF385B | NM_001113398.1 | CTGACAAATCAGAAGATAAAGGGAAGTTAAAAGCCAGCAGTTCCAGTCAGCCATCAAGCTCTGAAAGTGGCTCATTTCTCCTCAAATCTGGCACAACACC (SEQ ID NO: 2272) | CTGACTGGAACTGCTGGCTTTTAACTTCCCTTTATCTTCTGATTTGTCAG (SEQ ID NO: 2273) | GGTGTTGTGCCAGATTTGAGGAGAAATGAGCCACTTTCAGAGCTTGATGG (SEQ ID NO: 2274) |
| ZNF598 | NM_178167.2 | TCAGACAGGGCCTGATCTCCGCAGCCCAGTATTACAAGAGTTGCCGGGACCTGCTGGGGGAGAATTTCCAGAAGGTCTTTAATGAGCTGCTGGTCCTGCT (SEQ ID NO: 2275) | GTCCCGGCAACTCTTGTAATACTGGGCTGCGGAGATCAGG (SEQ ID NO: 2276) | ACCAGCAGCTCATTAAAGACCTTCTGGAAATTCTCCCCCAGCAG (SEQ ID NO: 2277) |
| ZNF608 | NM_020747.2 | CAGCACAATCATCTCAACTGAAAGAGTCCCATTCTCCCTATTACCACAGCTATGATCCTTATTATTCTCCAAGTTACATGCACCCTGGGCAGGTCGGTGC (SEQ ID NO: 2278) | GCTGTGGTAATAGGGAGAATGGGACTCTTTCAGTTGAGATGATTGTGCTG (SEQ ID NO: 2279) | GCACCGACCTGCCCAGGGTGCATGTAACTTGGAGAATAATAAGGATCATA (SEQ ID NO: 2280) |
| ZNRF1 | NM_032268.4 | ATAGCTTTGTCACCACAAAGGGCACTGTTCTATTCACAGCACCTCCTGCTTCTGCCTGGCAACTGTGTCTCCCTGTGCTATATTTAATTCCACCAGCAAA (SEQ ID NO: 2281) | AGCAGGAGGTGCTGTGAATAGAACAGTGCCCTTTGTGGTGACAAAGCTAT (SEQ ID NO: 2282) | TTTGCTGGTGGAATTAAATATAGCACAGGGAGACACAGTTGCCAGGCAGA (SEQ ID NO: 2283) |
| ZPBP2 | NM_198844.2 | TGCAAGTAGTACGTCTGGATAGCTGTCGACCAGGCTTTGGAAAAAATGAACGTCTACACAGTAATTGCGCTAGCTGTTGTGTGGTTTGTAGTCCTGCGAC (SEQ ID NO: 2284) | TTCATTTTTTCCAAAGCCTGGTCGACAGCTATCCAGACGTACTACTTGCA (SEQ ID NO: 2285) | GTCGCAGGACTACAAACCACACAACAGCTAGCGCAATTACTGTGTAGACG (SEQ ID NO: 2286) |
| ZWINT | NM_007057.3 | GGAGATGTAAATTTGCCATGACTTCCTGGAGGACAGCAGCATGGAGAAAGATCCTAGAAAAGGCCTCTGACTTCCCTCACCTCCCAACCATCATTACAGG (SEQ ID NO: 2287) | CTTTCTCCATGCTGCTGTCCTCCAGGAAGTCATGGCAAATTTACA (SEQ ID NO: 2288) | TAATGATGGTTGGGAGGTGAGGGAAGTCAGAGGCCTTTTCTAGGAT (SEQ ID NO: 2289) |

TABLE 1-continued

| Gene | GenBank Accession No. | Target Sequence | Capture Probe Sequence | Reporter Probe Sequence |
|---|---|---|---|---|
| IgG2 constant region | NCI_Lih_1_008.1 | TCCCCAGGCTCTCGGGGTCGCGCGAGGATGCTTGGCACGTACCCCGTCTACATACTTCCCGGGCACCCAGCATGGAAATAAAGCACCCAGCGCTGCCCTG (SEQ ID NO: 2290) | TAGACGGGGTACGTGCCAAGCATCCTCGCGCGACCCCGAG (SEQ ID NO: 2291) | CTGGGTGCTTTATTTCCATGCTGGGTGCCCGGAAGTATG (SEQ ID NO: 2292) |
| IgG4 constant region | NCI_Lih_1_034.1 | GATGGCGTGGAGGTGCATAATGCCAAGACAAAGCCGCGGGAGGAGCAGTTCAACAGCACGTACCGTGTGGTCAGCGTCCTCACCGTCCTGCACCAGGACT (SEQ ID NO: 2293) | AACTGCTCCTCCCGCGGCTTTGTCTTGGCATTATG (SEQ ID NO: 2294) | TGCAGGACGGTGAGGACGCTGACCACACGGTACGTGCTGTTG (SEQ ID NO: 2295) |
| IgA2 constant region | NCI_Lih_1_017.1 | GCCGCTGGCCTTCACACAGAAGACCATCGACCGCTTGGCGGTAAACCCACCCATGTCAATGTGTCTGTTGTCATGGCGGAGGTGGACGGCACCTGCTAC (SEQ ID NO: 2296) | TGGGTTTACCCGCCAAGCGGTCGATGGTCTTCTGTGTGAAGG (SEQ ID NO: 2297) | AGGTGCCGTCCACCTCCGCCATGACAACAGACACATTGACATGGG (SEQ ID NO: 2298) |
| IgE constant region | NCI_Lih_1_009.1 | AAGACCAAGGGCTCCGGCTTCTTCGTCTTCAGCCGCCTGGAGGTGACCAGGGCCGAATGGGAGCAGAAAGATGAGTTCATCTGCCGTGCAGTCCATGAGG (SEQ ID NO: 2299) | CTGGICACCTCCAGGCGGCTGAAGACGAAGAAGCCGGAGC (SEQ ID NO: 2300) | CACGGCAGATGAACTCATCTTTCTGCTCCCATTCGGCC (SEQ ID NO: 2301) |
| EBV EMP1 unique | NCI_Lih_1_001.1 | TTGCTTTCCATCTTGTGCCAATACACATTTGGATTCAGCCCAAGCCACACCTAACTCATGCCAGCAGAGGCAGGAACACCTGTTGTTGACACATTCTTTG (SEQ ID NO: 2302) | GTGTGGCTTGGGCTGAATCCAAATGTGTATTGGCACAAGATGGAAAGCAA (SEQ ID NO: 2303) | CAAAGAATGTGTCAACAACAGGTGTTCCTGCCTCTGCTGGCATGAGTTAG (SEQ ID NO: 2304) |
| EBV LMP1 3' end | NCI_Lih_1_025.1 | CTGTTTGGACTTTTATGCCTGCTCCTCATCTAAGAAGCCACCATGCGACCGGGTAGACCACTGGCTGGATTCTACGCTACTCTCCGCCGTTCCTTCAGAA (SEQ ID NO: 2305) | GGTCGCATGGTGGCTTCTTAGATGAGGAGCAGGCATAAAAGTCCAAACAG (SEQ ID NO: 2306) | TGAAGGAACGGCGGAGAGTAGCGTAGAATCCAGCCAGTGGTCTACC (SEQ ID NO: 2307) |
| EBV EBNA2 3' end | NCI_Lih_1_043.1 | AATTCACACACGGCAACCCCTAACGTTTCACCAATACATGAACCGGAGTCCCATAATAGCCCAGAGGCTCCCATTCTCTTCCCCGATGATTGGTATCCTC (SEQ ID NO: 2308) | GACTCCGGTTCATGTATTGGTGAAACGTTAGGGGTTGCCGTGTGTGAATT (SEQ ID NO: 2309) | GAGGATACCAATCATCGGGGAAGAGAATGGGAGCTCTGGGCTATTATGG (SEQ ID NO: 2310) |

TABLE 1-continued

| Gene | GenBank Accession No. | Target Sequence | Capture Probe Sequence | Reporter Probe Sequence |
|---|---|---|---|---|
| EBV EBNA2 long | NCI_Lih_1_006.1 | AATTGTTGACACGGATAGTCTTGGAAACCCGTCACTCTCAGTAATTCCCTCGAATCCCTACCAGGAACAACTGTCAGACACTCCATTAATTCCACTAACA (SEQ ID NO: 2311) | AGGGAATTACTGAGAGTGACGGGTTTCCAAGACTATCCGTGTCAACAATT (SEQ ID NO: 2312) | TGTTAGTGGAATTAATGGAGTGTCTGACAGTTGTTCCTGGTAGGGATTCG (SEQ ID NO: 2313) |
| EBV EBNA1 CDS | NCI_Lih_1_024.1 | GAGGTTTTGAAGGATGCGATTAAGGACCTTGTTATGACAAAGCCCGCTCCTACCTGCAATATCAGGGTGACTGTGTGCAGCTTTGACGATGGAGTAGATT (SEQ ID NO: 2314) | GGAGCGGGCTTTGTCATAACAAGGTCCTTAATCGCATCCTTCAAAACCTC (SEQ ID NO: 2315) | AATCTACTCCATCGTCAAAGCTGCACACGTCACCCTGATATTGCAGGTA (SEQ ID NO: 2316) |
| EBV LPM2A | NCI_Lih_1_004.1 | GAGGAAGTATGAATCCAGTATGCCTGCCTGTAATTGTTGCGCCCTACCTCTTTTGGCTGGCGGCTATTGCCGCCTCGTGTTTCACGGCCTCAGTTAGTAC (SEQ ID NO: 2317) | GAGGTAGGGCGCAACAATTACAGGCAGGCATACTGGATTCATACTTCCTC (SEQ ID NO: 2318) | GTACTAACTGAGGCCGTGAAACACGAGGCGGCAATAGCCGCCAGCCAAAA (SEQ ID NO: 2319) |
| EBV BZLF1 | NCI_Lih_1_027.1 | TGCCCAAGCCTGGATGTTGACTCCATTATCCGCCGGACACCAGATGTTTTACACGAGGATCTCTTAAATTTCTAACTCCCGTTATTGAAACCACGCCTGC (SEQ ID NO: 2320) | AAAACATCTGGTGTCCGGCGGATAATGGAGTCAACATCCAGGCTTGGGCA (SEQ ID NO: 2321) | GCAGGCGTGGTTTCAATAACGGGAGTTAGAAATTTAAGAGATCCTCGTGT (SEQ ID NO: 2322) |
| EBV EBNA3A | NCI_Lih_1_020.1 | CCAACATCAGCTGGATGCTTTGGGGTATACACTCCATGGTCTTAACCATCCCGGGGTTCCCGTGTCTCCTGCCGTTAACCAATATCATCTCAGCCAGGCT (SEQ ID NO: 2323) | GATGGTTAAGACCATGGAGTGTATACCCCAAAGCATCCAGCTGATGTTGG (SEQ ID NO: 2324) | AGCCTGGCTGAGATGATATTGGTTAACGGCAGGAGACACGGGAACCCCGG (SEQ ID NO: 2325) |
| EBV EBNA3C | NCI_Lih_1_022.1 | ACAATCGGAAACTTTAAGCCATATTACCCGTGGAATGCACCACCTAATGAAAATCCATATCACGCGCGGAGAGGCATAAAAGAACACGTAATCCAGAACG (SEQ ID NO: 2326) | TCATTAGGTGGTGCATTCCACGGGTAATATGGCTTAAAGTTTCCGATTGT (SEQ ID NO: 2327) | CGTTCTGGATTACGTGTTCTTTTATGCCTCTCCGCGCGTGATATGGATT (SEQ ID NO: 2328) |
| EBV EBNA3B | NCI_Lih_1_003.1 | CTCCCGTCGTTATCTTGGAGAATGTCGGCCAGGGGCAACAGCAGACTCTGGAGTGCGGAGGAACTGCTAAACAGGAAAGGGACATGTTGGGGCTGGGGGA (SEQ ID NO: 2329) | CAGAGTCTGCTGTTGCCCCTGGCCAACATTCTCCAAGATAACGACGGGAG (SEQ ID NO: 2330) | CAACATGTCCCTTTCCTGTTTAGCAGTTCCTCCGCACTC (SEQ ID NO: 2331) |

TABLE 1-continued

| Gene | GenBank Accession No. | Target Sequence | Capture Probe Sequence | Reporter Probe Sequence |
|---|---|---|---|---|
| HHV8 T0.7/P6 | NCI_Lih_1_040.1 | CGGTGTTTGTGGCAGTTCATGTCCCGGATGTGTTACTAAATGGGTGGCGCTGGAGGCTTGGGGCGATACCACCACTCGTTTGTCTGTTGGCGATTGGTGT (SEQ ID NO: 2332) | GCGCCACCCATTTAGTAACACATCCGGGACATGAACTGCCACAAACACCG (SEQ ID NO: 2333) | ACACCAATCGCCAACAGACAAACGAGTGGTGGTATCGCCCCAAGCCTCCA (SEQ ID NO: 2334) |
| HHV8 T1.1 | NCI_Lih_1_007.1 | AGCAAGTCGATTTGAATGACATAGGCGACAAAGTGAGGTGGCATTTGTCAGAAGTTTCAAAGTCGTGTAAGAACATTGGACTAAAGTGGTGTGCGGCAGC (SEQ ID NO: 2335) | TGACAAATGCCACCTCACTTTGTCGCCTATGTCATTCAAATCGACTTGCT (SEQ ID NO: 2336) | GCTGCCGCACACCACTTTAGTCCAATGTTCTTACACGACTTTGAAACTTC (SEQ ID NO: 2337) |
| HHV8 ORF73/ LANA | NCI_Lih_1_037.1 | CCATAATCTTGCACGGGTCGTCATCCGAGGACGAAATGGAAGTGGATTACCCTGTTGTTAGCACACATGAACAAATTGCCAGTAGCCCACCAGGAGATAA (SEQ ID NO: 2338) | GTAATCCACTTCCATTTCGTCCTCGGATGACGACCCGTGCAAGATTATGG (SEQ ID NO: 2339) | TTATCTCCTGGTGGGCTACTGGCAATTTGTTCATGTGTGCTAACAACAGG (SEQ ID NO: 2340) |
| HHV8 vFLIP ORF71 | NCI_Lih_1_021.1 | TGTTCTCCACGTAGACGGGGAGCTGTGTGCGAGGGATATTAGGTCTTTGATATTTTAAGCAAGGACACTATAGGGTCTCGCAGCACACCACAGACATTC (SEQ ID NO: 2341) | TCAAAGACCTAATATCCCTCGCACACAGCTCCCCGTCTACGTGGAGAACA (SEQ ID NO: 2342) | GAATGTCTGTGGTGTGCTGCGAGACCCTATAGTGTCCTTGCTTAAAAATA (SEQ ID NO: 2343) |
| HHV8 BCL2 homologue | NCI_Lih_1_010.1 | ATCACAGGCTTAATGCGAGACAAGGAGTCTTTTATTCGAGGCCATGTTGGCTAATGTGAGATTTCACAGCACCACCGGTATAAACCAGCTTGGGTTGAGCA (SEQ ID NO: 2344) | GCCAACATGGCCTCGAATAAAGACTCCTTGTCTCGCATTAAGCCTGTGAT (SEQ ID NO: 2345) | TGCTCAACCCAAGCTGGTTTATACCGGTGGTGCTGTGAAATCTCACATTA (SEQ ID NO: 2346) |
| HHV8 vMIP1b ORFK4.2 KIE-3 | NCI_Lih_1_041.1 | ATTAGCGCATGCAAATTAGCTTTGCCGAAGTTCTCGGAAAGCCGGTGGGGCGCGCTGGATTTTTGGACCGTGGGAAATGGGACCGGTGTCCTCTCTATGA (SEQ ID NO: 2347) | CCCCACCGGCTTTCCGAGAACTTCGGCAAAGCTAATTTGCATGCGCTAAT (SEQ ID NO: 2348) | TCATAGAGAGGACACCGGTCCCATTTCCCACGGTCCAAAAATCCAGCGCG (SEQ ID NO: 2349) |
| HHV8 vIL6 | NCI_Lih_1_026.1 | CGTACCGGCATCTGCAAGGGTATTCTAGAGCCCGCTGCTATTTTTCATCTGAAACTACCAGCCATCAACGATACTGATCACTGCGGGTTAATAGGATTTA (SEQ ID NO: 2350) | AGATGAAAAATAGCAGCGGGCTCTAGAATACCCTTGCAGATGCCGGTACG (SEQ ID NO: 2351) | TAAATCCTATTAACCCGCAGTGATCAGTATCGTTGATGGCTGGTAGTTTC (SEQ ID NO: 2352) |

TABLE 1-continued

| Gene | GenBank Accession No. | Target Sequence | Capture Probe Sequence | Reporter Probe Sequence |
|---|---|---|---|---|
| HHV8 K1-32 Bcb K1 protein | NCI_Lih_1_015.1 | TCGGATTCATCCTTGCCAATATCCTGGTATTGCAACGATACTCGGCTTTGGCGACTGACGAAGCCAACACTCACTATTGACATCATTACCTGCAATTTTA (SEQ ID NO: 2353) | CAAAGCCGAGTATCGTTGCAATACCAGGATATTGGCAAGGATGAATCCGA (SEQ ID NO: 2354) | TAAAATTGCAGGTAATGATGTCAATAGTGAGTGTTGGCTTCGTCAGTCGC (SEQ ID NO: 2355) |
| EBV EBER1 | NCI_Lih_1_016.1 | TGTAGCCACCCGTCCCGGGTACAAGTCCCGGGTGGTGAGGACGGTGTCTGTGGTTGTCTTCCCAGACTCTGCTTTCTGCCGTCTTCGGTCAAGTACCAGC (SEQ ID NO: 2356) | CAGACACCGTCCTCACCACCCGGGACTTGTACCCG (SEQ ID NO: 2357) | GCTGGTACTTGACCGAAGACGGCAGAAAGCAGAGTCTGGGAAGACAACCA (SEQ ID NO: 2358) |
| EBV EBER2 | NCI_Lih_1_014.1 | GTCCCGGGGGAGGAGAAGAGAGGCTTCCCGCCTAGAGCATTTGCAAGTCAGGATTCTCTAATCCCTCTGGGAGAAGGGTATTCGGCTTGTCCGCTATTTT (SEQ ID NO: 2359) | TGACTTGCAAATGCTCTAGGCGGGAAGCCTCTCTTCTCCTC (SEQ ID NO: 2360) | AAAATAGCGGACAAGCCGAATACCCTTCTCCCAGAGGGATTAGAGAATCC (SEQ ID NO: 2361) |
| BCL2_1 | NCI_Lih_1_013.1 | TCTTGATTCTTCAAAAGCATTCTGAGAAGGTGAGATAAGCCCTGAGTCTCAGCTACCTAAGAAAAACCTGGATGTCACTGGCCACTGAGGAGCTTTGTTT (SEQ ID NO: 2362) | GAGACTCAGGGCTTATCTCACCTTCTCAGAATGCTTTTGAAGAATCAAGA (SEQ ID NO: 2363) | AAACAAAGCTCCTCAGTGGCCAGTGACATCCAGGTTTTTCTTAGGTAGCT (SEQ ID NO: 2364) |
| BCL2_2 | NCI_Lih_1_028.1 | TGGCCTTCTTTGAGTTCGGTGGGGTCATGTGTGTGGAGAGCGTCAACCGGGAGATGTCGCCCCTGGTGGACAACATCGCCCTGTGGATGACTGAGTACCT (SEQ ID NO: 2365) | CCGGTTGACGCTCTCCACACACATGACCCCACCGAACTCAAAGAAGGCCA (SEQ ID NO: 2366) | CACAGGGCGATGTTGTCCACCAGGGGCGACATCTC (SEQ ID NO: 2367) |
| BCL2_3 | NCI_Lih_1_038.1 | ATTCTGCAACACTGTACACATAAAAATACGGTAAGGATACTTTACATGGTTAAGGTAAAGTAAGTCTCCAGTTGGCCACCATTAGCTATAATGGCACTT (SEQ ID NO: 2368) | CCATGTAAAGTATCCTTACCGTATTTTTTATGTGTACAGTGTTGCAGAAT (SEQ ID NO: 2369) | AAGTGCCATTATAGCTAATGGTGGCCAACTGGAGACTTACTTTACCTTAA (SEQ ID NO: 2370) |
| BCL2_4 | NCI_Lih_1_035.1 | GAACTTGAGGAAGTGAACATTTCGGTGACTTCCGCATCAGGAAGGCTAGAGTTACCCAGAGCATCAGGCCGCCACAAGTGCCTGCTTTTAGGAGACCGAA (SEQ ID NO: 2371) | TCTAGCCTTCCTGATGCGGAAGTCACCGAAATGTTCACTTCCTCAAGTTC (SEQ ID NO: 2372) | TCTCCTAAAAGCAGGCACTTGTGGCGGCCTGATGCTCTGGGTAAC (SEQ ID NO: 2373) |

TABLE 1-continued

| Gene | GenBank Accession No. | Target Sequence | Capture Probe Sequence | Reporter Probe Sequence |
|---|---|---|---|---|
| BCL2_5 | NCI_Lih_1_011.1 | TCAGGGAGTTGGAAGTTTTCAGAATAACCAGAACTAAGGGTATGAAGGACCTGTATTGGGGTCGATGTGATGCCTCTGCGAAGAACCTTGTGTGACAAAT (SEQ ID NO: 2374) | GTCCTTCATACCCTTAGTTCTGGTTATTCTGAAAACTTCCAACTCCCTGA (SEQ ID NO: 2375) | ATTTGTCACACAAGGTTCTTCGCAGAGGCATCCATCGACCCCAATACAG (SEQ ID NO: 2376) |
| BCL2_6 | NCI_Lih_1_032.1 | CGGCCCCAGCATGCGGCCTCTGTTTGATTTCTCCTGGCTGTCTCTGAAGACTCTGCTCAGTTTGGCCCTGGTGGGAGCTTGCATCACCCTGGGTGCCTAT (SEQ ID NO: 2377) | TCTTCAGAGACAGCCAGGAGAAATCAAACAGAGGCCGCATGCTGGGGCCG (SEQ ID NO: 2378) | AGGGTGATGCAAGCTCCCACCAGGGCCAAACTGGAGAG (SEQ ID NO: 2379) |
| CCND1_2 | NCI_Lih_1_030.1 | TGCTAATTTAAAGAGACTCCAAATCTCAATGAAGCCAGCTCACAGTGCTGTGTGCCCCGGTCACCTAGCAAGCTGCCGAACCAAAAGAATTTGCACCCCG (SEQ ID NO: 2380) | CAGCACTGTGAGCTGGCTTCATTGAGATTTGGAGTCTCTTTAAATTAGCA (SEQ ID NO: 2381) | TGCAAATTCTTTTGGTTCGGCAGCTTGCTAGGTGACCGGGGCACA (SEQ ID NO: 2382) |
| CCND1_3 | NCI_Lih_1_002.1 | CGCGCCGGTGTCCCCAGAGACCAGGCTGTGTCCCTCTTCTCTTCCCTGCGCCTGTGATGCTGGGCACTTCATCTGATCGGGGCGTAGCATCATAGTAGT (SEQ ID NO: 2383) | CGCAGGGAAGAGAAGAGGGACACAGCCTGGTCTCTGGGGACACCG (SEQ ID NO: 2384) | ACTACTATGATGCTACGCCCCGATCAGATGAAGTGCCCAGCATCACAGG (SEQ ID NO: 2385) |
| CCND1_4 | NCI_Lih_1_005.1 | ATTGATTCAGCCTGTTTGGCGTTTCCCAGAGTCATCTGATTGGACAGGCATGGTGCAAGGAAAATTAGGGTACTCAACCTAAGTTCGGTTCCGATGAAT (SEQ ID NO: 2386) | TGCCTGTCCAATCAGATGACTCTGGGAAACGCCAAACAGGCTGAATCAAT (SEQ ID NO: 2387) | ATTCATCGGAACCGAACTTAGGTTGAGTACCCTAATTTTCCTTGCACCCA (SEQ ID NO: 2388) |
| CCND1_5 | NCI_Lih_1_029.1 | GTTGTGTGTGCAGGGAGGGCAGTTTTCTAATGGAATGGTTTGGGAATATCCATGTACTTGTTTGCAAGCAGGACTTTGAGGCAAGTGTGGGCCACTGTGG (SEQ ID NO: 2389) | GATATTCCCAAACCATTCCATTAGAAAACTGCCCTCCCTGCACACACAAC (SEQ ID NO: 2390) | CCACAGTGGCCCACACTTGCCTCAAAGTCCTGCTTGCAAACAAGTACATG (SEQ ID NO: 2391) |
| CCND1_6 | NCI_Lih_1_019.1 | TCATGGCTGAAGTCACCTCTTGGTTACAGTAGCGTAGCGTGGCCGTGTGCATGTCCTTTGCGCCTGTGACCACCACCCCAACAAACCATCCAGTGACAAA (SEQ ID NO: 2392) | GCACACGGCCACGCTACGCTACTGTAACCAAGAGGTGACTTCAGCCATGA (SEQ ID NO: 2393) | CACTGGATGGTTTGTTGGGGTGGTGGTCACAGGCGCAAAGGACAT (SEQ ID NO: 2394) |

TABLE 1-continued

| Gene | GenBank Accession No. | Target Sequence | Capture Probe Sequence | Reporter Probe Sequence |
|---|---|---|---|---|
| CDKN2A_1 | NCI_Lih_1_018.1 | GCACTCACGCCCTAAGCGCACATTCATGTGGGCATTTCTTGCGAGCCTCGCAGCCTCCGGAAGCTGTCGACTTCATGACAAGCATTTTGTGAACTAGGGA (SEQ ID NO: 2395) | CGAGGCTCGCAAGAAATGCCCACATGAATGTGCGCTTAGGGCGTGAGTGC (SEQ ID NO: 2396) | TCCCTAGTTCACAAAATGCTTGTCATGAAGTCGACAGCTTCCGGAGGCTG (SEQ ID NO: 2397) |
| CDKN2A_2 | NCI_Lih_1_042.1 | AAAGATACCGCGGTCCCTCCAGAGGATTTGAGGGACAGGGTCGGAGGGGGCTCTTCCGCCAGCACCGGAGGAAGAAAGAGGAGGGGCTGGCTGGTCACCA (SEQ ID NO: 2398) | CCCCCTCCGACCCTGTCCCTCAAATCCTCTGGAGG (SEQ ID NO: 2399) | CCCTCCTCTTTCTTCCTCCGGTGCTGGCGGAAGAG (SEQ ID NO: 2400) |

Gene expression signatures based on novel combinations of genes derived from the 800 gene array can be used to diagnose a patient as having activated B cell-like diffuse large B cell lymphoma (ABC DLBCL), germinal center B cell-like diffuse large B cell lymphoma (GCB DLBCL), primary mediastinal B cell lymphoma (PMBL), Burkitt lymphoma (BL), or mantle cell lymphoma (MCL). For example, a gene expression signature that can be used to diagnose a patient as having one of the aforementioned lymphoma types includes at least one, but preferably two or more of the genes set forth in Table 1 (e.g., 2, 5, 10, 50, 75, 100, 125, 150, 175, 200, 225, 250, 275, 300, 400, 500, 600, or 700 genes, or a range defined by any two of the foregoing values). Desirably, the gene expression signature that can be used to diagnose a patient as having ABC DLBCL, GCB DLBCL, PMBL, BL, or MCL includes 15-200 of the genes set forth in Table 1 (e.g., 15, 30, 50, 75, 100, 125, 150, 175, or 200 genes, or a range defined by any two of the foregoing values). In one embodiment, the gene expression signature used to diagnose a patient as having ABC DLBCL, GCB DLBCL, PMBL, BL, or MCL includes the genes set forth in Table 2, or a subset of the genes set forth in Table 2 (e.g., 10, 15, 30, 50, 75, 100, 125, 150, or 190 of the genes set forth in Table 2, or a range defined by any two of the foregoing values).

TABLE 2

| Gene | GenBank Accession No. |
|---|---|
| ACSL5 | NM_016234.3 |
| ADAM12 | NM_003474.4 |
| AHCYL2 | NM_001130723.2 |
| AHR | NM_001621.3 |
| AKAP2 | NM_001136562.2 |
| AKAP9 | NM_005751.3 |
| ALOX5 | NM_000698.2 |
| ANKRD13A | NM_033121.1 |
| ANTXR1 | NM_018153.3 |
| ARID3A | NM_005224.2 |
| ARID3B | NM_006465.2 |
| ASB13 | NM_024701.3 |
| ATXN7L2 | NM_153340.4 |
| AUH | NM_001698.2 |
| AUTS2 | NM_001127231.1 |
| BANK1 | NM_001083907.1 |
| BATF | NM_006399.3 |

TABLE 2-continued

| Gene | GenBank Accession No. |
|---|---|
| BCAT1 | NM_005504.4 |
| BCL2 | NM_053056.2 |
| BCL2A1 | NM_004049.2 |
| BCL2L10 | NM_020396.2 |
| BCL6 | NM_001706.2 |
| BIRC3 | NM_001165.3 |
| BPGM | NM_199186.1 |
| BPNT1 | NM_006085.4 |
| BSPRY | NM_017688.2 |
| BUB1B | NM_001211.4 |
| C10orf18 | NM_017782.3 |
| C13orf18 | NM_025113.2 |
| C3orf37 | NM_020187.2 |
| CALD1 | NM_033138.2 |
| CARD11 | NM_032415.2 |
| CCDC50 | NM_174908.3 |
| CCL17 | NM_002987.2 |
| CCND1 | NM_053056.2 |
| CCND2 | NM_001759.2 |
| CCR7 | NM_001838.2 |
| CD44 | NM_000610.3 |
| CDH11 | NM_001797.2 |
| CDK5RAP2 | NM_001011649.1 |
| CDK6 | NM_001259.5 |
| CFLAR | NM_003879.3 |
| CGNL1 | NM_032866.3 |
| CHD4 | NM_001273.2 |
| CLIP2 | NM_003388.4 |
| CPA6 | NM_001127445.1 |
| CPNE3 | NM_003909.2 |
| CR2 | NM_001006658.1 |
| CREB3L2 | NM_194071.2 |
| CSF2RA | NM_006140.3 |
| CSTA | NM_005213.3 |
| CTHRC1 | NM_138455.2 |
| CTSH | NM_148979.2 |
| CTSK | NM_000396.2 |
| CYB5R2 | NM_016229.3 |
| CYP27A1 | NM_000784.3 |
| DAZAP2 | NM_014764.3 |
| DCTD | NM_001012732.1 |
| DENND4A | NM_005848.3 |
| DNAJB12 | NM_017626.4 |
| DNAJC10 | NM_018981.1 |
| DOCK10 | NM_014689.1 |
| DPYSL3 | NM_001387.2 |
| E2F2 | NM_004091.2 |
| EEPD1 | NM_030636.2 |
| EFEMP2 | NM_016938.3 |

TABLE 2-continued

| Gene | GenBank Accession No. |
|---|---|
| ELL2 | NM_012081.5 |
| EML1 | NM_004434.2 |
| ENTPD1 | NM_001776.4 |
| ERBB2IP | NM_018695.2 |
| ERP29 | NM_001034025.1 |
| ETV6 | NM_001987.4 |
| FAM108C1 | NM_021214.1 |
| FAM159A | NM_001042693.1 |
| FAM171B | NM_177454.3 |
| FAM46C | NM_017709.3 |
| FAM69A | NM_001006605.3 |
| FAP | NM_004460.2 |
| FAS | NM_000043.3 |
| FBXO41 | NM_001080410.1 |
| FCER2 | NM_002002.4 |
| FKBP11 | NM_016594.2 |
| FLJ42418 | NM_001001695.1 |
| FN1 | NM_212482.1 |
| FNDC1 | NM_032532.2 |
| FUT8 | NM_004480.3 |
| GCET2 | NM_001008756.1 |
| GIT2 | NM_057169.2 |
| GNA13 | NM_006572.4 |
| GNL3 | NM_014366.4 |
| GORASP1 | NM_031899.2 |
| GSK3B | NM_002093.2 |
| GYPC | NM_016815.2 |
| HARBI1 | NM_173811.3 |
| HCK | NM_002110.2 |
| HDAC1 | NM_004964.2 |
| HDGF | NM_004494.2 |
| HEG1 | NM_020733.1 |
| HLA-DMA | NM_006120.3 |
| HOMER2 | NM_004839.2 |
| HOPX | NM_001145460.1 |
| HPCAL1 | NM_134421.1 |
| HSP90AA1 | NM_005348.3 |
| HSP90B1 | NM_003299.1 |
| HSPA9 | NM_004134.4 |
| HSPB8 | NM_014365.2 |
| HTRA1 | NM_002775.4 |
| ICAM1 | NM_000201.1 |
| IFIH1 | NM_022168.2 |
| IGSF3 | NM_001542.2 |
| IK | NM_006083.3 |
| IL12A | NM_000882.2 |
| IL13RA1 | NM_001560.2 |
| IL16 | NM_004513.4 |
| IL17RB | NM_018725.3 |
| IRF4 | NM_002460.1 |
| ISG15 | NM_005101.3 |
| ISY1 | NM_020701.2 |
| ITGAV | NM_002210.2 |
| ITGAX | NM_000887.3 |
| ITGB2 | NM_000211.2 |
| ITPKB | NM_002221.3 |
| JAK2 | NM_004972.2 |
| JAK3 | NM_000215.2 |
| KCNK12 | NM_022055.1 |
| KIAA0746 | NM_015187.3 |
| KIAA1274 | NM_014431.2 |
| KLHL5 | NM_015990.4 |
| KRAS | NM_033360.2 |
| KYNU | NM_003937.2 |
| LANCL1 | NM_006055.1 |
| LDHA | NM_005566.1 |
| LIMA1 | NM_001113547.1 |
| LIMD1 | NM_014240.2 |
| LMO2 | NM_005574.3 |
| LRMP | NM_006152.2 |
| LRRC15 | NM_001135057.2 |
| LRRC33 | NM_198565.1 |
| LTBP2 | NM_000428.2 |
| LYPD6B | NM_177964.3 |
| LYZ | NM_000239.2 |
| MAL | NM_002371.2 |
| MAML3 | NM_018717.4 |
| MAP3K1 | NM_005921.1 |
| MAP4K4 | NM_004834.3 |
| MAPK10 | NM_002753.2 |
| MARCKSL1 | NM_023009.5 |
| MAST2 | NM_015112.1 |
| MDFIC | NM_199072.2 |
| MLL2 | NM_003482.3 |
| MLLT10 | NM_004641.2 |
| MME | NM_000902.2 |
| MMP2 | NM_004530.2 |
| MMP9 | NM_004994.2 |
| MOBKL2C | NM_145279.4 |
| MPEG1 | XM_937323.1 |
| MTHFD2 | NM_006636.3 |
| MYB | NM_005375.2 |
| MYBL1 | XM_034274.14 |
| MYC | NM_002467.3 |
| NAIF1 | NM_197956.3 |
| NANS | NM_018946.3 |
| NCF2 | NM_000433.2 |
| NECAP2 | NM_018090.4 |
| NEIL1 | NM_024608.2 |
| NEK6 | NM_014397.3 |
| NEU3 | NM_006656.5 |
| NFIL3 | NM_005384.2 |
| NFKBIZ | NM_001005474.1 |
| NIPA2 | NM_001008860.1 |
| NOC3L | NM_022451.9 |
| NOL5A | NM_006392.2 |
| NP | NM_000270.3 |
| OPA1 | NM_130837.1 |
| OSBPL3 | NM_145320.1 |
| PAG1 | NM_018440.3 |
| PDE9A | NM_001001567.1 |
| PDIA5 | NM_006810.2 |
| PDLIM1 | NM_020992.2 |
| PDPN | NM_006474.4 |
| PFTK1 | NM_012395.2 |
| PHF16 | NM_014735.3 |
| PHF23 | NM_024297.2 |
| PIM1 | NM_002648.2 |
| PIM2 | NM_006875.2 |
| PLAU | NM_002658.2 |
| PLEK | NM_002664.2 |
| PLEKHF2 | NM_024613.2 |
| PMEPA1 | NM_020182.3 |
| PPA1 | NM_021129.3 |
| PPP3CC | NM_005605.3 |
| PRDX2 | NM_005809.4 |
| PRICKLE1 | NM_153026.1 |
| PRKCB | NM_212535.1 |
| PRPSAP2 | NM_002767.2 |
| PRR6 | NM_181716.2 |
| PTGIR | NM_000960.3 |
| PTK2 | NM_005607.3 |
| PTPN1 | NM_002827.2 |
| PTRH1 | NM_001002913.1 |
| R3HDM1 | NM_015361.2 |
| RAB20 | NM_017817.1 |
| RAB33A | NM_004794.2 |
| RAB7L1 | NM_001135664.1 |
| RANBP9 | NM_005493.2 |
| RAPGEF5 | NM_012294.3 |
| RARRES2 | NM_002889.2 |
| RASGRP3 | NM_015376.2 |
| RC3H2 | NM_018835.2 |
| RCL1 | NM_005772.3 |
| REL | NM_002908.2 |
| RFTN1 | NM_015150.1 |
| RGS9 | NM_003835.1 |
| RHOF | NM_019034.2 |
| RNF214 | NM_207343.2 |
| RNUXA | NM_032177.3 |
| ROBO1 | NM_002941.2 |
| RRP1B | NM_015056.2 |
| S100Z | NM_130772.3 |
| S1PR2 | NM_004230.2 |

TABLE 2-continued

| Gene | GenBank Accession No. |
|---|---|
| SACS | NM_014363.4 |
| SAMSN1 | NM_022136.3 |
| SCARA5 | NM_173833.4 |
| SERPINA9 | NM_001042518.1 |
| SGK1 | NM_005627.2 |
| SH3BP5 | NM_001018009.2 |
| SIDT1 | NM_017699.2 |
| SLA | NM_001045556.2 |
| SLAMF1 | NM_003037.2 |
| SLC38A5 | NM_033518.2 |
| SMARCA4 | NM_003072.3 |
| SNN | NM_003498.4 |
| SNX11 | NM_152244.1 |
| SNX22 | NM_024798.2 |
| SNX29 | NM_001080530.2 |
| SOX11 | NM_003108.3 |
| SPARC | NM_003118.2 |
| SPINK2 | NM_021114.2 |
| SPINT2 | NM_021102.2 |
| SPRED2 | NM_181784.2 |
| SSBP2 | NM_012446.2 |
| STAMBPL1 | NM_020799.2 |
| STAP1 | NM_012108.2 |
| STAT3 | NM_139276.2 |
| STK17A | NM_004760.1 |
| STS | NM_000351.4 |
| STX11 | NM_003764.3 |
| SUFU | NM_016169.2 |
| SULF1 | NM_015170.2 |
| TARS | NM_152295.3 |
| TBC1D9 | NM_015130.2 |
| TCF3 | NM_003200.2 |
| TCF4 | NM_001083962.1 |
| TCTN3 | NM_015631.5 |
| TERT | NM_198253.1 |
| TEX9 | NM_198524.1 |
| THBS2 | NM_003247.2 |
| THOC5 | NM_001002878.1 |
| THY1 | NM_006288.2 |
| TIAM2 | NM_001010927.2 |
| TICAM2 | NM_021649.4 |
| TLE4 | NM_007005.3 |
| TLK1 | NM_012290.3 |
| TLR7 | NM_016562.3 |
| TMEM119 | NM_181724.2 |
| TMOD1 | NM_003275.2 |
| TNFRSF13B | NM_012452.2 |
| TNFRSF17 | NM_001192.2 |
| TNFSF4 | NM_003326.2 |
| TOX | NM_014729.2 |
| TPM1 | NM_000366.5 |
| TRAF1 | NM_005658.3 |
| TRIM56 | NM_030961.1 |
| TRIM62 | NM_018207.2 |
| TRIP13 | NM_004237.2 |
| TTC9 | NM_015351.1 |
| TUBB2C | NM_006088.5 |
| UBXN4 | NM_014607.3 |
| USP12 | NM_182488.3 |
| USP46 | NM_022832.2 |
| VAC14 | NM_018052.3 |
| VASH2 | NM_024749.3 |
| VGLL4 | NM_001128220.1 |
| VRK3 | NM_016440.3 |
| WAC | NM_100486.2 |
| WDR55 | NM_017706.4 |
| WNT3 | NM_030753.3 |
| XBP1 | NM_005080.2 |
| ZBTB32 | NM_014383.1 |
| ZBTB37 | NM_001122770.1 |
| ZBTB8 | NM_001040441.1 |
| ZCCHC2 | NM_017742.4 |
| ZCCHC7 | NM_032226.2 |
| ZNF281 | NM_012482.3 |
| ZNF318 | NM_014345.2 |
| ZNF598 | NM_178167.2 |
| ZNF608 | NM_020747.2 |

The invention also provides a method for selecting a treatment option for a subject who already has been diagnosed with a diffuse large B cell lymphoma (DLBCL). The method comprises isolating a gene expression product from a biopsy sample from a DLBCL subject, and obtaining digital gene expression data from the isolated gene expression product. The method comprises isolating a gene expression product from a biopsy sample from a DLBCL subject, and obtaining digital gene expression data from the isolated gene expression product. Descriptions of the gene expression product, digital gene expression data, and gene expression signature set forth above in connection with other embodiments of the invention also are applicable to those same aspects of the aforesaid inventive method for selecting a treatment option for a subject who already has been diagnosed with a DLBCL.

The invention further provides a method for selecting a GCB DLBCL subject for treatment with R-CHOP (rituxan, cyclophosphamide, hydroxydaunorubicin, oncovin (vincristine), and prednisone) therapy. The method comprises (a) isolating a gene expression product from a biopsy sample from a DLBCL subject; (b) obtaining digital gene expression data from the isolated gene expression product, wherein the digital gene expression data comprises data for genes in a gene expression signature (c) generating a weighted average of the expression levels of genes from the gene expression signature to thereby obtain a gene expression signature value; (d) calculating a predictor score based on the gene expression signature value; (e) classifying the subject as belonging to ABC DLBCL or GCB DLBCL based on the predictor score of (d); (f) selecting a GCB DLBCL subject for R-CHOP therapy; and (g) providing R-CHOP therapy to the GCB DLBCL subject and providing a different therapy to an ABC DLBCL subject. Descriptions of the gene expression product, digital gene expression data, and gene expression signature set forth above in connection with other embodiments of the invention also are applicable to those same aspects of the aforesaid inventive method for selecting a GCB DLBCL subject for treatment with R-CHOP therapy.

The invention provides gene expression signatures that can be used to classify a DLBCL as belonging to the GCB subtype or the ABC subtype and then select an appropriate treatment option based on that classification. In this respect, the invention provides a novel 20 gene array for the identification and diagnosis of various lymphoma types. The 20 gene array contains 15 genes of interest and 5 housekeeping genes, and is based on a pilot study described in Lenz et al., *N Engl. J. Med.*, 359: 2313-2323 (2008) (see also the Example herein). The genes and probe sequences that comprise the 20 gene array are set forth in Table 3. Gene expression signatures based on all or combinations of the genes from the 20 gene array can be used to diagnose a patient has having ABC DLBCL or GCB DLBCL. For example, a gene expression signature that can be used to diagnose a patient as having ABC DLBCL or GCB DLBCL includes at least one, but preferably two or more (e.g., 2, 3, 4, 5, 6, 7, 8, 9, 10, 11, 12, 13, 14, 15, 16, 17, 18, 19, or 20) of the genes set forth in Table 3.

TABLE 3

| Gene | GenBank Accession No. | Target Sequence | Capture Probe Sequence | Reporter Probe Sequence |
|---|---|---|---|---|
| ASB13 | NM_024701.3 | GGACACGTAGGCGGTACCACTAAGGTTTTGGTAATGAGCCATTCAAACCGACAGCAGTGTGAAGGTGTGTCAAGGTGTATATTCTCGTGGCTCGGCATTC (SEQ ID NO: 2401) | CGGTTTGAATGGCTCATTACCAAAACCTTAGTGGTACCGCCTACGTGTCC (SEQ ID NO: 2402) | GAATGCCGAGCCACGAGAATATACACCTTGACACACCTTCACACTGCTGT (SEQ ID NO: 2403) |
| CCDC50 | NM_174908.3 | AAACACTTTCCAGAGTTCCCTGCAACCCGTGCTTATGCAGATAGTTACTATTATGAAGATGGAGGAATGAAGCCAAGAGTGATGAAAGAAGCTGTATCTA (SEQ ID NO: 2404) | TAGTAACTATCTGCATAAGCACGGGTTGCAGGGAACTCTGGAAAGTGTTT (SEQ ID NO: 2405) | TAGATACAGCTTCTTTCATCACTCTTGGCTTCATTCCTCCATCTTCATAA (SEQ ID NO: 2406) |
| CREB3L2 | NM_194071.2 | ATGCCTGAGGGGATCAGGCTTTTCTACTCCAGGCAAACCTGCCCCATCTTGTCGCTTTTAGGACCTCCCACAACCTGGTTCCCCACACATCCATAGTTCT (SEQ ID NO: 2407) | AAGATGGGGCAGGTTTGCCTGGAGTAGAAAAGCCTGATCCCCT (SEQ ID NO: 2408) | AGAACTATGGATGTGTGGGGAACCAGGTTGTGGGAGGTCCTAAAAGCGAC (SEQ ID NO: 2409) |
| CYB5R2 | NM_016229.3 | CCATGTCTTAGGGCTTCCTGTAGGTAACTATGTCCAGCTCTTGGCAAAAATCGATAATGAATTGGTGGTCAGGGCTTACACCCCTGTCTCCAGTGATGAT (SEQ ID NO: 2410) | TTTTTGCCAAGAGCTGGACATAGTTACCTACAGGAAGCCCTAAGACATGG (SEQ ID NO: 2411) | ATCATCACTGGAGACAGGGGTGTAAGCCCTGACCACCAATTCATTATCGA (SEQ ID NO: 2412) |
| IRF4 | NM_002460.1 | GGGCACTGTTTAAAGGAAAGTTCCGAGAAGGCATCGACAAGCCGGACCCTCCCACCTGGAAGACGCGCCTGCGGTGCGCTTTGAACAAGAGCAATGACTT (SEQ ID NO: 2413) | AGGGTCCGGCTTGTCGATGCCTTCTCGGAACTTTCCTTTAAACAGTGCCC (SEQ ID NO: 2414) | TTGTTCAAAGCGCACCGCAGGCGCGTCTTCCAGGTGGG (SEQ ID NO: 2415) |
| ISY1 | NM_020701.2 | GGCAAAACATCAGTGTCTGTGGGTAGTTGGAATCTTCAGTTCCTGTGAGCGTCGGCGTCTTCTGGGCCTGTGGAGTTTCTTGGACAGGGGCCGCGGGGCT (SEQ ID NO: 2416) | GCTCACAGGAACTGAAGATTCCAACTACCCACAGACACTGATGTTTTGCC (SEQ ID NO: 2417) | CCCCTGTCCAAGAAACTCCACAGGCCCAGAAGACGCCGAC (SEQ ID NO: 2418) |
| ITPKB | NM_002221.3 | GTGGCCTCCTGGCATCATTTGTTATTGCCTCTGAAACAAGCCTTACTGCCTGGAGGGCTTAGATTCCTGCTTCTCCAATGTAGTGTGGGTATCTTGTAGG (SEQ ID NO: 2419) | GGCAGTAAGGCTTGTTTCAGAGGCAATAACAAATGATGCCAGGAGGCCAC (SEQ ID NO: 2420) | CCTACAAGATACCCACACTACATTGGAGAAGCAGGAATCTAAGCCCTCCA (SEQ ID NO: 2421) |
| LIMD1 | NM_014240.2 | AAGGCAAGTCTCAGGAACCCATGCAGGTACATCGCTTGCACCTGTTTTTAGCTTATTTAATGACGGGCTTTTGGGAAGAGCTGCCCGCATACTGAGAGAC (SEQ ID NO: 2422) | TAAAAACAGGTGCAAGCGATGTACCTGCATGGGTTCCTGAGACTTGCCTT (SEQ ID NO: 2423) | TCTCTCAGTATGCGGGCAGCTCTTCCCAAAAGCCCGTCATTAAATAAGC (SEQ ID NO: 2424) |

TABLE 3-continued

| Gene | GenBank Accession No. | Target Sequence | Capture Probe Sequence | Reporter Probe Sequence |
|---|---|---|---|---|
| MAML3 | NM_018717.4 | TGGAAGCCATCAACAATTTGCCCAGTAACATGCCACTGCCTTCAGCTTCTCCTCTTCACCAACTTGACCTGAAACCTTCTTTGCCCTTGCAGAACAGTGG (SEQ ID NO: 2425) | AGAAGCTGAAGGCAGTGGCATGTTACTGGGCAAATTGTTGATGGCTTCCA (SEQ ID NO: 2426) | CCACTGTTCTGCAAGGGCAAAGAAGGTTTCAGGTCAAGTTGGTGAAGAGG (SEQ ID NO: 2427) |
| MME | NM_000902.2 | GGATTGTAGGTGCAAGCTGTCCAGAGAAAAGAGTCCTTGTTCCAGCCCTATTCTGCCACTCCTGACAGGGTGACCTTGGGTATTTGCAATATTCCTTTGG (SEQ ID NO: 2428) | TAGGGCTGGAACAAGGACTCTTTTCTCTGGACAGCTTGCACCTACAATCC (SEQ ID NO: 2429) | CCAAAGGAATATTGCAAATACCCAAGGTCACCCTGTCAGGAGTGGCAGAA (SEQ ID NO: 2430) |
| MYBL1 | XM_034274.14 | GGCAAACGCTGTGTTATCCTCTTTGCAGACCATCCCAGAATTTGCAGAGACTCTAGAACTTATTGAATCTGATCCTGTAGCATGGAGTGACGTTACCAGT (SEQ ID NO: 2431) | TCTCTGCAAATTCTGGGATGGTCTGCAAAGAGGATAACACAGCGTTTGCC (SEQ ID NO: 2432) | ACTGGTAACGTCACTCCATGCTACAGGATCAGATTCAATAAGTTCTAGAG (SEQ ID NO: 2433) |
| PIM2 | NM_006875.2 | GCCATCCAGCACTGCCATTCCCGTGGAGTTGTCCATCGTGACATCAAGGATGAGAACATCCTGATAGACCTACGCCGTGGCTGTGCCAAACTCATTGATT (SEQ ID NO: 2434) | TCCTTGATGTCACGATGGACAACTCCACGGGAATGGCAGTGCTGGATG (SEQ ID NO: 2435) | AATCAATGAGTTTGGCACAGCCACGGCGTAGGTCTATCAGGATGTTCTCA (SEQ ID NO: 2436) |
| R3HDM1 | NM_015361.2 | CCTGTGTTCCCAAGAGAATTACATTATTGACAAAAGACTCCAAGACGAGGATGCCAGTAGTACCCAGCAGAGGCGCCAGATATTTAGAGTTAATAAAGAT (SEQ ID NO: 2437) | CCTCGTCTTGGAGTCTTTTGTCAATAATGTAATTCTCTTGGGAACACAGG (SEQ ID NO: 2438) | ATCTTTATTAACTCTAAATATCGGCGCCTCTGCTGGGTACTACTGGCAT (SEQ ID NO: 2439) |
| RAB7L1 | NM_001135664.1 | CATTTGAATTGTCTCCTGACTACTGTCCAGTAAGGAGGCCCATTGTCACTTAGAAAAGACACCTGGAACCCATGTCATTTCTGCATCTCCTGGATTAGC (SEQ ID NO: 2440) | AGTGACAATGGGCCTCCTTACTGGACAGTAGTCAGGAGACAATTCAAATG (SEQ ID NO: 2441) | CTAATCCAGGAGATGCAGAAATGCACATGGGTTCCAGGTGTCTTTTCTA (SEQ ID NO: 2442) |
| S1PR2 | NM_004230.2 | TCCCGCCAGGTGGCCTCGGCCTTCATCGTCATCCTCTGTTGCGCCGAAGGCCGAGGCCATTGTGGTGGAAAACCTTCTGGTGCTCATTGCGGTGGCCCGAAACAGCAAGTTCC (SEQ ID NO: 2443) | ACAATGGCGCAACAGAGGATGACGATGAAGGCCGAGGCCACCTGG (SEQ ID NO: 2444) | GGAACTTGCTGTTTCGGGCCACCGCAATGAGCACCAGAAGGTTTTCCACC (SEQ ID NO: 2445) |
| SERPINA9 | NM_001042518.1 | CCACTAAATCCTAGGTGGGAAATGGCCTGTTAACTGATGGCACATTGCTAATGCACAAGAAATAACAAACCACATCCCTCTTTCTGTTCTGAGGGTGCAT (SEQ ID NO: 2446) | TAGCAATGTGCCATCAGTTAACAGGCCATTTCCCACCTAGGATTTAG (SEQ ID NO: 2447) | ATGCACCCTCAGAACAGAAAGAGGGATGTGGTTTGTTATTTCTTGTGCAT (SEQ ID NO: 2448) |

TABLE 3-continued

| Gene | GenBank Accession No. | Target Sequence | Capture Probe Sequence | Reporter Probe Sequence |
|---|---|---|---|---|
| TNFRSF13B | NM_012452.2 | TGCAAAACCATTTGC AACCATCAGAGCCAG CGCACCTGTGCAGCC TTCTGCAGGTCACTC AGCTGCCGCAAGGAG CAAGGCAAGTTCTAT GACCATCTCC (SEQ ID NO: 2449) | CAGAAGGCTGCAC AGGTGCGCTGGCT CTGATGGTTGCAA ATGGTTTTGCA (SEQ ID NO: 2450) | TCATAGAACTTGC CTTGCTCCTTGCG GCAGCTGAGTGA CCTG (SEQ ID NO: 2451) |
| TRIM56 | NM_030961.1 | GTGGAGGCCGAGGAC ATTTTCCTGAAGGGC AGGGGTTGGCAACTT TTCAACATGGAGTGC CAAACTGCTAACCCG TCTTCTAGTGTGTGA GAATAGGGAC (SEQ ID NO: 2452) | TTGAAAAGTTGCC AACCCCTGCCCTT CAGGAAAATGTCC TCGGCCT (SEQ ID NO: 2453) | CCTATTCTCACAC ACTAGAAGACGG GTTAGCAGTTTGG CACTCCATG (SEQ ID NO: 2454) |
| UBXN4 | NM_014607.3 | CATCGCGACGGCCAA AAGGAGCGGCGCGGT CTTCGTGGTGTTCGTG GCAGGTGATGATGAA CAGTCTACACAGATG GCTGCAAGTTGGGAA GATGATAAA (SEQ ID NO: 2455) | CTGCCACGAACAC CACGAAGACCGCG CCGCTCCTTTTGGC CG (SEQ ID NO: 2456) | TTTATCATCTTCC CAACTTGCAGCC ATCTGTGTAGACT GTTCATCATCAC (SEQ ID NO: 2457) |
| WDR55 | NM_017706.4 | CTACCTCTTCAATTGG AATGGCTTTGGGGCC ACAAGTGACCGCTTT GCCCTGAGAGCTGAA TCTATCGACTGCATG GTTCCAGTCACCGAG AGTCTGCTG (SEQ ID NO: 2458) | GGGCAAAGCGGTC ACTTGTGGCCCCA AAGCCATTCCAAT TGAAGAG (SEQ ID NO: 2459) | GACTCTCGGTGA CTGGAACCATGC AGTCGATAGATT CAGCTCTCA (SEQ ID NO: 2460) |

In one embodiment, a method used to evaluate the likelihood that a particular sample belongs to ABC DLBCL, GCB DLBCL, PMBL, BL, or MCL involves (1) normalizing and transforming gene expression data from the gene expression signature and performing quality control, (2) forming individual trinary submodels, and (3) combining submodels into a final prediction. The gene expression data can be transformed by associating with each probe set a value equal to $\log_2$ of the counts reported for that probe set. A weighted average of the expression levels of genes from the gene expression signature can then be generated by multiplying the transformed data by their respective normalization weights (as set forth in Table 4) and summed to arrive at a normalization factor. If the normalization factor is less than 4.5, the sample is excluded as being of poor quality. Otherwise, the noalization factor can be subtracted from each of the log transformed data counts. If a reference array for the chip batch and a reference gold standard array are available, then for each probe set the $\log_2$ of the score for the reference array counts for that gene is subtracted and the $\log_2$ of the gold standard counts for that gene is added. These aforementioned steps are summarized in the following equation, which calculates a predictor score $y_i$ (the final output signal used for probe set i):

$$y_i = \log_2(x_i) - \sum_j \log_2(x_j) h_j - \log_2(r_i) + \log_2(g_i)$$

wherein $x_i$ is the counts for probe set i on the array of the sample being tested, $h_j$ is the housekeeping weight for probe set j, $r_i$ is the counts for probe set i on the reference array, and $g_i$ is the counts for probe set i on the gold-standard array.

The final classification of the subject as belonging to (i) ABC DLBCL, (ii) GCB DLBCL, (iii) PMBL, (iv) BL, or (v) MCL is based on a combination of five trinary submodels for each lymphoma type (i.e., MCL, BL non-myc, BL myc, PMBL, ABC DLBCL, and GCB DLBCL), each of which produces three possible output values (i.e., −1,0,1) according to the following formula:

$$\text{Submodel call} = \begin{cases} -1 & \text{if } \sum_i y_i w_i \leq \text{Lower cutpoint} \\ 0 & \text{Lower cutpoint} < \sum_i y_i w_i < \text{Upper cutpoint} \\ 1 & \text{if } \sum_i y_i w_i \geq \text{Upper cutpoint} \end{cases}$$

wherein $y_i$ is the predictor score $y_i$ assigned to probe set i as described above, $w_i$ are the weights associated with that probe set for the particular model as presented in Table 4, and the upper and lower cutpoints for a particular submodel are set forth in Table 5.

TABLE 4

| Gene | Normalization weights | ABC/GCB weights | BL non-Myc weights | BL myc weights | PMBL Weights | MCL Weights |
|---|---|---|---|---|---|---|
| ACPP | 0 | 0 | 0 | 0 | 0 | 0 |
| ACTG2 | 0 | 0 | 0 | 0 | 0 | 0 |
| ADAM12 | 0 | 0 | 0 | 0 | −2.166433184 | 0 |
| ADAM28 | 0 | 0 | 0 | 0 | 0 | 0 |
| ADH1B | 0 | 0 | 0 | 0 | 0 | 0 |
| ADIPOQ | 0 | 0 | 0 | 0 | 0 | 0 |
| ADO | 0 | 0 | 0 | 0 | 0 | 0 |
| AHR | 0 | 0 | 0 | −4.866117918 | 0 | 0 |
| AICDA | 0 | 0 | 0 | 0 | 0 | 0 |
| AKAP2 | 0 | 0 | 0 | 0 | 19.33144328 | 0 |
| AKR1C2 | 0 | 0 | 0 | 0 | 0 | 0 |
| ALOX5 | 0 | −11.14191131 | 0 | 0 | 0 | 59.14375571 |
| AMIGO2 | 0 | 0 | 0 | 0 | 0 | 0 |
| ANKRD13A | 0 | −13.1144441 | 0 | 0 | 0 | 0 |
| ANLN | 0 | 0 | 0 | 0 | 0 | 0 |
| ANO3 | 0 | 0 | 0 | 0 | 0 | 0 |
| ANTXR1 | 0 | 0 | 0 | 0 | −2.443912822 | 0 |
| ANUBL1 | 0 | 0 | 0 | 0 | 0 | 0 |
| APOL | 0 | 0 | 0 | 0 | 0 | 0 |
| ARID3A | 0 | 16.99118469 | 0 | 0 | 0 | 0 |
| ARID3B | 0 | 12.66080868 | 0 | 0 | 0 | 0 |
| ARID5A | 0 | 0 | 0 | 0 | 0 | 0 |
| ARL6IP1 | 0 | 0 | 0 | 0 | 0 | 0 |
| ARNT2 | 0 | 0 | 0 | 0 | 0 | 0 |
| ARNTL | 0 | 0 | 0 | 0 | 0 | 0 |
| ASB13 | 0 | −19.64578147 | 0 | 0 | 0 | 0 |
| ASPM | 0 | 0 | 0 | 0 | 0 | 0 |
| ATF3 | 0 | 0 | 0 | 0 | 0 | 0 |
| ATM | 0 | 0 | 0 | 0 | 0 | 0 |
| ATP6V0E1 | 0 | 0 | 0 | 0 | 0 | 0 |
| AUH | 0 | 0 | 0 | 0 | 20.46302485 | 0 |
| AURKA | 0 | 0 | 0 | 0 | 0 | 0 |
| AUTS2 | 0 | −15.20513307 | 0 | 0 | 0 | 0 |
| BANK1 | 0 | 0 | 0 | 0 | −24.53325693 | 0 |
| BASP1 | 0 | 0 | 0 | 0 | 0 | 0 |
| BATF | 0 | 17.98245577 | 0 | 0 | 0 | 0 |
| BATF3 | 0 | 0 | 0 | 0 | 0 | 0 |
| BCAT1 | 0 | 0 | 0 | 0 | 0 | −74.11099391 |
| BCL10 | 0 | 0 | 0 | 0 | 0 | 0 |
| BCL2 | 0 | 0 | 0 | 0 | 0 | 0 |
| BCL2 | 0 | 0 | 0 | 0 | 0 | 0 |
| BCL2 | 0 | 0 | 0 | 0 | 0 | 0 |
| BCL2 | 0 | 0 | 0 | 0 | 0 | 0 |
| BCL2 | 0 | 14.07216258 | 0 | 0 | 0 | 0 |
| BCL2 | 0 | 0 | 0 | 0 | 0 | 0 |
| BCL2A1 | 0 | 0 | 0 | −5.947560928 | 0 | 0 |
| BCL2L10 | 0 | 9.91380548 | 0 | 0 | 0 | 0 |
| BCL6 | 0 | −17.29479012 | 0 | −5.383296889 | 0 | 0 |
| BEST3 | 0 | 0 | 0 | 0 | 0 | 0 |
| BIRC2 | 0 | 0 | 0 | 0 | 0 | 0 |
| BIRC3 | 0 | 0 | 0 | −5.663158028 | 0 | 0 |
| BIRC5 | 0 | 0 | 0 | 0 | 0 | 0 |
| BMP7 | 0 | 0 | 0 | 0 | 0 | 0 |
| BPGM | 0 | 10.51166906 | 0 | 0 | 0 | 0 |
| BPNT1 | 0 | −11.94204992 | 0 | 0 | 0 | 0 |
| BSPRY | 0 | 12.55890968 | 0 | 0 | 0 | 0 |
| BST2 | 0 | 0 | 0 | 0 | 0 | 0 |
| BTBD19 | 0 | 0 | 0 | 0 | 0 | 0 |
| BTG1 | 0 | 0 | 0 | 0 | 0 | 0 |
| BTG2 | 0 | 0 | 0 | 0 | 0 | 0 |
| BTK | 0 | 0 | 0 | 0 | 0 | 0 |
| BUB1 | 0 | 0 | 0 | 0 | 0 | 0 |
| BUB1B | 0 | 0 | 0.129449175 | −6.543666003 | 0 | 0 |
| C10orf18 | 0 | −11.23438924 | 0 | 0 | 0 | 0 |
| C13orf18 | 0 | 14.60869443 | 0 | 6.676459404 | 0 | 0 |
| C15orf41 | 0 | 0 | 0 | 0 | 0 | 0 |
| C3orf37 | 0 | −13.2892376 | 0 | 0 | 0 | 0 |
| C5AR1 | 0 | 0 | 0 | 0 | 0 | 0 |
| C5orf41 | 0 | 0 | 0 | 0 | 0 | 0 |
| C7orf68 | 0 | 0 | 0 | 0 | 0 | 0 |
| CACNA1D | 0 | 0 | 0 | 0 | 0 | 0 |
| CALD1 | 0 | 0 | 0 | 0 | −2.249574505 | 0 |
| CAMK2B | 0 | 0 | 0 | 0 | 0 | 0 |
| CARD11 | 0 | 13.81862222 | 0 | 0 | −18.72040556 | 0 |
| CAV1 | 0 | 0 | 0 | 0 | 0 | 0 |
| CAV2 | 0 | 0 | 0 | 0 | 0 | 0 |
| CCDC50 | 0 | 18.68358953 | 0 | 5.320661402 | 0 | 68.6051667 |

TABLE 4-continued

| Gene | Normalization weights | ABC/GCB weights | BL non-Myc weights | BL myc weights | PMBL Weights | MCL Weights |
|---|---|---|---|---|---|---|
| CCDC75 | 0 | 0 | 0 | 0 | 0 | 0 |
| CCL17 | 0 | 0 | 0 | 0 | 25.50999568 | 0 |
| CCNA2 | 0 | 0 | 0 | 0 | 0 | 0 |
| CCNB1 | 0 | 0 | 0 | 0 | 0 | 0 |
| CCNB2 | 0 | 0 | 0 | 0 | 0 | 0 |
| CCND1 | 0 | 0 | 0 | 0 | 0 | 0 |
| CCND1 | 0 | 0 | 0 | 0 | 0 | 0 |
| CCND1 | 0 | 0 | 0 | 0 | 0 | 0 |
| CCND1 | 0 | 0 | 0 | 0 | 0 | 0 |
| CCND1 | 0 | 0 | 0 | 0 | 0 | 0 |
| CCND1 | 0 | 0 | 0 | 0 | 0 | 87.99680321 |
| CCND2 | 0 | 13.55862157 | 0 | 0 | 0 | 0 |
| CCND3 | 0 | 0 | 0 | 0 | 0 | 0 |
| CCR7 | 0 | 11.22811168 | 0 | −4.862612697 | 0 | 0 |
| CD2 | 0 | 0 | 0 | 0 | 0 | 0 |
| CD200 | 0 | 0 | 0 | 0 | 0 | 0 |
| CD22 | 0 | 0 | 0 | 0 | 0 | 0 |
| CD247 | 0 | 0 | 0 | 0 | 0 | 0 |
| CD274 | 0 | 0 | 0 | 0 | 0 | 0 |
| CD3D | 0 | 0 | 0 | 0 | 0 | 0 |
| CD3E | 0 | 0 | 0 | 0 | 0 | 0 |
| CD3G | 0 | 0 | 0 | 0 | 0 | 0 |
| CD40 | 0 | 0 | 0 | 0 | 0 | 0 |
| CD44 | 0 | 13.50378135 | 0 | −5.782231847 | 0 | 0 |
| CD47 | 0 | 0 | 0 | 0 | 0 | 0 |
| CD5 | 0 | 0 | 0 | 0 | 0 | 0 |
| CD58 | 0 | 0 | 0 | 0 | 0 | 0 |
| CD6 | 0 | 0 | 0 | 0 | 0 | 0 |
| CD74 | 0 | 0 | 0 | 0 | 0 | 0 |
| CD79A | 0 | 0 | 0 | 0 | 0 | 0 |
| CD79B | 0 | 0 | 0 | 0 | 0 | 0 |
| CD8A | 0 | 0 | 0 | 0 | 0 | 0 |
| CD8B | 0 | 0 | 0 | 0 | 0 | 0 |
| CDC20 | 0 | 0 | 0 | 0 | 0 | 0 |
| CDC25B | 0 | 0 | 0 | 0 | 0 | 0 |
| CDC25C | 0 | 0 | 0 | 0 | 0 | 0 |
| CDCA3 | 0 | 0 | 0 | 0 | 0 | 0 |
| CDCA5 | 0 | 0 | 0 | 0 | 0 | 0 |
| CDCA8 | 0 | 0 | 0 | 0 | 0 | 0 |
| CDH11 | 0 | 0 | 0 | 0 | −2.338738276 | 0 |
| CDC2 | 0 | 0 | 0 | 0 | 0 | 0 |
| PFTK1 | 0 | −15.92270263 | 0 | 0 | 0 | 0 |
| CDK4 | 0 | 0 | 0 | 0 | 0 | 0 |
| CDK6 | 0 | 0 | 0 | 0 | 0 | −65.86959926 |
| CDKN2A | 0 | 0 | 0 | 0 | 0 | 0 |
| CDKN2A | 0 | 0 | 0 | 0 | 0 | 0 |
| CDKN3 | 0 | 0 | 0 | 0 | 0 | 0 |
| CELSR1 | 0 | 0 | 0 | 0 | 0 | 0 |
| CENPA | 0 | 0 | 0 | 0 | 0 | 0 |
| CENPE | 0 | 0 | 0 | 0 | 0 | 0 |
| CENPF | 0 | 0 | 0 | 0 | 0 | 0 |
| CENPN | 0 | 0 | 0 | 0 | 0 | 0 |
| PRR6 | 0 | 0 | 0 | 0 | 22.43680643 | 0 |
| CEP55 | 0 | 0 | 0 | 0 | 0 | 0 |
| CFLAR | 0 | 16.61287119 | 0 | −5.100315997 | 0 | 0 |
| CGNL1 | 0 | 0 | 0 | 0 | −2.156504887 | 0 |
| CIITA | 0 | 0 | 0 | 0 | 0 | 0 |
| CKS2 | 0 | 0 | 0 | 0 | 0 | 0 |
| CLIP2 | 0 | 0 | 0 | 0 | 20.2768953 | 0 |
| CLMN | 0 | 0 | 0 | 0 | 0 | 0 |
| CPNE3 | 0 | −11.49752906 | 0 | 0 | 0 | 0 |
| CR2 | 0 | −12.2225611 | 0 | −5.465732584 | −19.63179827 | 0 |
| CREB3L2 | 0 | 19.29029329 | 0 | 0 | 0 | 0 |
| CREBBP | 0 | 0 | 0 | 0 | 0 | 0 |
| CSF2RA | 0 | 0 | 0 | 0 | −2.424880636 | 0 |
| CSTA | 0 | 0 | 0 | 0 | −2.543864326 | 0 |
| CTGF | 0 | 0 | 0 | 0 | 0 | 0 |
| CTH | 0 | 0 | 0 | 0 | 0 | 0 |
| CTHRC1 | 0 | 0 | 0 | 0 | −2.518684898 | 0 |
| CTLA4 | 0 | 0 | 0 | 0 | 0 | 0 |
| CTNNA2 | 0 | 0 | 0 | 0 | 0 | 0 |
| CTPS | 0 | 0 | 0 | 0 | 0 | 0 |
| CTSH | 0 | 0 | 0 | −5.145507824 | 0 | 0 |
| CTSK | 0 | 0 | 0 | 0 | −2.572873829 | 0 |
| CXCL10 | 0 | 0 | 0 | 0 | 0 | 0 |
| CXCL12 | 0 | 0 | 0 | 0 | 0 | 0 |
| CXCL9 | 0 | 0 | 0 | 0 | 0 | 0 |

TABLE 4-continued

| Gene | Normalization weights | ABC/GCB weights | BL non-Myc weights | BL myc weights | PMBL Weights | MCL Weights |
|---|---|---|---|---|---|---|
| CYB5R2 | 0 | 19.12600362 | 0 | 0 | 0 | 0 |
| CYP27A1 | 0 | 0 | 0 | 0 | −2.635085165 | 0 |
| CYP2J2 | 0 | 0 | 0 | 0 | 0 | 0 |
| CYSLTR1 | 0 | 0 | 0 | 0 | 0 | 0 |
| DCBLD1 | 0 | 0 | 0 | 0 | 0 | 0 |
| DCTD | 0 | 15.98936135 | 0 | 0 | 0 | 0 |
| DDAH2 | 0 | 0 | 0 | 0 | 0 | 0 |
| DDX58 | 0 | 0 | 0 | 0 | 0 | 0 |
| DENND4 | 0 | 0 | 0 | 0 | 21.20254474 | 0 |
| DLC1 | 0 | 0 | 0 | 0 | 0 | 0 |
| DLEU1 | 0 | 0 | 0 | 0 | 0 | 0 |
| DLGAP5 | 0 | 0 | 0 | 0 | 0 | 0 |
| DNAJA1 | 0 | 0 | 0 | 0 | 0 | 0 |
| DNAJB9 | 0 | 0 | 0 | 0 | 0 | 0 |
| DNAJC10 | 0 | −12.209423 | 0 | 0 | 0 | 0 |
| DNMT3A | 0 | 0 | 0 | 0 | 0 | 0 |
| DOCK10 | 0 | 15.87228876 | 0 | 0 | 17.13938941 | 0 |
| DPY19L1 | 0 | 0 | 0 | 0 | 0 | 0 |
| DPYSL3 | 0 | 0 | 0 | 0 | −2.427210322 | 0 |
| DRAM | 0 | 0 | 0 | 0 | 0 | 0 |
| DTX1 | 0 | 0 | 0 | 0 | 0 | 0 |
| E2F2 | 0 | 0 | 0 | 4.871853059 | 0 | 0 |
| E2F8 | 0 | 0 | 0 | 0 | 0 | 0 |
| EBV_BZLF1 | 0 | 0 | 0 | 0 | 0 | 0 |
| EBV_EBER1 | 0 | 0 | 0 | 0 | 0 | 0 |
| EBV_EBER2 | 0 | 0 | 0 | 0 | 0 | 0 |
| EBV_EBNA1_CDS | 0 | 0 | 0 | 0 | 0 | 0 |
| EBV_EBNA2_3'_end | 0 | 0 | 0 | 0 | 0 | 0 |
| EBV_EBNA2_long | 0 | 0 | 0 | 0 | 0 | 0 |
| EBV_EBNA3A | 0 | 0 | 0 | 0 | 0 | 0 |
| EBV_EBNA3B | 0 | 0 | 0 | 0 | 0 | 0 |
| EBV_EBNA3C | 0 | 0 | 0 | 0 | 0 | 0 |
| EBV_LMP1_3'_end | 0 | 0 | 0 | 0 | 0 | 0 |
| EBV_LMP1_unique | 0 | 0 | 0 | 0 | 0 | 0 |
| EBV_LPM2A | 0 | 0 | 0 | 0 | 0 | 0 |
| EEPD1 | 0 | −14.43898719 | 0 | 0 | 0 | 0 |
| EFEMP2 | 0 | 0 | 0 | 0 | −2.309390981 | 0 |
| EGFL7 | 0 | 0 | 0 | 0 | 0 | 0 |
| EHD2 | 0 | 0 | 0 | 0 | 0 | 0 |
| EIF5AL1 | 0 | 0 | 0 | 0 | 0 | 0 |
| ELL2 | 0 | 12.74051826 | 0 | −5.784944094 | 0 | 0 |
| EML1 | 0 | 0 | 0 | 0 | −2.370584039 | 0 |
| EMR | 0 | 0 | 0 | 0 | 0 | 0 |
| ENO1 | 0 | 0 | 0 | 0 | 0 | 0 |
| ENPP3 | 0 | 0 | 0 | 0 | 0 | 0 |
| ENTPD1 | 0 | 12.50562718 | 0 | 0 | 0 | 0 |
| EP300 | 0 | 0 | 0 | 0 | 0 | 0 |
| EPHB1 | 0 | 0 | 0 | 0 | 0 | 0 |
| EPSTI1 | 0 | 0 | 0 | 0 | 0 | 0 |
| ERG | 0 | 0 | 0 | 0 | 0 | 0 |
| ERP29 | 0 | 14.40630514 | 0 | 0 | 0 | 0 |
| TXNDC4 | 0 | 0 | 0 | 0 | 0 | 0 |
| ESPL1 | 0 | 0 | 0 | 0 | 0 | 0 |
| ETV6 | 0 | 17.10124803 | 0 | 0 | 0 | 0 |
| EXO1 | 0 | 0 | 0 | 0 | 0 | 0 |
| FABP4 | 0 | 0 | 0 | 0 | 0 | 0 |
| FAM108C1 | 0 | 13.9119712 | 0 | 0 | 0 | 0 |
| FAM159A | 0 | 0 | 0 | 0 | −19.09112771 | 0 |
| FAM171B | 0 | 0 | 0 | 0 | 20.15840479 | 0 |
| FAM46C | 0 | 16.04589049 | 0 | 0 | 0 | 0 |
| FAM69A | 0 | 0 | 0 | 0 | 20.26920874 | 0 |
| FAM83D | 0 | 0 | 0 | 0 | 0 | 0 |
| FAP | 0 | 0 | 0 | 0 | −2.448537997 | 0 |
| FAS | 0 | 0 | 0 | 0 | 19.4917463 | 0 |
| FBP2 | 0 | 0 | 0 | 0 | 0 | 0 |
| FBXO10 | 0 | 0 | 0 | 0 | 0 | 0 |
| FBXO11 | 0 | 0 | 0 | 0 | 0 | 0 |
| FCER2 | 0 | 0 | 0 | 0 | 19.36530173 | 0 |
| FEZ1 | 0 | 0 | 0 | 0 | 0 | 0 |
| FGL2 | 0 | 0 | 0 | 0 | 0 | 0 |
| FKBP11 | 0 | 10.77110305 | 0 | 0 | 0 | 0 |
| FKBP2 | 0 | 0 | 0 | 0 | 0 | 0 |
| FLJ42418 | 0 | −13.07282539 | 0 | 0 | 0 | 0 |
| FLNA | 0 | 0 | 0 | 0 | 0 | 0 |
| FN1 | 0 | 0 | 0 | 0 | −2.515692387 | 0 |
| FNBP1 | 0 | 0 | 0 | 0 | 0 | 0 |
| FNDC1 | 0 | −9.924277783 | 0 | 0 | −2.337279029 | 0 |

TABLE 4-continued

| Gene | Normalization weights | ABC/GCB weights | BL non-Myc weights | BL myc weights | PMBL Weights | MCL Weights |
|---|---|---|---|---|---|---|
| FOXM1 | 0 | 0 | 0 | 0 | 0 | 0 |
| FOXO1 | 0 | 0 | 0 | 0 | 0 | 0 |
| FOXP1 | 0 | 0 | 0 | 0 | 0 | 0 |
| FSCN1 | 0 | 0 | 0 | 0 | 0 | 0 |
| FUT8 | 0 | 12.89311878 | 0 | 0 | 0 | 0 |
| FYB | 0 | 0 | 0 | 0 | 0 | 0 |
| GBP1 | 0 | 0 | 0 | 0 | 0 | 0 |
| GBP4 | 0 | 0 | 0 | 0 | 0 | 0 |
| GCET2 | 0 | 0 | 0 | 0 | 17.14715594 | 0 |
| GGT1 | 0 | 0 | 0 | 0 | 0 | 0 |
| GHR | 0 | 0 | 0 | 0 | 0 | 0 |
| GLDC | 0 | 0 | 0 | 0 | 0 | 0 |
| GLRX | 0 | 0 | 0 | 0 | 0 | 0 |
| GNA13 | 0 | −13.98237394 | 0 | 0 | 0 | 0 |
| GNB4 | 0 | 0 | 0 | 0 | 0 | 0 |
| GNG10 | 0 | 0 | 0 | 0 | 0 | 0 |
| GNL3 | 0 | 13.0455436 | 0.131002027 | −6.622162805 | 0 | 0 |
| GPR116 | 0 | 0 | 0 | 0 | 0 | 0 |
| GPR176 | 0 | 0 | 0 | 0 | 0 | 0 |
| GPR183 | 0 | 0 | 0 | 0 | 0 | 0 |
| GRAMD1B | 0 | 0 | 0 | 0 | 0 | 0 |
| GRB10 | 0 | 0 | 0 | 0 | 0 | 0 |
| GRSF1 | 0 | 0 | 0 | 0 | 0 | 0 |
| GTSE1 | 0 | 0 | 0 | 0 | 0 | 0 |
| GLT8D4 | 0 | 0 | 0 | 0 | 0 | 0 |
| GYPC | 0 | 0 | 0 | 0 | 17.83003931 | 0 |
| H2AFV | 0 | 0 | 0 | 0 | 0 | 0 |
| H2AFX | 0 | 0 | 0 | 0 | 0 | 0 |
| HCK | 0 | 15.54344514 | 0 | −5.412764958 | 0 | 0 |
| HDAC1 | 0 | −15.02975702 | 0 | 0 | 0 | 0 |
| HDAC2 | 0 | 0 | 0 | 0 | 0 | 0 |
| HDGF | 0 | 0 | 0.116000721 | −5.863845581 | 0 | 0 |
| HEG1 | 0 | 0 | 0 | 0 | −2.46106726 | 0 |
| HHV8_BCL2_homologue | 0 | 0 | 0 | 0 | 0 | 0 |
| HHV8_K1-32_Bcb_K1_protein | 0 | 0 | 0 | 0 | 0 | 0 |
| HHV8_ORF73-LANA | 0 | 0 | 0 | 0 | 0 | 0 |
| HHV8_T0.7/P6 | 0 | 0 | 0 | 0 | 0 | 0 |
| HHV8_T1.1 | 0 | 0 | 0 | 0 | 0 | 0 |
| HHV8_vFLIP_ORF71 | 0 | 0 | 0 | 0 | 0 | 0 |
| HHV8_vIL6 | 0 | 0 | 0 | 0 | 0 | 0 |
| HHV8_vMIP1b_ORFK4.2_KIE-3 | 0 | 0 | 0 | 0 | 0 | 0 |
| HJURP | 0 | 0 | 0 | 0 | 0 | 0 |
| HLA-A | 0 | 0 | 0 | 0 | 0 | 0 |
| HLA-B | 0 | 0 | 0 | 0 | 0 | 0 |
| HLA-C | 0 | 0 | 0 | 0 | 0 | 0 |
| HLA-DMA | 0 | 0 | 0 | −4.825417012 | 0 | 0 |
| HLA-DPA1 | 0 | 0 | 0 | 0 | 0 | 0 |
| HLA-DPB1 | 0 | 0 | 0 | 0 | 0 | 0 |
| HLA-DQA1 | 0 | 0 | 0 | 0 | 0 | 0 |
| HLA-DRA | 0 | 0 | 0 | 0 | 0 | 0 |
| HLA-E | 0 | 0 | 0 | 0 | 0 | 0 |
| HLA-F | 0 | 0 | 0 | 0 | 0 | 0 |
| HOMER2 | 0 | 0 | 0 | 0 | 19.38721241 | 0 |
| HOPX | 0 | −14.01730842 | 0 | 0 | 0 | 0 |
| HPCAL1 | 0 | 0 | 0 | 0 | 0 | 59.25326244 |
| HSP90B1 | 0 | 15.53130763 | 0 | 0 | 0 | 0 |
| HSPB8 | 0 | 0 | 0 | 0 | −2.192325405 | 0 |
| HTRA1 | 0 | 0 | 0 | 0 | −2.354416381 | 0 |
| HYOU1 | 0 | 0 | 0 | 0 | 0 | 0 |
| ICAM1 | 0 | 0 | 0 | −5.307124944 | 0 | 0 |
| ID1 | 0 | 0 | 0 | 0 | 0 | 0 |
| ID2 | 0 | 0 | 0 | 0 | 0 | 0 |
| ID3 | 0 | 0 | 0 | 0 | 0 | 0 |
| IDS | 0 | 0 | 0 | 0 | 0 | 0 |
| IER3 | 0 | 0 | 0 | 0 | 0 | 0 |
| IFI16 | 0 | 0 | 0 | 0 | 0 | 0 |
| IFI35 | 0 | 0 | 0 | 0 | 0 | 0 |
| IFI44L | 0 | 0 | 0 | 0 | 0 | 0 |
| IFI6 | 0 | 0 | 0 | 0 | 0 | 0 |
| IFIH1 | 0 | 0 | 0 | 0 | 21.31413442 | 0 |
| IFIT1 | 0 | 0 | 0 | 0 | 0 | 0 |
| IFIT2 | 0 | 0 | 0 | 0 | 0 | 0 |
| IFIT3 | 0 | 0 | 0 | 0 | 0 | 0 |
| IFITM1 | 0 | 0 | 0 | 0 | 0 | 0 |
| IFNAR1 | 0 | 0 | 0 | 0 | 0 | 0 |
| IFNAR2 | 0 | 0 | 0 | 0 | 0 | 0 |
| IFNB1 | 0 | 0 | 0 | 0 | 0 | 0 |

TABLE 4-continued

| Gene | Normalization weights | ABC/GCB weights | BL non-Myc weights | BL myc weights | PMBL Weights | MCL Weights |
|---|---|---|---|---|---|---|
| IgA2_constant_region | 0 | 0 | 0 | 0 | 0 | 0 |
| IgE_constant_region | 0 | 0 | 0 | 0 | 0 | 0 |
| IGFBP5 | 0 | 0 | 0 | 0 | 0 | 0 |
| IgG2_constant_region | 0 | 0 | 0 | 0 | 0 | 0 |
| IgG4_constant_region | 0 | 0 | 0 | 0 | 0 | 0 |
| IGSF3 | 0 | 11.04304441 | 0 | 0 | 18.36718646 | 0 |
| IL10 | 0 | 0 | 0 | 0 | 0 | 0 |
| IL12A | 0 | 10.87451224 | 0 | 0 | 0 | 0 |
| IL13 | 0 | 0 | 0 | 0 | 0 | 0 |
| IL13RA1 | 0 | 0 | 0 | −5.477834924 | 22.21511102 | 0 |
| IL16 | 0 | 15.38015948 | 0 | 0 | 0 | 0 |
| IL17RB | 0 | 10.16999574 | 0 | 0 | 0 | 0 |
| IL4I1 | 0 | 0 | 0 | 0 | 0 | 0 |
| IL6 | 0 | 0 | 0 | 0 | 0 | 0 |
| ING1 | 0 | 0 | 0 | 0 | 0 | 0 |
| INPP5D | 0 | 0 | 0 | 0 | 0 | 0 |
| IRAK1 | 0 | 0 | 0 | 0 | 0 | 0 |
| IRAK2 | 0 | 0 | 0 | 0 | 0 | 0 |
| IRAK3 | 0 | 0 | 0 | 0 | 0 | 0 |
| IRAK4 | 0 | 0 | 0 | 0 | 0 | 0 |
| IRF1 | 0 | 0 | 0 | 0 | 0 | 0 |
| IRF3 | 0 | 0 | 0 | 0 | 0 | 0 |
| IRF4 | 0 | 21.21696785 | 0 | 0 | 0 | 0 |
| IRF5 | 0 | 0 | 0 | 0 | 0 | 0 |
| IRF7 | 0 | 0 | 0 | 0 | 0 | 0 |
| ISG15 | 0 | 0 | 0 | 0 | 18.22975543 | 0 |
| ITGA9 | 0 | 0 | 0 | 0 | 0 | 0 |
| ITGAV | 0 | 0 | 0 | 0 | −2.502427838 | 0 |
| ITGAX | 0 | 0 | 0 | 0 | −2.527107115 | 0 |
| ITGB2 | 0 | 0 | 0 | −5.354319759 | 0 | 0 |
| ITPKB | 0 | −19.39129721 | 0 | 0 | 0 | 0 |
| JAK1 | 0 | 0 | 0 | 0 | 0 | 0 |
| JAK2 | 0 | 0 | 0 | 0 | 18.78741327 | 0 |
| JAK3 | 0 | 0 | 0 | −4.911758111 | 0 | 0 |
| KCNJ1 | 0 | 0 | 0 | 0 | 0 | 0 |
| KCNK12 | 0 | −12.19178395 | 0 | 0 | 0 | 0 |
| KCNMA1 | 0 | 0 | 0 | 0 | 0 | 0 |
| JMJD2C | 0 | 0 | 0 | 0 | 0 | 0 |
| KDR | 0 | 0 | 0 | 0 | 0 | 0 |
| KIAA1147 | 0 | 0 | 0 | 0 | 0 | 0 |
| KIAA1274 | 0 | −11.88673995 | 0 | 0 | 0 | 0 |
| KIF11 | 0 | 0 | 0 | 0 | 0 | 0 |
| KIF14 | 0 | 0 | 0 | 0 | 0 | 0 |
| KIF15 | 0 | 0 | 0 | 0 | 0 | 0 |
| KIF18A | 0 | 0 | 0 | 0 | 0 | 0 |
| KIF18B | 0 | 0 | 0 | 0 | 0 | 0 |
| KIF20A | 0 | 0 | 0 | 0 | 0 | 0 |
| KIF23 | 0 | 0 | 0 | 0 | 0 | 0 |
| KIF2C | 0 | 0 | 0 | 0 | 0 | 0 |
| KIF4A | 0 | 0 | 0 | 0 | 0 | 0 |
| KLHL5 | 0 | −10.77233553 | 0 | 0 | 0 | 0 |
| KPNA2 | 0 | 0 | 0 | 0 | 0 | 0 |
| KYNU | 0 | 0 | 0 | 0 | 23.67824397 | 0 |
| LAMB1 | 0 | 0 | 0 | 0 | 0 | 0 |
| LAMP3 | 0 | 0 | 0 | 0 | 0 | 0 |
| LANCL1 | 0 | −11.96529389 | 0 | 0 | 0 | 0 |
| LAT | 0 | 0 | 0 | 0 | 0 | 0 |
| LAT2 | 0 | 0 | 0 | 0 | 0 | 0 |
| LDHA | 0 | 0 | 0 | 0 | 0 | −62.43798035 |
| LHFPL3 | 0 | 0 | 0 | 0 | 0 | 0 |
| LHX2 | 0 | 0 | 0 | 0 | 0 | 0 |
| LIMA1 | 0 | 0 | 0 | 0 | 22.38509346 | 0 |
| LIMD1 | 0 | 17.83248768 | 0 | 0 | 0 | 0 |
| LMAN2 | 0 | 0 | 0 | 0 | 0 | 0 |
| LMO2 | 0 | −16.98695863 | 0 | −9.427107802 | 0 | 0 |
| LOC643529 | 0 | 0 | 0 | 0 | 0 | 0 |
| LOXL2 | 0 | 0 | 0 | 0 | 0 | 0 |
| LPCAT3 | 0 | 0 | 0 | 0 | 0 | 0 |
| LRMP | 0 | −15.8755653 | 0 | 0 | 0 | 0 |
| LRPPRC | 0 | 0 | 0 | 0 | 0 | 0 |
| LRRC15 | 0 | −12.69088474 | 0 | 0 | −2.555292482 | 0 |
| LRRC33 | 0 | 15.08028382 | 0 | 0 | 0 | 0 |
| LTBP2 | 0 | 0 | 0 | 0 | −2.274436223 | 0 |
| LYPD6B | 0 | −12.18942045 | 0 | 0 | 0 | 0 |
| LYZ | 0 | 0 | 0 | 0 | −2.548310761 | 0 |
| MACROD2 | 0 | 0 | 0 | 0 | 0 | 0 |
| MAL | 0 | 0 | 0 | 0 | 21.94306064 | 0 |

TABLE 4-continued

| Gene | Normalization weights | ABC/GCB weights | BL non-Myc weights | BL myc weights | PMBL Weights | MCL Weights |
|---|---|---|---|---|---|---|
| MALT1 | 0 | 0 | 0 | 0 | 0 | 0 |
| MAML3 | 0 | −17.94799886 | 0 | 0 | 0 | 0 |
| MAP3K1 | 0 | 0 | 0 | 0 | 0 | 55.17626389 |
| MAP3K8 | 0 | 0 | 0 | 0 | 0 | 0 |
| MAP4K4 | 0 | −10.29136026 | 0 | 0 | 0 | 0 |
| MAPK10 | 0 | −14.19048558 | 0 | 0 | 0 | 0 |
| MAPKAPK5 | 0 | 0 | 0 | 0 | 0 | 0 |
| MARCKS | 0 | 0 | 0 | 0 | 0 | 0 |
| MARCKSL1 | 0 | −16.15992041 | 0 | −5.183663919 | 0 | 0 |
| MAST2 | 0 | −13.37445723 | 0 | 0 | 0 | 0 |
| MATR3 | 0 | 0 | 0 | 0 | 0 | 0 |
| MCL1 | 0 | 0 | 0 | 0 | 0 | 0 |
| MCM10 | 0 | 0 | 0 | 0 | 0 | 0 |
| MCM7 | 0 | 0 | 0 | 0 | 0 | 0 |
| MDFIC | 0 | 0 | 0 | −6.830814658 | 0 | 0 |
| MDM2 | 0 | 0 | 0 | 0 | 0 | 0 |
| MFAP5 | 0 | 0 | 0 | 0 | 0 | 0 |
| MFNG | 0 | 0 | 0 | 0 | 0 | 0 |
| MFSD2A | 0 | 0 | 0 | 0 | 0 | 0 |
| MGC87042 | 0 | 0 | 0 | 0 | 0 | 0 |
| MIR17HG | 0 | 0 | 0 | 0 | 0 | 0 |
| MKI67 | 0 | 0 | 0 | 0 | 0 | 0 |
| MME | 0 | −18.26084621 | 0 | 0 | 0 | 0 |
| MMP1 | 0 | 0 | 0 | 0 | 0 | 0 |
| MMP2 | 0 | 0 | 0 | 0 | −2.575770684 | 0 |
| MMP9 | 0 | 0 | 0 | 0 | −2.62062289 | 0 |
| MMRN2 | 0 | 0 | 0 | 0 | 0 | 0 |
| MNDA | 0 | 0 | 0 | 0 | 0 | 0 |
| MOBKL2C | 0 | 0 | 0 | 0 | 24.05195347 | 0 |
| MPEG1 | 0 | 13.61757622 | 0 | 0 | 0 | 0 |
| MS4A1 | 0 | 0 | 0 | 0 | 0 | 0 |
| MST1R | 0 | 0 | 0 | 0 | 0 | 0 |
| MTHFD2 | 0 | 0 | 0 | 0 | 0 | −64.88192756 |
| MUC16 | 0 | 0 | 0 | 0 | 0 | 0 |
| MYB | 0 | 0 | 0 | 6.206314452 | 0 | 0 |
| MYBL1 | 0 | −19.42564163 | 0 | 0 | 0 | 0 |
| MYC | 0 | 0 | 0.129410593 | −6.541715697 | 0 | 0 |
| MYD88 | 0 | 0 | 0 | 0 | 0 | 0 |
| MYO7A | 0 | 0 | 0 | 0 | 0 | 0 |
| FAM128B | 0 | 0 | 0 | 0 | 0 | 0 |
| NANS | 0 | 0 | 0 | −5.411187191 | 0 | −62.00052085 |
| NASP | 0 | 0 | 0 | 0 | 0 | 0 |
| NBN | 0 | 0 | 0 | 0 | 0 | 0 |
| NCAPG | 0 | 0 | 0 | 0 | 0 | 0 |
| NCAPH | 0 | 0 | 0 | 0 | 0 | 0 |
| NCF2 | 0 | 0 | 0 | 0 | 17.12736383 | 0 |
| NCRNA00158 | 0 | 0 | 0 | 0 | 0 | 0 |
| NDST4 | 0 | 0 | 0 | 0 | 0 | 0 |
| NECAP2 | 0 | 0 | 0 | 0 | 17.90953211 | 0 |
| NEIL1 | 0 | −16.14074081 | 0 | 0 | 0 | 0 |
| NEK6 | 0 | −14.536944 | 0 | 0 | 0 | 0 |
| NFATC1 | 0 | 0 | 0 | 0 | 0 | 0 |
| NFIL3 | 0 | 0 | 0 | 0 | 23.55828096 | 0 |
| NFKBIA | 0 | 0 | 0 | 0 | 0 | 0 |
| NFKBIZ | 0 | 14.96909754 | 0 | 0 | 0 | 0 |
| NIPA2 | 0 | 12.59506241 | 0 | 0 | 0 | 0 |
| NOC3L | 0 | 11.52493513 | 0 | 0 | 0 | 0 |
| NOL14 | 0 | 0 | 0 | 0 | 0 | 0 |
| NOL5A | 0 | 0 | 0.123010002 | −6.218165306 | 0 | 0 |
| NOTCH1 | 0 | 0 | 0 | 0 | 0 | 0 |
| NOTCH2 | 0 | 0 | 0 | 0 | 0 | 0 |
| NUF2 | 0 | 0 | 0 | 0 | 0 | 0 |
| NUP62 | 0 | 0 | 0 | 0 | 0 | 0 |
| NUSAP1 | 0 | 0 | 0 | 0 | 0 | 0 |
| OAS2 | 0 | 0 | 0 | 0 | 0 | 0 |
| OAS3 | 0 | 0 | 0 | 0 | 0 | 0 |
| OPN3 | 0 | 0 | 0 | 0 | 0 | 0 |
| OSBPL3 | 0 | −13.37500509 | 0 | 0 | 0 | 0 |
| PA2G4 | 0 | 0 | 0 | 0 | 0 | 0 |
| PAG1 | 0 | −16.35818989 | 0 | 0 | 0 | 0 |
| DKFZP564O0823 | 0 | 0 | 0 | 0 | 0 | 0 |
| PAX6 | 0 | 0 | 0 | 0 | 0 | 0 |
| PCNA | 0 | 0 | 0 | 0 | 0 | 0 |
| PDCD1LG2 | 0 | 0 | 0 | 0 | 0 | 0 |
| PDE9A | 0 | −12.58569832 | 0 | 0 | 0 | 0 |
| PDGFRA | 0 | 0 | 0 | 0 | 0 | 0 |
| PDIA4 | 0 | 0 | 0 | 0 | 0 | 0 |

TABLE 4-continued

| Gene | Normalization weights | ABC/GCB weights | BL non-Myc weights | BL myc weights | PMBL Weights | MCL Weights |
|---|---|---|---|---|---|---|
| PDIA5 | 0 | 11.45635103 | 0 | 0 | 0 | 0 |
| PDK4 | 0 | 0 | 0 | 0 | 0 | 0 |
| PDLIM1 | 0 | 14.15712166 | 0 | 0 | 0 | 0 |
| PDLIM3 | 0 | 0 | 0 | 0 | 0 | 0 |
| PDPN | 0 | 0 | 0 | 0 | −2.469335735 | 0 |
| PECAM1 | 0 | 0 | 0 | 0 | 0 | 0 |
| PECR | 0 | 0 | 0 | 0 | 0 | 0 |
| PGAM1 | 0 | 0 | 0 | 0 | 0 | 0 |
| PHC3 | 0 | 0 | 0 | 0 | 0 | 0 |
| PHF16 | 0 | 15.59828263 | 0 | 0 | 0 | 0 |
| PIK3CA | 0 | 0 | 0 | 0 | 0 | 0 |
| PIK3CD | 0 | 0 | 0 | 0 | 0 | 0 |
| PIM1 | 0 | 13.17752239 | 0 | 0 | 0 | 0 |
| PIM2 | 0 | 19.17848124 | 0 | 0 | 0 | 0 |
| PLAU | 0 | 0 | 0 | −4.942137646 | −2.638406534 | 0 |
| PLEK | 0 | 0 | 0 | −5.140753466 | 0 | 0 |
| PLEKHF2 | 0 | −14.32290025 | 0 | 0 | 0 | 0 |
| PLEKHG4B | 0 | 0 | 0 | 0 | 0 | 0 |
| PLXNB1 | 0 | 0 | 0 | 0 | 0 | 0 |
| PMEPA1 | 0 | −11.10781933 | 0 | 0 | −2.5144432 | 0 |
| PMP22 | 0 | 0 | 0 | 0 | 0 | 0 |
| NP | 0 | 11.18914667 | 0 | 0 | 0 | 0 |
| POU2AF1 | 0 | 0 | 0 | 0 | 0 | 0 |
| POU2F1 | 0 | 0 | 0 | 0 | 0 | 0 |
| POU2F2 | 0 | 0 | 0 | 0 | 0 | 0 |
| PPA1 | 0 | 0 | 0 | 0 | 0 | −58.07910524 |
| PPP2R3B | 0 | 0 | 0 | 0 | 0 | 0 |
| FAM152B | 0 | 0 | 0 | 0 | 0 | 0 |
| PRDM1 | 0 | 0 | 0 | 0 | 0 | 0 |
| PRDM12 | 0 | 0 | 0 | 0 | 0 | 0 |
| PRDX2 | 0 | 0 | 0 | 0 | −23.58686384 | 0 |
| PRDX4 | 0 | 0 | 0 | 0 | 0 | 0 |
| PRICKLE1 | 0 | 0 | 0 | 0 | 0 | 56.2707098 |
| PRKCB | 0 | 0 | 0 | 0 | −16.97009784 | 0 |
| PRMT1 | 0 | 0 | 0 | 0 | 0 | 0 |
| PRPSAP2 | 0 | −12.13413417 | 0 | 0 | 0 | 0 |
| PRSS1 | 0 | 0 | 0 | 0 | 0 | 0 |
| PSMG1 | 0 | 0 | 0 | 0 | 0 | 0 |
| PTEN | 0 | 0 | 0 | 0 | 0 | 0 |
| PTGER4 | 0 | 0 | 0 | 0 | 0 | 0 |
| PTGIR | 0 | 0 | 0 | 0 | 26.72740141 | 0 |
| PTK2 | 0 | −13.78968685 | 0 | −4.948036735 | 0 | 0 |
| PTPN1 | 0 | 13.38225581 | 0 | 0 | 0 | 0 |
| PTPRB | 0 | 0 | 0 | 0 | 0 | 0 |
| PVRL1 | 0 | 0 | 0 | 0 | 0 | 0 |
| PXDN | 0 | 0 | 0 | 0 | 0 | 0 |
| QSOX1 | 0 | 0 | 0 | 0 | 0 | 0 |
| RAB31 | 0 | 0 | 0 | 0 | 0 | 0 |
| RAB33A | 0 | 0 | 0 | −4.912839787 | 0 | 0 |
| RAB3A | 0 | 0 | 0 | 0 | 0 | 0 |
| RAB7L1 | 0 | 20.66492996 | 0 | 0 | 0 | 0 |
| RAPGEF5 | 0 | −14.68045686 | 0 | 0 | 0 | 0 |
| RARRES2 | 0 | 0 | 0 | 0 | −2.570678175 | 0 |
| RASGRP3 | 0 | 0 | 0 | −6.000117265 | 0 | 0 |
| RASSF4 | 0 | 0 | 0 | 0 | 0 | 0 |
| RBCK1 | 0 | 0 | 0 | 0 | 0 | 0 |
| RCL1 | 0 | 0 | 0 | 0 | 19.91410729 | 0 |
| REL | 0 | −10.88675527 | 0 | 0 | 0 | 0 |
| RFTN1 | 0 | −10.08136072 | 0 | 0 | 0 | 0 |
| RGL1 | 0 | 0 | 0 | 0 | 0 | 0 |
| RGS9 | 0 | 0 | 0 | 0 | 18.38318043 | 0 |
| RHEBL1 | 0 | 0 | 0 | 0 | 0 | 0 |
| RHOF | 0 | 0 | 0 | 0 | 19.45176982 | 0 |
| RHOXF1 | 0 | 0 | 0 | 0 | 0 | 0 |
| RNASEH2B | 0 | 0 | 0 | 0 | 0 | 0 |
| RNF31 | 0 | 0 | 0 | 0 | 0 | 0 |
| RNGTT | 0 | 0 | 0 | 0 | 0 | 0 |
| ROBO1 | 0 | 0 | 0 | 0 | −2.163573921 | 0 |
| ROBO4 | 0 | 0 | 0 | 0 | 0 | 0 |
| RPN2 | 0 | 0 | 0 | 0 | 0 | 0 |
| RPS6KA5 | 0 | 0 | 0 | 0 | 0 | 0 |
| RSAD2 | 0 | 0 | 0 | 0 | 0 | 0 |
| RTCD1 | 0 | 0 | 0 | 0 | 0 | 0 |
| RUNDC2B | 0 | 0 | 0 | 0 | 0 | 0 |
| RXRA | 0 | 0 | 0 | 0 | 0 | 0 |
| S100Z | 0 | −12.22316337 | 0 | 0 | 0 | 0 |
| S1PR2 | 0 | −21.44566507 | 0 | 0 | 0 | 0 |

TABLE 4-continued

| Gene | Normalization weights | ABC/GCB weights | BL non-Myc weights | BL myc weights | PMBL Weights | MCL Weights |
|---|---|---|---|---|---|---|
| SAA1 | 0 | 0 | 0 | 0 | 0 | 0 |
| SACS | 0 | 12.97435391 | 0 | 0 | 0 | 0 |
| SAE1 | 0 | 0 | 0 | 0 | 0 | 0 |
| SAMSN1 | 0 | 0 | 0 | −5.803971429 | 22.68315196 | 0 |
| SAP30 | 0 | 0 | 0 | 0 | 0 | 0 |
| SCARA5 | 0 | 0 | 0 | 0 | −2.335496267 | 0 |
| SDC1 | 0 | 0 | 0 | 0 | 0 | 0 |
| SDCCAG8 | 0 | 0 | 0 | 0 | 0 | 0 |
| KIAA0746 | 0 | −15.04224714 | 0 | 0 | 0 | 0 |
| SEMA7A | 0 | 0 | 0 | 0 | 0 | 0 |
| SEPHS1 | 0 | 0 | 0 | 0 | 0 | 0 |
| SERBP1 | 0 | 0 | 0 | 0 | 0 | 0 |
| SERPINA9 | 0 | −17.70615386 | 0 | −4.937282176 | 0 | 0 |
| SERPINB1 | 0 | 0 | 0 | 0 | 0 | 0 |
| SFN | 0 | 0 | 0 | 0 | 0 | 0 |
| SFPQ | 0 | 0 | 0 | 0 | 0 | 0 |
| SGK1 | 0 | −9.835329752 | 0 | −5.684745402 | 0 | 0 |
| SGOL2 | 0 | 0 | 0 | 0 | 0 | 0 |
| SH2D1A | 0 | 0 | 0 | 0 | 0 | 0 |
| SH3BP5 | 0 | 17.2475192 | 0 | 0 | 0 | 0 |
| SHARPIN | 0 | 0 | 0 | 0 | 0 | 0 |
| SIDT1 | 0 | 10.70030882 | 0 | 0 | 0 | 0 |
| SIRPA | 0 | 0 | 0 | 0 | 0 | 0 |
| SIRPB1 | 0 | 0 | 0 | 0 | 0 | 0 |
| SLA | 0 | 16.00267223 | 0 | 0 | 0 | 0 |
| SLAMF1 | 0 | −13.70193031 | 0 | −5.135970135 | 20.7055292 | 0 |
| SLC12A8 | 0 | 0 | 0 | 0 | 0 | 0 |
| SLC16A9 | 0 | 0 | 0 | 0 | 0 | 0 |
| SLC1A4 | 0 | 0 | 0 | 0 | 0 | 0 |
| SLC31A1 | 0 | 0 | 0 | 0 | 0 | 0 |
| SLC35E2B | 0 | 0 | 0 | 0 | 0 | 0 |
| SLC38A5 | 0 | 16.76798547 | 0 | 0 | 0 | 0 |
| SMAD1 | 0 | 0 | 0 | 0 | 0 | 0 |
| SMAD7 | 0 | 0 | 0 | 0 | 0 | 0 |
| SMARCA4 | 0 | −13.90289239 | 0 | 5.037186022 | 0 | 0 |
| SNAP23 | 0 | 0 | 0 | 0 | 0 | 0 |
| SNN | 0 | 0 | 0 | 0 | 0 | 67.01976847 |
| SNX11 | 0 | 0 | 0 | 0 | 22.05768278 | 0 |
| SNX22 | 0 | −13.10658722 | 0 | 0 | 0 | 0 |
| SNX29 | 0 | 0 | 0 | 0 | 19.13395502 | 0 |
| SOCS1 | 0 | 0 | 0 | 0 | 0 | 0 |
| SOCS2 | 0 | 0 | 0 | 0 | 0 | 0 |
| SOCS3 | 0 | 0 | 0 | 0 | 0 | 0 |
| SORBS1 | 0 | 0 | 0 | 0 | 0 | 0 |
| SOX11 | 0 | 0 | 0 | 0 | 0 | 54.39896926 |
| SOX5 | 0 | 0 | 0 | 0 | 0 | 0 |
| SPAG5 | 0 | 0 | 0 | 0 | 0 | 0 |
| SPARC | 0 | 0 | 0 | 0 | −2.470075697 | 0 |
| SPARCL1 | 0 | 0 | 0 | 0 | 0 | 0 |
| SPIB | 0 | 0 | 0 | 0 | 0 | 0 |
| SPINK2 | 0 | −10.030466 | 0 | 0 | 0 | 0 |
| SPINT2 | 0 | 0 | 0 | 0 | 19.59153543 | 0 |
| SPON1 | 0 | 0 | 0 | 0 | 0 | 0 |
| SPRED2 | 0 | −11.78392433 | 0 | 0 | 0 | 0 |
| SPRY1 | 0 | 0 | 0 | 0 | 0 | 0 |
| SRPK1 | 0 | 0 | 0 | 0 | 0 | 0 |
| SRPX | 0 | 0 | 0 | 0 | 0 | 0 |
| SRSF1 | 0 | 0 | 0 | 0 | 0 | 0 |
| SSBP2 | 0 | −16.54355885 | 0 | 0 | 0 | 0 |
| STAG3 | 0 | 0 | 0 | 0 | 0 | 0 |
| STAMBPL1 | 0 | 14.49186031 | 0 | 0 | 0 | 0 |
| STAP1 | 0 | −12.71264348 | 0 | 0 | 0 | 0 |
| STAT1 | 0 | 0 | 0 | 0 | 0 | 0 |
| STAT3 | 0 | 10.99589419 | 0 | −5.30437752 | 0 | 0 |
| STEAP1 | 0 | 0 | 0 | 0 | 0 | 0 |
| STK17A | 0 | −12.60874641 | 0 | 0 | 0 | 0 |
| STK38L | 0 | 0 | 0 | 0 | 0 | 0 |
| STMN1 | 0 | 0 | 0 | 0 | 0 | 0 |
| STS | 0 | −9.978596163 | 0 | 0 | 0 | 0 |
| STX11 | 0 | 0 | 0 | −5.423455974 | 0 | 0 |
| SULF1 | 0 | 0 | 0 | 0 | −2.512044172 | 0 |
| SYK | 0 | 0 | 0 | 0 | 0 | 0 |
| SYPL1 | 0 | 0 | 0 | 0 | 0 | 0 |
| SYT17 | 0 | 0 | 0 | 0 | 0 | 0 |
| SYTL4 | 0 | 0 | 0 | 0 | 0 | 0 |
| TARS | 0 | 13.55653507 | 0 | 0 | 0 | 0 |
| TAX1BP1 | 0 | 0 | 0 | 0 | 0 | 0 |

TABLE 4-continued

| Gene | Normalization weights | ABC/GCB weights | BL non-Myc weights | BL myc weights | PMBL Weights | MCL Weights |
|---|---|---|---|---|---|---|
| TBC1D27 | 0 | 0 | 0 | 0 | 0 | 0 |
| TBC1D9 | 0 | 0 | 0 | 0 | 0 | 61.55561013 |
| TCF3 | 0 | 0 | 0 | 5.046896623 | 0 | 0 |
| TCF4 | 0 | 15.61877166 | 0 | 0 | 0 | 0 |
| TCTN3 | 0 | 13.00379932 | 0 | 0 | 0 | 0 |
| TEAD1 | 0 | 0 | 0 | 0 | 0 | 0 |
| TEK | 0 | 0 | 0 | 0 | 0 | 0 |
| TERT | 0 | 0 | 0.125565268 | −6.347334222 | 0 | 0 |
| TEX9 | 0 | −12.41661821 | 0 | 0 | 0 | 0 |
| TFDP2 | 0 | 0 | 0 | 0 | 0 | 0 |
| TFPI2 | 0 | 0 | 0 | 0 | 0 | 0 |
| TGFBR1 | 0 | 0 | 0 | 0 | 0 | 0 |
| THBS2 | 0 | 0 | 0 | 0 | −2.458163143 | 0 |
| THY1 | 0 | 0 | 0 | 0 | −2.435821946 | 0 |
| TIAM2 | 0 | −10.50158544 | 0 | 0 | 0 | 0 |
| TICAM2 | 0 | 10.36653445 | 0 | −4.996251154 | 0 | 0 |
| TJP2 | 0 | 0 | 0 | 0 | 0 | 0 |
| TK1 | 0 | 0 | 0 | 0 | 0 | 0 |
| TLE4 | 0 | 0 | 0 | 0 | 17.47264051 | 0 |
| TLK1 | 0 | 12.28505922 | 0 | 0 | 0 | 0 |
| TLR7 | 0 | 0 | 0 | 0 | 19.4679966 | 0 |
| TM4SF1 | 0 | 0 | 0 | 0 | 0 | 0 |
| TMBIM6 | 0 | 0 | 0 | 0 | 0 | 0 |
| TMEM109 | 0 | 0 | 0 | 0 | 0 | 0 |
| TMEM119 | 0 | −10.5658305 | 0 | −5.379086543 | −2.658347176 | 0 |
| TMOD1 | 0 | 0 | 0 | 0 | 19.102924 | 0 |
| IMPRSS6 | 0 | 0 | 0 | 0 | 0 | 0 |
| TNT | 0 | 0 | 0 | 0 | 0 | 0 |
| TNFAIP2 | 0 | 0 | 0 | 0 | 0 | 0 |
| TNFAIP3 | 0 | 0 | 0 | 0 | 0 | 0 |
| TNFRSF13B | 0 | 19.52210849 | 0 | 0 | 0 | 0 |
| TNFRSF14 | 0 | 0 | 0 | 0 | 0 | 0 |
| TNFRSF17 | 0 | 0 | 0 | 0 | 20.07405253 | 0 |
| TNFRSF19 | 0 | 0 | 0 | 0 | 0 | 0 |
| TNFSF10 | 0 | 0 | 0 | 0 | 0 | 0 |
| TNFSF4 | 0 | 0 | 0 | 0 | 27.41538607 | 0 |
| TNIP2 | 0 | 0 | 0 | 0 | 0 | 0 |
| TNXB | 0 | 0 | 0 | 0 | 0 | 0 |
| TOP2A | 0 | 0 | 0 | 0 | 0 | 0 |
| TOX | 0 | −11.9192864 | 0 | 0 | 0 | 0 |
| TP53 | 0 | 0 | 0 | 0 | 0 | 0 |
| TP73 | 0 | 0 | 0 | 0 | 0 | 0 |
| TPM1 | 0 | 0 | 0 | 0 | −2.197810042 | 0 |
| TPX2 | 0 | 0 | 0 | 0 | 0 | 0 |
| TRAF1 | 0 | 0 | 0 | 0 | 21.57006782 | 0 |
| TRAF3 | 0 | 0 | 0 | 0 | 0 | 0 |
| TRIM25 | 0 | 0 | 0 | 0 | 0 | 0 |
| TRIM6-TRIM34 | 0 | 0 | 0 | 0 | 0 | 0 |
| TRIP13 | 0 | 0 | 0.122871716 | −6.211174921 | 0 | 0 |
| TTC9 | 0 | −12.56263701 | 0 | 0 | 0 | 0 |
| TUBG1 | 0 | 0 | 0 | 0 | 0 | 0 |
| TXN | 0 | 0 | 0 | 0 | 0 | 0 |
| TXNDC5 | 0 | 0 | 0 | 0 | 0 | 0 |
| TYK2 | 0 | 0 | 0 | 0 | 0 | 0 |
| TYMS | 0 | 0 | 0 | 0 | 0 | 0 |
| UBE2I | 0 | 0 | 0 | 0 | 0 | 0 |
| UBE2S | 0 | 0 | 0 | 0 | 0 | 0 |
| USP12 | 0 | −11.66057366 | 0 | 0 | 0 | 0 |
| USP18 | 0 | 0 | 0 | 0 | 0 | 0 |
| USP46 | 0 | 13.42760916 | 0 | 0 | 0 | 0 |
| VASH2 | 0 | 0 | 0 | 0 | 20.35631229 | 0 |
| VGLL4 | 0 | −12.24069542 | 0 | 0 | 0 | 0 |
| TMEM49 | 0 | 0 | 0 | 0 | 0 | 0 |
| VWF | 0 | 0 | 0 | 0 | 0 | 0 |
| WASF1 | 0 | 0 | 0 | 0 | 0 | 0 |
| WDR25 | 0 | 0 | 0 | 0 | 0 | 0 |
| WHSC1 | 0 | 0 | 0 | 0 | 0 | 0 |
| WNT3 | 0 | 0 | 0 | 0 | 0 | 55.5970345 |
| XAF1 | 0 | 0 | 0 | 0 | 0 | 0 |
| XBP1 | 0 | 10.72031521 | 0 | 0 | 0 | 0 |
| YPEL1 | 0 | 0 | 0 | 0 | 0 | 0 |
| ZAP70 | 0 | 0 | 0 | 0 | 0 | 0 |
| ZBTB32 | 0 | 12.89819312 | 0 | 0 | 0 | 0 |
| ZBTB38 | 0 | 0 | 0 | 0 | 0 | 0 |
| ZBTB8 | 0 | 0 | 0 | 0 | 22.31265521 | 0 |
| ZCCHC7 | 0 | −10.53054134 | 0 | 0 | 0 | 0 |
| ZFP36L1 | 0 | 0 | 0 | 0 | 0 | 0 |

TABLE 4-continued

| Gene | Normalization weights | ABC/GCB weights | BL non-Myc weights | BL myc weights | PMBL Weights | MCL Weights |
|---|---|---|---|---|---|---|
| ZMYND8 | 0 | 0 | 0 | 0 | 0 | 0 |
| ZNF238 | 0 | 0 | 0 | 0 | 0 | 0 |
| ZNF281 | 0 | 0 | 0 | 0 | 17.18038245 | 0 |
| ZNF318 | 0 | −14.69750421 | 0 | 0 | 0 | 0 |
| ZNF385B | 0 | 0 | 0 | 0 | 0 | 0 |
| ZNF608 | 0 | −12.02764268 | 0 | 0 | 0 | 0 |
| ZNRF1 | 0 | 0 | 0 | 0 | 0 | 0 |
| ZPBP2 | 0 | 0 | 0 | 0 | 0 | 0 |
| ZWINT | 0 | 0 | 0 | 0 | 0 | 0 |
| A2LD1 | 0 | 0 | 0 | 0 | 0 | 0 |
| ABCA12 | 0 | 0 | 0 | 0 | 0 | 0 |
| ACSL5 | 0.021276596 | 0 | 0 | 0 | 0 | 0 |
| AHCYL2 | 0.021276596 | 0 | 0 | 0 | 0 | 0 |
| AKAP9 | 0.021276596 | 0 | 0 | 0 | 0 | 0 |
| ASCL2 | 0 | 0 | 0 | 0 | 0 | 0 |
| ASMTL-AS1 | 0 | 0 | 0 | 0 | 0 | 0 |
| ATOH8 | 0 | 0 | 0 | 0 | 0 | 0 |
| ATXN7L2 | 0.021276596 | 0 | 0 | 0 | 0 | 0 |
| C19orf26 | 0 | 0 | 0 | 0 | 0 | 0 |
| C4orf31 | 0 | 0 | 0 | 0 | 0 | 0 |
| CA7 | 0 | 0 | 0 | 0 | 0 | 0 |
| CAMKK1 | 0 | 0 | 0 | 0 | 0 | 0 |
| CDK5RAP2 | 0.021276596 | 0 | 0 | 0 | 0 | 0 |
| CHD4 | 0.021276596 | 0 | 0 | 0 | 0 | 0 |
| CHST5 | 0 | 0 | 0 | 0 | 0 | 0 |
| CPA6 | 0 | −10.24419002 | 0 | 0 | 0 | 0 |
| DAZAP2 | 0.021276596 | 0 | 0 | 0 | 0 | 0 |
| DCLK3 | 0 | 0 | 0 | 0 | 0 | 0 |
| DNAJB12 | 0.021276596 | 0 | 0 | 0 | 0 | 0 |
| ERBB2IP | 0.021276596 | 0 | 0 | 0 | 0 | 0 |
| ERN2 | 0 | 0 | 0 | 0 | 0 | 0 |
| KIAA0574 | 0 | 0 | 0 | 0 | 0 | 0 |
| FAR2 | 0 | 0 | 0 | 0 | 0 | 0 |
| FARP1 | 0 | 0 | 0 | 0 | 0 | 0 |
| FBXL13 | 0 | 0 | 0 | 0 | 0 | 0 |
| FBXO36 | 0 | 0 | 0 | 0 | 0 | 0 |
| FBXO41 | 0.021276596 | 0 | 0 | 0 | 0 | 0 |
| FCN2 | 0 | 0 | 0 | 0 | 0 | 0 |
| GAD2 | 0 | 0 | 0 | 0 | 0 | 0 |
| GATA1 | 0 | 0 | 0 | 0 | 0 | 0 |
| GATA2 | 0 | 0 | 0 | 0 | 0 | 0 |
| GIT2 | 0.021276596 | 0 | 0 | 0 | 0 | 0 |
| GNG4 | 0 | 0 | 0 | 0 | 0 | 0 |
| GORASP1 | 0.021276596 | 0 | 0 | 0 | 0 | 0 |
| GSK3B | 0.021276596 | 0 | 0 | 0 | 0 | 0 |
| GYG2 | 0 | 0 | 0 | 0 | 0 | 0 |
| H1FOO | 0 | 0 | 0 | 0 | 0 | 0 |
| HARBI1 | 0.021276596 | 0 | 0 | 0 | 0 | 0 |
| HHIP | 0 | 0 | 0 | 0 | 0 | 0 |
| HSP90AA1 | 0.021276596 | 0 | 0 | 0 | 0 | 0 |
| HSPA12B | 0 | 0 | 0 | 0 | 0 | 0 |
| HSPA9 | 0.021276596 | 0 | 0 | 0 | 0 | 0 |
| IK | 0.021276596 | 0 | 0 | 0 | 0 | 0 |
| ISY1 | 0.021276596 | 0 | 0 | 0 | 0 | 0 |
| KCNQ3 | 0 | 0 | 0 | 0 | 0 | 0 |
| KCP | 0 | 0 | 0 | 0 | 0 | 0 |
| KIF6 | 0 | 0 | 0 | 0 | 0 | 0 |
| KRAS | 0.021276596 | 0 | 0 | 0 | 0 | 0 |
| LRP3 | 0 | 0 | 0 | 0 | 0 | 0 |
| MLL2 | 0.021276596 | 0 | 0 | 0 | 0 | 0 |
| MLLT10 | 0.021276596 | 0 | 0 | 0 | 0 | 0 |
| MSX2 | 0 | 0 | 0 | 0 | 0 | 0 |
| KIAA0774 | 0 | 0 | 0 | 0 | 0 | 0 |
| NAIF1 | 0.021276596 | 0 | 0 | 0 | 0 | 0 |
| NEBL | 0 | 0 | 0 | 0 | 0 | 0 |
| NEU3 | 0.021276596 | 0 | 0 | 0 | 0 | 0 |
| NHLH2 | 0 | 0 | 0 | 0 | 0 | 0 |
| NRG1 | 0 | 0 | 0 | 0 | 0 | 0 |
| OPA1 | 0.021276596 | 0 | 0 | 0 | 0 | 0 |
| PDE4DIP | 0 | 0 | 0 | 0 | 0 | 0 |
| RNUXA | 0.021276596 | 0 | 0 | 0 | 0 | 0 |
| PHF23 | 0.021276596 | 0 | 0 | 0 | 0 | 0 |
| PMCHL1 | 0 | 0 | 0 | 0 | 0 | 0 |
| PNLIP | 0 | 0 | 0 | 0 | 0 | 0 |
| PPP3CC | 0.021276596 | 0 | 0 | 0 | 0 | 0 |
| PTENP1 | 0 | 0 | 0 | 0 | 0 | 0 |
| PTPN21 | 0 | 0 | 0 | 0 | 0 | 0 |

TABLE 4-continued

| Gene | Normalization weights | ABC/GCB weights | BL non-Myc weights | BL myc weights | PMBL Weights | MCL Weights |
|---|---|---|---|---|---|---|
| PTRH1 | 0.021276596 | 0 | 0 | 0 | 0 | 0 |
| R3HDM1 | 0.021276596 | 0 | 0 | 0 | 0 | 0 |
| RAB20 | 0.021276596 | 0 | 0 | 0 | 0 | 0 |
| RANBP9 | 0.021276596 | 0 | 0 | 0 | 0 | 0 |
| RC3H2 | 0.021276596 | 0 | 0 | 0 | 0 | 0 |
| RETNLB | 0 | 0 | 0 | 0 | 0 | 0 |
| RHCE | 0 | 0 | 0 | 0 | 0 | 0 |
| RNF214 | 0.021276596 | 0 | 0 | 0 | 0 | 0 |
| RRP1B | 0.021276596 | 0 | 0 | 0 | 0 | 0 |
| SPATA6 | 0 | 0 | 0 | 0 | 0 | 0 |
| SPATS1 | 0 | 0 | 0 | 0 | 0 | 0 |
| SSPN | 0 | 0 | 0 | 0 | 0 | 0 |
| SUFU | 0.021276596 | 0 | 0 | 0 | 0 | 0 |
| SPAG4L | 0 | 0 | 0 | 0 | 0 | 0 |
| SYCP1 | 0 | 0 | 0 | 0 | 0 | 0 |
| THOC5 | 0.021276596 | 0 | 0 | 0 | 0 | 0 |
| TRIM56 | 0.021276596 | 0 | 0 | 0 | 0 | 0 |
| TRIM62 | 0.021276596 | 0 | 0 | 0 | 0 | 0 |
| TUBB2C | 0.021276596 | 0 | 0 | 0 | 0 | 0 |
| UBXN4 | 0.021276596 | 0 | 0 | 0 | 0 | 0 |
| VAC14 | 0.021276596 | 0 | 0 | 0 | 0 | 0 |
| VRK3 | 0.021276596 | 0 | 0 | 0 | 0 | 0 |
| WAC | 0.021276596 | 0 | 0 | 0 | 0 | 0 |
| WDR55 | 0.021276596 | 0 | 0 | 0 | 0 | 0 |
| WFDC9 | 0 | 0 | 0 | 0 | 0 | 0 |
| ZBTB37 | 0.021276596 | 0 | 0 | 0 | 0 | 0 |
| ZCCHC2 | 0.021276596 | 0 | 0 | 0 | 0 | 0 |
| ZFP42 | 0 | 0 | 0 | 0 | 0 | 0 |
| ZNF135 | 0 | 0 | 0 | 0 | 0 | 0 |
| ZNF598 | 0.021276596 | 0 | 0 | 0 | 0 | 0 |

TABLE 5

| Submodel | Lower Cut-point | Upper Cut-point |
|---|---|---|
| ABC/GCB | 712.91 | 1238.61 |
| BL Non-Myc | −89.39 | −60.39 |
| BL Myc | 1.11 | 1.11 |
| PMBL | −400.06 | −150.06 |
| MCL | −51.92 | 359.08 |

The five submodels can then be combined according to the logic set forth below and summarized in the FIGURE.
(1) If the MCL submodel has a value of 1, the sample is called MCL.
  If the MCL submodel has a value of 0, the sample is called unclassifiable but borderline MCL.
  If the MCL submodel has a value of −1, proceed to step 2.
(2) If the BL non-myc submodel has a value of 1, proceed to step 3.
  If the BL non-myc submodel has a value of 0, the sample is called unclassifiable but borderline BL.
  If the BL non-myc submodel has a value of −1, proceed to step 4.
(3) If the BL myc submodel has a value of 0 or 1, the sample is called BL.
  If the BL myc submodel has a value of −1, the sample is called unclassifiable but borderline BL.
(4) If the PMBL submodel has a value of 1, the sample is called PMBL.
  If the PMBL submodel has a value of 0, the sample is called unclassifiable but borderline PMBL.
  If the PMBL submodel has a value of −1, proceed to step 5.
(5) If the ABC/GCB submodel has a value of 1, the sample is called ABC.
  If the ABC/GCB submodel has a value of 0, the sample is called unclassified DLBCL.
  If the ABC/GCB submodel has a value of −1, the sample is called GCB.

A similar analysis can be performed to predict whether a subject already diagnosed with DLBCL has the germinal center B cell (GCB) subtype or the activated B cell (ABC) subtype using the 800 gene array. In this respect, the sample is assumed to be of non-PMBL DLBCL, so only a ABC/GCB submodel is used employing the following logic:
  If the ABC/GCB submodel has a value of 1, the sample is called ABC
  If the ABC/GCB submodel has a value of 0, the sample is called unclassified DLBCL
  If the ABC/GCB submodel has a value of −1, the sample is called GCB.

In another embodiment, evaluating the likelihood that a particular DLBCL sample belongs to either the ABC subtype or the GCB subtype can involve calculating a predictor score using the 20 gene array containing the genes set forth in Table 3. The predictor score can be calculated using the algorithms described above with respect to the classification of ABC DLBCL, GCB DLBCL, PMBL, BL, or MCL, but using a different set of model weights, housekeeping weights, and cut points. For example, the weights ($w_i$) associated with the 20 gene probe set for the particular submodel are set forth in Table 6. In this example, the lower cutpoint for the ABC/GCB submodel is 1988.2, while the upper cutpoint for the ABC/GCB submodel is 2513.9.

TABLE 6

| Gene | Normalization weights | ABC/GCB weights |
|---|---|---|
| ASB13 | 0 | −66.35 |
| CCDC50 | 0 | 40.54 |
| CREB3L2 | 0 | 65.79 |
| CYB5R2 | 0 | 67.72 |

TABLE 6-continued

| Gene | Normalization weights | ABC/GCB weights |
|---|---|---|
| IRF4 | 0 | 71.92 |
| ISY1 | 0.2 | 0.00 |
| ITPKB | 0 | −67.78 |
| LIMD1 | 0 | 61.92 |
| MAML3 | 0 | −58.59 |
| MME | 0 | −56.55 |
| MYBL1 | 0 | −72.92 |
| PIM2 | 0 | 71.80 |
| R3HDM1 | 0.2 | 0.00 |
| RAB7L1 | 0 | 70.45 |
| S1PR2 | 0 | −78.74 |
| SERPINA9 | 0 | −61.81 |
| TNFRSF13B | 0 | 66.49 |
| TRIM56 | 0.2 | 0.00 |
| UBXN4 | 0.2 | 0 |
| WDR55 | 0.2 | 0 |

An alternative method to report the likelihood that a particular sample belongs to ABC DLBCL, GCB DLBCL, PMBL, BL, or MCL avoids assigning discrete prediction class labels to each sample and instead provides a vector of five confidence values. Each confidence value indicates the likelihood that the sample is of one of the five lymphoma types. For example, linear predictor scores are first created for each submodel $$z = \sum_i y_i w_i$$

as described above. However, rather than using discrete cut-points to indicate one of three discrete groups, the following transformation can be used to define a Bayesian sub-model score:

$$B_{submodel} = \frac{\phi\left(\sum_i y_i w_i; m_1, v_1\right)}{\phi\left(\sum_i y_i w_i; m_1, v_1\right) + \phi\left(\sum_i y_i w_i; m_2, v_2\right)}.$$

wherein $y_i$ is the value assigned probe set i as described above; $w_i$ are the weights associated with that probe set for the particular model as presented in Table 4; $m_1$, $v_1$, $m_2$, and $v_2$ are values associated with the submodel as set forth in Table 7, and $\Phi$ is the Gaussian density defined as follows:

$$\phi(y; m, v) = \frac{1}{v\sqrt{2\pi}} e^{-\frac{1}{2}\left(\frac{y-m}{v}\right)^2}.$$

TABLE 7

| Submodel | $m_1$ | $m_2$ | $v_1$ | $v_2$ |
|---|---|---|---|---|
| ABC/GCB | 2021.11 | −302.89 | 469.00 | 596.00 |
| BL non-myc | 78.02 | −201.94 | 47.60 | 38.88 |
| BL myc | 1.88 | 0.27 | 0.26 | 0.47 |
| PMBL | 571.94 | −1080.06 | 315.00 | 294.00 |
| MCL | 1610.08 | −916.92 | 582.00 | 412.00 |

The two Bayesian submodels can then be combined into the following single Bayesian score, $B_{BL}$:

$$B_{BL} = \begin{cases} B_{BLnon-myc} & \text{if } B_{BLmyc} > 0.1 \\ \min(B_{BLnon-myc}, 0.5) & \text{if } B_{BLmyc} \leq 0.1 \end{cases}.$$

The confidence values of each subtype can then be calculated as follows:

MCL confidence=$B_{MCL}$

BL confidence=$(B_{BL})(1-B_{MCL})$

PMBL confidence=$(B_{PMBL})(1-B_{BL})(1-B_{MCL})$

ABC confidence=$(B_{ABC/GCB})(1-B_{PMBL})(1-B_{BL})(1-B_{MCL})$

GCB confidence=$(1-B_{ABC/GCB})(1-B_{PMBL})(1-B_{BL})(1-B_{MCL})$.

A similar confidence value analysis can be performed to predict whether a subject already diagnosed with DLBCL has the germinal center B cell (GCB) subtype or the activated B cell (ABC) subtype using the 800 gene array. In this respect, the sample is assumed to be of non-PMBL DLBCL, so only a ABC/GCB Bayesian submodel is used which employs the following logic:

ABC confidence=$(B_{ABC/GCB})$

GCB confidence=$(1-B_{ABC/GCB})$.

In another embodiment, evaluating the likelihood that a particular DLBCL sample belongs to either the ABC subtype or the GCB subtype can involve calculating confidence values using the 20 gene array containing the genes set forth in Table 3. The confidence values can be calculated using the algorithms described above with respect to ABC DLBCL, GCB DLBCL, PMBL, BL, or MCL, but using a different set of model weights, housekeeping weights, and cut points. For example, the weights ($w_i$) associated with the 20 gene probe set for the particular submodel are set forth in Table 6. The $m_1$, $m_2$, $v_1$, and $v_2$ values for this model are, for example, 916.74, −449.76, 294.24, and 343.55, respectively.

The classification of a lymphoproliferative disorder in accordance with embodiments of the invention may be used in combination with any other effective classification feature or set of features. For example, a disorder may be classified by a method of the invention in conjunction with WHO suggested guidelines, morphological properties, histochemical properties, chromosomal structure, genetic mutation, cellular proliferation rates, immunoreactivity, clinical presentation, and/or response to chemical, biological, or other agents. Embodiments of the invention may be used in lieu of or in conjunction with other methods for lymphoma diagnosis, such as immunohistochemistry, flow cytometry, FISH for translocations, or viral diagnostics.

The inventive methods further comprise selecting a treatment option for the subject based on the subject's lymphoma classification. Accurate determination of lymphoma type in a subject allows for better selection and application of therapeutic methods. Knowledge about the exact lymphoma affecting a subject allows a clinician to select therapies or treatments that are most appropriate and useful for that subject, while avoiding therapies that are nonproductive or even counterproductive. For example, central nervous system (CNS) prophylaxis may be useful for treating BL but not DLBCL, CHOP therapy (cyclophosphamide, hydroxydaunorubicin, oncovin (vincristine), and prednisone) may be useful for treating DLBCL but not blastic MCL (see, e.g., Fisher et al., *N. Engl. J. Med.*, 328: 1002-1006 (1993); and Khouri et al., *J. Clin. Oncol.*, 12: 3803-3809 (1998)), and subjects with follicular lymphoma frequently receive treatment while subjects with follicular hyperplasia do not.

The treatment option selected can comprise any suitable therapeutic regimen or phaiinaceutical agent that shows efficacy in treating the particular lymphoma type. For example, the current standard of care for the treatment of diffuse large B cell lymphoma (DLBCL) includes anthracycline-based chemotherapy regimens such as CHOP in combination with the administration of the anti-CD20 monoclonal antibody rituximab (RITUXAN™, Genentech, Inc., South San Francisco, Calif.) ("R-CHOP"), CODOX-M/IVAC therapy (cyclophosphamide, doxorubicin, vincristine, methotrexate/ifosfamide, etoposide, high dose cytarabine), CNS prophylaxis, and radiotherapy. In one embodiment, the invention comprises providing R-CHOP therapy to a GCB DLBCL subject, while providing a different therapy to an ABC DLBCL subject, as an ABC DLBCL diagnosis can have a worse prognosis in response to R-CHOP chemotherapy as compared to a GCB DLBCL diagnosis. In this embodiment, the ABC DLBCL subject can be provided with any of the treatment options described herein or otherwise known in the art to be effective against lymphoma.

Treatment options for MCL include, for example, chemotherapy (e.g., CHOP), immune based therapy (e.g., rituximab), radioimmunotherapy, and biologic agents (e.g., protoesome inhibitors and mTor inhibitors). Treatment options for BL include, for example, R-EPOCH therapy (i.e., rituximab, etoposide, prednisone, oncovirin (vincristine)-doxorubicin-cyclophosphamide), CODOX-M/IVAC therapy, immunotherapy, bone marrow transplantation, stem cell transplantation, surgery, and radiotherapy. Treatment options for PBML are similar to those for DLBCL, and also can include high-dose chemotherapy, radiotherapy, and/or stem cell transplantation. Other lymphoma treatments include drugs which target specific pathways that sustain lymphoma survival, such as, e.g., ibrutinib.

The following examples further illustrates the invention but, of course, should not be construed as in any way limiting its scope.

Example 1

This example demonstrates a method for determining subtypes of diffuse large B-cell lymphoma (DLBCL) using gene expression profiling on formalin-fixed paraffin embedded tissue.

Although the ABC DLBCL and GCB DLBCL subtypes were originally defined using gene expression profiling (GEP) on snap-frozen tissues (referred to herein as "frozen-GEP"), it has become common practice to use less precise but relatively inexpensive and broadly applicable immunohistochemical (IHC) methods using formalin-fixed paraffin embedded tissues (FFPET). The inventive method allows for a robust, highly accurate, molecular assay for cell-of-origin (COO) distinction using new GEP techniques applicable to FFPET. Studies were performed on centrally reviewed DLBCL FFPET biopsies from the Lymphoma/Leukemia Molecular Profiling Project (LLMPP) matching cases that had "gold standard" COO assigned by frozen-GEP using GENECHIP™ U133 plus 2.0 microarrays (Affymetrix, Santa Clara, Calif.). The training cohort consisted of 51 cases comprising 20 GCB DLBCL, 19 ABC DLBCL and 12 unclassifiable (U) cases. An independent validation cohort, which includes 68 cases (28 GCB DLBCL, 30 ABC DLBCL, and 10 U) drawn from the validation cohort described in Lenz et al., *N Engl. J Med.*, 359: 2313-2323 (2008), had the typical proportions of COO subtypes seen in DLBCL populations.

Nucleic acids were extracted from 10 µm FFPET scrolls. Digital gene expression was performed on 200 ng of RNA using the NANOSTRING™ assay (NanoString Technologies, Seattle, Wash.). All FFPET GEP studies were performed in parallel at two independent sites (BC Cancer Agency, Vancouver and NCI, Bethesda, Md.) using different FFPET scrolls to determine inter-site concordance, which assesses the robustness and portability of the assay. To assign COO by IHC, tissue microarrays were made using 0.6 mm duplicate cores for the validation cohort and stained for antibodies for CD10, BCL6, MUM1, FOXP1, GCET1, and LMO2. Two hematopathologists independently assessed the proportion of tumor cells stained, with consensus on discordant cases reached with a third hematopathologist. For the validation studies, those producing and analyzing the GEP and IHC data were blinded to the "gold standard" COO.

All 119 FFPET biopsies yielded sufficient RNA. A pilot study using the training cohort identified 20 genes (i.e., 15 genes of interest and 5 housekeeping genes) whose expression, measured using the NANOSTRING™ assay, would allow accurate replication of the COO assignment model described in Lenz et al., supra. The NANOSTRING™ assay was then used to quantify expression of these 20 genes in the training cohort, thereby allowing the COO model to be optimized. Despite the age of the FFPET blocks (6 to 32 years old), 95% (49/51) of the training samples produced gene expression data of sufficient quality. The COO model, including coefficients, thresholds, and QC parameters was then "locked" and applied to the independent validation cohort. Ninety-nine percent (67/68) of the samples from the validation cohort (5 to 12 years old) provided gene expression of adequate quality. When considering the "gold standard" ABC DLBCL and GCB DLBCL cases, the COO assignments by the NANOSTRING™ assay at the NCI site were 93% concordant, with 5% labeled U and 1 ABC misclassified as GCB, as shown in Table 8.

TABLE 8

|  |  | NANOSTRING™ GEP Assay-NCI | | | Hans Algorithm | | Tally Algorithm | | Choi Algorithm | |
| --- | --- | --- | --- | --- | --- | --- | --- | --- | --- | --- |
|  |  | GCB | U | ABC | GCB | Non-GCB | GCB | ABC | GCB | ABC |
| Frozen-GEP | GCB | 28 | 0 | 0 | 21 | 0 | 18 | 3 | 19 | 2 |
|  | U | 7 | 2 | 1 | 5 | 5 | 2 | 8 | 6 | 4 |
|  | ABC | 1 | 3 | 25 | 4 | 22 | 0 | 26 | 6 | 20 |

Thus, 119 highly characterized DLBCL cases from the LLMPP, which were previously subtyped by a published disease-defining algorithm using frozen-GEP, were highly accurately analyzed in accordance with the inventive method. These results demonstrate that the inventive method, which utilized RNA from FFPET that is routinely obtained for diagnosis, provides a desirable alternative to existing techniques for the analysis of DLBCL cases. The 2% rate of misclassification of ABC and GCB cases by the inventive method compares favorably with the 9%, 6% and 17% rates for the Hans, Tally and Choi algorithms, respectively (see Hans et al. *Blood,* 103(1): 275-82 (2004); Meyer et al., *J. Clin. Oncol.,* 29(2): 200-207 (2011); and Choi et al., *Clin. Cancer Res.,* 15(17): 5494-502 (2009)). Furthermore, the 100% concordance of COO assignment (95% if "gold standard" U cases also are included) between the NCI and BC Cancer Agency sites indicates that, in contrast to the IHC algorithms, the inventive method is robust.

The inventive method exhibits high performance with archival FFPET and allows for rapid turn-around time (<36 hours from FFPET block to result), which is highly desirable in clinical practice.

Example 2

This example demonstrates a method for determining subtypes of aggressive B cell non-Hodgkin lymphomas (agg-B-NHL) using gene expression profiling on formalin-fixed paraffin embedded tissue.

Formalin-fixed, paraffin-embedded tissue (FFPET) biopsies qualified by an expert Hematopathology review panel as having a tumor content of ≥60% and confirmed B cell immunophenotype were evaluated. Diagnostic categories included diffuse large B cell lymphoma (DLBCL) including the activated B cell-like (ABC) and germinal center B cell-like (GCB) subtypes, unclassifiable (UNC) DLBCL, primary mediastinal B cell lymphoma (PMBCL), Burkitt lymphoma (BL), and mantle cell lymphoma (MCL). Using previous GEP data, diagnostic signatures, the NCOUNTER™ gene expression assay (NanoString Technologies, Seattle, Wash.), and employing published procedures (Scott et al, *Blood,* (January 2014); DOI: 10.1182/blood-2013-11-536433), probes to 800 genes (shown in Table 4) were designed with utility in distinguishing between these pathological entities.

The training cohort comprised 107 unique cases, whose FFPET biopsies were independently assayed at the Molecular Characterization Laboratory, Frederick National Laboratory for Cancer Research (Frederick, Md.) and the Centre for Lymphoid Cancer, BC Cancer Agency (Vancouver, BC). The resulting algorithm was locked down and applied to an independent cohort of 199 cases. The nucleic acids from FFPET biopsies from these cases were extracted and run across the two independent laboratories, with 83 cases run at both laboratories to assess inter-laboratory performance. The "gold standard" by which the NANOSTRING™ classification was compared was based on Affymetrix gene expression profiling of matched frozen biopsies in the cases of ABC, GCB, and UNC DLBCL (Lenz et al., supra) and on the pathological diagnosis by the Hematopathology review panel in the cases of BL, MCL, and PMBCL. The use of human tissues and clinical data for this study was approved by the University of Arizona Institutional Review Board in accordance with the Declaration of Helsinki.

The final locked algorithm consisted of 297 gene probes (shown in Table 2) including 47 housekeeping genes. Thirty-six cases from the training cohort were run again on the new lot of NANOSTRING™ code set to allow for cross code set calibration of the assay. The laboratory procedure and algorithm, together termed the "Lymph5Cx" test, consists of a hierarchical series of pair-wise comparisons. In the independent validation set, 257/282 (91.1%) of assays yielded gene expression data of sufficient quality (total of 185 of the 199 cases). A classification summary is given in Table 9.

TABLE 9

| Lymphoma Subtype | # cases | % accurate | % borderline | % error |
|---|---|---|---|---|
| ABC | 26 | 76.9% | 23.1% | 0.0% |
| GCB | 27 | 88.9% | 7.4% | 3.7% |
| BL | 48 | 68.8% | 19.8% | 11.5% |
| PMBL | 30 | 80.0% | 6.7% | 13.3% |
| MCL | 34 | 100.0% | 0.0% | 0.0% |

In this cohort, 136 cases (82%) were correctly assigned while 12 cases (6%) were assigned incorrect diagnoses as follows: 6 BL assigned to GCB, 1 GCB labeled a PMBCL, 1 UNC DLBCL called a PMBCL and 4 PMBCL assigned to DLBCL subtypes. The Lymph5Cx test included categories of indeterminate results between two diagnostic entities and were declared borderline. The agreement between the two laboratory sites was 71/72 (99%) of cases that yielded adequate gene expression data at both sites.

Therefore, the results of this example demonstrate that the Lymph5Cx test was robust and able to discriminate the often clinically difficult diagnostic categories of agg-B-NHL using a single methodology for cases with histologic and immunophenotypic features of an agg-B-NHL. Misclassification errors were low, suggesting that this test would be useful adjunct to current diagnostic methods. In addition, targetable pathways, as well as genes associated with known prognostic signatures in DLBCL (stromal) and MCL (proliferation) were quantified.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US11574704B2). An electronic copy of the "Sequence Listing" will also be available from the USPTO upon request and payment of the fee set forth in 37 CFR 1.19(b)(3).

The invention claimed is:

1. A method for treating an activated B cell-like diffuse large B cell lymphoma (ABC DLBCL) in a human subject, a germinal center B cell-like diffuse large B cell lymphoma (GCB DLBCL) in a human subject, a primary mediastinal B cell lymphoma (PMBL) in a human subject, a Burkitt lymphoma (BL) in a human subject, or a mantle cell lymphoma (MCL) in a human subject, the method comprising:

(a) isolating RNA gene expression product from a biopsy sample from a lymphoma human subject;

(b) obtaining digital gene expression data from the isolated gene expression product, wherein the digital gene expression data comprises data for genes in a gene expression signature, and wherein the gene expression signature comprises at least one of the genes listed in Table 2;

(c) optionally obtaining digital gene expression data from a first and second reference set of probe sets, the first and second reference set of probe sets being known for classifying ABC DLBCL, GCB DLBCL, PMBL, BL, or MCL;

(d) calculating a predictor score using the equation:

$$y_i = \log_2(x_i) - \sum_j \log_2(x_j) h_j - \log_2(r_i) + \log_2(g_i)$$

wherein $y_i$ is a predictor score for gene i, $x_i$ is the counts for probe set i for gene i on the sample being tested, $x_j$ is the counts for probe set j for gene j, probe set j is the set of normalization genes of the sample being tested, $h_j$ is the normalization weight for probe set j as listed in Table 4, $r_i$ is the counts for probe set i for gene i on the first reference set of probe sets, and $g_i$ is the counts for probe set i for gene i on the second reference set of probe sets, the mathematical terms with $r_i$ and $g_i$ being equal to zero if no digital gene expression data is obtained from a first and second reference set of probe sets;

(e) calculating a Bayesian sub-model score for each of ABC/GCB DLBCL, BL non-myc, BL myc, PMBL, and MCL using the equation:

$$B_{submodel} = \frac{\phi\left(\sum_i y_i w_i; m_1, v_1\right)}{\phi\left(\sum_i y_i w_i; m_1, v_1\right) + \phi\left(\sum_i y_i w_i; m_2, v_2\right)}$$

wherein $y_i$ is the value assigned probe set i in (d); $w_i$ are the weights associated with that probe set for the particular model as listed in Table 4; $m_1$, $v_1$, $m_2$, and $v_2$ are values associated with the submodel as listed in Table 7, and $\Phi$ is the Gaussian density defined as:

$$\phi(y; m, v) = \frac{1}{v\sqrt{2\pi}} e^{-\frac{1}{2}\left(\frac{y-m}{v}\right)^2};$$

(f) combining the Bayesian sub-model scores for BL non-myc and BL myc using the formula:

$$B_{BL} = \begin{cases} B_{BLnon-myc} & \text{if } B_{BLmyc} > 0.1 \\ \min(B_{BLnon-myc}, 0.5) & \text{if } B_{BLmyc} \leq 0.1 \end{cases};$$

(g) calculating the confidence values of each subtype using:

MCL confidence=$B_{MCL}$

BL confidence=$(B_{BL})(1-B_{MCL})$

PMBL confidence=$(B_{PMBL})(1-B_{BL})(1-B_{MCL})$

ABC confidence=$(B_{ABc/GCB})(1-B_{PMBL})(1-B_{BL})(1-B_{MCL})$

GCB confidence=$(1-B_{ABc/GCB})(1-B_{PMBL})(1-B_{BL})(1-B_{MCL})$;

(h) classifying the subject based on the confidence values of (g) as belonging to one of the following groups: (1) ABC DLBCL, (2) GCB DLBCL, (3) PMBL, (4) BL, or (5) MCL; and (i) providing treatment to the subject, wherein the treatment is (i) R-CHOP or ibrutinib if the classification of (h) is GCB DLBCL, (ii) ibrutinib if the classification of (h) is ABC DLBCL, (iii) CHOP, ibrutinib, immunotherapy, radioimmunotherapy, protoesome inhibitors, or mTor inhibitors if the classification of (h) is MCL, (iv) EPOCH, ibrutinib, CODOX-M/IVAC therapy, immunotherapy, bone marrow transplantation, stem cell transplantation, surgery, or radiotherapy if the classification of (h) is BL, or (v) R-CHOP, ibrutinib, high-dose chemotherapy, radiotherapy, or stem cell transplantation if the classification of (h) is PMBL.

2. The method of claim 1, wherein the gene expression signature comprises the genes listed in Table 2.

3. The method of claim 1, wherein the gene expression product is isolated from a formalin-fixed and paraffin-embedded (FFPE) biopsy sample from the subject.

4. The method of claim 1, wherein the digital gene expression data is obtained using an assay comprising color-coded probes.

5. A method for treating a diffuse large B cell lymphoma (DLBCL) in a human subject, comprising the steps of:
(a) isolating RNA gene expression product from a biopsy sample from a lymphoma human subject;
(b) obtaining digital gene expression data from the isolated gene expression product, wherein the digital gene expression data comprises data for genes in a gene expression signature, and wherein the gene expression signature comprises at least one of the genes listed in Table 1;
(c) optionally obtaining digital gene expression data from a first and second reference set of probe sets, the first and second reference set of probe sets being known for classifying ABC DLBCL or GCB DLBCL;
(d) calculating a predictor score using the equation:

$$y_i = \log_2(x_i) - \sum_j \log_2(x_j) h_j - \log_2(r_i) + \log_2(g_i)$$

wherein $y_i$ is a predictor score for gene i, $x_i$ is the counts for probe set i for gene i on the sample being tested, $x_j$ is the counts for probe set j for gene j, probe set j is the set of normalization genes of the sample being tested, $h_j$ is the normalization weight for probe set j as listed in Table 4, $r_i$ is the counts for probe set i for gene i on the first reference set of probe sets, and $g_i$ is the counts for probe set i for gene i on the second reference set of probe sets, the mathematical terms with $r_i$ and $g_i$ being equal to zero if no digital gene expression data is obtained from a first and second reference set of probe sets;
(e) calculating a ABC/GCB Bayesian sub-model score using the equation:

$$B_{submodel} = \frac{\phi\left(\sum_i y_i w_i; m_1, v_1\right)}{\phi\left(\sum_i y_i w_i; m_1, v_1\right) + \phi\left(\sum_i y_i w_i; m_2, v_2\right)}$$

wherein $y_i$ is the value assigned probe set i in (d); $w_i$ are the weights associated with that probe set for the particular model as listed in Table 4; $m_1$, $v_1$, $m_2$, and $v_2$ are values associated with the submodel as listed in Table 7, and $\Phi$ is the Gaussian density defined as:

$$\phi(y; m, v) = \frac{1}{v\sqrt{2\pi}} e^{-\frac{1}{2}\left(\frac{y-m}{v}\right)^2};$$

(f) calculating the confidence values of each subtype using:

ABC confidence=$(B_{ABC/GCB})$

GCB confidence=$(1-B_{ABC/GCB})$;

(g) classifying the subject based on the confidence values of (f) as belonging to ABC DLBCL or GCB DLBCL;
(h) providing treatment to the subject, wherein the treatment is (i) R-CHOP or ibrutinib if the classification of (g) is GCB DLBCL or (ii) ibrutinib if the classification of (g) is ABC DLBCL.

6. The method of claim 5, wherein the gene expression signature comprises the genes listed in Table 1.

7. The method of claim 5, wherein the gene expression product is isolated from a formalin-fixed and paraffin-embedded (FFPE) biopsy sample from the subject.

8. The method of claim 5, wherein the digital gene expression data is obtained using an assay comprising color-coded probes.

9. A method for treating a diffuse large B cell lymphoma (DLBCL) in a human subject, comprising the steps of:
(a) isolating RNA gene expression product from a biopsy sample from a lymphoma human subject;
(b) obtaining digital gene expression data from the isolated gene expression product, wherein the digital gene expression data comprises data for genes in a gene expression signature, and wherein the gene expression signature comprises at least one of the genes listed in Table 3;
(c) optionally obtaining digital gene expression data from a first and second reference set of probe sets, the first and second reference set of probe sets being known for classifying ABC DLBCL or GCB DLBCL;
(d) calculating a predictor score using the equation:

$$y_i = \log_2(x_i) - \sum_j \log_2(x_j) h_j - \log_2(r_i) + \log_2(g_i)$$

wherein $y_i$ is a predictor score for gene i, $x_i$ is the counts for probe set i for gene i on the sample being tested, $x_j$ is the counts for probe set j for gene j, probe set j is the set of normalization genes of the sample being tested, $h_j$ is the normalization weight for probe set j as listed in Table 4, $r_i$ is the counts for probe set i for gene i on the first reference set of probe sets, and $g_i$ is the counts for probe set i for gene i on the second reference set of probe sets, the mathematical terms with $r_i$ and $g_i$ being equal to zero if no digital gene expression data is obtained from a first and second reference set of probe sets;
(e) calculating a ABC/GCB Bayesian sub-model score using the equation:

$$B_{submodel} = \frac{\phi\left(\sum_i y_i w_i; m_1, v_1\right)}{\phi\left(\sum_i y_i w_i; m_1, v_1\right) + \phi\left(\sum_i y_i w_i; m_2, v_2\right)}$$

wherein $y_i$ is the value assigned probe set i in (d); $w_i$ are the weights associated with that probe set for the particular model as listed in Table 6; $m_1$, $v_1$, $m_2$, and $v_2$ are 916.74, −449.76, 294.24, and 343.55, respectively, and $\Phi$ is the Gaussian density defined as:

$$\phi(y; m, v) = \frac{1}{v\sqrt{2\pi}} e^{-\frac{1}{2}(\frac{y-m}{v})^2};$$

(f) calculating the confidence values of each subtype using:

ABC confidence=$(B_{ABC/GCB})$

GCB confidence=$(1-B_{ABC/GCB})$;

(g) classifying the subject based on the confidence values of (f) as belonging to ABC DLBCL or GCB DLBCL;

(h) providing treatment to the subject, wherein the treatment is (i) R-CHOP or ibrutinib if the classification of (g) is GCB DLBCL or (ii) ibrutinib if the classification of (g) is ABC DLBCL.

10. The method of claim 9, wherein the gene expression signature comprises the genes listed in Table 3.

11. The method of claim 9, wherein the gene expression product is isolated from a formalin-fixed and paraffin-embedded (FFPE) biopsy sample from the subject.

12. The method of claim 9, wherein the digital gene expression data is obtained using an assay comprising color-coded probes.

\* \* \* \* \*